US012774349B2

(12) United States Patent
Arathoon et al.

(10) Patent No.: US 12,774,349 B2
(45) Date of Patent: Oct. 27, 2026

(54) ANTI ABCC1 ANTIBODIES AND USES THEREOF

(71) Applicant: William Robert Arathoon living Trust Dated August 29, 2016, Tiburon, CA (US)

(72) Inventors: William Robert Arathoon, Tiburon, CA (US); Raffaella Briante, Burlingame, CA (US); Paul David Ponath, San Francisco, CA (US); Cindy Tan, San Jose, CA (US); Richard Theolis, Santa Cruz, CA (US); Qianting Zhai, South San Francisco, CA (US); Pingping Zhang, Cupertino, CA (US)

(73) Assignee: William Robert Arathoon Living Trust Dated August 29, 2016, Tiburon, CA (US)

( * ) Notice: Subject to any disclaimer, the term of this patent is extended or adjusted under 35 U.S.C. 154(b) by 814 days.

(21) Appl. No.: 18/043,675

(22) PCT Filed: Sep. 1, 2021

(86) PCT No.: PCT/US2021/048701
§ 371 (c)(1),
(2) Date: Mar. 1, 2023

(87) PCT Pub. No.: WO2022/051390
PCT Pub. Date: Mar. 10, 2022

(65) Prior Publication Data

US 2023/0272117 A1 Aug. 31, 2023

Related U.S. Application Data

(60) Provisional application No. 63/073,826, filed on Sep. 2, 2020.

(51) Int. Cl.
*C07K 16/46* (2006.01)
*A61P 35/00* (2006.01)

(52) U.S. Cl.
CPC ............ *C07K 16/468* (2013.01); *A61P 35/00* (2018.01); *C07K 2317/31* (2013.01); *C07K 2317/565* (2013.01); *C07K 2317/622* (2013.01)

(58) Field of Classification Search
CPC .............. C07K 16/468; C07K 2317/31; C07K 2317/565; C07K 2317/622; C07K 2317/76; C07K 2317/92; C07K 16/2827; C07K 16/32; C07K 2317/24; C07K 2317/33; C07K 2317/73; C07K 16/3023; C07K 16/28; A61P 35/00; A61K 2039/505; A61K 2039/86
See application file for complete search history.

(56) References Cited

U.S. PATENT DOCUMENTS

| | | | |
|---|---|---|---|
| 6,063,621 | A | 5/2000 | Deeley et al. |
| 2019/0248912 | A1 | 8/2019 | Zhen |

FOREIGN PATENT DOCUMENTS

| | | |
|---|---|---|
| CN | 106432490 A | 2/2017 |
| JP | 2004051553 | 2/2004 |

OTHER PUBLICATIONS

Scheffer et al. Cancer Res (2000) 60 (18): 5269-5277 (Year: 2000).*
Binyamin et al. Int. J. Cancer, 110: 882-890, 2004 (Year: 2004).*
"Purified anti-human/mouse MRP1 (ABCC1) Antibody", (2016), Biolegend, 1-2.
(Sep. 6, 2009) "ABCC1 Gene—ATP Binding Cassette Subfamily C Member 1", Retrieved from:—"https://www.genecards.org/cgi-bin/carddisp.pl?gene=ABCC1&keywords=ABCC1,GENE", 27 pages.
Biolegend (Aug. 4, 2019) "Anti-MRP1 (ABCC1) Antibody (Previously Covance catalog# SIG—38760)", Catalog #907201, Version 4, 8 pages.
Godinot et al. (Mar. 2003) "Cloning and functional characterization of the multidrug resistance-associated protein (MRP1/ABCC1) from the cynomolgus monkey", Molecular Cancer Therapeutics, vol. 2, No. 3, pp. 307-316.
Rudikoff et al. (Mar. 1982) "Single amino acid substitution altering antigen-binding specificity", Proc. Natl Acad. Sci., vol. 79, pp. 1979-1983.
Van Dijk et al. (1989) "Bispecific antibodies reactive with the multidrug-resistance-related glycoprotein and CD3 induce lysis of multidrug-resistant tumor cells", International Journal of Cancer, vol. 44, pp. 738-743.
Yang et al. (2015) "Target therapy of multiple myeloma by PTX-NPs and ABCG2 antibody in a mouse xenograft model", Oncotarget, vol. 6, No. 29, pp. 27714-27724.

* cited by examiner

*Primary Examiner* — Sean E Aeder
*Assistant Examiner* — Yie Chia Lee
(74) *Attorney, Agent, or Firm* — Shweta Chandra; Bozicevic, Field & Francis LLP

(57) ABSTRACT

Provided are antibodies that target the cellular efflux pump ABCC1. Also provided are pharmaceutical compositions, nucleic acids, recombinant expression vectors, cells, and kits that include or encode such antibodies. Methods of using the antibodies for detecting presence or absence of ABCC1 expression in cells, e.g., tumor cells, Level of ABCC1 expression, and/or inhibiting ABCC1 function are also disclosed. Also provided are methods for treating a subject for a cancer that include administering to the subject an anti-ABCC1 antibody disclosed herein. The subject antibody may be a bispecific antibody. The bispecific antibody may bind to ABCC1 and a tumor associated antigen (TAA).

20 Claims, 34 Drawing Sheets

Specification includes a Sequence Listing.

| | C1.773A | C1.773 | C1.777A | C1.778B | C1.784A | C1.786A | C1.787A | C1.779B | C1.309 | C1.505 |
|---|---|---|---|---|---|---|---|---|---|---|
| H69ADR Kd(nM) | 3.2 | 2.5 | 4.2 | 8.7 | 7.0 | 8.3 | 4.3 | 10.1 | 10.0 | 7.1 |

mAbs binding to the human and Cyno C1 overexpression cell line

| | C1.773 | C1.773A | C1.777A | C1.778B | C1.781A | C1.7 84A | C1.786A | C1.787A | C1.779B | C1.505.hu 11 | 786A | 787A | C1.505 | C1.309 |
|---|---|---|---|---|---|---|---|---|---|---|---|---|---|---|
| C6.hC1 Kd(nM) | 6.5 | 33.0 | 41.2 | 666.8 | 115.8 | 38.2 | 12.4 | 17.2 | 83.3 | 157.9 | 13.8 | 24.3 | 81.2 | 132.7 |
| C6.cC1 | | | | | | | | | | | | | | |

mAbs binding to the human and Cyno C1 overexpression cell line

| | C1.876 | C1778b | C1.879A | C1.861 | C1.877 | C1.773 |
|---|---|---|---|---|---|---|
| C6.hC1 Kd(nM) | 6.5 | 33.0 | 41.2 | 666.8 | 115.8 | 17.2 |
| C6.cC1 Kd(nM) | 3.7 | 28.2 | 27.2 | 60.1 | 66.8 | 19.1 |
| 293T.hC1 Kd(nM) | 14.5 | 16.5 | 8.5 | 9.5 | 6.9 | 4.5 |

mAbs binding to the human and Cyno C1 overexpression cell line

| | C1.835 | C1.831 | C1.827 | C1.505 | C1.773 |
|---|---|---|---|---|---|
| C6.hC1 Kd(nM) | 144.4 | 11.4 | 133.9 | 35.2 | 1.9 |
| C6.cC1 Kd(nM) | 575.1 | 8.7 | 67.3 | NB | 2.7 |

mAbs binding to the human and Cyno C1 overexpression cell line

| | C1.830B | C1.841 | C1.844 | C1.845 | C1.847 | C1.851 | C1.855 | C1.773 |
|---|---|---|---|---|---|---|---|---|
| C6.hC1 Kd(nM) | 14.4 | 102.9 | 65.1 | 21.8 | 21.7 | 98.0 | >1000 | 12.7 |
| C6.cC1 Kd(nM) | 8.6 | 42.3 | 34.1 | 20.1 | 23.3 | 28.0 | 278.8 | 5.9 |

mAbs binding to the human and Cyno C1 overexpression cell line

| | C1.861 | C1.863 | C1.787a | C1.773 |
|---|---|---|---|---|
| C6.hC1 Kd(nM) | 14.7 | 11.7 | 7.8 | 3.7 |
| C6.cC1 Kd(nM) | 28.0 | 27.3 | 27.6 | 4.6 |

C1 Efflux Assay results

Characterization of humanized C1 mAbs

| | C1.831.hu11 | C1.861.hu11 | C1.861.hu21 | C1.844.hu21 | C1.773 |
|---|---|---|---|---|---|
| C6.hC1 Kd(nM) | 14 | 19 | 16 | 14 | 5 |
| C6.cC1 Kd(nM) | 11 | 11 | 11 | 11 | 4 |
| 293T.hC1 Kd(nM) | 11 | 14 | 10 | 8 | 6 |

Humanized mAbs binding the human and Cyno C1 overexpression cell line

| | C1.831.hu11 | C1.831.hu21 | C1.831.hu31 | C1.831.hu41 | C1.831.hu51 | C1.861.hu11 | C1.861.hu21 | C1.861.hu31 | C1.861.hu41 | C1.861.hu51 | C1.861.hu61 | C1.844.hu21 | C1.844.hu31 | C1.844.hu41 |
|---|---|---|---|---|---|---|---|---|---|---|---|---|---|---|
| C6.hC1 Kd(nM) | 21 | NB | NB | 21 | NB | 21 | 38 | NB | 156 | NB | 218 | 103 | 518 | 94 |
| C6.cC1 Kd(nM) | 27 | NB | 1071 | 20 | NB | 29 | 37 | 110 | 64 | 125 | 135 | 83 | 253 | 107 |

Humanized C1.851 mAbs binding the human and Cyno C1 overexpression cell line

| | C1.851.hu14 | C1.851.hu15 | C1.851.hu12 |
|---|---|---|---|
| C6.hC1 Kd(nM) | 148.5 | 118.9 | 152.9 |
| C6.cC1 Kd(nM) | 2030 | 210.5 | 181.2 |

C1/KT9 Bispecific antibodies

C1/KT1 Bispecific Antibodies

Cytotoxicity Assay

FIG. 13B

| Treatment | IC50 (uM) | IC50 (nM) | % IgG | % Vin |
|---|---|---|---|---|
| Vin | 0.0003835 | 0.384 | 219.1 | 99.9 |
| Vin+MK571 | 0.0000467 | 0.047 | 26.7 | 12.2 |
| Vin+hIgG | 0.0001751 | 0.175 | 100.1 | 45.6 |
| Vin+C1-505 | 0.0000305 | 0.031 | 17.4 | 7.9 |
| Vin+ C1-787a | 0.0001019 | 0.102 | 58.2 | 26.5 |
| Vin+C1-845 | 0.0001630 | 0.163 | 93.1 | 42.4 |
| Vin+C1-847 | 0.0001845 | 0.185 | 105.4 | 48.0 |
| Vin+ C1-851 | 0.0000007 | 0.001 | 0.4 | 0.2 |
| Vin+C1-841 | 0.0000001 | 0.000 | 0.04 | 0.02 |

Cytotoxicity Assay

| Treatment | IC50 (pM) |
|---|---|
| Vin | 335.0 |
| MK571 | 0.002 |
| hIgG | 175.1 |
| C1-505 | 99.4 |
| C1-787a | 99.0 |
| C1-845 | 127.8 |
| C1-847 | 80.1 |
| C1-851 | 58.3 |
| C1-841 | 65.7 |
| C1-830B | 291.1 |
| C1-861 | 3.6 |
| C1-831 | 13.6 |

| Treatment | IC50 (pM) |
|---|---|
| Vin | 335.0 |
| MK571 | 0.002 |
| hIgG | 175.1 |
| C1-505 | 99.4 |
| C1-787a | 99.0 |
| C1-845 | 127.8 |
| C1-847 | 80.1 |
| C1-851 | 58.3 |
| C1-841 | 65.7 |
| C1-830B | 291.1 |
| C1-861 | 3.6 |
| C1-831 | 13.6 |

| TA | IC50 (pM) |
|---|---|
| Vin | 5.7 |
| MK571 | 3.1 |
| hIgG | 13.0 |
| C1-505d | 6.6 |
| C1-505 | 34.3 |
| C1-773 | 38.9 |
| C1-773A | 24.9 |
| C1-786A | 0.1 |
| C1-787A | 0.5 |
| C1-777A | 0.2 |
| C1-778B | 19.2 |

C1 Monoclonals Inhibit Tumor Growth in vivo

C1 Monoclonals Inhibit Tumor Growth in vivo

ANTI ABCC1 ANTIBODIES AND USES THEREOF

CROSS-REFERENCE TO RELATED APPLICATIONS

This application claims the benefit of priority to U.S. Provisional Patent Application No. 63/073,826 filed on Sep. 2, 2020, which application is incorporated herein by reference in its entirety.

INCORPORATION BY REFERENCE OF SEQUENCE LISTING PROVIDED AS TEXT FILE

A Sequence Listing is provided herewith as a text file, "KNJY-006WO SEQ LIST_ST25.txt," created on Aug. 24, 2021 and having a size of 151 KB. The contents of the text file are incorporated by reference herein in their entirety.

INTRODUCTION

Drug resistance, a well-known phenomenon that results when diseases become tolerant to pharmaceutical treatments, is a major and increasing challenge in various fields of medicine, including oncology. Although many types of cancers are initially susceptible to chemotherapy, over time they can develop resistance through these and other mechanisms, including DNA mutations and metabolic changes that promote drug inhibition, degradation and enhanced efflux.

Efflux pumps (EP) are proteins expressed by living cells and have evolved to naturally expel various compounds from the cells. Members of the ATP-binding cassette (ABC) transporter family proteins are examples of EPs that enable drug efflux. Though a transporter's structure varies from protein to protein (e.g., there are 49 known members of the ABC family in humans), they are all classified by the presence of two distinct domains—a highly conserved nucleotide binding domain and a more variable transmembrane domain. Multidrug resistance protein 1 (MDR1), encoded by the ATP Binding Cassette Subfamily B Member 1 (ABCB1) gene, was the first of these to be identified and has been studied extensively. ATP Binding Cassette Subfamily C Member 1 (ABCC1) expression is increased in response to treatment with certain chemotherapeutics.

EPs enable tumors to develop resistance to chemotherapeutic agents. Such resistance is frequently associated with enhanced efflux of the chemotherapeutic agent from the drug resistant cells. This chemotherapy resistance is termed multi drug resistance (MDR) when it applies to more than one chemotherapeutic agent.

As such there is a need to develop reagents that may be used for assaying for expression of EPs and/or inhibiting EPs.

SUMMARY

Provided are antibodies that target the cellular efflux pump ATP Binding Cassette Subfamily C Member 1 (ABCC1). Also provided are pharmaceutical compositions, nucleic acids, recombinant expression vectors, cells, and kits that include or encode such antibodies. Methods of using the antibodies for detecting presence or absence of ABCC1 expression in cells, e.g., tumor cells, level of ABCC1 expression, and/or inhibiting ABCC1 function are also disclosed. Also provided are methods for treating a subject for a cancer that include administering to the subject an anti-ABCC1 antibody disclosed herein.

BRIEF DESCRIPTION OF THE FIGURES

FIGS. 13A-13B, 14A-14B, and 15 show the effect of the tested anti-ABCC1 monoclonal antibodies on vincristine cytotoxicity in the 293T cytotoxicity assay.

DEFINITIONS

Figure 1:
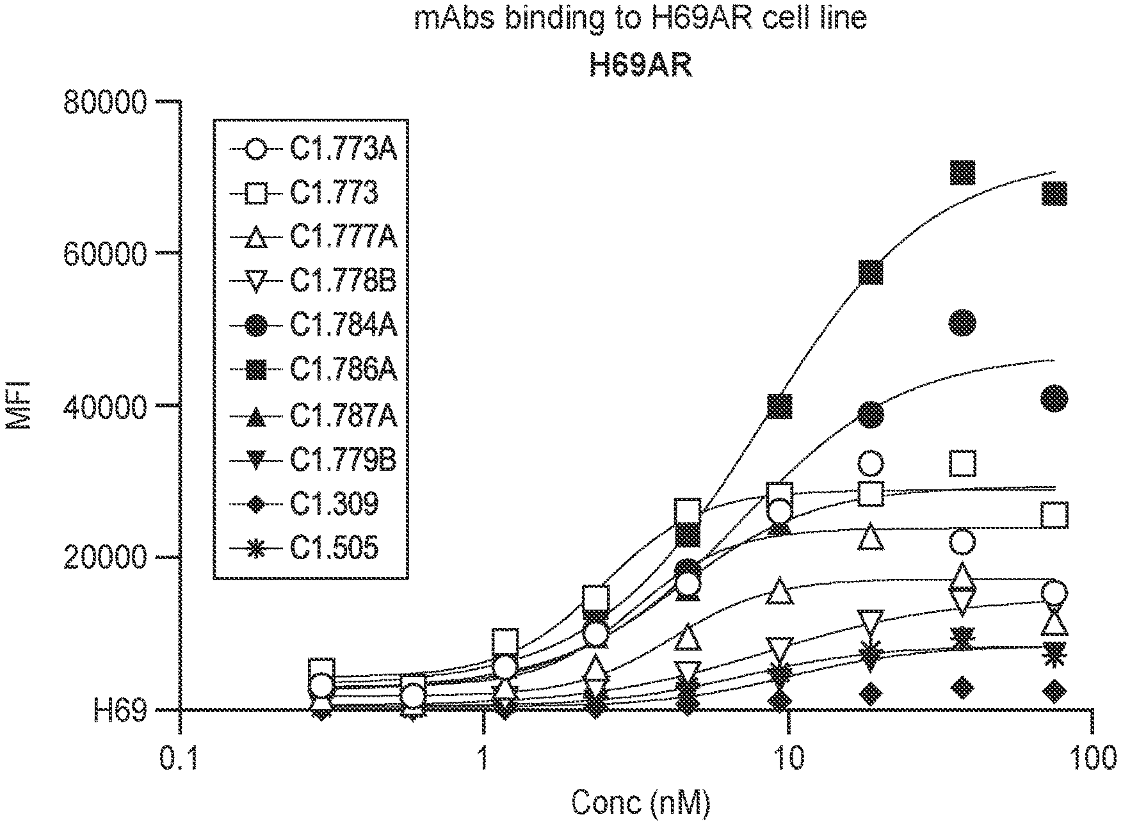
FIG. 1 depicts the results of titration binding of the indicated anti-ABCC1 monoclonal antibodies to the doxorubic n-resistant lung carcinoma cell line H69AR (ATCC® CRL-11351) that endogenously expresses ABCC1. H69AR (ATCC CRL-11351) was established from NCI-H69 cells that were grown in the presence of increasing concentrations of Adriamycin (doxorubicin) over a total of 14 months.
Figure 2A:
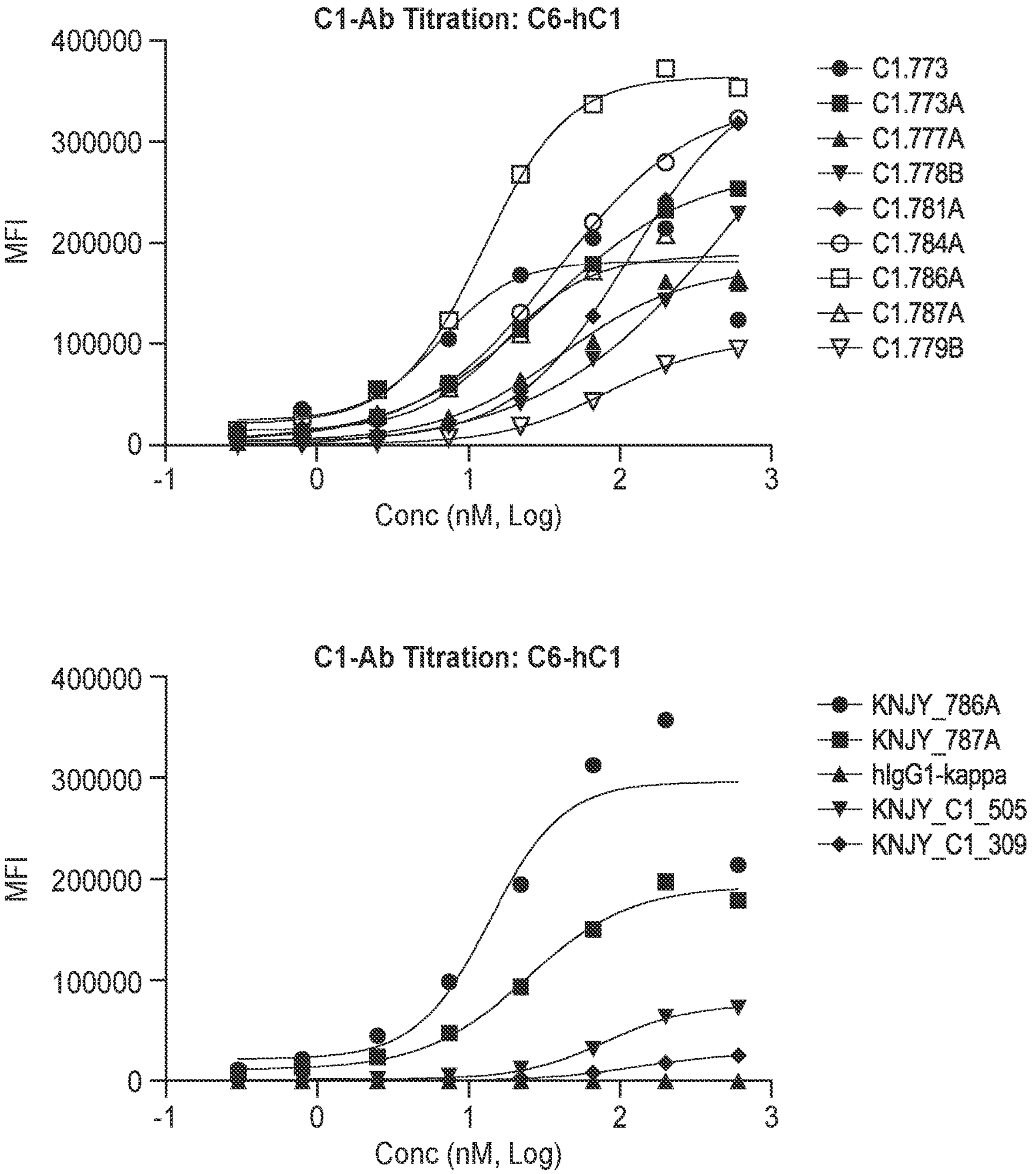
FIGS. 2A-2B depict the results of titration binding of the indicated anti-ABCC1 monoclonal antibodies to human and cynomolgus ABCC1-overexpressing rat C6 glioma cell lines.
Figure 2B:
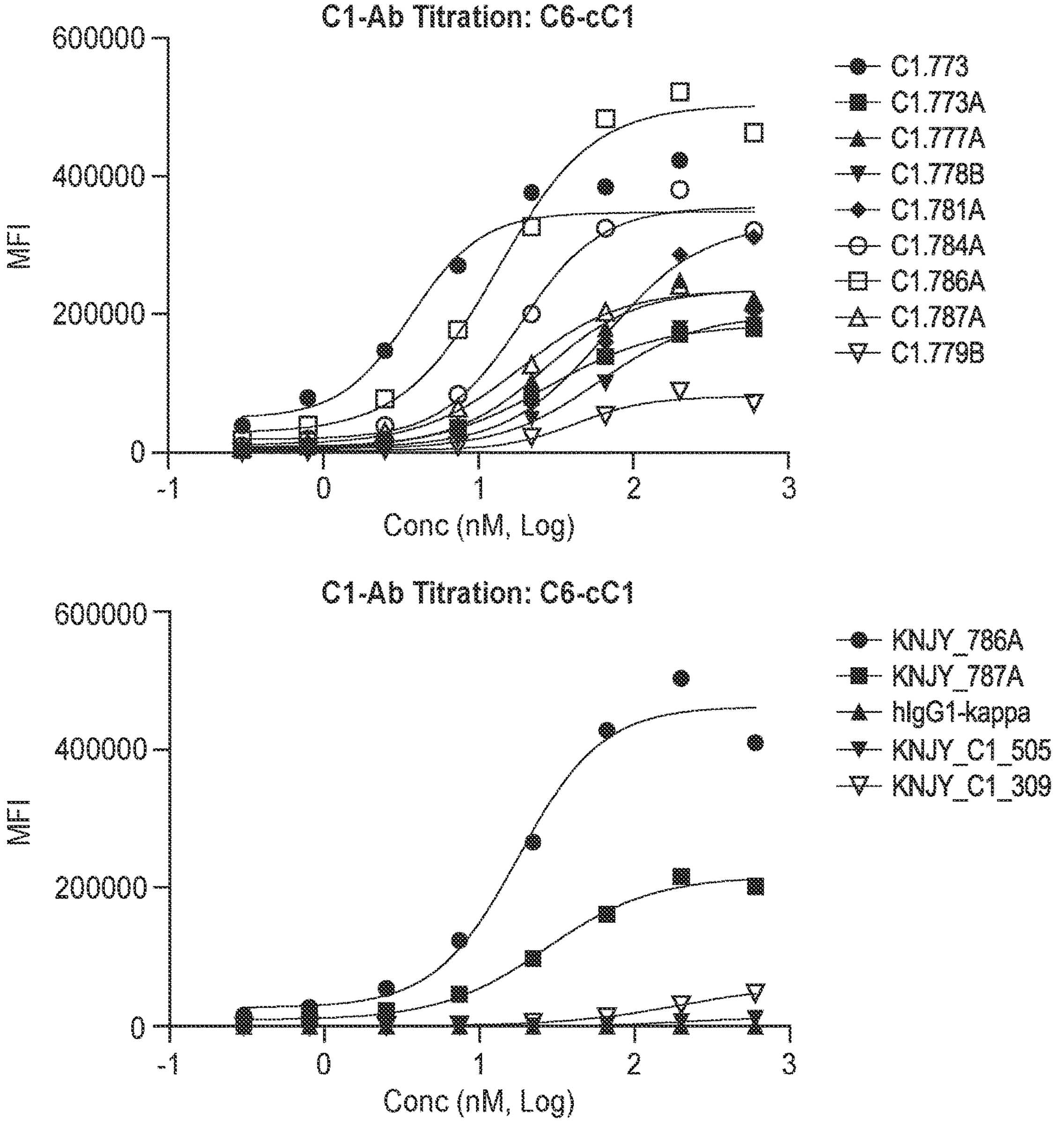
Figure 3A:
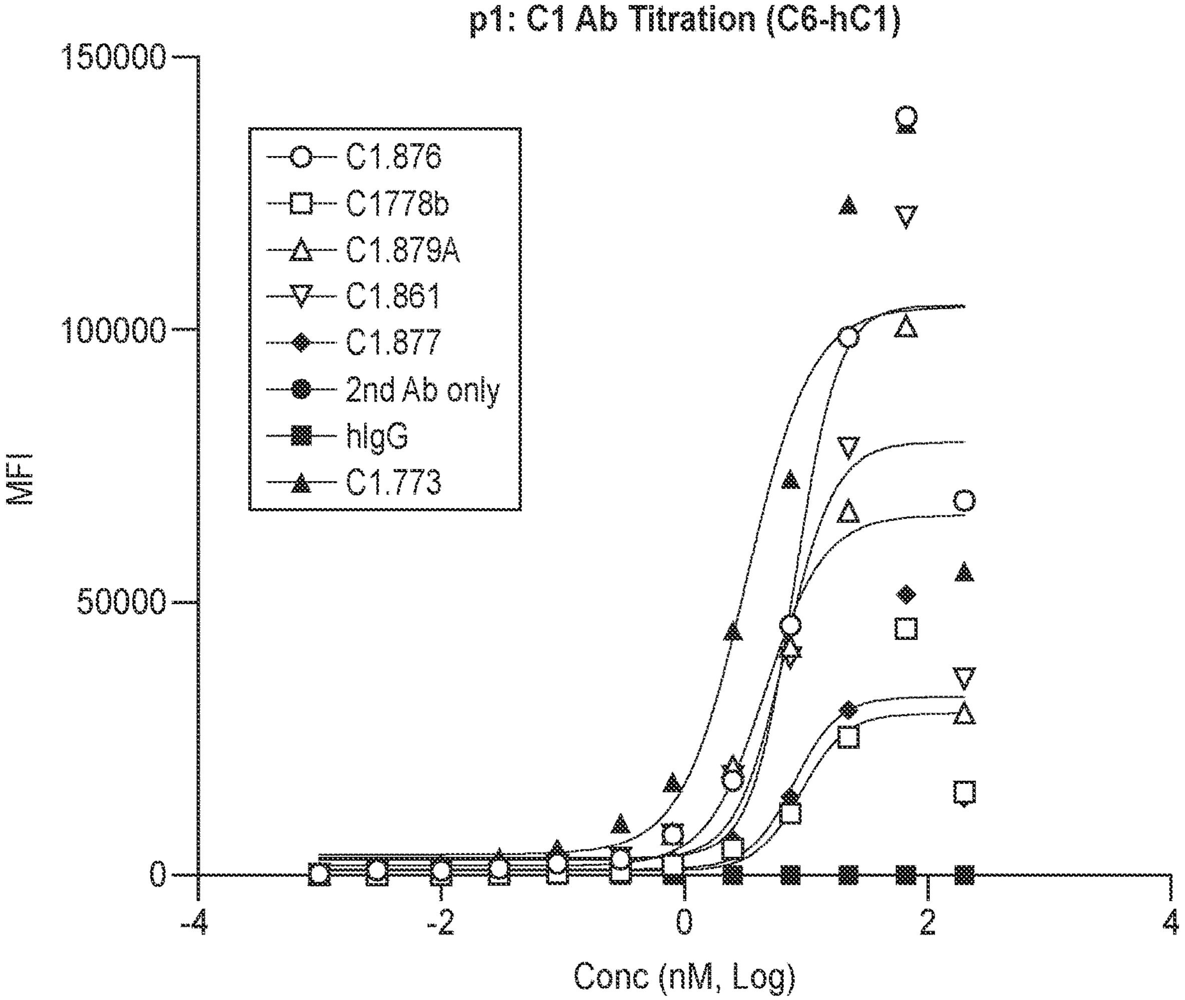
FIGS. 3A-3C, 4, 5A-5B, and 6A-6B show the results of titration binding of further anti-ABCC1 monocional antibodies to human and cynomolgus ABCC1-overexpressing rat C6 glioma cell lines. "2$^{nd}$ Ab only" refers to not adding a primary antibody before binding with secondary antibody (i.e., 2$^{nd}$ Ab) to provide a negative control.
Figure 3B:
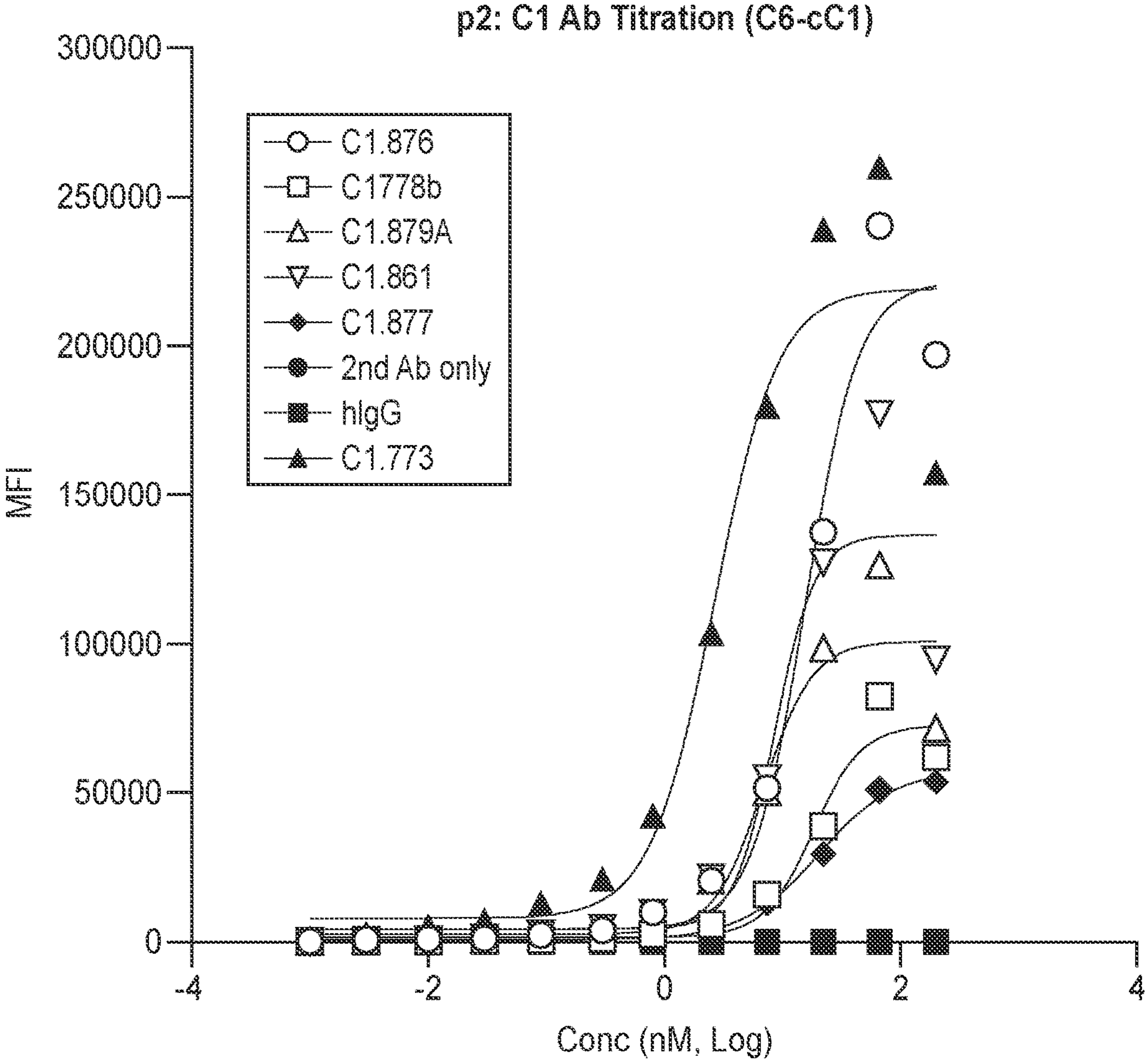
Figure 3C:
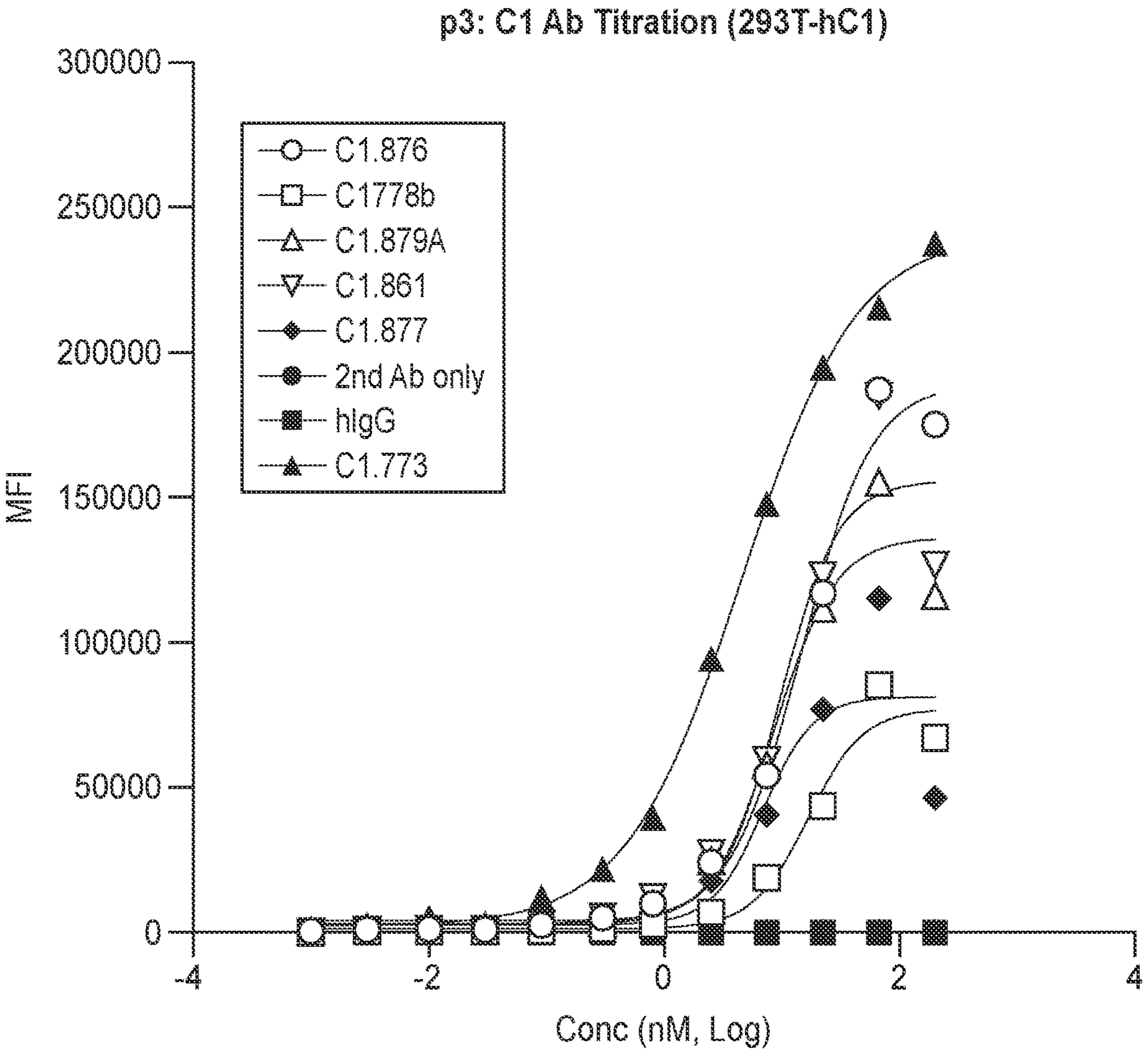
Figure 4:
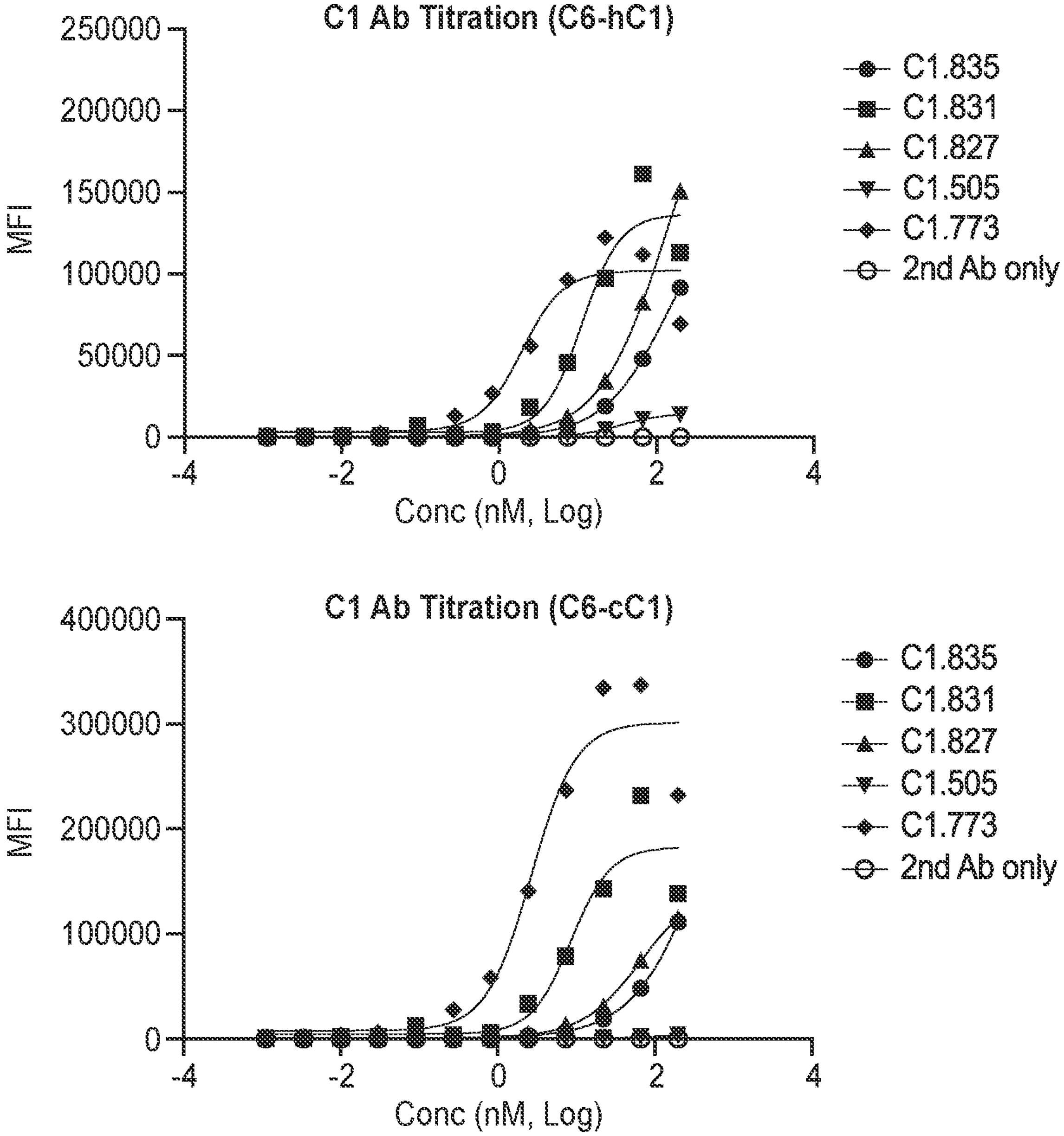
Figure 5A:
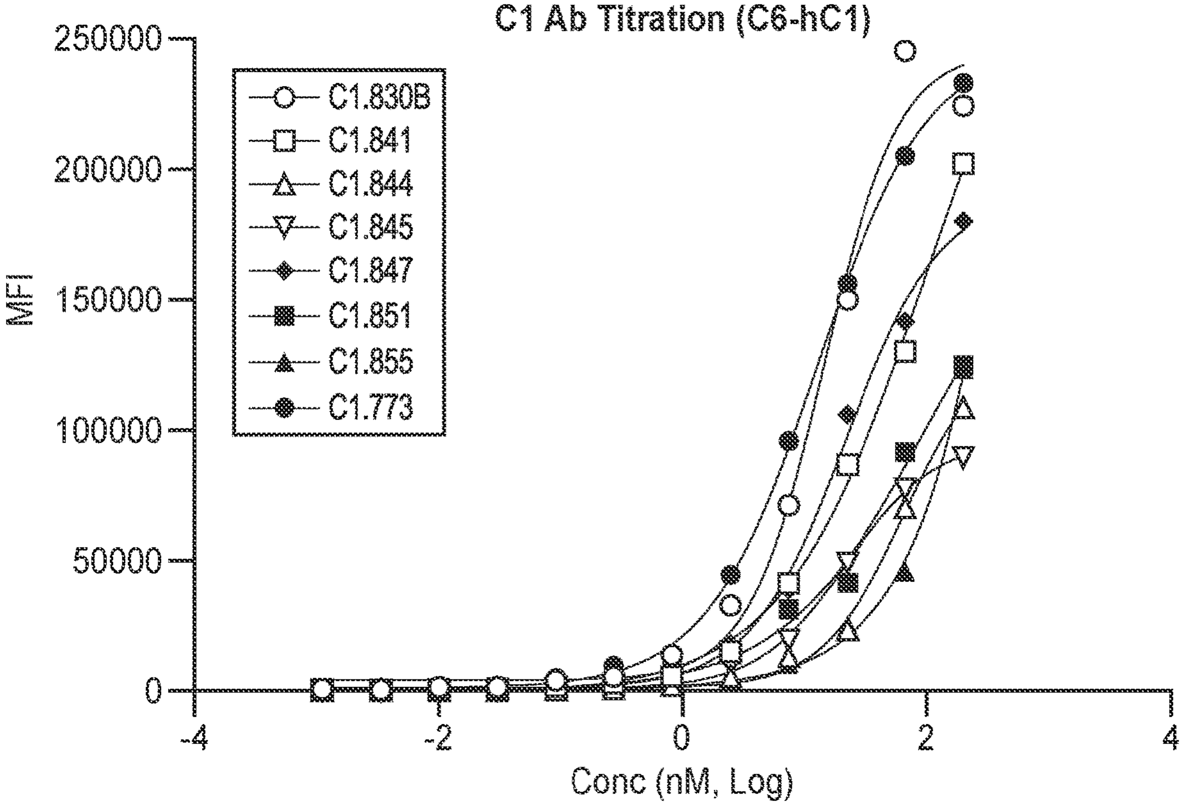
Figure 5B:
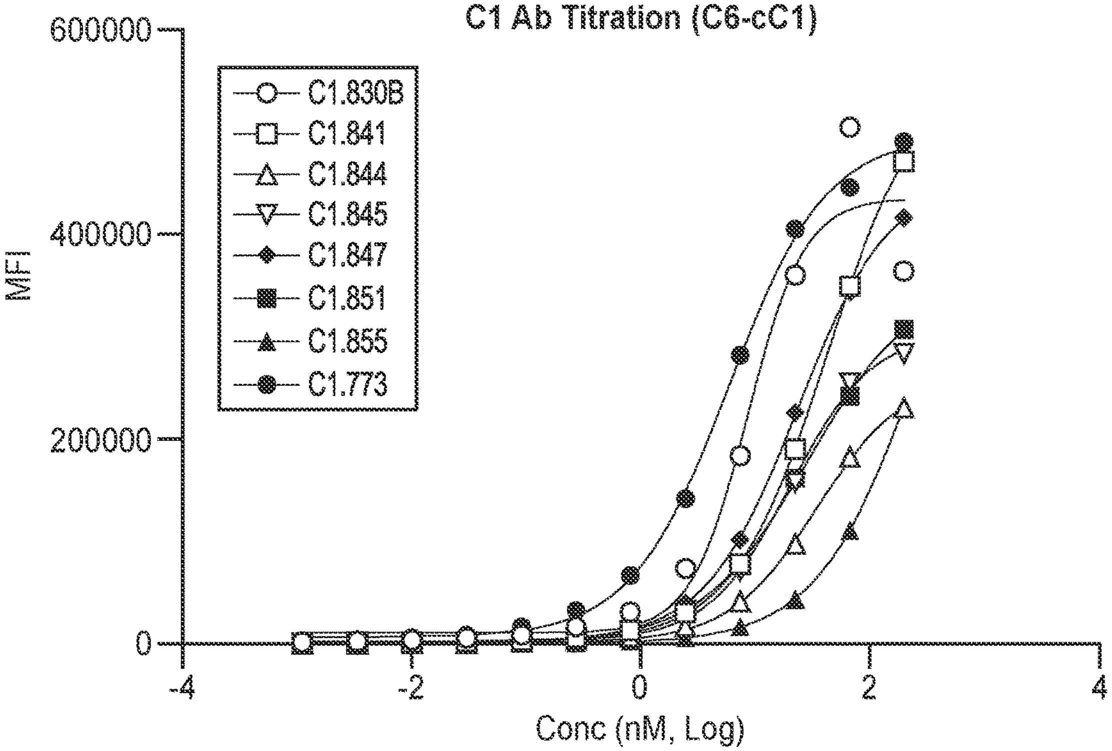
Figure 6A:
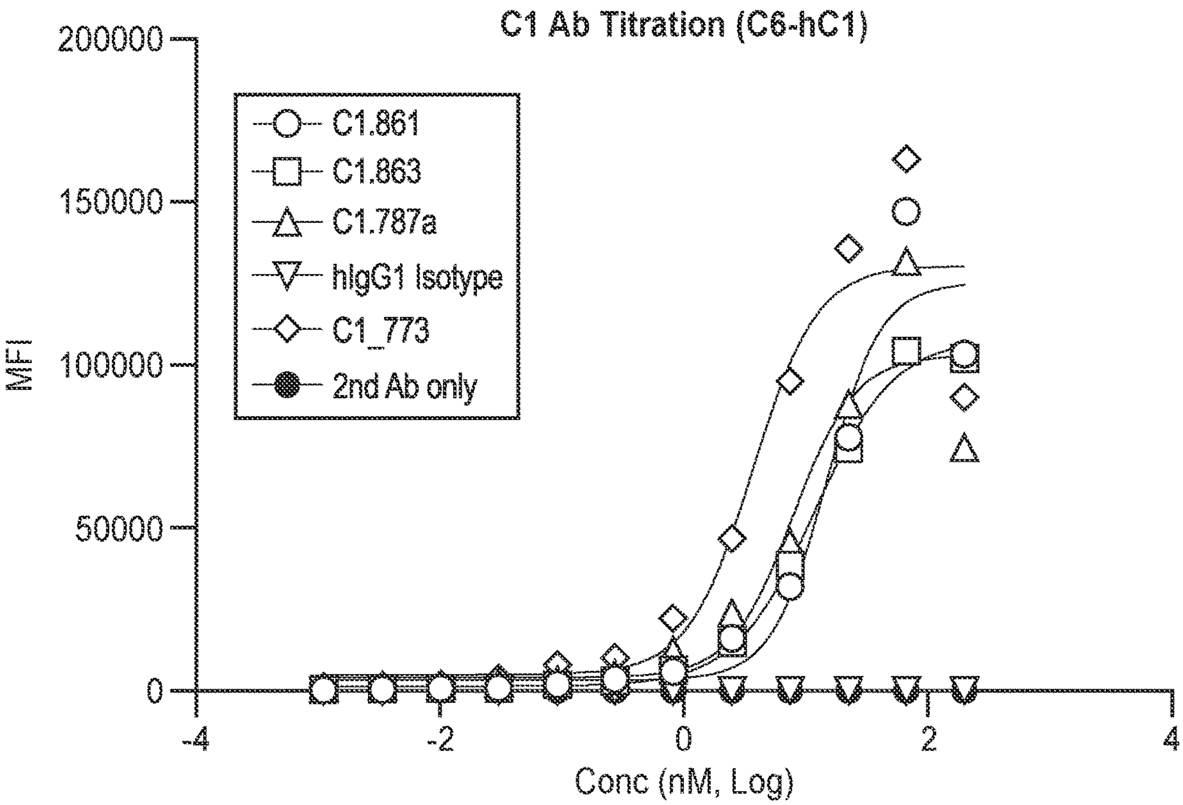
Figure 6B:
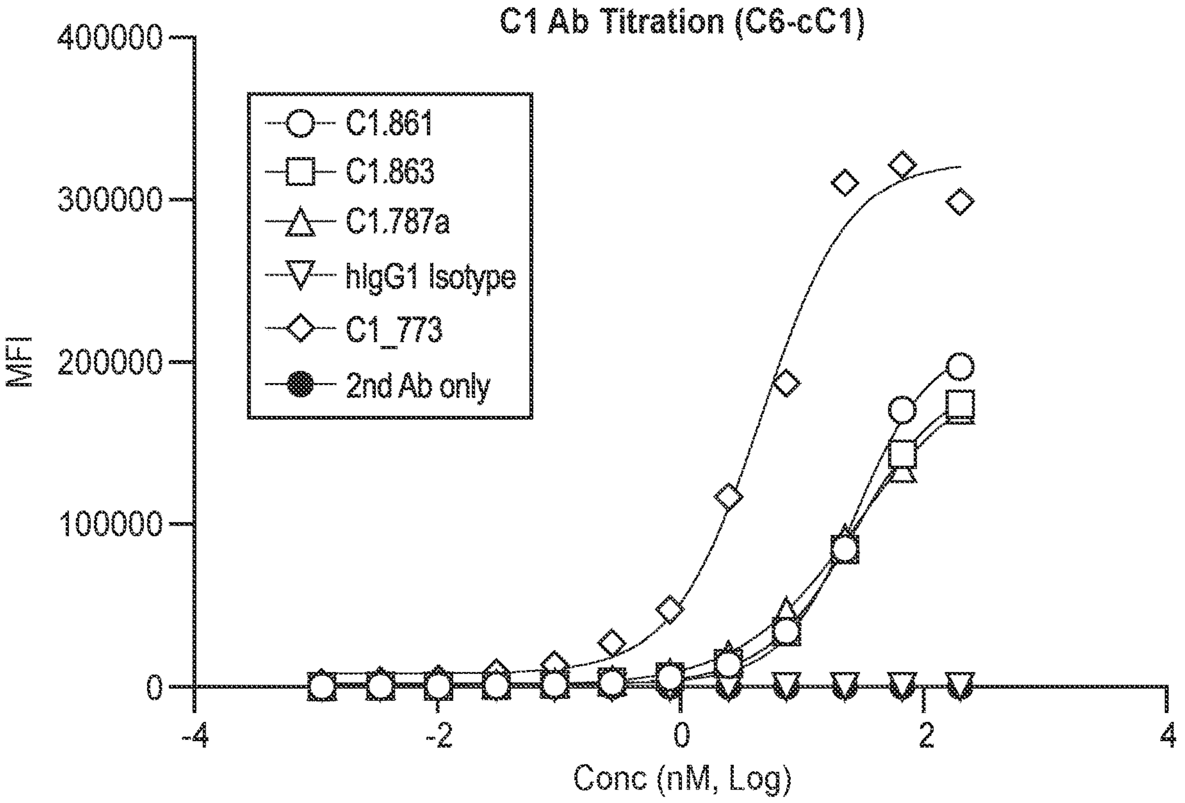

The terms "antibody" and "immunoglobulin" include antibodies or immunoglobulins of any isotype, fragments of antibodies which retain specific binding to antigen, including, but not limited to, Fab, Fv, scFv, Fd, Fab', Fv, $F(ab')_2$, chimeric antibodies, humanized antibodies, monoclonal antibodies, single-chain antibodies, including antibodies comprising only heavy chains (e.g. VHH camelid antibodies), bispecific antibodies, and fusion proteins comprising an antigen-binding portion of an antibody and a non-antibody protein. The antibodies may be detectably labeled, e.g., with a radioisotope, an enzyme which generates a detectable product, a fluorescent protein, and the like. The antibodies may be further conjugated to other moieties, such as members of specific binding pairs. e.g., biotin (member of biotin-avidin specific binding pair), and the like. The antibodies may also be bound to a solid support, including, but not limited to, polystyrene plates or beads, and the like. An antibody may be monovalent or bivalent. An antibody may be conjugated to a toxic moiety, such as, a chemotherapeutic agent.

"Antibody fragments" comprise a portion of an intact antibody, for example, the antigen binding or variable region of the intact antibody. Examples of antibody fragments include Fab, Fab', $F(ab')_2$, and Fv fragments; diabodies; linear antibodies (Zapata et al., Protein Eng. 8(10): 1057-1062 (1995)); single-chain antibody molecules, including antibodies comprising only heavy chains (e.g. VHH camelid antibodies); and multispecific antibodies formed from antibody fragments. Papain digestion of antibodies produces two identical antigen-binding fragments, called "Fab" fragments, each with a single antigen-binding site, and a residual "Fc" fragment, a designation reflecting the ability to crystallize readily. Pepsin treatment yields an $F(ab')_2$ fragment that has two antigen combining sites and is still capable of cross-linking antigen.

"Fv" is the minimum antibody fragment which contains a complete antigen-recognition and -binding site. This region consists of a dimer of one heavy- and one light-chain variable domain in tight, non-covalent association. It is in this configuration that the three CDRs of each variable domain interact to define an antigen-binding site on the surface of the VH-VL dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site comprising the three CDRs of each variable domain.

The "Fab" fragment also contains the constant domain of the light chain and the first constant domain ($CH_1$) of the heavy chain. Fab fragments differ from Fab' fragments by the addition of a few residues at the carboxyl terminus of the heavy chain $CH_1$ domain including one or more cysteines from the antibody hinge region. Fab'-SH is the designation herein for Fab' in which the cysteine residue(s) of the constant domains bear a free thiol group. $F(ab')_2$ antibody fragments originally were produced as pairs of Fab' fragments which have hinge cysteines between them. Other chemical couplings of antibody fragments are also known.

The "light chains" of antibodies (immunoglobulins) from any vertebrate species can be assigned to one of two clearly distinct types, called kappa and lambda, based on the amino acid sequences of their constant domains. Depending on the amino acid sequence of the constant domain of their heavy chains, immunoglobulins can be assigned to different classes. There are five major classes of immunoglobulins: IgA, IgD, IgE. IgG, and IgM, and several of these may be further divided into subclasses (isotypes), e.g., IgG1, IgG2, IgG3, IgG4, IgA, and IgA2.

"Single-chain Fv" "sFv" or "scFv" antibody fragments comprise the $V_H$ and $V_L$ domains of antibody, wherein these domains are present in a single polypeptide chain. In some embodiments, the Fv polypeptide further comprises a polypeptide linker between the $V_H$ and $V_L$ domains, which enables the sFv to form the desired structure for antigen binding. For a review of sFv, see *Pluckthun in The Pharmacology of Monoclonal Antibodies*, vol. 113, Rosenburg and Moore eds., Springer-Verlag, New York, pp. 269-315 (1994).

The term "diabodies" refers to small antibody fragments with two antigen-binding sites, which fragments comprise a heavy-chain variable domain (VH) connected to alight-chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., *Proc. Natl. Acad. Sci. USA,* 90:6444-6448 (1993).

As used herein, the term "affinity" refers to the equilibrium constant for the reversible binding of two agents and is expressed as a dissociation constant (Kd). Affinity can be at least 1-fold greater, at least 2-fold greater, at least 3-fold greater, at least 4-fold greater, at least 5-fold greater, at least 6-fold greater, at least 7-fold greater, at least 8-fold greater, at least 9-fold greater, at least 10-fold greater, at least 20-fold greater, at least 30-fold greater, at least 40-fold greater, at least 50-fold greater, at least 60-fold greater, at least 70-fold greater, at least 80-fold greater, at least 90-fold greater, at least 100-fold greater, or at least 1000-fold greater, or more, than the affinity of an antibody for unrelated amino acid sequences. Affinity of an antibody to a target protein can be, for example, from about 100 nanomolar (nM) to about 0.1 nM, from about 100 nM to about 1 picomolar (pM), or from about 100 nM to about 1 femtomolar (fM) or more. As used herein, the term "avidity" refers to the resistance of a complex of two or more agents to dissociation after dilution. The terms "immunoreactive" and "preferentially binds" are used interchangeably herein with respect to antibodies and/or antigen-binding fragments.

The term "binding" refers to a direct association between two molecules, due to, for example, covalent, electrostatic, hydrophobic, and ionic and/or hydrogen-bond interactions, including interactions such as salt bridges and water bridges. An ABCC1-specific antibody binds specifically to an epitope within a ABCC1 polypeptide. The epitope may be a linear epitope formed by a contiguous stretch of amino acids or a non-linear or a conformational epitope formed by non-contiguous stretches of amino acids. Non-specific binding would refer to binding with an affinity of less than about $10^{-7}$ M, e.g., binding with an affinity of $10^{-6}$ M, $10^{-5}$ M, $10^{-4}$ M, etc.

As used herein, the term "CDR" or "complementarity determining region" is intended to mean the non-contiguous antigen combining sites found within the variable region of both heavy and light chain polypeptides. CDRs are hypervariable regions and are interspersed with regions that are more conserved, termed "framework regions (FR)". CDRs have been described by Kabat et al., J. Biol. Chem. 252: 6609-6616 (1977); Kabat et al., U.S. Dept. of Health and Human Services. "Sequences of proteins of immunological interest" (1991); by Chothia et al., J. Mol. Biol. 196:901-917 (1987); and MacCallum et al., J. Mol. Biol. 262:732-745 (1996), where the definitions include overlapping or subsets of amino acid residues when compared against each other.

Nevertheless, application of either definition to refer to a CDR of an antibody or grafted antibodies or variants thereof is intended to be within the scope of the term as defined and used herein. The amino acid residues which encompass the CDRs as defined by each of the above cited references are set forth below in Table 1 as a comparison.

TABLE 1

| CDR Definitions | | | |
|---|---|---|---|
| | Kabat[1] | Chothia[2] | MacCallum[3] |
| $V_H$ CDR1 | 31-35 | 26-32 | 30-35 |
| $V_H$ CDR2 | 50-65 | 53-55 | 47-58 |
| $V_H$ CDR3 | 95-102 | 96-101 | 93-101 |
| $V_L$ CDR1 | 24-34 | 26-32 | 30-36 |
| $V_L$ CDR2 | 50-56 | 50-52 | 46-55 |
| $V_L$ CDR3 | 89-97 | 91-96 | 89-96 |

[1]Residue numbering follows the nomenclature of Kabat et al., supra
[2]Residue numbering follows the nomenclature of Chothia et al., supra
[3]Residue numbering follows the nomenclature of MacCallum et al., supra As used herein, the term "framework" when used in reference to an antibody variable region is intended to mean all amino acid residues outside the CDR regions within the variable region of an antibody. A variable region framework is generally a discontinuous amino acid sequence between about 100-120 amino acids in length but is intended to reference only those amino acids outside of the CDRs. As used herein, the term "framework region" is intended to mean each domain of the framework that is separated by the CDRs. A VH chain can comprise three CDRs and four FRs arranged from N-terminus to C-terminus in the following order: FR1, CDR1, FR2, CDR2, FR3. CDR3, FR4. Similarly, a VL chain can comprise three CDRs and four FRs arranged from N-terminus to C-terminus in the following order: FR1, CDR1, FR2, CDR2, FR3, CDR3, FR4. The terms VH chain and VH region are used interchangeably herein. The terms VL chain and VL region are used interchangeably herein.

As used herein, the term antibody encompasses a tetramer of two heavy and two light chains, wherein the heavy and light chains are interconnected by, for example, disulphide bonds. The heavy chain constant region is comprised of three domains, CH1, CH2 and CH3. The light chain constant region is comprised of one domain, CL. The variable regions of the heavy and light chains comprise binding regions that interact with antigen. The constant regions of the antibodies typically mediate the binding of the antibody to host tissues and factors, including various cells of the immune system and the first component of the complement system. The term "antibody" includes immunoglobulins of types IgA, IgG, IgE, IgD, IgM and subtypes thereof. In some embodiments, a subject antibody is an IgG isotype, e.g., IgG1.

As used herein the term "immunoglobulin" refers to a protein including one or more polypeptides substantially encoded by immunoglobulin genes. The recognized human immunoglobulin genes include the kappa, lambda, alpha (IgA1 and IgA2), gamma (IgG1, IgG2, IgG3, IgG4), delta, epsilon and mu constant region genes; and numerous immunoglobulin variable region genes. Full-length immunoglobulin light chains (about 25 kD or 214 amino acids) are encoded by a variable region gene at the N-terminus (about 110 amino acids) and a kappa or lambda constant region at the C-terminus. Full-length immunoglobulin heavy chains (about 50 kD or 446 amino acids) are encoded by a variable region gene at the N-terminus (about 116 amino acids) and one of the other aforementioned constant region genes at the C-terminus, e.g. gamma (encoding about 330 amino acids). In some embodiments, a subject antibody comprises full-length immunoglobulin heavy chain and a full-length immunoglobulin light chain.

The term "antigen-binding fragment" refers to one or more fragments of a full-length antibody that are capable of specifically binding to an antigen. Examples of binding fragments include (i) a Fab fragment (a monovalent fragment including, e.g., consisting of, the VL, VH, CL and CH1 domains; (ii) a $F(ab')_2$ fragment (a bivalent fragment comprising two Fab fragments linked by a disulfide bridge at the hinge region: (iii) a Fd fragment (including, e.g., consisting of, the VH and CH1 domains); (iv) a Fv fragment (including, e.g., consisting of, the VH and VL domains of a single arm of an antibody); (v) a dAb fragment (including, e.g., consisting of, the VH domain); (vi) an isolated CDR; (vii) a single chain Fv (scFv) (including, e.g., consisting of, the VH and VL domains of a single arm of an antibody joined by a synthetic linker using recombinant means such that the VH and VL domains pair to form a monovalent molecule); (viii) diabodies (including, e.g., consisting of, two scFvs in which the VH and VL domains are joined such that they do not pair to form a monovalent molecule; the VH of each one of the scFv pairs with the VL domain of the other scFv to form a bivalent molecule).

The term "chimeric" antibody refers to an antibody in which a portion of the heavy and/or light chain is derived from a particular source or species, while the remainder of the heavy and/or light chain is derived from a different source or species.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "human consensus framework" is a framework (FR) which represents the most commonly occurring amino acid residues in a selection of human immunoglobulin variable light chain (VL) or variable heavy chain (VH) framework sequences. Generally, the selection of human immunoglobulin VL or VH sequences is from a subgroup of variable domain sequences. Generally, the subgroup of sequences is a subgroup as in Kabat et al., Sequences of Proteins of Immunological Interest, Fifth Edition, NIH Publication 91-3242, Bethesda Md. (1991), vols. 1-3. In one embodiment, for the VL, the subgroup is subgroup kappa I as in Kabat et al., supra. In one embodiment, for the VH, the subgroup is subgroup III as in Kabat et al., supra.

A "humanized" antibody refers to a chimeric antibody comprising amino acid residues from non-human CDRs and amino acid residues from human frameworks (FRs). At least a portion of a humanized antibody constant region is derived from a human antibody, e.g., a human IgG1 antibody. In preferred embodiments, the antibody molecules disclosed herein include a heavy chain comprising a variable heavy chain region as provided herein and a human IgG1 constant region having the amino acid sequence sequence set forth in UniProt: P01857-1, version 1. In preferred embodiments, the antibody molecules disclosed herein include a light chain comprising a variable light chain region as provided herein and a human light chain constant region. In preferred embodiments, the human light chain constant region is a human kappa light chain constant region having the amino acid set forth in UniProtKB/Swiss-Prot: P01834.2. In certain embodiments, the human IgG1 heavy chain constant region present in the subject antibodies may include mutations, e.g., substitutions to modulate Fc function. For example, the LALAPG effector function mutations (L234A, L235A, and P329G) or the N297A mutation may be introduced to reduce antibody dependent cellular cytotoxicity (ADCC). The numbering of the substitutions is based on the EU numbering system. The "EU numbering system" or "EU index" is generally used when referring to a residue in an immunoglobulin heavy chain constant region (e.g., the EU index reported in Kabat et al., Sequences of Proteins of Immunological Interest, 5th Ed. Public Health Service, National Institutes of Health, Bethesda, Md. (1991)). The "EU index as in Kabat" refers to the residue numbering of the human IgG 1 EU antibody.

A "humanized form" of an antibody, e.g., a non-human antibody, refers to an antibody that has undergone humanization.

The term "epitope" refers to a region of an antigen that is recognized by the immune system, for example by antibodies, B cells, or T cells. For example, the epitope is the specific region of the antigen to which an antibody binds.

An "isolated" antibody is one that has been identified and separated and/or recovered from a component of its natural environment. Contaminant components of its natural environment are materials that would interfere with diagnostic or therapeutic uses for the antibody, and may include enzymes, hormones, and other proteinaceous or nonproteinaceous solutes. In some embodiments, the antibody will be purified (1) to greater than 90%, greater than 95%, or greater than 98%, by weight of antibody as determined by the Lowry method, for example, more than 99% by weight, (2) to a degree sufficient to obtain at least 15 residues of N-terminal or internal amino acid sequence by use of a spinning cup sequenator, or (3) to homogeneity by sodium dodecyl sulfate-polyacrylamide gel electrophoresis (SDS-PAGE) under reducing or nonreducing conditions using Coomassie blue or silver stain. Isolated antibody includes the antibody in situ within recombinant cells since at least one component of the antibody's natural environment will not be present. In some instances, isolated antibody will be prepared by at least one purification step.

The term "cytotoxic agent" as used herein refers to a substance that inhibits or prevents a cellular function and/or causes cell death or destruction. A "chemotherapeutic agent," also referred to an "antineoplastic agent," can be a cytotoxic agent which is used for treating a cancer or other disease or disorder.

As used herein, the terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment," as used herein, covers any treatment of a disease in a mammal, including in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease.

The terms "individual," "subject," "host," and "patient," used interchangeably herein, refer to a mammal, including, but not limited to, murines (rats, mice), non-human primates, humans, canines, felines, ungulates (e.g., equines, bovines, ovines, porcines, caprines), etc.

A "therapeutically effective amount" or "efficacious amount" refers to the amount of a target-specific antibody that, when administered to a mammal or other subject for treating a disease, is sufficient to affect such treatment for the disease. The "therapeutically effective amount" will vary depending on the antibody, the disease and its severity and the age, weight, etc., of the subject to be treated.

The term "refractory", used herein, refers to a disease or condition that does not respond to treatment. With regard to cancer "refractory cancer", as used herein, refers to cancer that does not respond to treatment. A refractory cancer may be resistant at the beginning of treatment or it may become resistant during treatment. Refractory cancer may also be called resistant cancer.

A "biological sample" encompasses a variety of sample types obtained from an individual and can be used in a diagnostic or monitoring assay. The definition encompasses blood and other liquid samples of biological origin, solid tissue samples such as a biopsy specimen or tissue cultures or cells derived therefrom and the progeny thereof. The definition also includes samples that have been manipulated in any way after their procurement, such as by treatment with reagents, solubilization, or enrichment for certain components, such as polynucleotides. The term "biological sample" encompasses a clinical sample, and also includes cells in culture, cell supernatants, cell lysates, serum, plasma, biological fluid, and tissue samples.

Percent identity between a pair of sequences may be calculated by multiplying the number of matches in the pair by 100 and dividing by the length of the aligned region, including gaps. Identity scoring only counts perfect matches and does not consider the degree of similarity of amino acids to one another. Only internal gaps are included in the length, not gaps at the sequence ends. Percent Identity=(Matches× 100)/Length of aligned region (with gaps)

The phrase "conservative amino acid substitution" refers to substitution of amino acid residues within the following groups: 1) L, I, M, V, F; 2) R, K; 3) F, Y, H, W, R; 4) G, A, T, S; 5) Q, N; and 6) D, E. Conservative amino acid substitutions may preserve the activity of the protein by replacing an amino acid(s) in the protein with an amino acid with a side chain of similar acidity, basicity, charge, polarity, or size of the side chain.

Guidance for substitutions, insertions, or deletions may be based on alignments of amino acid sequences of proteins from different species or from a consensus sequence based on a plurality of proteins having the same or similar function.

The term "vector" means any molecule or entity (e.g., nucleic acid, plasmid, bacteriophage or virus) used to transfer protein coding information into a host cell.

The term "expression vector" or "expression construct" refers to a vector that is suitable for transformation of a host cell and contains nucleic acid sequences that direct and/or control (in conjunction with the host cell) expression of one or more heterologous coding regions operatively linked thereto. An expression construct may include, but is not limited to, sequences that affect or control transcription, translation, and, if introns are present, affect RNA splicing of a coding region operably linked thereto.

The term "stimulation," refers to a primary response induced by binding of a stimulatory molecule (e.g., a TCR/CD3 complex or CAR) with its cognate ligand (or tumor antigen in the case of a CAR) thereby mediating a signal transduction event, such as, but not limited to, signal transduction via the TCR/CD3 complex or signal transduction via the appropriate NK receptor or signaling domains of the CAR. Stimulation can mediate altered expression of certain molecules.

The term "stimulatory molecule," refers to a molecule expressed by an immune cell (e.g., T cell, NK cell, B cell) that provides the cytoplasmic signaling sequence(s) that regulate activation of the immune cell in a stimulatory way for at least some aspect of the immune cell signaling pathway. In one embodiment, the signal is a primary signal that is initiated by, for instance, binding of a TCR/CD3 complex with an MHC molecule loaded with peptide, and which leads to mediation of a T cell response, including, but not limited to, proliferation, activation, differentiation, and the like. A primary cytoplasmic signaling sequence (also referred to as a "primary signaling domain") that acts in a stimulatory manner may contain a signaling motif which is known as immunoreceptor tyrosine-based activation motif or ITAM. Examples of an ITAM containing cytoplasmic signaling sequence that is of particular use in the invention includes, but is not limited to, those derived from CD3 zeta, common FcR gamma (FCER1G), Fc gamma RIIa, FcR beta (Fc Epsilon R1b), CD3 gamma, CD3 delta, CD3 epsilon, CD79a. CD79b, DAP10, and DAP12.

The term a "costimulatory molecule" refers to a cognate binding partner on a T cell that specifically binds with a costimulatory ligand, thereby mediating a costimulatory response by the T cell, such as, but not limited to, proliferation. Costimulatory molecules are cell surface molecules other than antigen receptors or their ligands that are contribute to an efficient immune response. Costimulatory molecules include, but are not limited to an MHC class I molecule, BTLA and a Toll ligand receptor, as well as OX40, CD27, CD28, CDS, ICAM-1, LFA-1 (CD11a/CD18), ICOS (CD278), and 4-1BB (CD137).

The term "autologous" refers to any material derived from the same individual to whom it is later to be re-introduced into the individual.

An "intracellular signaling domain," as the term is used herein, refers to an intracellular portion of a molecule. The intracellular signaling domain generates a signal that promotes an immune effector function of the CAR containing cell, e.g., a CAR-T cell. Examples of immune effector function, e.g., in a CAR-T cell, include cytolytic activity and helper activity, including the secretion of cytokines.

"Immune effector cell," as that term is used herein, refers to a cell that is involved in an immune response. e.g., in the promotion of an immune effector response. Examples of immune effector cells include T cells, e.g., alpha/beta T cells and gamma/delta T cells, B cells, natural killer (NK) cells, natural killer T (NKT) cells, mast cells, and myeloid-derived phagocytes.

DETAILED DESCRIPTION

Provided are antibodies that bind to the cellular efflux pump ABCC1. Also provided are pharmaceutical compositions, nucleic acids, recombinant expression vectors, cells, and kits that include or encode such antibodies. Methods of using the antibodies for detecting presence or absence of ABCC1 expression in cells, e.g., tumor cells, level of ABCC1 expression, and/or inhibiting ABCC1 function are also disclosed. Also provided are methods for treating a subject for a cancer that include administering to the subject an anti-ABCC1 antibody as disclosed herein.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely." "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

While the methods and compositions have or will be described for the sake of grammatical fluidity with functional explanations, it is to be expressly understood that the claims, unless expressly formulated under 35 U.S.C. § 112(f), are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 U.S.C. § 112(f) are to be accorded full statutory equivalents under 35 U.S.C. § 112(f).

Antibodies

As summarized above, the present disclosure provides antibodies that bind a cellular efflux pump ABCC1 expressed on surface of a mammalian cell, e.g., a human cell. ABCC1, also known as Glutathione-S-Conjugate-Translocating ATPase ABCC1 or Multidrug Resistance-Associated Protein 1 (MRP1), is an energy-dependent pump that effluxes drugs and organic anions across the plasma membrane. It includes 17 transmembrane helices linked by extracellular and cytoplasmic loops. ABCC1 mediates resistance to doxorubicin, etoposide, and vincristine among others.

In some embodiments, the antibodies disclosed herein bind to one or more sites on an extracellular region of ABCC1. In certain embodiments, the anti-ABCC1 antibodies of the present disclosure bind to human ABCC1. In certain embodiments, the anti-ABCC1 antibodies of the present disclosure bind to human ABCC1 expressed on the cell surface of a human cell, e.g., a cancer cell.

Antibodies of the present disclosure may have one or more of the following properties:

i) Inhibits efflux from ABCC1;
ii) increases sensitivity of cancer cell to treatment with a chemotherapeutic agent thereby lowering the IC50 of the chemotherapeutic agent by at least a factor of 2;
iii) binds to human and cynomolgus ABCC1 on cell surface;
iv) is effective in in vitro cell killing assays;
v) is effective in inhibiting tumor growth even in absence of chemotherapy; and
vi) has an affinity for ABCC1 in a lower range such that it binds to cancer cells that express ABCC1 at a higher level as compared to non-cancer cells and binds significantly less to non-cancer cells.

As used herein, EC50 refers to the concentration of an antibody that provides half maximal response (e.g., half of the maximum fluorescence intensity). The antibodies of the present disclosure may have an EC50 of 100 nM or lower, e.g., 100 nM-4 nM, 80 nM-4 nM, 60 nM-4 nM, 40 nM-4 nM, 30 nM-4 nM, 20 nM-4 nM, 15 nM-4 nM, or 10 nM-4 nM. EC50 of a test antibody many be determined by flow cytometry or ELISA. For example, flow cytometry may involve contacting a cell expressing ABCC1 (e.g. human ABCC1) with the antibody in a flow cytometry buffer, where the antibody is serially diluted, and incubating at room temperature or 4° C. for a period of time sufficient for the antibody to bind to the cells (e.g. 10 min-1 hr). After incubating, the cells may optionally be washed to remove and non-specifically bound antibody and/or the cells may be contacted with a fluorescently labeled secondary antibody that specifically binds to the test antibody. After incubation, the fluorescently labeled secondary antibody may be removed and the cells washed. The washed cells may be sorted by flow cytometry and the number of cells bound to the fluorescently labeled secondary antibody counted. The concentration that provides half maximal response (e.g., half of the maximum fluorescence intensity) is measured as the EC50. In variations of the flow cytometry assay, the cell may be a 293T cell overexpressing ABCC1.

The IC50 of a test antibody may be determined by measuring inhibition of cell growth. IC50 may be measured by using the test antibody alone to determine the concentration of the antibody that produced half maximal response. The IC50 of a chemotherapeutic agent may be measured in the absence and in the presence of the test antibody to determine the effect of the antibody on the IC50 chemotherapeutic agent. The chemotherapeutic agent may be doxorubicin, daunorubicin, etoposide, vincristine etc. The cell may be a cancer cell line. The cancer cell line may be H69AR, a doxorubicin-selected, C1-positive variant of the lung cancer cell line, H69. Cells may be contacted with antibody alone if determining the IC50 of the antibody, wherein the antibody is tested at serial dilutions. Cells may be contacted with antibody and the chemotherapeutic agent to determine the effect of the antibody on the IC50 of the agent, where the agent is tested at serial dilutions. The cells may be incubated at 37° C. for a period of time (e.g. 24 hr-84 hr) and cell viability assessed using standard reagents and methods. The antibodies disclosed herein may increase sensitivity of cancer cell to treatment with a chemotherapeutic agent thereby lowering the IC50 of the chemotherapeutic agent by at least a factor of 5. In certain embodiments, the antibodies of the present disclosure may lower the IC50 of the chemotherapeutic agent by factor of 5 or more, e.g., factor of 6 or more, factor of 7 or more, factor of 8 or more, factor of 9 or more, or factor of 10 or more, e.g., by a factor of 5 to 10.

In certain embodiments, one or more of the anti-ABCC1 antibodies disclosed herein bind to both human and cynomolgus ABCC1. This property may be utilized in determining safety of the antibody in an animal model.

In certain embodiments, the anti-ABCC1 antibodies disclosed herein are specific for ABCC1 and do not show significant binding to other antigens.

In some embodiments, one or more of the subject antibodies may, when bound to a cell expressing ABCC1, prevent the functioning of the cellular ABCC1 protein. Accordingly, one or more antibodies of the present disclosure may inhibit efflux by the ABCC1 protein, including e.g., where efflux is reduced by 5% or more, including e.g., 10% or more, 15% or more, 20% or more, 25% or more, 30% or more, 40% or more, 50% or more, 60% or more, 70% or more, 80% or more, or 90% or more, as compared to efflux by ABCC1 in the absence of the subject antibody. In some embodiments, the subject antibodies may, when bound to a cell expressing ABCC1 may otherwise impede the action of ABCC1 by other mechanisms, e.g., rendering ABCC1 leaky which in turn may enhance uptake of a chemotherapeutic agent and/or decrease viability of the cell.

In certain embodiments, an anti-ABCC1 antibody that competes for binding to ABCC1 with an antibody comprising heavy chain complementarity determining regions (HCDRs) and light chain CDRs (LCDRs) of the variable heavy chain (VH) region and the variable light chain (VL) region pair, respectively, of an antibody listed in Table 2 is provided. For example, in one embodiment, an anti-ABCC1 antibody of the present disclosure competes for binding to ABCC1 with the C1.309 antibody listed in Table 2. In certain embodiments, HCDRs 1-3 and LCDRs 1-3 are defined as per Kabat nomenclature.

In certain embodiments, the anti-ABCC1 antibody comprises the HCDR1, HCDR2, and HCDR3 of the VH region of the antibody listed in Table 2. In certain embodiments, the HCDR1, HCDR2, and HCDR3 are defined as per Kabat nomenclature. For example, in one embodiment, the anti-ABCC1 antibody of the present disclosure that competes for binding to ABCC1 with the C1.309 antibody listed in Table 2 comprises the HCDR1, HCDR2, and HCDR3 of the VH region of the C1.309 antibody.

Any suitable approach for determining whether a first antibody competes with a second antibody for binding to ABCC1 may be employed. Whether a first antibody "competes with" a second antibody for binding to an antigen may be readily determined using competitive binding assays known in the art. Competing antibodies may be identified, for example, via an antibody competition assay. For example, a sample of a first antibody can be bound to a solid support. Then, a sample of a second antibody suspected of being able to compete with such first antibody is added. One of the two antibodies is labelled. If the labeled antibody and the unlabeled antibody bind to separate and discrete sites on the antigen, the labeled antibody will bind to the same level whether or not the suspected competing antibody is present. However, if the sites of interaction are identical or overlapping, the unlabeled antibody will compete, and the amount of labeled antibody bound to the antigen will be lowered. If the unlabeled antibody is present in excess, very little, if any, labeled antibody will bind.

For purposes of the present disclosure, competing antibodies are those that decrease the binding of an antibody to the antigen by about 30% or more, about 40% or more, about 50% or more, about 60% or more, about 70% or more, about 80% or more, about 85% or more, about 90% or more, about 95% or more, or about 99% or more. Details of procedures for carrying out such competition assays are well known in the art and can be found, for example, in Harlow and Lane, Antibodies, A Laboratory Manual, Cold Spring Harbor Laboratory Press, Cold Spring Harbor, N.Y., 1988, 567-569, 1988, ISBN 0-87969-314-2. Such assays can be made quantitative by using purified antibodies. A standard curve may be established by titrating one antibody against itself, i.e., the same antibody is used for both the label and the competitor. The capacity of an unlabeled competing antibody to inhibit the binding of the labeled antibody to the antigen may be titrated. The results may be plotted, and the concentrations necessary to achieve the desired degree of binding inhibition may be compared.

In certain embodiments, an antibody that specifically binds to ABCC1 comprises (i) HCDRs 1-3 and light chain CDRs (LCDRs 1-3) of a pair of variable heavy chain (VH) region and variable light chain (VL) region of an antibody listed in Table 2; (ii) HCDRs 1-3 of a VH region of an antibody listed in Table 2; (iii) LCDRs 1-3 of a VH region of an antibody listed in Table 2; or (iv) HCDRs 1-3 of a VH region of a first antibody listed in Table 2 and LCDRs 1-3 of a VL region of second antibody listed in Table 2. The HCDRs and the LCDRs may be defined based on the Kabat nomenclature.

In certain embodiments, an antibody of the present disclosure that binds specifically to human ABCC1 comprises the HCDR1, HCDR2, and HCDR3 sequences and the LCDR1, LCDR2, and LCDR3 sequences of an antibody listed in Table 2. In addition to binding to human ABCC1, one or more of the antibodies provided herein may bind to ABCC1 from other mammalian species, such as, mouse, monkey, chimpanzee, etc. The antibodies may be raised in mouse or rat. In Table 2, the animal in which the antibody was generated is indicated.

TABLE 2

From left to right, 1st column: Anti-ABCC1 antibody name, 2nd column: VH region, 3rd column: HCDR1, 4th column: HCDR2, 5th column: HCDR3, 6th column: VL region, 7th column: LCDR1, 8th column: LCDR2, 9th column: LCDR3.

| Antibody | Heavy Chain Variable Region | CDRH1 | CDRH2 | CDRH3 | Light Chain Variable Region | CDRL1 | CDRL2 | CDRL3 |
|---|---|---|---|---|---|---|---|---|
| C1.309 | QVQLKESGPGLVAPSQSLSITCTV<br>SGFSLTSYDITWIRQPPGKGLEW<br>LGVIWTGGGTNYNSAFMSRLSIS<br>KDSSKSQVFLKMNSLRTDDTAIY<br>YCVRDLRYGYDGFWYFDVWGA<br>GTTVTVSS (SEQ ID NO: 1) | SYDIT (SEQ<br>ID NO: 37) | VIWTGGGTNY<br>NSAPMS (SEQ<br>ID NO: 47) | DLRYGYDGF<br>WYFDV (SEQ<br>ID NO: 64) | DVVMTQTPLSLPVSLGDQASISCRS<br>SQSIVHSNGNTYLEWYLQKPGQSP<br>KLLIYKVSNRFSGVPDRESGSGTGT<br>DFTLKISRVEAEDLGVYYCFQGSHV<br>PRTFGGGTKLEIK (SEQ ID NO: 76) | RSSQSIVHS<br>NGNTYLE<br>(SEQ ID<br>NO: 111) | KVSNRFS<br>(SEQ ID<br>NO: 124) | FQGSHVPRT<br>(SEQ ID<br>NO: 135) |
| C1.310 | QVQMKQSGPGLVAPSQSLSITC<br>TVSGFSLTSYDITWIRQPPGKGLE<br>WLGVIWTGGGTNYNSAFMSRL<br>SISKDSSKSQVFLKMNSLRTDDT<br>AIYYCVRDLRYGYDGFWYFDVW<br>GTGTTVTVSS (SEQ ID NO: 2) | SYDIT (SEQ<br>ID NO: 37) | VIWTGGGTNY<br>NSAFMS (SEQ<br>ID NO: 47) | DLRYGYDGF<br>WYEDV (SEQ<br>ID NO: 64) | DVVMTQAPSSLSASLGERISLTCRA<br>SQDIYGSLNWFQQKPDGTIKLLIYG<br>TSSLDSGVPKRFSGSRSGSDYSLTIS<br>SLESEDFADYYCLQYASSPYTFGGG<br>TKLEIK (SEQ ID NO: 77) | RASQDIYGS<br>LN (SEQ ID<br>NO: 112) | GTSSLDS<br>(SEQ ID<br>NO: 125) | LQYASYPYT<br>(SEQ ID<br>NO: 136) |
| C1.499 | EVELKESGPGLVQPSQTLSLTCTV<br>SGFSLTSNGVSWVRQPPGKGLE<br>WIAAISSGGNIYYNSAFKSRLSISR<br>HTSKSQVLLKMNSLQTEDTAMY<br>FCVRHRGYYGYNWGYFDYWGQ<br>GASVTVSS (SEQ ID NO: 3) | SNGVS<br>(SEQ ID<br>NO: 38) | AISSGGNIYYN<br>SAFKS (SEQ<br>ID NO: 48) | HRGYYGYN<br>WGYFDY<br>(SEQ ID<br>NO: 65) | DIQMTQSPSLLSASVGDRVTLSCKG<br>SQNINNYLAWYQQKLGGAPKLLIY<br>KTNSLQTGIPSRFSGSGSGTDYTLTI<br>SSLHSEDLATYYCYQYNNWYTFGP<br>GTKLELK (SEQ ID NO: 78) | KGSQNINN<br>YLA (SEQ<br>ID<br>NO: 113) | KTNSLQT<br>(SEQ ID<br>NO: 126) | YQYNNWYT<br>(SEQ ID<br>NO: 137) |
| C1.505 | EVQLTESGPGLVQPSQTLSLTCT<br>VSGFSLTSNGVSWVRLPPGKGLE<br>WIAAISSGGNIYYNSALKSRLSISR<br>DISKSQVFLKMNSLQTEDTAIYF<br>CTRERGWNYPGITNGYYFDYW<br>GQGASVTVSS (SEQ ID NO: 4) | SNGVS<br>(SEQ ID<br>NO: 38) | AISSGGNIYYN<br>SALKS (SEQ<br>ID NO: 49) | ERGWNYPGI<br>TNGYYFDY<br>(SEQ ID<br>NO: 66) | DIVLTQSPSLLSASVGDRVILSCKAG<br>QKINNYLAWYQQKLGEAPKLLIYN<br>ANSLQTGIPSRESGSGSGTDYTLTIS<br>SLQPEDVATYFCQQYNSWYTFGA<br>GTKLEIK (SEQ ID NO: 79) | KAGQKINN<br>YLA (SEQ<br>ID<br>NO: 114) | NANSLQT<br>(SEQ ID<br>NO: 127) | QQYNSWYT<br>(SEQ ID<br>NO: 138) |
| C1.773 | EIQLAQSGPELVKPGASVKMSCK<br>ASGYSFIGYFMNWVKQSHGKSL<br>EWIGRINPYNGDTFYNQKFKGK<br>ATLTVDKSSSTAHMELRSLTSED<br>SALYYCTRSGWGYDVYSFDYWG<br>QGTLVTVSS (SEQ ID NO: 5) | GYFMN<br>(SEQ ID<br>NO: 39) | RINPYNGDTF<br>YNQKFKG<br>(SEQ ID<br>NO: 50) | SGWGYDVYS<br>FDY (SEQ ID<br>NO: 67) | DIQMTQTPSSLSASLGQRVTISCRA<br>SQDISNYLNWYQQKPDGTVKLLIYY<br>TSRLHSGVPSRESGSGSGTDYSLTIS<br>NLEQEDIATYFCQQGNTLPWTFGG<br>GTKLEIK (SEQ ID NO: 80) | RASQDISNY<br>LN (SEQ ID<br>NO: 115) | YTSRLHS<br>(SEQ ID<br>NO: 128) | QQGNTLPW<br>T (SEQ ID<br>NO: 139) |
| C1.773a | EVQLKESGPGLVQPSQTLSLTCT<br>VSGFSLTSNGVSWVRQPPGKGL<br>EWIAAISSGGSIYYNSAFKSRLSIS<br>RHTSKSQVLLKMNSLQTEDTAM<br>YFCARHRGYYGYNWGYFDYWG<br>QGASVTVSS (SEQ ID NO: 6) | SNGVS<br>(SEQ ID<br>NO: 38) | AISSGGSIYYN<br>SAFKS (SEQ<br>ID NO: 51) | HRGYYGYN<br>WGYFDY<br>(SEQ ID<br>NO: 65) | NIQLTQSPSLLSASVGDRVTLSCKGS<br>QNINNYLAWYQQKLGEAPKLLIYK<br>TNSLQTGIPSRFSGSGSGTDYTLTIS<br>SLHSEDLATYYCSQYNINGYTFGAG<br>TKLEIK (SEQ ID NO: 81) | KGSQNINN<br>YLA (SEQ<br>ID<br>NO: 113) | KINSLQT<br>(SEQ ID<br>NO: 126) | SQYNNGYT<br>(SEQ ID<br>NO: 140) |
| C1.777a | EVQLVESGPGLVQPSQTLSLTCT<br>VSGFSLTNNGVSWVRQPPGKGL<br>EWIAAISSGGSIYYNLAFKSRLSIS | NNGVS<br>(SEQ ID<br>NO: 40) | AISSGGSIYYN<br>LAFKS (SEQ<br>ID NO: 52) | HRGYYGEN<br>WGYFDY<br>(SEQ ID | NIQLTQSPSLLSASVGDRVTLSCKGS<br>QNINNYLAWYQQKLGEAPKLLIYK<br>TNSLQTGIPSRFSGSGSGTDYTLTIS | KGSQNINN<br>YLA (SEQ<br>ID | KINSLQT<br>(SEQ ID<br>NO: 126) | YQYNDGYT<br>(SEQ ID<br>NO: 141) |

TABLE 2-continued

From left to right, 1st column: Anti-ABCC1 antibody name, 2nd column: VH region, 3rd column: HCDR1, 4th column: HCDR2, 5th column: HCDR3, 6th column: VL region, 7th column: LCDR1, 8th column: LCDR2, 9th column: LCDR3.

| Antibody | Heavy Chain Variable Region | CDRH1 | CDRH2 | CDRH3 | Light Chain Variable Region | CDRL1 | CDRL2 | CDRL3 |
|---|---|---|---|---|---|---|---|---|
| | RNTSKGHVLLKMNSLQTEDTAM YFCVRHRGYYGFNWGYFDYWG QGVMVTVSS (SEQ ID NO: 7) | | | NO: 68) | SLHSEDLATYYCYQYNDGYTFGAG TKLELK (SEQ ID NO: 82) | NO: 113) | | |
| C1.778b | EVQRKESGPGLVQPSQTLSLTCT VSGFSLTNNGVSWVRQPPGKGL EWIAAISSGGSIVYNSAFKSRLSIS RITSKSQVLLKMINSLQTEDTAMY FCARHRGYYGYNWGYFDYWG QGVMVTVSS (SEQ ID NO: 8) | NNGVS (SEQ ID NO: 40) | AISSGGSIYYN SAFKS (SEQ ID NO: 51) | HRGYYGYN WGYFDY (SEQ ID NO: 65) | NIQLTQSPSLLSASVGQRVTLSCKGS QNIDNYLAWYQQKLGEPPKLLIYKT NSLQTGIPSRFSGSGSGTDYTLTISS LHSEDLATYYCYQYNNGYTFGAGT KLELKRADA (SEQ ID NO: 83) | KGSQNIDN YLA (SEQ ID NO: 116) | KINSLQT (SEQ ID NO: 126) | YQYNNGYT (SEQ ID NO: 142) |
| C1.7848 | EVKLEESGPGLVQPSQTLSLTCTV SGFSLTNNGVSWVRQPPGKGLE WIAAMSSGGNIYYNSAFKSRLSI SRDTSKSQVLLKMSSLQTEDTA MYFCGRHRGYYWYNWGFFDY WGQGASVTVSS (SEQ ID NO: 9) | NNGVS (SEQ ID NO: 40) | AMSSGGNIYY NSAFKS (SEQ ID NO: 53) | HRGYYWYN WGFPDY (SEQ ID NO: 69) | NIQLTQSPSLLSASVGDRVTLSCKGS QNINNYLAWYQQKLGEAPKLLIYK TNSLQTGIPSRFSGSGSGTDFTLTIS SLHSEDLATYYCCQYNNGYTFGAG TKLELK (SEQ ID NO: 84) | KGSQNINN YLA (SEQ ID NO: 113) | KINSLQT (SEQ ID NO: 126) | CQYNNGYT (SEQ ID NO: 143) |
| C1.786a | EVQLTESGLGLVQPSQTLSLTCSV SGFSLTSYNVHWVRQPTGKGLE WMGVIWTGGYTDSNSPLKSRLS ITRQTSKSQVFLKMNSLQSEDIAT YYCARERHTMGITKSWYFDYW GQGVMVTVSS (SEQ ID NO: 10) | SYNVH (SEQ ID NO: 41) | VIWTGGYTDS NSPLKS (SEQ ID NO: 54) | ERHTMGITK SWYFDY (SEQ ID NO: 70) | DVQMTQSPASLSASLGETISIECLAS EGIFSYLAWYQQKPGKSPQLLIYGA NTLQAGVPSRFSGSGSGTQYSLKIS SMQPEDEGDYFCQQSYKFPVTFGS GTKLELK (SEQ ID NO: 85) | LASEGIFSYL A (SEQ ID NO: 117) | GANTLQA (SEQ ID NO: 129) | QQSYKFPVT (SEQ ID NO: 144) |
| C1.787a | EVQLTESGPGLVQPSQTLSLTCT VSGFSLTSNGVSWVRQPPGKGL EWIAAISSGGSTYYNSAFKSRLSIS RHTSKSQVLENMINSLQTEDTAM YFCARHRGYYWSNWGYFDYW GQGVMVTVSS (SEQ ID NO: 11) | SNGVS (SEQ ID NO: 38) | AISSGGSTYYN SAFKS (SEQ ID NO: 55) | HRGYYWSN WGYFDY (SEQ ID NO: 71) | NIQLTQSPSLLSASVGDRVTLSCKGS QNINNYLAWYQQKLGEAPKLLIYK TNSLQTGIPSRFSGSGSGTDYTLILS SLHSEDLATYYCCQYNDGYTFGAG TKLELK (SEQ ID NO: 86) | KGSQNINN YLA (SEQ ID NO: 113) | KINSLQT (SEQ ID NO: 126) | CQYNDGYT (SEQ ID NO: 145) |
| C.779b | EVKLLESGPGLVQPSQTLSLTCTV SGFSLTSNGVIWVRQPPGKGLE WIAAISSGGNIYYNSGLKSRLGIS RDTSKSQVFLKMNSLQTEDTAIY FCTRARGTTTAYFMDAWGQGA SVTVSS (SEQ ID NO: 12) | SNGVI (SEQ ID NO: 42) | AISSGGNIYYN SGLKS (SEQ ID NO: 56) | ARGTTTAYF MDA (SEQ ID NO: 72) | ETVMITQSPSSLAVSAGETVTMNCK SSQSLLYSGNQKNYLAWYQQKPG QSPKLLIYWASTRQSGVPDRFIGSG SGTDFTLTISSVQAEDLAIYYCQQYY DTLMKMFGAGTKLEIK (SEQ ID NO: 87) | KSSQSLLYS GNQKNYLA (SEQ ID NO: 118) | WASTRQS (SEQ ID NO: 130) | QQYYDTLMK M (SEQ ID NO: 146) |
| C1.505 | EVQLTESGPGLVQPSQTLSLTCT VSGFSLTSNGVSWVRLPPGKGLE WIAAISSGGNIYYNSALKSRLSISR DISKSQVFLKMNSLQTEDTAIYF CTRERGWNYPGITNGYYFDYW GQGTSVTVSS (SEQ ID NO: 13) | SNGVS (SEQ ID NO: 38) | AISSGGNIYYN SALKS (SEQ ID NO: 49) | ERGWNYPGI TNGYYFDY (SEQ ID NO: 66) | DIVLTQSPSLLSASVGDRVILSCKAG QKINNYLAWYQQKLGEAPKLLIYN ANSLQTGIPSRESGSGSGTDYTLTIS SLQPEDVATYFCQQYNSWYTFGA GTKLEIK (SEQ ID NO: 79) | KAGQKINN YLA (SEQ ID NO: 114) | NANSLQT (SEQ ID NO: 127) | QQYNSWYT (SEQ ID NO: 138) |

TABLE 2-continued

From left to right, 1st column: Anti-ABCC1 antibody name, 2nd column: VH region, 3rd column: HCDR1, 4th column: HCDR2, 5th column: HCDR3, 6th column: VL region, 7th column: LCDR1, 8th column: LCDR2, 9th column: LCDR3.

| Antibody | Heavy Chain Variable Region | CDRH1 | CDRH2 | CDRH3 | Light Chain Variable Region | CDRL1 | CDRL2 | CDRL3 |
|---|---|---|---|---|---|---|---|---|
| C1.827 | EVQLVESGPGLVQPSQTLSLTCTVSGFSLTNNGVSWVRQPPGKGLEWIAAISNGGNIYHNSALKSRLSISRNTAKSQVLIKMNSLQTEDTAMYFCARHRGYYGYNWGYFDYWGQGASVTVSS (SEQ ID NO: 14) | NNGVS (SEQ ID NO: 40) | AISNGGNIYHNSALKS (SEQ ID NO: 57) | HRGYYGYNWGYFDY (SEQ ID NO: 65) | NIQVTQSPSLLSASVGDRVTLSCKGSQNIYNYLAWYQQKLGEAPKLLIYKTNSLQTGIPSRFSGSGSGTDYTLTISSLHSEDLATYYCCQYNNGYTFGAGTKLELK (SEQ ID NO: 88) | KGSQNIYNYLA (SEQ ID NO: 119) | KTNSLQT (SEQ ID NO: 126) | CQYNNGYT (SEQ ID NO: 143) |
| C1.830B | EVQLKESGPGLVRPSQTLSLTCSVSGFSLTNYNVHWVRQPTGKGLEWMGIIWTGGYTDYNSDLKSRLSITRQTSKSQVFLKMINGLQTEDVATYYCARERHTMGITKSWYFDYWGQGASVTVSS (SEQ ID NO: 15) | NYNVH (SEQ ID NO: 43) | IIWTGGYTDYNSDLKS (SEQ ID NO: 58) | ERHTMGITKSWYFDY (SEQ ID NO: 70) | DILMTQSPASLSASLGETISIECLASEGIFSYLGWYQQKPGKSPQLLIYGANSLQAGVPSRFSGSGSGTQYSLKISSMQPEDEGDYFCQQSYKFPVTFGSGTKLELK (SEQ ID NO: 89) | LASEGIFSYLG (SEQ ID NO: 120) | GANSLQA (SEQ ID NO: 131) | QQSYKFPVT (SEQ ID NO: 144) |
| C1.831 | EVQLTESGPGLVQPSQTLSLTCTVSGFSLTSNGVSWVRQPPGKGLEWIAAISSGGNIYYNSVLKSRLSISRDTSKSQVFLKMSSVQTEDTAIFCTRERGWNYPFITNGYYFDYWGQGVMVTVSS (SEQ ID NO: 16) | SNGVS (SEQ ID NO: 38) | AISSGGNIYYNSVLKS (SEQID NO: 59) | ERGWNYPFITNGYYFDY (SEQ ID NO: 73) | EIMILTQSPSLLSASVGDRVTLSCKAGQNINNYLAWYQQKLGEAPKLLIYNANSLQTGIPSRESGSGSGTDYTLTISSLQPEDVATYFCQQYNSWYTFGAGTKLEIK (SEQ ID NO: 90) | KAGQNINNYLA (SEQ ID NO: 121) | NANSLQT (SEQ ID NO: 127) | QQYNSWYT (SEQ ID NO: 138) |
| C1.835 | EVQLLESGPGLVQPSQTLSLTCTVSGFSLTNINGVSWVRQPPGKGLEWVAAMSSGGNIYYNSAFKSRLSISRHTSKSQVLLKMNSLQTEDTAMYFCARHRGYYGYNWGYFDYWGQGVMVTVSS (SEQ ID NO: 17) | NNGVS (SEQ ID NO: 40) | AMSSGGNIYYNSAFKS (SEQ ID NO: 53) | HRGYYGYNWGYFDY (SEQ ID NO: 65) | NIQLTQSPSLLSASVGDRVTLSCKGSQNIYNYLAWYQQKLGEAPKLLIYKTNSLQTDIPSRESGSGSGTDYTLTISSLHSEDLATYYCCQYNNGYTFGAGTKLELK (SEQ ID NO: 91) | KGSQNIYNYLA (SEQ ID NO: 119) | KINSLQT (SEQ ID NO: 126) | CQYNNGYT (SEQ ID NO: 143) |
| C1.841 | EVQLLESGPGLVQPSQTLSLTCTVSGFSLTNNGVSWVRQPPGKGLEWVAAMSSGGNIYYNSAFKSRLSISRHTSKSQVLLKMNSLQTEDTAMYFCARHRGYYGYNWGYFDYWGQGVMVTVSS (SEQ ID NO: 17) | NNGVS (SEQ ID NO: 40) | AMSSGGNIYYNSAFKS (SEQ ID NO: 53) | HRGYYGYNWGYFDY (SEQ ID NO: 65) | NIQLTQSPSLLSASVGDSVSLRCKGSQNIYNYLAWYQQKLGEAPKLLIYKTNNLQTGIPSRESGSGSGTDYTLTISSLNSEDLATYYCCQYNNGYTFGAGTKLELK (SEQ ID NO: 92) | KGSQNIYNYLA (SEQ ID NO: 119) | KINNLQT (SEQ ID NO: 132) | CQYNNGYT (SEQ ID NO: 143) |
| C1.844 | EVQLKESGPGLVQPSQTLSLTCTVSGFSLTSNGVIWVRQPPGKGLEWIAAISSGGNIVYNSGLKSRLGISRDTSKSQVFLKMNSLQTEDTAIYFCTRARGTTTAYVMDAWGQGASVTVSS (SEQ ID NO: 18) | SNGVI (SEQ ID NO: 42) | AISSGGNIYYNSGLKS (SEQ ID NO: 56) | ARGTTTAYVMDA (SEQ ID NO: 74) | DIVMITQSPSSLAVSAGETVNINCKSSQSLLYSVNQKNYLAWYQQKPGQSPKLLIYWASTRQSGVPDRFIGSGSGTDFTLTISSVQAEDLAIYYCQQYYDTLMKMFGAGTKLELK (SEQ ID NO: 93) | KSSQSLLYSVNQKNYLA (SEQ ID NO: 122) | WASTRQS (SEQ ID NO: 130) | QQYYDTLMKM (SEQ ID NO: 146) |

TABLE 2-continued

From left to right, 1st column: Anti-ABCC1 antibody name, 2nd column: VH region, 3rd column: HCDR1, 4th column: HCDR2, 5th column: HCDR3, 6th column: VL region, 7th column: LCDR1, 8th column: LCDR2, 9th column: LCDR3.

| Antibody | Heavy Chain Variable Region | CDRH1 | CDRH2 | CDRH3 | Light Chain Variable Region | CDRL1 | CDRL2 | CDRL3 |
|---|---|---|---|---|---|---|---|---|
| C1.845 | EVQLVESGPGLVQPSQTLSLTCTVSGFSLTNINGVSWVRQPPGKGLEWIAAISSGGSIYYNLAFKSRLSISRNTSKGQVLLKMNSLQTEDTAMYFCARHRGYYGYNWGYFDYWGQGASVTVSS (SEQ NO: 19) | NNGVS (SEQ ID NO: 40) | AISSGGSIYYNLAFKS (SEQ ID NO: 52) | HRGYYGYNWGYFDY (SEQ ID NO: 65) | NIQLTQSPSLLSASVGDRVTLSCKGSQNINNYLAWYQQKLGEAPKLLIYKTNSLQTGIPSRFSGSGSGSDYTLTISSLHSEDLATYYCYQYNDGYTFGAGTKLELK (SEQ ID NO: 94) | KGSQNINNYLA (SEQ ID NO: 113) | KINSLQT (SEQ ID NO: 126) | YQYNDGYT (SEQ ID NO: 141) |
| C1.847 | EVQLKESGPGLVQPSQTLSLTCTVSGFSLTNNGVSWVRQPPGKGLEWIAAISSGGNIYHNSALKSRLSISRNTAQSQVLLKMNSLQTEDTAMYFCARHRGYYGYNWGYFDYWGQGTLVTVSS (SEQ ID NO: 20) | NNGVS (SEQ ID NO: 40) | AISSGGNIYHNSALKS (SEQ ID NO: 60) | HRGYYGYNWGYFDY (SEQ ID NO: 65) | NIQLTQSPSLLSASVGDRVTLSCKGSQNIYNYLAWYQQKIGEAPKLLIYKTNSLQTGIPSRFSGSGSGTDYTLTISSLHSEDLATYYCCQYNNGYTFGAGTKLELK (SEQ ID NO: 95) | KGSQNIYNYLA (SEQ ID NO: 119) | KINSLQT (SEQ ID NO: 126) | CQYNNGYT (SEQ ID NO: 143) |
| C1.851 | EVQLKESGPGLVQPSQTLSLTCTVSGFSLTNNGVSWIRQPPGKGLEWIAAISSGQNIYYNSAFKSRLSISRNTSKRQVLLKMNSLQTEDTAMYFCARHRGYYGYNWGYFDYWGQGASVTVSS (SEQ ID NO: 21) | NNGVS (SEQ ID NO: 40) | AISSGGNIYYNSAFKS (SEQ ID NO: 48) | HRGYYGYNWGYFDY (SEQ ID NO: 65) | NIQLTQSPSLLSASVGDRVTLSCKGSQNINNYLAWYQQKLGEAPKLLIYKTNSLQTGIPSRESGSGSGTDYTLTISSLHSEDLATYYCCQYNNGYTFGAGTKLELKR (SEQ ID NO: 96) | KGSQNINNYLA (SEQ ID NO: 113) | KINSLQT (SEQ ID NO: 126) | CQYNNGYT (SEQ ID NO: 143) |
| C1.855 | EVQLKESGPGLVQPSQTLSLTCTVSGFSLTSNGVSWVRQPPGKGLEWIAAISNGGNIYYNSAFKSRLSISRHTSKSQVLLKMNSLQTEDTAMYFCARHRGYYGYNWGYFDYWGQGASVTVSS (SEQ ID NO: 22) | SNGVS (SEQ ID NO: 38) | AISNGGNIYYNSAFKS (SEQ ID NO: 61) | HRGYYGYNWGYFDY (SEQ ID NO: 65) | NIQLTQSPSLLSASVGDRVTLSCKGSQNINNYLGWYQQKLGEAPRLLIYKTNSLQTGIPSRESGSGSGTDYTLTISSLHSEDLATYYCYQYNNGYTFGAGTKLELK (SEQ ID NO: 97) | KGSQNINNYEG (SEQ ID NO: 123) | KINSLQT (SEQ ID NO: 126) | YQYNNGYT (SEQ ID NO: 142) |
| C1.861 | EVQLKESGPGLVQPSQTLSLTCTVSGFSLTSNGVTWVRQPPGKGLEWIAAISSGGNIYYNSAVKSRLSISRDTSKSQVFLKMNSLQTEDTAIYFCTRARGTTTAYVMDAWGQGASVTVSS (SEQ ID NO: 23) | SNGVT (SEQ ID NO: 44) | AISSQGNIYYNSAVKS (SEQ ID NO: 62) | ARGTTTAYVMDA (SEQ ID NO: 74) | DVVLTQSPSSLAVSAGETVTINCKS5QSLLYSGNQKNYLAWYQQKPGQSPKLLIYWASTRQSGVPDRFIGSGSGTDFTLTISSVQAEDLAIYYCQQYYDVLMNMFGAGTKLEIK (SEQ ID NO: 98) | KSSQSLLYSGNQKNYLA (SEQ ID NO: 118) | WASTRQS (SEQ ID NO: 130) | QQYYDVLMNM (SEQ ID NO: 147) |
| C1.863 | EVQRKESGPGLVQPSQTLSLTCTVSGFSLTNNGVSWVRQPPGKGLEWIAAISSGGSIYYNSAFKSRLSISRITSKSQVLLKMNSLQTEDTAMYFCARHRGYYGYNWGYFDYWGQGVMVTVSS (SEQ ID NO: 8) | NNGVS (SEQ ID NO: 40) | AISSGGSIYYNSAFKS (SEQ ID NO: 51) | HRGYYGYNWGYFDY (SEQ ID NO: 65) | NIQMTQSPSLLSASVGDRVTLSCKGSQNIYNYLAWYQQKLGEAPKLLIYKTSSLQAGIPSRFSGSGSDTDYTLTISSLHSEDLATYYCCQYNNGYTFGAGTKLEIK (SEQ ID NO: 99) | KGSQNIYNYLA (SEQ ID NO: 119) | KISSLQA (SEQ ID NO: 133) | CQYNNGYT (SEQ ID NO: 143) |

TABLE 2-continued

From left to right, 1st column: Anti-ABCC1 antibody name, 2nd column: VH region, 3rd column: HCDR1, 4th column: HCDR2, 5th column: HCDR3, 6th column: VL region, 7th column: LCDR1, 8th column: LCDR2, 9th column: LCDR3.

| Antibody | Heavy Chain Variable Region | CDRH1 | CDRH2 | CDRH3 | Light Chain Variable Region | CDRL1 | CDRL2 | CDRL3 |
|---|---|---|---|---|---|---|---|---|
| C1.876 | QVQLKESGPGLVQPSQTLSLTCTVSGFSLTNINGVSWVRQPPGKGLEWIAAMSSGGSIYYNSAFKSRLSISRHTSKSQVLLQMNSLQTEDTAMYFCTRHRGYYGYNWGYFDYWGQGVMVTVSS (SEQ ID NO: 24) | NNGVS (SEQ ID NO: 40) | AMSSGGSIYYNSAFKS (SEQ ID NO: 63) | HRGYYGYNWGYFDY (SEQ ID NO: 65) | DIQLTQSPSLLSASVGDSVSLRCKGSQNIYNYLAWYQQKLGEAPKLLIYKTNNLQTGIPSRFSGSGSGTDYTLTISSLNSEDLATYYCCQYNNGYTFGAGTKVELK (SEQ ID NO: 100) | KGSQNIYNYLA (SEQ ID NO: 119) | KINNLQT (SEQ ID NO: 132) | CQYNNGYT (SEQ ID NO: 143) |
| C1.877 | EVQLTESGPGLVQPSQTLSLTCTVSGFSLTSNGVSWVRQPPGKGLEWIAAISSGGSTYYNSAFKSRLSISRHTSKSQVLLNMNSLQTEDTAMYFCARHRGYYWSNWGYFDYWGQGVMVTVSS (SEQ ID NO: 11) | SNGVS (SEQ ID NO: 38) | AISSGGSTYYNSAFKS (SEQ ID NO: 55) | HRGYYWSNWGYFDY (SEQ ID NO: 71) | DIVMTQSPSLLSASVGDRVTLSCKGSQNINNYLAWYQQKLGEAPKLLIYETNSLQTGIPSRESGSGSGTDYTLTLSSLHSEDLATYYCYQYNDGYTFGAGTKLEIK (SEQ ID NO: 101) | KGSQNINNYLA (SEQ ID NO: 113) | ETNSLQT (SEQ ID NO: 134) | YQYNDGYT (SEQ ID NO: 141) |
| C1.879A | EVQLTESGPGLVQPSQTLSLTCTVSGFSLTSNGVSWVRQPPGKGLEWIAAISSGGSTYYNSAFKSRLSISRHTSKSQVLLNMNSLQTEDTAMYFCARHRGYYWSNWGYFDYWGQGVMVTVSS (SEQ ID NO: 11) | SNGVS (SEQ ID NO: 38) | AISSGGSTYYNSAFKS (SEQ ID NO: 55) | HRGYYWSNWGYFDY (SEQ ID NO: 71) | DIQLTQSPSLLSASVGDRVTLSCKGSQNINNYLAWYQQKVGEAPKLLIYKTNSLQTGIPSRFSGSGSGTDYTLTISSLHSEDLATYYCYQYNNGYTFGAGTKLELKRADAAPTV (SEQ ID NO: 102) | KGSQNINNYLA (SEQ ID NO: 113) | KINSLQT (SEQ ID NO: 126) | YQYNNGYT (SEQ ID NO: 142) |
| C1.830B. hu11 Human-ized | EVQLQESGPGLVKPSQTLSLTCAVYGFSLTNYNVHWVRQPPGKGLEWMGIIWTGGYTDYNSDLKSRLTISRDTSKNQVSLKLSSVTAADTAVYYCARERHTMIGITKSWYFDYWGQGTLVTVSS (SEQ ID NO: 26) | NYNVH (SEQ ID NO: 43) | NWTGGYTDYNSDEKS (SEQ ID NO: 58) | ERHTMGITKSWYFDY (SEQ ID NO: 70) | DIQMTQSPSSLSASVGDRVTITCLASEGIFSYLGWYQQKPGKSPKLLIYGANSLQAGVPSRESGSGSGTDYTLTISSLQPEDFATYYCQQSYKFPVTFGQGTKLEIK (SEQ ID NO: 103) | LASEGIFSYLG (SEQ ID NO: 120) | GANSLQA (2) | QQSYKFPVT (SEQ ID NO: 144) |
| C1.851. hu11 Human-ized | EVQLQESGPGLVKPSETLSLTCTVSGFSLTNNGVSWIRQPPGKGLEWIAAISSGGNIYYNSAFKSRLTISRDTSKNQVSLKLSSVTAADTAVYYCARHRGYYGYNWGYFDYWGQGTLVTVSS (SEQ ID NO: 27) | NNGVS (SEQ ID NO: 40) | AISSGGNIYYNSAFKS (SEQ ID NO: 48) | HRGYYGYNWGYFDY (SEQ ID NO: 65) | DIQLTQSPSSLSASVGDRVTITCKGSQNINNYLAWYQQKPGKAPKLLIYKTNSLQTGIPSRFSGSGSGTDYTLTISSLQPEDFATYYCCQYNNGYTFGQGTKLEIK (SEQ ID NO: 104) | KGSQNINNYLA (SEQ ID NO: 113) | KTNSLQT (SEQ ID NO: 126) | CQYNNGYT (SEQ ID NO: 143) |
| C1.851. hu12 Human-ized | EVQLQESGPGLVKPSETLSLTCTVSGFSLTNNGVSWIRQPPGKGLEWIAAISSGGNIYYNSAFKSRLTISRDTSKNQVSLKLSSVTAADTAVYYCARHRGYYGYNWGYFDYWGQGTLVTVSS (SEQ ID NO: 27) | NNGVS (SEQ ID NO: 40) | AISSGGNIYYNSAFKS (SEQ ID NO: 48) | HRGYYGYNWGYFDY (SEQ ID NO: 65) | DIQLTQSPSSLSASVGDRVTITCKGSQNINNYLAWYQQKPGKAPKLLIYKTNSLQTGIPSRFSGSGSGTDYTLTISSLQPEDFATYYCYQYNNGYTFGQGTKLEIK (SEQ ID NO: 105) | KGSQNINNYLA (SEQ ID NO: 113) | KINSLQT (SEQ ID NO: 126) | YQYNNGYT (SEQ ID NO: 142) |

TABLE 2-continued

From left to right, 1st column: Anti-ABCC1 antibody name, 2nd column: VH region, 3rd column: HCDR1, 4th column: HCDR2, 5th column: HCDR3, 6th column: VL region, 7th column: LCDR1, 8th column: LCDR2, 9th column: LCDR3.

| Antibody | Heavy Chain Variable Region | CDRH1 | CDRH2 | CDRH3 | Light Chain Variable Region | CDRL1 | CDRL2 | CDRL3 |
|---|---|---|---|---|---|---|---|---|
| C1.851.hu13 Human-ized | EVQLQESGPGLVKPSETLSLTCTVSGFSLTNNGVSWIRQPPGKGLEWIAAISSGGNIYYNSAFKSRLTISRDTSKNQVSLKLSSVTAADTAVYYCARHRGYYGYNWGYFDYWGQGTLVTVSS (SEQ ID NO: 27) | NNGVS (SEQ ID NO: 40) | AISSGGNIYYNSAFKS (SEQ ID NO: 48) | HRGYYGYNWGYFDY (SEQ ID NO: 65) | DIQLTQSPSSLSASVGDRVTITCKGSQNINNYLAWYQQKPGKAPKLLIYKTNSLQTGIPSRFSGSGSGTDYTLTISSLQPEDFATYYCSQYNNGYTFGQGTKLEIK (SEQ ID NO: 106) | KGSQNINNYIA (SEQ ID NO: 113) | KTNSLQT (SEQ ID NO: 126) | SQYNINGYT (SEQ ID NO: 140) |
| C1.787a.hu11 Human-ized | EVQLQESGPGLVKPSETLSLTCTVSGFSLTSNGVSWVRQPPGKGLEWIAAISSGGSTYYNSAFKSRLTISRQTSKNQVSLKLSSVTAADTAVYYCARHRGYYWSNWGYFDYWGQGTLVTVSS (SEQ ID NO: 28) | SNGVS (SEQ ID NO: 38) | AISSGGSTYYNSAFKS (SEQ ID NO: 55) | HRGYYWSNWGYFDY (SEQ ID NO: 71) | DIQLTQSPSSLSASVGDRVTITCKGSQNINNYLAWYQQKPGKAPKLLIYKTNSLQTGIPSRFSGSGSGTDYTLTISSLQPEDFATYYCCQYNDGYTFGQGTKLEIK (SEQ ID NO: 107) | KGSQNINNYLA (SEQ ID NO: 113) | KINSLQT (SEQ ID NO: 126) | CQYNDGYT (SEQ ID NO: 145) |
| C1.831.hu11 Human-ized | EVQLQESGPGLVKPSETLSLTCTVSGFSLTSNGVSWVRQPPGKGLEWIAAISSGGNIYYNSVLKSRLTISRDISKNQVSLKLSSVTAADTAVYYCTRERGWNYPFITNGYYFDYWGQGTLVTVSS (SEQ ID NO: 29) | SNGVS (SEQ ID NO: 38) | AISSGGNIYYNSVIKS (SEQ ID NO: 59) | ERGWNYPFITNGYYFDY (SEQ ID NO: 73) | DIQLTQSPSSLSASVGDRVTITCKAGQNINNYLAWYQQKPGKAPKLLIYNANSLQTGIPSRFSGSGSGTDYTLTISSLQPEDFATYYCQQYNSWYTFGQGTKLEIK (SEQ ID NO: 108) | KAGQNINNYLA (SEQ ID NO: 121) | NANSLQT (SEQ ID NO: 127) | QQYNSWYT (SEQ ID NO: 138) |
| C1.831.hu41 Human-ized | EVQLQESGPGLVKPSETLSLTCTVSGFSLTSQGVSWVRQPPGKGLEWIAAISSGGNIYYNSVLKSRLTISRDISKNQVSLKLSSVTAADTAVYYCTRERGWNYPFITSGYYFDYWGQGTLVTVSS (SEQ ID NO: 30) | SQGVS (SEQ ID NO: 45) | AISSGGNIYYNSVLKS (SEQ ID NO: 59) | ERGWNYPFITSGYYFDY (SEQ ID NO: 75) | DIQLTQSPSSLSASVGDRVTITCKAGQNINNYLAWYQQKPGKAPKLLIYNANSLQTGIPSRFSGSGSGTDYTLTISSLQPEDFATYYCQQYNSWYTFGQGTKLEIK (SEQ ID NO: 108) | KAGQNINNYLA (SEQ ID NO: 121) | NANSLQT (SEQ ID NO: 127) | QQYNSWYT (SEQ ID NO: 138) |
| C1.844.hu11 Human-ized | EVQLQESGPGLVKPSETLSLTCTVSGFSLTSNGVIWVRQPPGKGLEWIAAISSGGNIVYNSGLKSRLTISRDTSKNQVSLKLSSVTAADTAVYYCTRARGTTTAYVMDAWGQGTLVTVSS (SEQ ID NO: 31) | SNGVI (SEQ ID NO: 42) | AISSGGNIYYNSGLKS (SEQ ID NO: 56) | ARGTTTAYVMDA (SEQ ID NO: 74) | DIVMTQSPDSLAVSLGERATINCKSSQSLLYSVNQKNYLAWYQQKPGQSPKLLIYWASTRQSGVPDRFSGSGSGTDFTLTISSLQAEDVAVYYCQQYYDTLMKMFGAGTKLELK (SEQ ID NO: 109) | KSSQSLLYSVNQKNYLA (SEQ ID NO: 122) | WASTRQS (SEQ ID NO: 130) | QQYYDTLMKM (SEQ ID NO: 146) |
| C1.844.hu21 Human-ized | EVQLVESGGGLIQPGGSLRLSCAVSGFSLTSNGVIWVRQPPGKGLEWIAAISSGGNIYYNSGLKSRLTISRDTSKNTVYLQMNSLRAEDTAVYYCTRARGTTTAYVMDAWGQGTLVTVSS (SEQ ID NO: 32) | SNGVI (SEQ ID NO: 42) | AISSGGNIYYNSGLKS (SEQ ID NO: 56) | ARGTTTAYVMDA (SEQ ID NO: 74) | DIVMTQSPDSLAVSLGERATINCKSSQSLLYSVNQKNYLAWYQQKPGQSPKLLIYWASTRQSGVPQRFSGSGSGTDFTLTISSLQAEDVAVYYCQQYYDTLMKMFGAGTKLELK (SEQ ID NO: 109) | KSSQSLLYSVNQKNYLA (SEQ ID NO: 122) | WASTRQS (SEQ ID NO: 130) | QQYYDTLMKM (SEQ ID NO: 146) |

TABLE 2-continued

From left to right, 1st column: Anti-ABCC1 antibody name, 2nd column: VH region, 3rd column: HCDR1, 4th column: HCDR2, 5th column: HCDR3, 6th column: VL region, 7th column: LCDR1, 8th column: LCDR2, 9th column: LCDR3.

| Antibody | Heavy Chain Variable Region | CDRH1 | CDRH2 | CDRH3 | Light Chain Variable Region | CDRL1 | CDRL2 | CDRL3 |
|---|---|---|---|---|---|---|---|---|
| C1.861.hu11 Humanized | EVQLQESGPGLVKPSETLSLTCTVSGFSLTSNGVTWVRQPPGKGLEWIAAISSGGNIYYNSAVKSRLTISRDTSKNQVSLKLSSVTAADTAVYYCTRARGTTTAYVMDAWGQGTTVTVSS (SEQ ID NO: 33) | SNGVT (SEQ ID NO: 44) | AISSGGNIYYNSAVKS (SEQ ID NO: 62) | ARGTTTAYVMDA (SEQ ID NO: 74) | DVQLTQSPSSLSASVGDRVTITCKSSQSLLYSGNQKNYLAWYQQKPGKSPKLLIYWASTRQSGVPSRFSGSGSGTDFTLTISSLQPEDVATYYCQQYYDVLMNMFGGGTKLEIK (SEQ ID NO: 110) | KSSQSLLYSGNQKNYLA (SEQ ID NO: 118) | WASTRQS (SEQ ID NO: 130) | QQYYDVLMNM (SEQ ID NO: 147) |
| C1.861.hu21 Humanized | EVQLVESGGGLIQPGGSLRLSCAVSGFSLTSNGVTWVRQPPGKGLEWIAAISSGGNIYYNSAVKSRLTISRDTSKNTVYLQMNSLRAEDTAVYFCTRARGTTTAYVMDAWGQGTTVTVSS (SEQ ID NO: 34) | SNGVT (SEQ ID NO: 44) | AISSGGNIYYNSAVKS (SEQ ID NO: 62) | ARGTTTAYVMDA (SEQ ID NO: 74) | DVQLTQSPSSLSASVGDRVTITCKSSQSLLYSGNQKNYLAWYQQKPGKSPKLLIYWASTRQSGVPSRFSGSGSGTDFTLTISSLQPEDVATYYCQQYYDVLMINMFGGGTKLEIK (SEQ ID NO: 110) | KSSQSLLYSGNQKNYLA (SEQ ID NO: 118) | WASTRQS (SEQ ID NO: 130) | QQYYDVLMNM (SEQ ID NO: 147) |
| C1.861.hu41 Humanized | EVQLQESGPGLVKPSETLSLTCTVSGFSLTSSGVTWVRQPPGKGLEWIAAISSGGNIYYNSAVKSRLTISRDTSKNQVSLKLSSVTAADTAVYYCTRARGTTTAYVMDAWGQGTTVTVSS (SEQ ID NO: 35) | SSGVT (SEQ ID NO: 46) | AISSGGNIYYNSAVKS (SEQ ID NO: 62) | ARGTTTAYVMDA (SEQ ID NO: 74) | DVQLTQSPSSLSASVGDRVTITCKSSQSLLYSGNQKNYLAWYQQKPGKSPKLLIYWASTRQSGVPSRFSGSGSGTDFTLTISSLQPEDVATYYCQQYYDVLMNMFGGGTKLEIK (SEQ ID NO: 110) | KSSQSLLYSGNQKNYLA (SEQ_ID NO: 118) | WASTRQS (SEQ ID NO: 130) | QQYYDVLMNM (SEQ ID NO: 147) |
| C1.861.hu61 Humanized | EVQLVESGGGLIQPGGSLRLSCAVSGFSLTSSGVTWVRQPPGKGLEWIAAISSGGNIYYNSAVKSRLTISRDTSKNTVYLQMNSLRAEDTAVYFCTRARGTTTAYVMDAWGQGTTVTVSS (SEQ ID NO: 36) | SSGVT (SEQ ID NO: 46) | AISSGGNIYYNSAVKS (SEQ ID NO: 62) | ARGTTTAYVMDA (SEQ ID NO: 74) | DVQLTQSPSSLSASVGDRVTITCKSSQSLLYSGNQKNYLAWYQQKPGKSPKLLIYWASTRQSGVPSRFSGSGSGTDFTLTISSLQPEDVATYYCQQYYDVLMINMFGGGTKLEIK (SEQ ID NO: 110) | KSSQSLLYSGNQKNYLA (SEQ ID NO: 118) | WASTRQS (SEQ ID NO: 130) | QQYYDVLMNM (SEQ ID NO: 147) |
| C1.851.hu14 Humanized | EVQLQESGPGLVKPSETLSLTCTVSGFSLTNNGVSWIRQPPGKGLEWIAAISSGGNIYYNSAFKSRLTISRDTSKNQVSLKLSSVTAADTAVYYCARHRGYYGYNWGYFDYWGQGTLVTVSS (SEQ ID NO: 27) | NNGVS (SEQ ID NO: 40) | AISSGGNIYYNSAFKS (SEQ ID NO: 48) | HRGYYGYNWGYFDY (SEQ ID NO: 65) | DVVMTQTPLSLPVSLGDQASISCRSSQSIVHSNGNTYLEWYLQKPGQSPKLLIYKVSNRFSGVPDRFSGSGTGTDFTLKISRVEAEDLGVYYCFQGSHVPRTFGGGTKLEIK (SEQ ID NO: 76) | KGSQNINNYLA (SEQ ID NO: 113) | KINSLQT (SEQ ID NO: 126) | YQYNQGYT (SEQ ID NO: 148) |
| C1.851.hu15 Humanized | EVQLQESGPGLVKPSETLSLTCTVSGFSLTNNGVSWIRQPPGKGLEWIAAISSGGNIYYNSAFKSRLTISRQTSKNQVSLKLSSVTAADTAVYYCARHRGYYGYNWGYFDYWGQGTLVTVSS (SEQ ID NO: 27) | NNGVS (SEQ ID NO: 40) | AISSGGNIYYNSAFKS (SEQ ID NO: 48) | HRGYYGYNWGYFDY (SEQ ID NO: 65) | DVVMTQAPSSLSASLGERISLTCRASQDIYGSLNWFQQKPDGTIKLLIYGTSSLDSGVPKRFSGSRSGSDYSLTISSLESEDFADYYCLQYASSPYTFGGGTKLEIK (SEQ ID NO: 77) | KGSQNINNYLA (SEQ ID NO: 113) | KINSLQT (SEQ ID NO: 126) | YQYNSGYT (SEQ ID NO: 149) |

The anti-ABCC1 antibodies listed in Table 2 are also referred to as anti-KPC1 antibodies or anti-C1 antibodies and can be referred to by the antibody number listed in Table 2.

In some embodiments, the antibody comprises a VL region and a VH region that are present in separate polypeptides; in other embodiments, the VL region and a VH region are contained within a single polypeptide.

The antibody of the present disclosure may be selected from the group consisting of an Ig monomer, a Fab fragment, a $F(ab')_2$ fragment, a Fd fragment, a scFv, a scAb, a dAb, and a Fv.

In some embodiments, a subject antibody is a recombinant or modified antibody, e.g., a chimeric, humanized, deimmunized or an in vitro generated antibody. The term "recombinant" or "modified" antibody as used herein is intended to include all antibodies that are prepared, expressed, created, or isolated by recombinant means, such as (i) antibodies expressed using a recombinant expression vector transfected into a host cell; (ii) antibodies isolated from a recombinant, combinatorial antibody library; (iii) antibodies isolated from an animal (e.g. a mouse) that is transgenic for human immunoglobulin genes; or (iv) antibodies prepared, expressed, created, or isolated by any other means that involves splicing of human immunoglobulin gene sequences to other DNA sequences. Such recombinant antibodies include humanized, CDR grafted, chimeric, deimmunized, and in vitro generated antibodies; and can optionally include constant regions derived from human germline immunoglobulin sequences.

As noted above, the subject anti-ABCC1 antibody specifically binds one or more epitopes of ABCC1. Thus, the epitope is an ABCC1 epitope. The size of a ABCC1 epitope bound by anti-ABCC1 antibody may vary, including where the ABCC1 epitope is formed by a polypeptide having a contiguous stretch of an ABCC1 sequence that may range from 3 aa or less to 12 aa or more, including but not limited to e.g., 4 aa, 5 aa, 6 aa, 7 aa, 8 aa, 9 aa, 10 aa, 11 aa, 12 aa, 4 aa to 10 aa, 5 aa to 10 aa, 6 as to 10 aa, 4 aa to 8 aa, 5 as to 8 aa, 6 as to 8 aa, etc.

In some embodiments, the ABCC1 epitope can be formed by a polypeptide having at least about 75%, at least about 80%, at least about 85%, at least about 90%, at least about 95%, at least about 98%, at least about 99%, or 100%, amino acid sequence identity to a contiguous stretch of a ABCC1 sequence, including but not limited to e.g., the human ABCC1 sequence: MALRGFCSADGSDPLWDWNVTWNTSNPDFTKCFQNTVLVWVPCFYLWACFPFYFLYLSRHD RGYIQMTPLNKTKTALGFLLWIVCWADLFYSFWERSRGIFLAPVFLVSP TLLGITMLLATFLIQLE RRKGVQSSGIMLTFWLVALVCALAILRSKIMTALKEDAQVDLFRDITFYVYFSLLLIQLVLSCFSD RSPLFSETIHDPNPCPESSASFLSRITFWWITGLIV RGYRQPLEGSDLWSLNKEDTSEQVVPVL VKNWKKECAKTRKQPVKVVYSSKDPAQPKESSKVDANEEVEALIVKSPQKEWNPSLFKVLYKT FGPYFLMSFFFKAIHDLMMFSGPQILKLLIKFVNDTKAPDWQGYFYTVLLFVTACLQTLVLHQYF HICFVSGMRIKTAVIGAVYRKALVITNSARKSSTVGEIVNLMSVDAQRFM DLATYINMIWSAPLQ VILALYLLWLNLGPSVLAGVAVMVLMVPVNAVMAMKTKTYQVAHMKSKDNRIKLMNEILNGIKV LKLYAWELAFKDKVLAIRQEELKVLKKSAYLSAVGTFTWVCT PFLVALCTFAVYVTIDENNILDA QTAFVSLALFNILRFPLNILPMVISSIVQASVSLKRLRIFLSHEELEPDSIERRPVKDGGGTNSITV RNATFTWARSDPPTLNGITFSIPEGALVAV VGQVGCGKSSLLSALLAEMDKVEGHVAIKGSVAY VPQQAWIQNDSLRENILFGCQLEEPYYRSVIQACALLPDLEILPSGDRTEIGEKGVNLSGGQKQ RVSLARAVYSNADIYLFDDPLSAVDAHVGKHIFENVIGPKGMLKNKTRILVTHSMSYLPQVDVIIV MSGGKISEMGSYQELLARDGAFAEFLRTYASTEQEQDAEENGVTGVSGPGKEAKQMENGML VTDSAGKQLQRQLSSSSSYSGDISRHHNSTAELQKAEAKKEETWKLMEADKAQTGQVKLSVY WDYMKAIGLFISFLSIFLFMCNHVSALASNYWLSLWTDDPIVNGTQEHTKVRLSVYGALGISQGI AVFGYSMAVSIGGILASRCLHVDLLHSILRSPMSFFERT PSGNLVNRFSKELDTVDSMIPEVIKM FMGSLFNVIGACIVILLATPIAAIIIPPLGLIYFFVQRFYVASSRQLKRLESVSRSPVYSHFNETLLG VSVIRAFEEQERFIHQSDLKVDENQKAYYPSIVA NRWLAVRLECVGNCIVLFAALFAVISRHSLS AGLVGLSVSYSLQVTTYLNWLVRMSSEMETNIVAVERLKEYSETEKEAPWQIQETAPPSSWPQ VGRVEFRNYCLRYREDLDFVLRHINVTINGGEKVGIVGRTGAGKSSLTLGLFRINESAEGEIIIDG INIAKIGLHDLRFKITIIPQDPVLFSGSLRMNLDPFSQYSDEEVWTSLELAHLKDFVSALPDKLDH ECAEGGENLSVGQRQLVCLARALLRKTKILVLDEATAAVDLETDDLIQSTIRTQFEDCTVLTIAHR LNTIMDYTRVIVLDKGEIQEYGAPSDLLQQRGLFYSMAKDAGLV (SEQ ID NO:150), or an extracellular region thereof, e.g., Loop 1 (amino acids 1-33): MALRGFCSADGSDPLWDWNVTWNTSNPDFTKCF (SEQ ID NO:151); Loop 2 (amino acids 96-100): RSRGI (SEQ ID NO:152); Loop 3 (amino acids 155-172): SKIMTALKEDAQVDLFRD (SEQ ID NO:153); Loop 4 (amino acids 338-363): MMFSGPQILKLLIKFVNDTKAPDWQG (SEQ ID NO:154): Loop 5 (amino acids 462-464): LGP; Loop 6 (amino acids 569-490): VTIDENNILDAQTAFVSLALFN (SEQ ID NO:155); Loop 7 (amino acids 989-1025): ALASNYWLSLWTDDPIVNGTQEHTKVRLSVYGALGIS (SEQ ID NO:156); Loop 8 (amino acid 1111): A; Loop 9 (amino acids 1225-1226): LS; or a fragment of human ABCC1, e.g., a fragment comprising amino acid residues 204-1531: MDPNPCPESSASFLSRITFWWITGLIVRGYRQPLEGSDLWSLNKEDTSEQVVPVLVKNWKKEC AKTRKQPVKVVYSSKDPAQPKESSKVDANEEVEALIVKSP QKEWNPSLFKVLYKTFGPYFLMS FFFKAIHDLMMFSGPQILKLLIKFVNDTKAPDWQGYFYTVLLFVTACLQTLVLHQYFHICFVSGM RIKTAVIGAVYRKALVITNSARKSSTVGEIVNLMSVDAQRFMDLATYINMIWSAPLQVILALYLLW LNLGPSVLAGVAVMVLMVPVNAVMAMKTKTYQVAHMKSKDN RIKLMNEILNGIKVLKLYAWEL AFKDKVLAIRQEELKVLKKSAYLSAVGTFTWVCTPFLVALCTFAVYVTIDENNILDAQTAFVSLAL FNILRFPLNILPMVISSIVQASVSLKRLRIFLSHEE LEPDSIERRPVKDGGGTNSITVRNATFTWAR SDPPTLNGITFSIPEGALVAWGQVGCGKSSLLSALLAEMDKVEGHVAIKGSVAYVPQQAWIQN DSLRENILFGCQLEEPYYRSVIQACALLPDLEILPSGDRTEIGEKGVNLSGGOKQRVSLARAVYS NADIYLFDDPLSAVDAHVGKHIFENVIGPKGMLKNKTRILVTHSMSYLPQVDVIIVMSGG- KISEM GSYQELLARDGAFAEFLRTYASTEQEQ-DAEENGVTGVSGPGKEAKQMENGMLVTDSAGKQLQRQLSSSSSYSGDISRHHNSTAELQKAEAK-KEETWKLMEADKAQTGQVKLSVYWDYMKAIGLFISFLSIFLFMCNHVSALASNYWLSLWTDDPIV-NGTQEHTKVRLSVYGALGISQGIAVFGYSMAV SIG-GILASRCLHVDLLHSILRSPMSFFER-TPSGNLVNRFSKELDTVDSMIPEVIKMFMGSLFNVIGACIVILLATPIAAIIPPLGLIYFFVQRFYVASSRQLKR-LESVSRSPVYSHFNETLLGVSVIRAFEEQERFIHQSDLKVDENQKAYYPSIVANRWLAVR-LECVGNCIVLFAALFAVISRHSLSAGLVGLSVSYSLQVTTYLNWLVRMSSEMETNIVAVERLKEY-SETEKEAPWQIQETAPPSSWPQVGRVEFRNYCLRYREDLDFVLRHINVTINGGEKVGIVGRT-GAGKSSLTLGLFRINESAEGEIIDGINIAKIGLHDLRFKITIIPQDPVLFSGSLRMNLDPFSQYS-DEEVWTSLELAHLKDFVSALPDKLDHECAEGGENLSVGQRQLVCLARALLRKTKILVLDEATAAVDLETD-DLIQSTIRTQFEDCTVLTIAHRLNTIMDYTRVIVLDKGEIQEYGAPSDLLQQRGLFYSMAKDAGLV (SEQ ID NO:157); or a cynomolgus monkey ABCC1 sequence: MALRGFCSADGSDPLWDWNVTWYTSNPDFTKCFQNTVLVWVPCFYLWACFPFYFLY-LSRHD RGYIQMTLLNKTKTALGFLL-WIVCWADLFYSFWERSRGIFLAPVFLVSPTLLGITML-LATFLIQLE RRKGVQSSGIMLTFWLVALLCALAILRS-KIMTALKEDVQVDLFRDMTFYVYFSLVLIQLVLSCFSDRSPLFSETIHDPNPCPESSASFLSRITFWWITGLIVR-GYRQPLEGSDLWSLNKEDTSEQVVPV LVKNWKKE-CAKTRKQPVKVVYSSKDPAQPKDSSKVDANEE-VEALIVKSPQKEWNPSLFKVLYKTFGPYFLMSFFFKAIHDLMMFSG-PEILKLLINFVNDTKAPDWQGYFYTALLFVAA-CLQTLVLHQY FHICFVSGMRIKTAVIGAVYRKALVIT-NAARKSSTVGEIVNLMSVDAQRFMDLATYINMIWSAPL QVILALYLLWRNLGP-PILAGVAVMVLMVPVNAVMAMKTKTYQVAHMK-SKDNRIKLMNEILNGIK VLKLYAWELAFKDKV-LAIRQEELKVLKKSAYLAAVGTFTWVCTPFLVALCTFAVYVTIDKNNVLDAQKAFVSLALFNILRFPLNILPMVISSIVQASVSLKRL-RIFLSHEELEPDSIERRPVKDGGDTNSIT VRNATFT-WARSDPPTLNGITFSIPEGALVAWGQVGCGKSSLL-SALLAEMDKVEGHVALKGSVAYVPQQAWIQNDSLQENILFGCQLEEPYYRSVIQA-CALLPDLEILPSGDRTEIGEKGVNLSGGQKQRVSLARAVYCNADIYLFDDPLSAVDAHVGKH-IFENVIGPKGMLKNKTRILVTHSMSYLPQVDVIIVMSGGKISEMGSYQELLARDGAFAEFLRTYA-SAEQEQDPEDNGVTGVSGPGKEAKQMEN GMLVTD-SAGKQLQRQLSSSSSYSGDVSRQHNSTAELQKD-GAKKEETWKLMEADKAQTGQVKLSVYWDYMKAIGLFISFLSIFL-FICNHVAALASNYWLSLWTDDPIV-NGTQEHTKVRLSVYGALGIS QGIAVFGYSMAVSIG-GILASRCLHVDLLHSILRSPMSFFERTPSGNLVNRFSKELDTVDSMIPEVI KMFMGSLFN-VIGACIVILLATPIAAIIPPLGLIYFFVQRFY-VASSRQLKRLESVSRSPVYSHFNETL LGVSVIRAFE-EQERFIHQSDLKVDENQKAYYPSIVANRWLAVRLECVGNCIVLFAALFAVISRHSLSAGLVGLSVSYSLQVTYLNWLVRMSSEMETNIVA-VERLKEYSETEKEAPWQIQETAPPSNW PQVGRVE-FRNYCLRYREDLDFVLRHINVTINGGEKVGIVGRT-GAGKSSLTLGLFRINESAEGEIIIDGINIARIGLHDLRFKITIIPDPVLF-SGSLRMNLDPFSQYSDEEAWTSLELAHLKGFVS-ALPDKL DHECAEGGENLSVGQRLVCLARALLRKT-KILVLDEATVDLETDDLIQSTIRTQFEDCTVLTIAHRLNTIMDYTRVIVLDKGEIQEYGAPSDLLQQRGL-FYNMARDAGLV (SEQ ID NO:158) an extracellular region thereof; or a fragment of cynomolgus monkey ABCC1, e.g., a fragment comprising amino acid residues 204-1531:

(SEQ ID NO: 159)

```
MDPNPCPESSASFLSRITFWWITGLIVRGYROPLEGSDLWSLNKEDTSEQVVPVLVKN

WKKECAKTRKQPVKVVYSSKDPAQPKDSSKVDANEEVEALIVKSPQKEWNPSLFKVLYKTFG

PYFLMSFFFKAIHDLMMFSGPEILKLLINFVNDTKAPDWQGYFYTALLFVAACLQTLVLHQYFHI

CFVSGMRIKTAVIGAVYRKALVITNAARKSSTVGEIVNLMSVDAQRFMDLATYINMIWSAPLQVI

LALYLLWRNLGPPILAGVAVMVLMVPVNAVMAMKTKTYQVAHMKSKONRIKLMNEILNGIKVLK

LYAWELAFKDKVLAIRQEELKVLKKSAYLAAVGTFTWVCTPFLVALCTFAVYVTIDKNNVLDAQK

AFVSLALFNILRFPLNILPMVISSIVQASVSLKRLRIFLSHEELEPDSIERRPVKDGGDTNSITVRN

ATFTWARSDPPTLNGITFSIPEGALVAVVGQVGCGKSSLLSALLAEMDKVEGHVALKGSVAYV

PQQAWIQNDSLOENILFGCOLEEPYYRSVIQACALLPDLEILPSGDRTEIGEKGVNLSGGQKOR

VSLARAVYCNADIYLFDDPLSAVDAHVGKHIFENVIGPKGMLKNKTRILVTHSMSYLPQVDVIIV

MSGGKISEMGSYQELLARDGAFAEFLRTYASAEQEQDPEDNGVTGVSGPGKEAKQMENGML

VTDSAGKQLQRQLSSSSSYSGDVSRQHNSTAELQKDGAKKEETWKLMEADKAQTGQVKLSV

YWDYMKAIGLFISFLSIFLFICNHVAALASNYWLSLWTDDPIVNGTQEHTKVRLSVYGALGISQGI

AVFGYSMAVSIGGILASRCLHVDLLHSILRSPMSFFERTPSGNLVNRFSKELDTVDSMIPEVIKM

FMGSLFNVIGACIVILLATPIAAIIPPLGLIYFFVQRFYVASSRQLKRLESVSRSPVYSHFNETLLG

VSVIRAFEEQERFIHQSDLKVDENQKAYYPSIVANRWLAVRLECVGNCIVLFAALFAVISRHSLS
```

-continued

```
AGLVGLSVSYSLQVTTYLNWLVRMSSEMETNIVAVERLKEYSETEKEAPWQIQETAPPSNWPQ

VGRVEFRNYCLRYREDLDFVLRHINVTINGGEKVGIVGRTGAGKSSLTLGLFRINESAEGEIIIDG

INIARIGLHDLRFKITIIPQDPVLFSGSLRMNLDPFSQYSDEEVWTSLELAHLKGFVSALPDKLDH

ECAEGGENLSVGQRQLVCLARALLRKTKILVLDEATAAVDLETDDLIQSTIRTQFEDCTVLTIAH

RLNTIMDYTRVIVLDKGEIQEYGAPSDLLQQRGLFYNMARDAGLV
```

A subject anti-ABCC1 antibody exhibits high affinity binding to ABCC1. For example, a subject anti-ABCC1 antibody binds to a human ABCC1 with an affinity of at least about $10^{-7}$ M, at least about $10^{-8}$ M, at least about $10^{-9}$ M, at least about $10^{-10}$ M, at least about $10^{-11}$ M, or at least about $10^{-12}$ M, or greater than $10^{-12}$ M. A subject anti-ABCC1 antibody binds to an epitope present on ABCC1 with an affinity of from about $10^{-7}$ M to about $10^{-8}$ M, from about $10^{-8}$ M to about $10^{-9}$ M, from about $10^{-9}$ M to about $10^{-10}$ M, from about $10^{-10}$ M to about $10^{-11}$ M. or from about $10^{-11}$ M to about $10^{-12}$ M, or greater than $10^{-12}$ M.

A subject anti-ABCC1 antibody exhibits substantially no binding to any epitopes formed by amino acids within other related, but sequence dissimilar, proteins such as related but sequence dissimilar EPs. Any binding of a subject anti-ABCC1 antibody to an epitope formed by amino acids within a related, but sequence dissimilar, protein is generally non-specific binding of a substantially lower affinity than the specific binding of the anti-ABCC1 antibody to the epitope on ABCC1. A substantially lower affinity is generally at least a 2 fold, 3 fold, 5 fold, 10 fold, 50 fold, 100 fold, 500 fold, or 1000 fold lower affinity.

A subject anti-ABCC1 antibody can reduce transport of molecules through an ABCC1 transporter, e.g., a human ABCC1. For example, a subject anti-ABCC1 antibody can reduce transport by at least about 5%, at least about 10%, at least about 15%, at least about 20%, at least about 25%, at least about 30%, at least about 40%, at least about 50%, at least about 60%, at least about 70%, at least about 80%, at least about 90%, or more, compared to the degree of transport in the absence of the anti-ABCC1 antibody.

In some embodiments, a subject antibody comprises FR regions that are mammalian sequences, including e.g., rodent, non-human primate, and human sequences (e.g., encoded by the respective heavy chain FR-encoding sequences).

A subject antibody can comprise a heavy chain variable (VH) region comprising an amino acid sequence that is 85%, 88%, 87%, 88%, 89%, 90%, 91%, 92%, 93%, 94%, 95%, 96%, 97%, 98%, 99%, or more, including 100%, identical to a sequence for a VH region of a VH-VL pair of an antibody set forth in Table 2. The subject antibody can comprise a light chain variable (VL) region comprising an amino acid sequence that is 85%, 86%, 87%, 88%, 89%, 90%, 91%, 92%, 93%, 94%, 95%, 96%, 97%, 98%, 99%, or more, including 100%, identical to a sequence for a VL of the VH-VL region pair of the antibody set forth in Table 2.

In one aspect, the antibody molecule comprises the HCDRs 1-3 and/or LCDRs 1-3 of one of the C1.844 antibody, the C1.851 antibody, the C1.831 antibody, or the C1.861 antibody listed in Table 2.

In one aspect, the antibody molecule comprises the HCDRs 1-3 and/or LCDRs 1-3 of one of the C1.773 antibody, the C1.773a antibody, the C1.777a antibody, the C1.784a antibody, the C1.786a antibody, the C1.787a antibody, the C1.827 antibody, the C1.830B antibody, the C1.831 antibody, the C1.835 antibody, the C1.841 antibody, the C1.844 antibody, the C1.845 antibody, the C1.847 antibody, the C1.851 antibody, the C1.855 antibody, the C1.861 antibody, the C1.863 antibody, the C1.876 antibody, the C1.877 antibody, or the C1.879A antibody listed in Table 2.

In certain embodiments, the antibodies of the present disclosure may lower the IC50 of the chemotherapeutic agent (e.g., vincristine) by factor of 5 or more, e.g., factor of 6 or more, factor of 7 or more, factor of 8 or more, factor of 9 or more, factor of 10 or more, or factor of 20 or more, e.g., by a factor of 5 to 50. In one aspect, the antibody molecule may lower the IC50 of the chemotherapeutic agent (e.g., vincristine) by factor of 5 or more and may comprises the HCDRs 1-3 and/or LCDRs 1-3 of the C1.851 antibody, the C1.841 antibody, the C1.861 antibody, the C1.831 antibody, C1.786a the antibody, the C1.787a antibody, or the C1.777 antibody, listed in Table 2.

Regions and/or chains of the subject antibodies may or may not be joined by one or more linker regions. Where present, the linker region can be from about 5 amino acids to about 50 amino acids in length, e.g., from about 5 aa to about 10 aa, from about 10 aa to about 15 aa, from about 15 aa to about 20 aa, from about 20 aa to about 25 aa, from about 25 aa to about 30 aa, from about 30 as to about 35 aa, from about 35 as to about 40 aa, from about 40 aa to about 45 aa, or from about 45 aa to about 50 aa in length.

Linkers suitable for use a subject antibody include "flexible linkers". If present, the linker molecules are generally of sufficient length to permit some flexible movement between linked regions. The linker molecules are generally about 6-50 atoms long. The linker molecules may also be, for example, aryl acetylene, ethylene glycol oligomers containing 2-10 monomer units, diamines, diacids, amino acids, or combinations thereof. Other linker molecules which can bind to polypeptides may be used in light of this disclosure.

Suitable linkers can be readily selected and can be of any of a suitable of different lengths, such as from 1 amino acid (e.g., Gly) to 20 amino acids, from 2 amino acids to 15 amino acids, from 3 amino acids to 12 amino acids, including 4 amino acids to 10 amino acids, 5 amino acids to 9 amino acids, 6 amino acids to 8 amino acids, or 7 amino acids to 8 amino acids, and may be 1, 2, 3, 4, 5, 6, or 7 amino acids.

Exemplary flexible linkers include glycine polymers $(G)_n$, glycine-serine polymers (including, for example, $(GS)_n$, $GSGGS_n$ (SEQ ID NO:160) and $GGGS_n$ (SEQ ID NO:161), where n is an integer of at least one), glycine-alanine polymers, alanine-serine polymers, and other flexible linkers known in the art. Glycine and glycine-serine polymers are of interest since both of these amino acids are relatively unstructured, and therefore may serve as a neutral tether between components. Glycine polymers are of particular interest since glycine accesses significantly more phi-psi space than even alanine, and is much less restricted than residues with longer side chains (see Scheraga, *Rev. Computational Chem.* 11173-142 (1992)). Exemplary flexible linkers include, but are not limited to GGSG (SEQ ID NO:162), GGSGG (SEQ ID NO:163), GSGSG (SEQ ID NO:164), GSGGG (SEQ ID NO:165), GGGSG (SEQ ID NO:166), GSSSG (SEQ ID NO:167), and the like. The ordinarily skilled artisan will recognize that design of a peptide conjugated to any elements described above can include linkers that are all or partially flexible, such that the linker can include a flexible linker as well as one or more portions that confer less flexible structure.

In other instances, the flexibility of the hinge region of an antibody of the present disclosure may be reduced by either mutating amino acid C220 to serine or any other natural amino acid, by removing C220, by removing the complete hinge, or by replacing the IgG1 hinge with an IgG3 hinge, an antibody is formed in which the light chains are connected via their C-terminal cysteines, analogous to the situation found in the human isotype IgA2m. This results in a reduced flexibility of the Fabs relative to the Fc and consequently reduced cross-linking capacity. Another strategy to reduce the flexibility of an IgG1 molecule is to replace the IgG1 hinge with the IgG2 hinge or IgG2-like hinge. Alternatively, a variant of the IgG1 hinge that resembles the IgG2 hinge can be introduced. This mutant (TH7 Δ6-9) contains mutation T223C and two deletions (K222 and T225) in order to create a shorter hinge with an additional cysteine.

The substitution of mouse CDRs into a human variable domain framework can result in retention of their correct spatial orientation where, e.g., the human variable domain framework adopts the same or similar conformation to the mouse variable framework from which the CDRs originated. This can be achieved by obtaining the human variable domains from human antibodies whose framework sequences exhibit a high degree of sequence identity with the murine variable framework domains from which the CDRs were derived. The heavy and light chain variable framework regions can be derived from the same or different human antibody sequences. The human antibody sequences can be the sequences of naturally occurring human antibodies or can be consensus sequences of several human antibodies. See Kettleborough et al., Protein Engineering 4:773 (1991); Kolbinger et al., Protein Engineering 6:971 (1993).

Having identified the complementarity determining regions of the murine donor immunoglobulin and appropriate human acceptor immunoglobulins, the next step is to determine which, if any, residues from these components should be substituted to optimize the properties of the resulting humanized antibody. In general, substitution of human amino acid residues with murine should be minimized, because introduction of murine residues increases the risk of the antibody eliciting a human-anti-mouse-antibody (HAMA) response in humans. Art-recognized methods of determining immune response can be performed to monitor a HAMA response in a particular patient or during clinical trials. Patients administered humanized antibodies can be given an immunogenicity assessment at the beginning and throughout the administration of said therapy. The HAMA response is measured, for example, by detecting antibodies to the humanized therapeutic reagent, in serum samples from the patient using a method known to one in the art, including surface plasmon resonance technology (BIACORE) and/or solid-phase ELISA analysis. In many embodiments, a subject humanized antibody does not substantially elicit a HAMA response in a human subject.

Certain amino acids from the human variable region framework residues are selected for substitution based on their possible influence on CDR conformation and/or binding to antigen. The unnatural juxtaposition of murine CDR regions with human variable framework region can result in conformational restraints, which, unless corrected by substitution of certain amino acid residues, lead to loss of binding affinity.

The selection of amino acid residues for substitution can be determined, in part, by computer modeling. Computer hardware and software for producing three-dimensional images of immunoglobulin molecules are known in the art. In general, molecular models are produced starting from solved structures for immunoglobulin chains or domains thereof. The chains to be modeled are compared for amino acid sequence similarity with chains or domains of solved three-dimensional structures, and the chains or domains showing the greatest sequence similarity is/are selected as starting points for construction of the molecular model. Chains or domains sharing at least 50% sequence identity are selected for modeling, and preferably those sharing at least 60%, 70%, 80%, 90% sequence identity or more are selected for modeling. The solved starting structures are modified to allow for differences between the actual amino acids in the immunoglobulin chains or domains being modeled, and those in the starting structure. The modified structures are then assembled into a composite immunoglobulin. Finally, the model is refined by energy minimization and by verifying that all atoms are within appropriate distances from one another and that bond lengths and angles are within chemically acceptable limits.

In some embodiments, a subject antibody comprises scFv multimers. For example, in some embodiments, a subject antibody is an scFv dimer (e.g., comprises two tandem scFv ($scFv_2$)), an scFv trimer (e.g., comprises three tandem scFv ($scFv_3$)), an scFv tetramer (e.g., comprises four tandem scFv ($scFv_4$)), or is a multimer of more than four scFv (e.g., in tandem). The scFv monomers can be linked in tandem via linkers of from about 2 amino acids to about 15 amino acids in length, e.g., 2 aa, 3 aa, 4 aa, 5 aa, 6 aa, 7 aa, 8 aa, 9 aa, 10 aa, 11 aa, 12 aa, 13 aa, 14 aa, or 15 as in length. Suitable linkers include, e.g., (Gly) (SEQ ID NO:168), where x is an integer from 2 to 15. Other suitable linkers are those discussed above. In some embodiments, each of the scFv monomers in a subject scFV multimer is humanized, as described above. In certain embodiments, a bispecific antibody may be in any molecular format known in the literature.

For example, a bispecific antibody of the present disclosure may have a molecular format described in Spiess C. et al., Mol Immunol. 2015 October; 67(2 Pt A):95-106.

In some embodiments, a subject antibody comprises a constant region of an immunoglobulin (e.g., an Fc region). The Fc region, if present, can be a human Fc region. If constant regions are present, the antibody can contain both light chain and heavy chain constant regions. Suitable heavy chain constant region include CH1, hinge, CH2, CH3, and CH4 regions. The antibodies described herein include antibodies having all types of constant regions, including IgM, IgG, IgD, IgA and IgE, and any isotype, including IgG1, IgG2, IgG3 and IgG4. An example of a suitable heavy chain Fc region is a human isotype IgG1 Fc. Light chain constant regions can be lambda or kappa. A subject antibody (e.g., a subject humanized antibody) can comprise sequences from more than one class or isotype. Antibodies can be expressed as tetramers containing two light and two heavy chains, as separate heavy chains, light chains, as Fab, Fab' F(ab')2, and Fv, or as single chain antibodies in which heavy and light chain variable domains are linked through a spacer.

In some embodiments, a subject antibody comprises a free thiol (—SH) group at the carboxyl terminus, where the free thiol group can be used to attach the antibody to a second polypeptide (e.g., another antibody, including a subject antibody), a scaffold, a carrier, etc.

A subject antibody can be covalently linked to a second moiety (e.g., a lipid, a polypeptide other than a subject antibody, a synthetic polymer, a carbohydrate, a toxin and the like) using for example, glutaraldehyde, a homobifunctional cross-linker, or a heterobifunctional cross-linker. Glutaraldehyde cross-links polypeptides via their amino moieties. Homobifunctional cross-linkers (e.g., a homobifunctional imidoester, a homobifunctional N-hydroxysuccinimidyl (NHS) ester, or a homobifunctional sulfhydryl reactive cross-linker) contain two or more identical reactive moieties and can be used in a one-step reaction procedure in which the cross-linker is added to a solution containing a mixture of the polypeptides to be linked. Homobifunctional NHS ester and imido esters cross-link amine containing polypeptides. In a mild alkaline pH, imido esters react only with primary amines to form imidoamides, and overall charge of the cross-linked polypeptides is not affected. Homobifunctional sulfhydryl reactive cross-linkers includes bismaleimidohexane (BMH), 1,5-difluoro-2,4-dinitrobenzene (DFDNB), and 1,4-Bis[3-(2-pyridyldithio)propionamido]butane (DPDPB).

Bispecific Antibodies

In certain aspects, the antibodies provided herein may be bispecific antibodies comprising a VH region and a VL region of an anti-ABCC1 antibody as set forth in the preceding section, and further comprises a second VH region comprising HCDRs1-3 of an antibody that binds to a tumor associated antigen (TAA).

The antibody may include a second VL region and wherein the second VH region and the second VL region bind to the TAA. In certain embodiments, the second VH region and the second VL region may be present in a single polypeptide. In certain embodiments, the second VH region and the second VL region are present in a scFv.

In certain embodiments, the bispecific antibody comprises a common light chain, wherein the common light chain comprises a VL region of an anti-ABCC1 antibody as set forth in the preceding section.

The TAA may be any antigen that is known to be overexpressed in cancer cells. For example, the TAA may be an antigen that is not expressed at detectable levels in a normal cell and is expressed in cancer cells, where the normal and cancer cells are the same cell type, e.g., epithelial cells. For example, TAAs may be neoantigens that are a class of tumor antigens that arise from a tumor-specific mutation(s) which alters the amino acid sequence of encoded proteins as compared to the amino acid sequence of the unmutated protein. In other aspects, a TAA is an antigen that Is expressed in normal cells but is expressed at higher levels in cancer cells.

In certain embodiments, the TAA may be PD-L1. PD-L1 is also known as cluster of differentiation 274 (CD274) or B7 homolog 1 (87-H1). In certain embodiments, the antibody that binds to PD-L1 may be atezolizumab.

In certain embodiments, the bispecific antibody may include a VH region comprising HCDRs1-3 and a VL region comprising LCDRs1-3 of the VH region and VL region, respectively, of the C1.844 antibody or the C1.851 antibody as listed in Table 2 and a second VH region and a second VL region comprising HCDRs1-3 and LCDRs1-3, respectively, of atezolizumab. In certain embodiments, the HCDRs1-3 and LCDRs1-3 are defined as per Kabat nomenclature.

In certain embodiments, the bispecific antibody comprises: a VH region and a VL region of the C1.844 antibody or the C1.851 antibody listed in Table 2 and a scFv comprising HCDRs1-3 and LCDRs1-3 of atezolizumab, where the HCDRs1-3 and LCDRs1-3 are defined as per Kabat nomenclature.

In certain embodiments, the bispecific antibody may include a VH region comprising HCDRs1-3 and a VL region comprising LCDRs1-3 of the VH region and VL region, respectively, of the C1.844hu21 antibody or the C1.851hu12 antibody as listed in Table 2 and a second VH region and a second VL region comprising HCDRs1-3 and LCDRs1-3, respectively, of atezolizumab. In certain embodiments, the HCDRs1-3 and LCDRs1-3 are defined as per Kabat nomenclature.

In certain embodiments, the bispecific antibody comprises: a VH region and a VL region of the C1.844hu21 antibody or the C1.851hu12 antibody listed in Table 2 and a scFv comprising HCDRs1-3 and LCDRs1-3 of atezolizumab, where the HCDRs1-3 and LCDRs1-3 are defined as per Kabat nomenclature.

In certain embodiments, the HCDRs1-3 present in the second VH region or the scFv region of the bispecific antibody are the HCDRs1-3 of atezolizumab, where the HCDR1 comprises the sequence DSWIH (SEQ ID NO:25), the HCDR2 comprises the sequence WISPYGGSTYYADSVKG (SEQ ID NO:169), and the HCDR3 comprises the sequence RHWPGGFDY (SEQ ID NO:170). In certain embodiments, the bispecific antibody that binds to ABCC1 and PD-L1 may further include a second VL region that includes the LCDRs1-3 of atezolizumab, where the LCDR1 comprises the sequence RASQDVSTAVA (SEQ ID NO:171), the LCDR2 comprises the sequence SASFLYS (SEQ ID NO:172), and the LCDR3 comprises the sequence QQYLYHPAT (SEQ ID NO:173). In certain embodiments, the LCDRs1-3 present in the scFv region include the LCDRs1-3 of atezolizumab, defined as per Kabat nomenclature.

In certain embodiments, the bispecific antibody that binds to ABCC1 and PD-L1 comprises a second VH region comprising an amino acid sequence at least 80%, at least 90%, at least 95%, or a 100% identical to the amino acid sequence of the VH region of atezolizumab as set forth below:

```
                                        (SEQ ID NO: 174)
EVQLVESGGGLVQPGGSLRLSCAASGFTFSDSWIHWVRQAPGKGLEWVA
WISPYGGSTYYADSVKGRFTISADTSKNTAYLQMNSLRAEDTAVYYCAR
RHWPGGFDYWGQGTLVTVSS
```

In certain embodiments, the bispecific antibody that binds to ABCC1 and PD-L1 comprises a second VL region comprising an amino acid sequence at least 80%, at least 90%, at least 95%, or a 100% identical to the amino acid sequence of the VL region of atezolizumab as set forth below:

```
                                        (SEQ ID NO: 175)
DIQMTQSPSSLSASVGDRVTITCRASQDVSTAVAWYQQKPGKAPKLLIY
SASFLYSGVPSRFSGSGSGTDFTLTISSLQPEDFATYYCQQYLYHPATF
GQGTKVEIK
```

In certain embodiments, the bispecific antibody that binds to ABCC1 and PD-1 comprises a scFv region that binds to PD-L1 and comprises an amino acid sequence at least 80%, at least 90%, at least 95%, or a 100% identical to the amino acid sequence set forth below:

(SEQ ID NO: 176)
EVQLVESGGGLVQPGGSLRLSCAASGFTFSDSWIHWVRQAPGKGLEWVA

WISPYGGSTYYADSVKGRFTISADTSKNTAYLQMNSLRAEDTAVYYCAR

RHWPGGFDYWGQGTLVTVSSGGGGSGGGGSGGGGSDIQMTQSPSSLSAS

VGDRVTITCRASQDVSTAVAWYQQKPGKAPKLLIYSASFLYSGVPSRFS

GSGSGTDFTLTISSLQPEDFATYYCQQYLYHPATFGQGTKVEIK.

The italicized sequence is a linker sequence between the VH and VL regions. Any other linker sequence may be used to connect the VH and VL regions.

In certain embodiments, the TAA is ErbB2 (HER2). ErbB2 is also known as Receptor Tyrosine Kinase 2 or HER2. In certain embodiments, the antibody that binds to ErbB2 is trastuzumab.

In certain embodiments, the bispecific antibody comprises: a VH region comprising HCDRs1-3 and a VL region comprising LCDRs1-3 of the VH region and VL region, respectively, of the C1.844 antibody, the C1.831 antibody, or the C1.851 antibody listed in Table 2 and a second VH region and a second VL region comprising HCDRs1-3 and LCDRs1-3, respectively, of trastuzumab. In certain embodiments, the HCDRs1-3 and LCDRs1-3 are defined as per Kabat nomenclature.

In certain embodiments, the bispecific antibody comprises: a VH region comprising HCDRs1-3 and a VL region comprising LCDRs1-3 of the VH region and VL region, respectively, of the C1.844 antibody, the C1.831 antibody, or the C1.851 antibody listed in Table 2 and a scFv comprising HCDRs1-3 and LCDRs1-3 of trastuzumab.

In certain embodiments, the bispecific antibody comprises: a VH region and a VL region of the C1.844hu21 antibody, the C1.831hu11 antibody, or the C1.851hu12 antibody and a scFv comprising HCDRs1-3 and LCDRs1-3 of trastuzumab, where the HCDRs1-3 and LCDRs1-3 are defined as per Kabat nomenclature.

In certain embodiments, the HCDRs1-3 present in the second VH region or the scFv region of the bispecific antibody are the HCDRs1-3 of trastuzumab, where the HCDR1 comprises the sequence DTYIH (SEQ ID NO:177), the HCDR2 comprises the sequence RIYPTNGYTRYADSVKG (SEQ ID NO:178), and the HCDR3 comprises the sequence WGGDGFYAMDY (SEQ ID NO:179). In certain embodiments, the bispecific antibody that binds to ABCC1 and HER2 may further include a second VL region that includes the LCDRs1-3 of trastuzumab, where the LCDR1 comprises the sequence RASQDVNTAVA (SEQ ID NO:180), the LCDR2 comprises the sequence SASFLYS (SEQ ID NO:172), and the LCDR3 comprises the sequence QQHYTTPPT (SEQ ID NO:181). In certain embodiments, the LCDRs1-3 present in the scFv region include the LCDRs1-3 of trastuzumab, defined as per Kabat nomenclature.

In certain embodiments, the bispecific antibody that binds to ABCC1 and HER2 comprises a second VH region comprising an amino acid sequence at least 80%, at least 90%, at least 95%, or a 100% identical to the amino acid sequence of the VH region of trastuzumab as set forth below:

(SEQ ID NO: 182)
EVQLVESGGGLVQPGGSLRLSCAASGFNIKDTYIHWVRQAPGKGLEWVA
RIYPTNGYTRYADSVKGRFTISADTSKNTAYLQMNSLRAEDTAVYYCSR
WGGDGFYAMDYWGQGTLVTVSS.

In certain embodiments, the bispecific antibody that binds to ABCC1 and HER2 comprises a second VL region comprising an amino acid sequence at least 80%, at least 90%, at least 95%, or a 100% identical to the amino acid sequence of the VL region of trastuzumab as set forth below:

(SEQ ID NO: 183)
DIQMTQSPSSLSASVGDRVTITCRASQDVNTAVAWYQQKPGKAPKLLIY
SASFLYSGVPSRFSGSRSGTDFTLTISSLQPEDFATYYCQQHYTTPPTF
GQGTKVEIK.

In certain embodiments, the bispecific antibody that binds to ABCC1 and HER2 comprises a scFv region that binds to HER2 and comprises an amino acid sequence at least 80%, at least 90%, at least 95%, or a 100% identical to the amino acid sequence set forth below:

(SEQ ID NO: 184)
RYADSVKGRFTISADTSKNTAYLQMNSLRAEDTAVYYCSRWGGDGFYAM

DYWGCGTLVTVSSGGGGSGGGGSGGGGSDIQMTQSPSSLSASVGDRVTI

TCRASQDVNTAVAWYQQKPGKCPKLLIYSASFLYSGVPSRFSGSRSGTD

FTLTISSLQPEDFATYYCQQHYTTPPTFGQGTKVEIK

The italicized sequence is a linker sequence between the VH and VL regions. Any other linker sequence may be used to connect the VH and VL regions.

In certain embodiments, the heavy chain of the bispecific antibodies may include a VH region as provided herein and a heavy chain constant region. In certain embodiments, the light chain of the bispecific antibodies may include a VL region as provided herein and a light chain constant region. In certain embodiments, the scFv may be conjugated to a heavy chain constant region.

The heavy chain constant region and the light chain constant region may be of a human IgG antibody, e.g., a human IgG1 antibody. The constant region may have a wild type sequence or a modified sequence. In some embodiments, the bispecific antibody may include a modified heavy chain, including a modified Fc domain, including a modified CH2 and/or modified CH3 domain. In some instances, modified Fc domains may employ electrostatic steering effects, including but not limited to e.g., through the use of the procedures described in Gunasekeran et al, (2010) Journal of Biological Chemistry 285, 19637-19646; the disclosure of which is incorporated herein by reference in its entirety. In some instances, a bispecific antibody is assembled through charge pair substitutions at the CH3 domain, including but not limited to e.g., where one heavy chain is modified to contain K392D and K409D substitutions and the other heavy chain is modified to contained E366K and D399K substitutions. Charge pair substituted chains may preferentially form a heterodimer with one another. The numbering of the amino acid substitutions is per EU numbering system for HCs.

In some instances, an antibody of the present disclosure includes charge pair substitutions. In some instances, an antibody of the present disclosure does not include charge pair substitutions. In some instances, an alternative means of promoting preferential heterodimer formation of desired chains may be employed.

In some instances, a modified heavy chain may include a knob-into-hole modification. "Knobs-into-holes" amino acid modification is a rational design strategy in antibody engineering, used for heterodimerization of the heavy chains, in the production of multi-specific antibodies, including bispecific IgG antibodies. For example, in incorporating the knobs-into-holes strategy into a bispecific antibody made from two monoclonal antibodies of different specificities, amino acid changes are engineered in order to create a "knob" on the CH3 of the heavy chain of monoclonal antibody 1 (mAb1) and a "hole" on the CH3 of the heavy chain of monoclonal antibody 2 (mAb2). The knob may be represented by a large amino acid, such as e.g., a tyrosine (Y), whereas the hole may be represented by small amino acid, such as a threonine (T). For example, a knobs-into-holes pair modification may be created a T22Y substitution in a first CH3 domain and Y86T substitution in the partner CH3 domain. Examples of knobs-into-holes modifications are described in Carter, J. Immunol. Methods, 248(1-2):7-15 (2001); Ridgway, J. B. et al. Protein Eng. 9(7):617-2 (1996); and Merchant, A. M. et al. Nat. Biotechnol. 16(7):677-81 (1998); the disclosures of which are incorporated herein in their entirety. In antibodies generated from paired knob-into-hole modified domains the bispecific heterodimer will generally represent the major fraction.

In certain embodiments, the bispecific antibodies provided herein bind to cancer cells expressing both ABCC1 and the TAA while showing reduced binding to non-cancer cells expressing ABCC1 and/or the TA. In other words, the bispecific antibodies provided herein bind with low affinity to (1) cells expressing TAA where ABCC1 expression is low or absent and (2) cells expressing ABCC1 where TAA expression is low or absent, and with high affinity to cancer cells that express at least one or both ABCC1 and TAA at relatively high levels, i.e., levels higher than normal cells.

Compositions and Formulations

The present disclosure provides a composition comprising a subject antibody. A subject antibody composition can comprise, in addition to a subject antibody, one or more of a salt, e.g., NaCl, $MgCl_2$, KCl, $MgSO_4$, etc.; a buffering agent, e.g., a Tris buffer, a histidine buffer. N-(2-Hydroxyethyl)piperazine-N'-(2-ethanesulfonic acid) (HEPES), 2-(N-Morpholino)ethanesulfonic acid (MES), 2-(N-Morpholino) ethanesulfonic acid sodium salt (MES), 3-(N-Morpholino) propanesulfonic acid (MOPS). N-tris[Hydroxymethyl] methyl-3-aminopropanesulfonic acid (TAPS), etc.; a solubilizing agent; a detergent, e.g., a non-ionic detergent such as Tween-20, etc.; a protease inhibitor; glycerol; and the like.

Compositions of the present disclosure also include pharmaceutical compositions that include an antibody described herein. In general, a formulation comprises an effective amount of the subject antibody. An "effective amount" means a dosage sufficient to produce a desired result, e.g., reduction in a cancer of a subject, reduction in the growth rate of a cancer in a subject, amelioration of a symptom of cancer, and the like. Generally, the desired result is at least a reduction in a symptom of a cancer, reduction in the growth of a cancer, reduction in the size of a cancer, etc., as compared to a control. A subject antibody can be delivered, or be formulated, in such a manner as to avoid the blood-brain barrier.

In some instances, an antibody may include a delivery enhancer, including where such enhancers may facilitate crossing of the blood-brain barrier, increased permeability, e.g., allowing for efficient transdermal delivery, and the like.

In some instances, the antibodies of the present disclosure may not be administered in a formulation with a delivery enhancer. In some instances, the antibodies of the present disclosure may themselves enhance permeability across the blood-brain barrier. In some instances, the antibodies of the present disclosure may be used as a delivery enhancer to facilitate crossing of the blood-brain barrier by an anti-neoplastic agent, e.g., an immunotherapeutic agent or a chemotherapeutic agent. In some instances, the antibodies of the present disclosure may be used as a delivery enhancer to facilitate crossing of the blood-brain barrier, blood-cerebrospinal fluid (CSF) barrier, blood-testis barrier, or blood-placenta barrier by an active agent, such as, another antibody or a chemotherapeutic agent.

In the subject methods, a subject antibody can be administered to the host using any convenient means capable of resulting in the desired therapeutic effect or diagnostic effect. Thus, the agent can be incorporated into a variety of formulations for therapeutic administration. More particularly, a subject antibody can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols.

In pharmaceutical dosage forms, a subject antibody can be administered in conjunction with a pharmaceutically acceptable excipient, or they may also be used alone or in appropriate association, as well as in combination, with other pharmaceutically active compounds. The following methods and excipients are merely exemplary and are in no way limiting.

A subject antibody can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

Pharmaceutical compositions comprising a subject antibody are prepared by mixing the antibody having the desired degree of purity with optional physiologically acceptable carriers, excipients, stabilizers, surfactants, buffers and/or tonicity agents. Acceptable carriers, excipients and/or stabilizers are nontoxic to recipients at the dosages and concentrations employed, and include buffers such as phosphate, citrate, and other organic acids; antioxidants including ascorbic acid, glutathione, cysteine, methionine and citric acid; preservatives (such as ethanol, benzyl alcohol, phenol, m-cresol, p-chlor-m-cresol, methyl or propyl parabens, benzalkonium chloride, or combinations thereof); amino acids such as arginine, glycine, ornithine, lysine, histidine, glutamic acid, aspartic acid, isoleucine, leucine, alanine, phenylalanine, tyrosine, tryptophan, methionine, serine, proline and combinations thereof; monosaccharides, disaccharides and other carbohydrates; low molecular weight (less than about 10 residues) polypeptides; proteins, such as gelatin or serum albumin; chelating agents such as EDTA; sugars such as trehalose, sucrose, lactose, glucose, mannose, maltose, galactose, fructose, sorbose, raffinose, glucosamine, N-methylglucosamine, galactosamine, and neuraminic acid; and/or non-ionic surfactants such as Tween, Brij Pluronics, Triton-X, or polyethylene glycol (PEG).

The pharmaceutical composition may be in a liquid form, a lyophilized form or a liquid form reconstituted from a lyophilized form, wherein the lyophilized preparation is to be reconstituted with a sterile solution prior to administration.

Exemplary antibody concentrations in a subject pharmaceutical composition may range from about 1 mg/mL to about 200 mg/mil or from about 50 mg/mL to about 200 mg/mL, or from about 150 mg/mL to about 200 mg/mL.

An aqueous formulation of the antibody may be prepared in a pH-buffered solution, e.g., at pH ranging from about 4.0 to about 7.5 or from about 5.0 to about 6.0, or alternatively about 5.5. Examples of buffers that are suitable for a pH within this range include phosphate-, histidine-, citrate-, succinate-, acetate-buffers and other organic acid buffers. The buffer concentration can be from about 1 mM to about 100 mM, or from about 5 mM to about 50 mM, depending, e.g., on the buffer and the desired tonicity of the formulation.

In some embodiments, the aqueous formulation is isotonic, although hypertonic or hypotonic solutions may be suitable. The term "isotonic" denotes a solution having the same tonicity as some other solution with which it is compared, such as physiological salt solution or serum. Tonicity agents may be used in an amount of about 5 mM to about 350 mM, e.g., in an amount of 100 mM to 350 nM.

A surfactant may also be added to the antibody formulation to reduce aggregation of the formulated antibody and/or minimize the formation of particulates in the formulation and/or reduce adsorption. Exemplary surfactants include polyoxyethylensorbitan fatty acid esters (Tween), polyoxyethylene alkyl ethers (Brij), alkylphenylpolyoxyethylene ethers (Triton-X), polyoxyethylene-polyoxypropylene copolymer (Poloxamer, Pluronic), and sodium dodecyl sulfate (SOS). Exemplary concentrations of surfactant may range from about 0.001% to about 1% w/v.

A lyoprotectant may also be added in order to protect the labile active ingredient (e.g. a protein) against destabilizing conditions during the lyophilization process. For example, known lyoprotectants include sugars (including glucose and sucrose); polyols (including mannitol, sorbitol and glycerol): and amino acids (including alanine, glycine and glutamic acid). Lyoprotectants can be included in an amount of about 10 mM to 500 nM.

In some embodiments, a subject formulation includes a subject antibody, and one or more of the above-identified agents (e.g., a surfactant, a buffer, a stabilizer, a tonicity agent) and is essentially free of one or more preservatives, such as ethanol, benzyl alcohol, phenol, m-cresol, p-chlor-m-cresol, methyl or propyl parabens, benzalkonium chloride, and combinations thereof.

In other embodiments, a preservative is included in the formulation, e.g., at concentrations ranging from about 0.001 to about 2% (w/v).

For example, a subject formulation can be a liquid or lyophilized formulation suitable for parenteral administration, and can comprise: about 1 mg/mL to about 200 mg/mL of a subject antibody; about 0.001% to about 1% of at least one surfactant; about 1 mM to about 100 mM of a buffer; optionally about 10 mM to about 500 mM of a stabilizer; and about 5 mM to about 305 mM of a tonicity agent; and has a pH of about 4.0 to about 7.0.

A subject antibody can be utilized in aerosol formulation to be administered via inhalation.

A subject antibody can be formulated into pressurized acceptable propellants such as dichlorodifluoromethane, propane, nitrogen and the like.

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for a subject antibody may depend on the particular antibody employed and the effect to be achieved, and the pharmacodynamics associated with each antibody in the host.

A subject antibody can be administered as an injectable formulation. Typically, injectable compositions are prepared as liquid solutions or suspensions; solid forms suitable for solution in, or suspension in, liquid vehicles prior to injection may also be prepared. The preparation may also be emulsified or the antibody encapsulated in liposome vehicles.

Suitable excipient vehicles are, for example, water, saline, dextrose, glycerol, ethanol, or the like, and combinations thereof. In addition, if desired, the vehicle may contain minor amounts of auxiliary substances such as wetting or emulsifying agents or pH buffering agents. Actual methods of preparing such dosage forms are known, or will be apparent, to those skilled in the art.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

In some embodiments, a subject antibody is formulated in a controlled release formulation. Sustained-release preparations may be prepared using methods well known in the art.

Dosages

A suitable dosage can be determined by an attending physician or by other qualified medical personnel, based on various clinical factors. As is well known in the medical arts, dosages for any one patient depend upon many factors, including the patient's size, body surface area, age, the particular compound to be administered, sex of the patient, time, and route of administration, general health, and other drugs being administered concurrently. A subject antibody may be administered in amounts between 1 ng/kg body weight and 20 mg/kg body weight per dose, e.g. between 0.1 mg/kg body weight to 10 mg/kg body weight, e.g. between 0.5 mg/kg body weight to 5 mg/kg body weight; however, doses below or above this exemplary range are envisioned, especially considering the aforementioned factors. If the regimen is a continuous infusion, it can also be in the range of 1 μg to 10 mg per kilogram of body weight per minute.

Those of skill will readily appreciate that dose levels can vary as a function of the specific antibody, the severity of the symptoms and the susceptibility of the subject to side effects. Preferred dosages for a given compound are readily determinable by those of skill in the art by a variety of means.

Routes of Administration

A subject antibody is administered to an individual using any available method and route suitable for drug delivery, including in vivo and ex vivo methods, as well as systemic and localized routes of administration.

Conventional and pharmaceutically acceptable routes of administration include intranasal, intramuscular, intratracheal, subcutaneous, intradermal, topical application, intravenous, intraarterial, rectal, nasal, oral, and other enteral and parenteral routes of administration. Routes of administration may be combined, if desired, or adjusted depending upon the antibody and/or the desired effect. A subject antibody composition can be administered in a single dose or in multiple doses. In some embodiments, a subject antibody composition is administered orally. In some embodiments, a subject antibody composition is administered via an inhalational route. In some embodiments, a subject antibody composition is administered intranasally. In some embodiments, a subject antibody composition is administered locally. In some embodiments, a subject antibody composition is administered intracranially. In some embodiments, a subject antibody composition is administered intravenously.

The agent can be administered to a host using any available conventional methods and routes suitable for delivery of conventional drugs, including systemic or localized routes. In general, routes of administration contemplated by the invention include, but are not necessarily limited to, enteral, parenteral, or inhalational routes.

Parenteral routes of administration other than inhalation administration include, but are not necessarily limited to, topical, transdermal, subcutaneous, intramuscular, intraorbital, intracapsular, intraspinal, intrasternal, and intravenous routes, i.e., any route of administration other than through the alimentary canal. Parenteral administration can be carried to effect systemic or local delivery of a subject antibody. Where systemic delivery is desired, administration typically involves invasive or systemically absorbed topical or mucosal administration of pharmaceutical preparations.

A subject antibody can also be delivered to the subject by enteral administration. Enteral routes of administration include, but are not necessarily limited to, oral and rectal (e.g., using a suppository) delivery.

By treatment is meant at least an amelioration of the symptoms associated with the pathological condition afflicting the host, where amelioration is used in a broad sense to refer to at least a reduction in the magnitude of a parameter, e.g. symptom, associated with the pathological condition being treated, such as cancer and/or the growth of a cancer and pain associated therewith. As such, treatment also includes situations where the pathological condition, or at least symptoms associated therewith, are completely inhibited, e.g. prevented from happening, or stopped, e.g. terminated, such that the host no longer suffers from the pathological condition, or at least the symptoms that characterize the pathological condition.

A variety of subjects (wherein the term "subject" is used interchangeably herein with the terms "individual" and "patient") are treatable according to the presently disclosed methods. Generally, such subjects are "mammals" or "mammalian," where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In some embodiments, the hosts will be humans.

Kits with unit doses of a subject antibody, e.g. in oral or injectable doses, are provided. In some embodiments, in addition to the containers containing the unit doses will be an informational package insert describing the use and attendant benefits of the antibody in treating pathological condition of interest.

Nucleic Acids

The present disclosure provides nucleic acids comprising nucleotide sequences encoding a subject antibody. A nucleotide sequence encoding a subject antibody can be operably linked to one or more regulatory elements, such as a promoter and enhancer, that allow expression of the nucleotide sequence in the intended target cells (e.g., a cell that is genetically modified to synthesize and/or secrete the encoded antibody).

Suitable promoter and enhancer elements are known in the art. For expression in a bacterial cell, suitable promoters include, but are not limited to, lacI, lacZ, T3, T7, gpt, lambda P and trc. For expression in a eukaryotic cell, suitable promoters include, but are not limited to, light and/or heavy chain immunoglobulin gene promoter and enhancer elements; cytomegalovirus immediate early promoter; herpes simplex virus thymidine kinase promoter; early and late SV40 promoters; promoter present in long terminal repeats from a retrovirus; mouse metallothionein-I promoter; and various art-known tissue specific promoters.

A nucleotide sequence encoding a subject antibody can be present in an expression vector and/or a cloning vector. Where a subject antibody comprises two or more separate polypeptides, nucleotide sequences encoding the two polypeptides can be cloned in the same or separate vectors. Separate polypeptides may be expressed from a single nucleic acid or single vector using various strategies, such as separate promoters, one or more internal ribosomal entry sites (IRES), one or more self-cleaving sequences (e.g., 2A cleavage sequences, e.g., P2A, T2A, E2A, and F2A), combinations thereof, and the like. An expression vector can include a selectable marker, an origin of replication, and other features that provide for replication and/or maintenance of the vector.

Large numbers of suitable vectors and promoters are known to those of skill in the art; many are commercially available for generating a subject recombinant construct. The following vectors are provided by way of example. Bacterial: pBs, phagescript, PsiX174, pBluescript SK, pBs KS, pNH8a, pNH16a, pNH18a, pNH46a (Stratagene, La Jolla, Calif., USA); pTrc99A, pKK223-3, pKK233-3, pDR540, and pRIT5 (Pharmacia. Uppsala, Sweden). Eukaryotic: pWLneo, pSV2cat, pOG44, PXR1, pSG (Stratagene) pSVK3, pBPV, pMSG and pSVL (Pharmacia).

Expression vectors generally have convenient restriction sites located near the promoter sequence to provide for the insertion of nucleic acid sequences encoding heterologous proteins. A selectable marker operative in the expression host may be present. Suitable expression vectors include, but are not limited to, viral vectors (e.g. viral vectors based on vaccinia virus; poliovirus; adenovirus; adeno-associated virus: SV40; herpes simplex virus; human immunodeficiency virus; a retroviral vector (e.g., Murine Leukemia Virus, spleen necrosis virus, and vectors derived from retroviruses such as Rous Sarcoma Virus, Harvey Sarcoma Virus, avian leukosis virus, human immunodeficiency virus, myeloproliferative sarcoma virus, and mammary tumor virus); and the like.

Nucleic acids, e.g., as described herein, may, in some instances, be introduced into a cell, e.g., by contacting the cell with the nucleic acid. Cells with introduced nucleic acids will generally be referred to herein as genetically modified cells. Various methods of nucleic acid delivery may be employed including but not limited to e.g., naked nucleic acid delivery, viral delivery, chemical transfection, biolistics, and the like.

Cells

The present disclosure provides isolated genetically modified cells (e.g., in vitro cells, ex vivo cells, cultured cells, etc.) that are genetically modified with a subject nucleic acid. In some embodiments, a subject isolated genetically modified cell can produce a subject antibody. In some instances, a genetically modified cell can deliver an antibody, e.g., to a subject in need thereof.

Suitable cells include eukaryotic cells, such as a mammalian cell, an insect cell, a yeast cell; and prokaryotic cells, such as a bacterial cell. Introduction of a subject nucleic acid into the host cell can be affected, for example by calcium phosphate precipitation, DEAE dextran mediated transfection, liposome-mediated transfection, electroporation, or other known method.

Suitable mammalian cells include primary cells and immortalized cell lines. Suitable mammalian cell lines include human cell lines, non-human primate cell lines, rodent (e.g., mouse, rat) cell lines, and the like. Suitable mammalian cell lines Include, but are not limited to, HeLa cells, CHO cells, 293 cells, 3T3 cells, Vero cells, Huh-7 cells, BHK cells, PC12 cells, COS cells, COS-7 cells, RAT1 cells, mouse L cells, human embryonic kidney (HEK) cells, HLHepG2 cells, and the like.

In some instances, useful mammalian cells may include cells derived from a mammalian tissue or organ. In some instances, cells employed are kidney cells, including e.g., kidney cells of an established kidney cell line, such as HEK 293T cells.

In some instances, cells of the present disclosure may be immune cells. As used herein, the term "immune cells" generally includes white blood cells (leukocytes) which are derived from hematopoietic stem cells (HSC) produced in the bone marrow. "Immune cells" Includes, e.g., lymphocytes (T cells, B cells, natural killer (NK) cells) and myeloid-derived cells (neutrophil, eosinophil, basophil, monocyte, macrophage, dendritic cells). "T cell" includes all types of immune cells expressing CD3 including T-helper cells (CD4+ cells), cytotoxic T-cells (CD8+ cells), T-regulatory cells (Treg) and gamma-delta T cells. A "cytotoxic cell" includes CD8+ T cells, natural-killer (NK) cells, and neutrophils, which cells are capable of mediating cytotoxicity responses.

In some instances, useful cells expressing an antibody such as a multi-specific antibody of the present disclosure may include producer T cells. Producer T cells engineered to include nucleic acid sequence encoding an antibody of the present disclosure may, in some instances, be employed to deliver the antibody to a subject in need thereof.

In some instances, immune cells of the present disclosure include immune effector cell comprising a chimeric antigen receptor (CAR) comprising an ABCC1 binding domain, a transmembrane domain, and an intracellular signaling domain, and wherein the ABCC1 binding domain comprises heavy chain complementarity determining regions (HCDRs) and light chain CDRs (LCDRs) of a pair of variable heavy chain (VH) region and variable light chain (VL) region of an antibody listed in Table 2. In one embodiment, the intracellular signaling domain may include one or more functional signaling domains derived from at least one costimulatory molecule. e.g., 4-18B (i.e., CD137), CD27 and/or CD28. The intracellular signaling domain may include a functional signaling domain derived from a costimulatory molecule and a functional signaling domain derived from a stimulatory molecule.

The immune effector cell may be a T-cell. The immune effector cell may be an autologous cell.

Methods

As summarized above, methods of the present disclosure include methods of contacting a cell with an antibody of the present disclosure, methods of treating a subject according to a method that involves administering to the subject an antibody of the present disclosure, methods of making elements described in the instant application, including e.g., antibodies, compositions and formulations, nucleic acids, expression vectors, cells, and the like.

As summarized above, methods of the present disclosure include contacting a cancer cell with an antibody of the present disclosure, e.g., to detect presence of expression of ABCC1 on the cancer cell, measure level of expression of ABCC1 on the cancer cell, or to facilitate and/or enhance killing of the cancer cell. In some instances, killing of the cancer cell is mediated by an immune response or immune cell acting upon the cancer cell bound by the antibody. In some instances, killing of the cancer cell is mediated by inhibition of cellular efflux of the cancer cell, e.g., as a result of ABCC1 inhibition by the antibody. In some instances, killing of the cancer cell is mediated by a combination of inhibition of cellular efflux of the cancer cell plus an immune mediated response (e.g., via Fc region of the antibody). Methods that involve contacting a cancer cell with an antibody of the present disclosure may or may not include contacting the cancer cell with an additional therapy or active agent, including e.g., a chemotherapeutic, an immunotherapy, radiation therapy, or the like.

Treatment Methods

The present disclosure provides methods of treating a cancer, the methods generally involving administering to an individual in need thereof (e.g., an individual having a cancer) an effective amount of an antibody as provided herein, alone (e.g., in monotherapy) or in combination (e.g., in combination therapy) with one or more additional therapeutic agents. Administration of an antibody of the present disclosure may be performed by any convenient and appropriate route of delivery.

Accordingly, administration includes but is not limited to e.g., delivery of the antibody by injection, delivery of the antibody by infusion, delivery of a nucleic acid or expression vector encoding the antibody, delivery of the antibody by administering to the subject a cell that expresses and secretes the antibody, delivery of an immune effector cell (e.g., a CAR-T cell) that expresses on the cell surface a chimeric antigen receptor (CAR) comprising a ABCC1 binding domain, a transmembrane domain, and an intracellular signaling domain, and wherein the ABCC1 binding domain comprises HCDRs and LCDRs of a pair of VH region and VL region of an antibody listed in Table 2, and the like. Administration of an agent, a nucleic acid encoding an agent, a cell expressing an agent, etc. may include contacting with the agent, contacting with the nucleic acid, contacting with the cell, and the like.

In some embodiments, an effective amount of a subject antibody is an amount that, when administered alone (e.g., in monotherapy) or in combination (e.g., in combination therapy) with one or more additional therapeutic agents, in one or more doses, is effective to reduce an adverse symptom of cancer by at least about 5%, at least about 10%, at least about 15%, at least about 20%, at least about 25%, at least about 30%, at least about 40%, at least about 50%, at least about 80%, at least about 70%, at least about 80%, at least about 90%, or more, compared to the severity of the adverse symptom in the absence of treatment with the antibody.

In some embodiments, an effective amount of a subject antibody is an amount that, when administered alone (e.g., in monotherapy) or in combination (e.g., in combination therapy) with one or more additional therapeutic agents, in one or more doses, is effective to improve the cancer (i.e., slow the growth of the cancer, stop the growth of the cancer, reverse the growth of the cancer, kill cancer cells (including tumor cells, or the like) in the individual being treated. For example, an effective amount of a subject antibody can reduce a cancer growth rate or reduce a cancer size in an individual by at least about 5%, at least about 10%, at least about 15%, at least about 20%, at least about 25%, at least about 30%, at least about 40%, at least about 50%, or more, compared to in the absence of treatment with an antibody.

In some instances, a subject may be treated systemically, including with the subject antibody, with or without one or more additional reagents. By "systemic treatment", as used herein, is meant a treatment that is not directed solely to target a specific tumor (such as e.g., a primary tumor or a defined secondary tumor) or a specific cancer containing tissue (such as e.g., the liver in the case of liver cancer, the blood in the case of a blood cancer, etc.). Systemic treatments will generally be directed to the subject's body as a whole and may include but are not limited to e.g., systemic radiation therapy, systemic chemotherapy, systemic immunotherapy, combinations thereof and the like.

In some instances, a subject may be treated locally, including with the subject antibody, with or without one or more additional reagents. By "local treatment", as used herein, is meant a treatment that is specifically directed to the location of a tumor (such as e.g., a primary tumor or a defined secondary tumor) or specifically directed to a cancer containing tissue (such as e.g., the liver in the case of liver cancer, the blood in the case of a blood cancer, etc.). In some instances, local treatment may also be administered in such a way as to affect the environment surrounding a tumor, such as tissue surrounding the tumor, such as tissue immediately adjacent to the tumor. Local treatment will generally not affect or not be targeted to tissues distant from the site of cancer including the site of a tumor, such as a primary tumor. Useful local treatments that may be administered in addition to or in combination with a subject antibody, e.g., include but are not limited to surgery, local radiation therapy, local cryotherapy, local laser therapy, local topical therapy, combinations thereof, and the like.

In some embodiments, a subject treatment method involves administering a subject antibody and one or more additional therapeutic agents. Suitable additional therapeutic agents include, but are not limited to, chemotherapeutic agents, radiation therapy reagents, immunotherapy reagents, other antibody agents, and the like. Additional therapies that may be administered to a subject before, during or after a subject administering an antibody of the present disclosure will vary depending on numerous factors including e.g., the type of cancer, the subject's medical history, general state of health and/or any co-morbidities, and the like. Useful cancer therapies include but are not limited to e.g., radiation therapy, chemotherapy, immunotherapy, and the like.

Radiation therapy includes, but is not limited to, x-rays or gamma rays that are delivered from either an externally applied source such as a beam, or by implantation of small radioactive sources.

Suitable antibodies for use in cancer treatment include, but are not limited to, naked antibodies, e.g., trastuzumab (Herceptin), bevacizumab (Avastin™), cetuximab (Erbitux™), panitumumab (Vectibix™), Ipilimumab (Yervoy™), rituximab (Rituxan), alemtuzumab (Lemtrada™), Ofatumumab (Arzerra™), Oregovomab (OvaRex™), Lambrolizumab (MK-3475), pertuzumab (Perjeta™), ranibizumab (Lucentis™) etc., and conjugated antibodies, e.g., gemtuzumab ozogamicin (Mylortarg™), Brentuximab vedotin (Adcetris™), 90Y-labelled ibritumomab tiuxetan (Zevalin™), 131I-labelled tositumoma (Bexxar™), etc.

Suitable antibodies for use in cancer treatment also include, but are not limited to, antibodies raised against tumor-associated antigens. Such antigens include, but are not limited to, CD20, CD30, CD33, CD52, EpCAM, CEA, gpA33, Mucins, TAG-72, CAIX, PSMA, Folate-binding protein, Gangliosides (e.g., GD2, GD3, GM2, etc.), Ley, VEGF, VEGFR, Integrin alpha-V-beta-3, Integrin alpha-5-beta-1, EGFR, ERBB2, ERBB3, MET, IGF1R, EPHA3, TRAILR1, TRAILR2, RANKL, FAP, Tenascin, Programmed Death-Ligand 1 (PD-L1), androgen receptor (AR), Bruton's Tyrosine Kinase (BTK), BCR-Abl, c-kit, PIK3CA, EML4-ALK, KRAS, ALK, ROS1, AKT1, BRAF, MEKJ, MEK2, NRAS, RAC1, ESR1, CTLA-4, LAG-3 and TIM-3, etc. These antibodies may be administered as a combination therapy with an anti-ABCC1 antibody provided herein.

Conventional cancer therapies also include targeted therapies for cancer including but not limited to e.g., Ado-trastuzumab emtansine (Kadcyla) targeting HER2 (ERBB2/neu) (approved for use in Breast cancer); Afatinib (Gilotrif) targeting EGFR (HER1/ERBB1), HER2 (ERBB2/neu) (approved for use in Non-small cell lung cancer); Aldesleukin (Proleukin) targeting (approved for use in Renal cell carcinoma, Melanoma); Alectinib (Alecensa) targeting ALK (approved for use in Non-small cell lung cancer); Alemtuzumab (Campath) targeting CD52 (approved for use in B-cell chronic lymphocytic leukemia); Atezolizumab (Tecentriq) targeting PD-L1 (approved for use in Urothelial carcinoma, Non-small cell lung cancer); Avelumab (Bavencio) targeting PD-L1 (approved for use in Merkel cell carcinoma); Axitinib (Inlyta) targeting KIT, PDGFRB. VEGFR1/2/3 (approved for use in Renal cell carcinoma); Belimumab (Benlysta) targeting BAFF (approved for use in Lupus erythematosus): Belinostat (Beleodaq) targeting HDAC (approved for use in Peripheral T-cell lymphoma); Bevacizumab (Avastin) targeting VEGF ligand (approved for use in Cervical cancer, Colorectal cancer, Fallopian tube cancer, Glioblastoma, Non-small cell lung cancer, Ovarian cancer, Peritoneal cancer, Renal cell carcinoma); Blinatumomab (Blincyto) targeting CD19/CD3 (approved for use in Acute lymphoblastic leukemia (precursor B-cell)); Bortezomib (Velcade) targeting Proteasome (approved for use in Multiple myeloma, Mantle cell lymphoma); Bosutinib (Bosulif) targeting ABL (approved for use in Chronic myelogenous leukemia); Brentuximab vedotin (Adcetris) targeting CD30 (approved for use in Hodgkin lymphoma, Anaplastic large cell lymphoma); Brigatinib (Alunbrig) targeting ALK (approved for use in Non-small cell lung cancer (ALK+)); Cabozantinib (Cabometyx, Cometriq) targeting FLT3, KIT, MET, RET, VEGFR2 (approved for use in Medullary thyroid cancer, Renal cell carcinoma); Carfilzomib (Kyprolis) targeting Proteasome (approved for use in Multiple myeloma); Ceritinib (Zykadia) targeting ALK (approved for use in Non-small cell lung cancer); Cetuximab (Erbitux) targeting EGFR (HER1/ERBB1) (approved for use in Colorectal cancer, Squamous cell cancer of the head and neck); Cobimetinib (Cotellic) targeting MEK (approved for use in Melanoma): Crizotinib (Xalkori) targeting ALK, MET, ROS1 (approved for use in Non-small cell lung cancer); Dabrafenib (Tafinlar) targeting BRAF (approved for use in Melanoma, Non-small cell lung cancer); Daratumumab (Darzalex) targeting CD38 (approved for use in Multiple myeloma): Dasatinib (Sprycel) targeting ABL (approved for use in Chronic myelogenous leukemia, Acute lymphoblastic leukemia); Denosumab (Xgeva) targeting RANKL (approved for use in Giant cell tumor of the bone); Dinutuximab (Unituxin) targeting B4GALNT1 (GD2) (approved for use in Pediatric neuroblastoma); Durvalumab (Imfinzi) targeting PD-L1 (approved for use in Urothelial carcinoma); Elotuzumab (Empliciti) targeting SLAMF7 (CS1/CD319/CRACC) (approved for use in Multiple myeloma); Enasidenib (Idhifa) targeting IDH2 (approved for use in Acute myeloid leukemia); Erlotinib (Tarceva) targeting EGFR (HER1/ERBB1) (approved for use in Non-small cell lung cancer, Pancreatic cancer); Everolimus (Afinitor) targeting mTOR (approved for use in Pancreatic, gastrointestinal, or lung origin neuroendocrine tumor, Renal cell carcinoma, Nonresectable subependymal giant cell astrocytoma, Breast cancer); Gefitinib (Iressa) targeting EGFR (HER1/ERBB1) (approved for use in Non-small cell lung cancer); Ibritumomab tiuxetan (Zevalin) targeting CD20 (approved for use in Non-Hodgkin's lymphoma); Ibrutinib (Imbruvica) targeting BTK (approved for use in Mantle cell lymphoma, Chronic lymphocytic leukemia, Waldenstrom's macroglobulinemia); Idelalisib (Zydelig) targeting PI3Kδ (approved for use in Chronic lymphocytic leukemia, Follicular B-cell non-Hodgkin lymphoma, Small lymphocytic lymphoma); Imatinib (Gleevec) targeting KIT, PDGFR, ABL (approved for use in GI stromal tumor (KIT+), Dermatofibrosarcoma protuberans, Multiple hematologic malignancies); Ipilimumab (Yervoy) targeting CTLA-4 (approved for use in Melanoma); Ixazomib (Ninlaro) targeting Proteasome (approved for use in Multiple Myeloma); Lapatinib (Tykerb) targeting HER2 (ERBB2/neu), EGFR (HER1/ERBB1) (approved for use in Breast cancer (HER2+)); Lenvatinib (Lenvima) targeting VEGFR2 (approved for use in Renal cell carcinoma, Thyroid cancer); Midostaurin (Rydapt) targeting FLT3 (approved for use in acute myeloid leukemia (FLT3+)); Necitumumab (Portrazza) targeting EGFR (HER1/ERBB1) (approved for use in Squamous non-small cell lung cancer): Neratinib (Nerlynx) targeting HER2 (ERBB2/neu) (approved for use in Breast cancer); Nilotinib (Tasigna) targeting ABL (approved for use in Chronic myelogenous leukemia); Niraparib (Zejula) targeting PARP (approved for use in Ovarian cancer, Fallopian tube cancer, Peritoneal cancer); Nivolumab (Opdivo) targeting PD-1 (approved for use in Colorectal cancer, Head and neck squamous cell carcinoma, Hodgkin lymphoma, Melanoma, Non-small cell lung cancer, Renal cell carcinoma, Urothelial carcinoma); Obinutuzumab (Gazyva) targeting CD20 (approved for use in Chronic lymphocytic leukemia, Follicular lymphoma); Ofatumumab (Arzerra, HuMax-CD20) targeting CD20 (approved for use in Chronic lymphocytic leukemia): Olaparib (Lynparza) targeting PARP (approved for use in Ovarian cancer); Olaratumab (Lartruvo) targeting PDGFRα (approved for use in Soft tissue sarcoma); Osimertinib (Tagrisso) targeting EGFR (approved for use in Non-small cell lung cancer); Pabociclib (Ibrance) targeting CDK4, CDK6 (approved for use in Breast cancer); Panitumumab (Vectibix) targeting EGFR (HER1/ERBB1) (approved for use in Colorectal cancer); Panobinostat (Farydak) targeting HDAC (approved for use in Multiple myeloma); Pazopanib (Votrient) targeting VEGFR, PDGFR, KIT (approved for use in Renal cell carcinoma); Pembrolizumab (Keytruda) targeting PD-1 (approved for use in Classical Hodgkin lymphoma, Melanoma, Non-small cell lung cancer (PD-L1+), Head and neck squamous cell carcinoma, Solid tumors (MSI-H)); Pertuzumab (Perjeta) targeting HER2 (ERBB2/neu) (approved for use in Breast cancer (HER2+)); Ponatinib (Iclusig) targeting ABL, FGFR1-3, FLT3, VEGFR2 (approved for use in Chronic myelogenous leukemia, Acute lymphoblastic leukemia); Ramucirumab (Cyramza) targeting VEGFR2 (approved for use in Colorectal cancer, Gastric cancer or Gastroesophageal junction (GEJ) adenocarcinoma, Non-small cell lung cancer); Regorafenib (Stivarga) targeting KIT, PDGFRP, RAF, RET, VEGFR1/2/3 (approved for use in Colorectal cancer, Gastrointestinal stromal tumors, Hepatocellular carcinoma); Ribociclib (Kisqali) targeting CDK4, CDK6 (approved for use in Breast cancer (HR+, HER2−)); Rituximab (Rituxan, Mabthera) targeting CD20 (approved for use in Non-Hodgkin's lymphoma, Chronic lymphocytic leukemia, Rheumatoid arthritis, Granulomatosis with polyangiitis); Rituximab/hyaluronidase human (Rituxan Hycela) targeting CD20 (approved for use in Chronic lymphocytic leukemia, Diffuse large B-cell lymphoma, Follicular lymphoma); Romidepsin (Istodax) targeting HDAC (approved for use in Cutaneous T-cell lymphoma. Peripheral T-cell lymphoma); Rucaparib (Rubraca) targeting PARP (approved for use in Ovarian cancer); Ruxolitinib (Jakafi) targeting JAK1/2 (approved for use in Myeloflbrosis); Siltuximab (Sylvant) targeting IL-6 (approved for use in Multicentric Castleman's disease); Sipuleucel-T (Provenge) targeting (approved for use in Prostate cancer); Sonidegib (Odomzo) targeting Smoothened (approved for use in Basal cell carcinoma); Sorafenib (Nexavar) targeting VEGFR, PDGFR. KIT, RAF (approved for use in Hepatocellular carcinoma, Renal cell carcinoma, Thyroid carcinoma): Temsirolimus (Torisel) targeting mTOR (approved for use in Renal cell carcinoma); Tositumomab (Bexxar) targeting CD20 (approved for use in Non-Hodgkin's lymphoma); Trametinib (Mekinist) targeting MEK (approved for use in Melanoma, Non-small cell lung cancer); Trastuzumab (Herceptin) targeting HER2 (ERBB2/neu) (approved for use in Breast cancer (HER2+), Gastric cancer (HER2+)); Vandetanib (Caprelsa) targeting EGFR (HER1/ERBB1), RET, VEGFR2 (approved for use in Medullary thyroid cancer); Vemurafenib (Zelboraf) targeting BRAF (approved for use in Melanoma); Venetoclax (Venclexta) targeting BCL2 (approved for use in Chronic lymphocytic leukemia): Vismodegib (Erivedge) targeting PTCH, Smoothened (approved for use in Basal cell carcinoma); Vorinostat (Zolinza) targeting HDAC (approved for use in Cutaneous T-cell lymphoma); Ziv-aflibercept (Zaltrap) targeting PIGF, VEGFA/B (approved for use in Colorectal cancer); and the like. These antibodies may be administered as a combination therapy with an anti-ABCC1 antibody provided herein.

Biological response modifiers suitable for use in connection with the methods of the present disclosure include, but are not limited to, (1) inhibitors of tyrosine kinase (RTK) activity; (2) inhibitors of serine/threonine kinase activity; (3) tumor-associated antigen antagonists, such as antibodies that bind specifically to a tumor antigen; (4) apoptosis receptor agonists; (5) interleukin-2; (8) interferon-α; (7) interferon-γ; (8) colony-stimulating factors; (9) inhibitors of angiogenesis; and (10) antagonists of tumor necrosis factor.

Chemotherapeutic agents or antineoplastic agents are non-peptidic (i.e., non-proteinaceous) compounds that reduce proliferation of cancer cells, and encompass cytotoxic agents and cytostatic agents. Non-limiting examples of chemotherapeutic agents include alkylating agents (e.g., nitrosoureas), antimetabolites (e.g., methotrexate), antitumor antibiotics (e.g., anthracyclins), plant alkaloids (e.g., vinca alkaloids, taxanes, etc.), toposiomerase inhibitors, and steroid hormones.

Agents that act to reduce cellular proliferation are known in the art and widely used. Such agents include alkylating agents, such as nitrogen mustards, nitrosoureas, ethylenimine derivatives, alkyl sulfonates, and triazenes, including, but not limited to, mechlorethamine, cyclophosphamide (Cytoxan™), melphalan (L-sarcolysin), carmustine (BCNU), lomustine (CCNU), semustine (methyl-CCNU), streptozocin, chlorozotocin, uracil mustard, chlormethine, ifosfamide, chlorambucil, pipobroman, triethylenemelamine, triethylenethiophosphoramine, busulfan, dacarbazine, and temozolomide.

Antimetabolite agents include folic acid analogs, pyrimidine analogs, purine analogs, and adenosine deaminase inhibitors, including, but not limited to, cytarabine (CYTOSAR-U), cytosine arabinoside, fluorouracil (5-FU), floxuridine (FudR), 8-thioguanine, 8-mercaptopurine (6-MP), pentostatin, 5-fluorouracil (5-FU), methotrexate, 10-propargyl-5,8-dideazafolate (PDDF, CB3717), 5,8-dideazatetrahydrofolic acid (DDATHF), leucovorin, fludarabine phosphate, pentostatine, and gemcitabine.

Suitable natural products and their derivatives, (e.g., vinca alkaloids, antitumor antibiotics, enzymes, lymphokines, and epipodophyllotoxins), include, but are not limited to, Ara-C, paclitaxel (Taxol®), docetaxel (Taxotere®), deoxycoformycin, mitomycin-C, L-asparaginase, azathioprine; brequinar, alkaloids, e.g. vincristine, vinblastine, vinorelbine, vindesine, etc.; podophyllotoxins, e.g. etoposide, teniposide, etc.; antibiotics, e.g. anthracycline, daunorubicin hydrochloride (daunomycin, rubidomycin, cerubidine), idarubicin, doxorubicin, epirubicin and morpholino derivatives, etc.; phenoxizone biscyclopeptides, e.g. dactinomycin; basic glycopeptides, e.g. bleomycin; anthraquinone glycosides, e.g. plicamycin (mithramycin); anthracenediones, e.g. mitoxantrone; azirinopyrrolo indolediones, e.g. mitomycin: macrocyclic immunosuppressants, e.g. cyclosporine, FK-506 (tacrolimus, prograf), rapamycin, etc.; and the like.

Other anti-proliferative cytotoxic agents are navelbene, CPT-11, anastrazole, letrazole, capecitabine, reloxafine, cyclophosphamide, ifosamide, and droloxafine.

Microtubule affecting agents that have antiproliferative activity are also suitable for use and include, but are not limited to, allocolchicine (NSC 406042), Halichondrin B (NSC 609395), colchicine (NSC 757), colchicine derivatives (e.g., NSC 33410), dolstatin 10 (NSC 376128), maytansine (NSC 153858), rhizoxin (NSC 332598), paclitaxel (Taxol®), Taxol® derivatives, docetaxel (Taxotere®), thiocolchicine (NSC 361792), trityl cysterin, vinblastine sulfate, vincristine sulfate, natural and synthetic epothilones including but not limited to, eopthilone A, epothilone B, discodermolide; estramustine, nocodazole, and the like.

Hormone modulators and steroids (including synthetic analogs) that are suitable for use include, but are not limited to, adrenocorticosteroids, e.g. prednisone, dexamethasone, etc.; estrogens and pregestins, e.g. hydroxyprogesterone caproate, medroxyprogesterone acetate, megestrol acetate, estradiol, clomiphene, tamoxifen; etc.; and adrenocortical suppressants, e.g. aminoglutethimide; 17α-ethinylestradiol; diethylstilbestrol, testosterone, fluoxymesterone, dromostanolone propionate, testolactone, methylprednisolone, methyl-testosterone, prednisolone, triamcinolone, chlorotrianisene, hydroxyprogesterone, aminoglutethimide, estramustine, medroxyprogesterone acetate, leuprolide, Flutamide (Drogenil). Toremifene (Fareston), and Zoladex. Estrogens stimulate proliferation and differentiation, therefore compounds that bind to the estrogen receptor are used to block this activity. Corticosteroids may inhibit T cell proliferation.

Other chemotherapeutic agents include metal complexes, e.g. cisplatin (cis-DDP), carboplatin, etc.; ureas, e.g. hydroxyurea; and hydrazines, e.g. N-methylhydrazine; epidophyllotoxin; a topoisomerase inhibitor; procarbazine; mitoxantrone; leucovorin; tegafur; etc. Other anti-proliferative agents of interest include immunosuppressants, e.g. mycophenolic acid, thalidomide, desoxyspergualin, azasporine, leflunomide, mizoribine, azaspirane (SKF 105685); Iressa® (ZD 1839, 4-(3-chloro-4-fluorophenylamino)-7-methoxy-6-(3-(4-morpholinyl)propoxy)quinazoline); etc.

"Taxanes" include paclitaxel, as well as any active taxane derivative or pro-drug. "Paclitaxel" (which should be understood herein to include analogues, formulations, and derivatives such as, for example, docetaxel, TAXOL™, TAXOTERE™ (a formulation of docetaxel), 10-desacetyl analogs of paclitaxel and 3'N-desbenzoyl-3'N-t-butoxycarbonyl analogs of paclitaxel) may be readily prepared utilizing techniques known to those skilled in the art (see also WO 94/07882, WO 94/07881, WO 94/07880, WO 94/07876, WO 93/23555, WO 93/10076; U.S. Pat. Nos. 5,294,637; 5,283,253; 5,279,949; 5,274,137; 5,202,448; 5,200,534; 5,229,529; and EP 590,267), or obtained from a variety of commercial sources, including for example, Sigma Chemical Co., St. Louis, Mo. (T7402 from *Taxus brevifolia*; or T-1912 from *Taxus yannanensis*).

Paclitaxel should be understood to refer to not only the common chemically available form of paditaxel, but analogs and derivatives (e.g., Taxotere™ docetaxel, as noted above) and pacitaxel conjugates (e.g., paclitaxel-PEG, paclitaxel-dextran, paclitaxel-xylose, or protein bound paclitaxel such as Abraxans®).

Also included within the term "taxane" are a variety of known derivatives, including both hydrophilic derivatives, and hydrophobic derivatives. Taxane derivatives include, but are not limited to, galactose and mannose derivatives described in International Patent Application No. WO 99/18113; piperazino and other derivatives described in WO 99/14209; taxane derivatives described in WO 99/09021. WO 98/22451, and U.S. Pat. No. 5,869,680; 6-thio derivatives described in WO 98/28288; sulfenamide derivatives described in U.S. Pat. No. 5,821,263; and taxol derivative described in U.S. Pat. No. 5,415,869. It further includes prodrugs of paclitaxel including, but not limited to, those described in WO 98/58927; WO 98/13059; and U.S. Pat. No. 5,824,701.

Useful immunotherapies include anti-PD-1/PD-L1 immunotherapies, and/or other immunotherapy targets, such as e.g., immune check point markers, such as CTLA-4, LAG-3 and TIM-3, that may be targeted in treatment methods. Anti-PD-1/PD-L1 immunotherapies which include but are not limited to e.g., those therapies that include administering to a subject an effective amount of one or more anti-PD-1/PD-L1 therapeutic antagonists where such antagonists include but are not limited to e.g., OPDIVO® (nivolumab), KEYTRUDA® (pembrolizumab), Tecentriq™ (atezolizumab), durvalumab (MED14736), avelumab (MSB0010718C), BMS-936559 (MDX-1105), CA-170, BMS-202, BMS-8, BMS-37, BMS-242 and the like. These antibodies may be administered as a combination therapy with an anti-ABCC1 antibody provided herein.

CTLA-4, also known as CD152, binds to CD80 and CD86. Antibodies against CTLA-4 have been approved for treating some cancer types. The co-inhibitory effect of CTLA-4 with other immunotherapies make CTLA-4 a good candidate for use in combination with other immunotherapies to treat certain cancers. TIM-3 may also be targeted for immunotherapy for several cancer types.

LAG-3 is in clinical trials for treating cancers. Anti-LAG-3 immunotherapies include those that employ antagonist LAG-3 antibodies that can both activate T effector cells (by downregulating the LAG-3 Inhibiting signal into pre-activated LAG-3+ cells) and Inhibit induced (i.e. antigen-specific) Treg suppressive activity. Useful LAG-3 antagonistic antibodies include relatlimab (BMS-986016; developed by Bristol-Myers Squibb), IMP701 (developed by Immutep), TSR-033 (anti-LAG-3 mAb; developed by TESARO, Inc.), and the like.

Immunotherapies also include T cell-based immunotherapies such as e.g., adoptive cell therapy (ACT) and chimeric antigen receptor (CAR) T cell therapies. For example, a subject may be administered a population of CAR T cells engineered to target an antigen expressed by the subject's cancer. A T cell-based therapy may involve, in some instances, obtaining a cellular sample from a subject, such as a blood sample or a tumor biopsy, and culturing immune cells from the sample ex vivo, with or without genetic modification of the cultured immune cells. As an example, immune cells may be obtained from a subject, cultured ex vivo and modified with a CAR specific for an antigen expressed by the cancer to produce a population of CAR T cells. Then, the CAR T cells may be reintroduced into the subject to target the cancer. T cell-based immunotherapies may be configured in various ways, e.g., by targeting various antigens, by collecting/culturing various cell types, etc., depending on a particular cancer to be treated. In addition, T cell-based immunotherapies may be administered systemically, e.g., by intravenous injection, or locally, e.g., by infusion (e.g., intraperitoneal infusion, pleural catheter infusion, etc.), direct injection, and the like.

In some instances, a method of treatment described herein may include administering to a subject one or more inhibitors of a multidrug resistance transporter, including but not limited to e.g., a multidrug resistance transporter other than ABCC1. Useful inhibitors of multidrug resistance transporters include e.g., tyrosine kinase inhibitors, natural products, microRNAs, and small molecule inhibitors. Inhibitors of multidrug resistance transporters include ABC transporter inhibitors.

Individuals suitable for treatment using a method of the present disclosure include an individual having a cancer; an individual diagnosed as having a cancer; an individual being treated for a cancer with chemotherapy, radiation therapy, antibody therapy, surgery, etc.); an individual who has been treated for a cancer (e.g., with one or more of chemotherapy, radiation therapy, antibody therapy, surgery, etc.), and who has failed to respond to the treatment; an individual who has been treated for a cancer (e.g., with one or more of chemotherapy, radiation therapy, antibody therapy, surgery, etc.), and who initially responded to the treatment but who subsequently relapsed, i.e., the cancer recurred.

The methods of the present disclosure may be employed to target and treat a variety of cancers, including e.g., primary cancer, secondary cancers, re-growing cancers, recurrent cancers, refractory cancers and the like. For example, in some instances, the methods of the present disclosure may be employed as an initial treatment of a primary cancer identified in a subject. In some instances, the methods of the present disclosure may be employed as a non-primary (e.g., secondary or later) treatment, e.g., in a subject with a cancer that is refractory to a prior treatment, in a subject with a cancer that is re-growing following a prior treatment, in a subject with a mixed response to a prior treatment (e.g., a positive response to at least one tumor in the subject and a negative or neutral response to at least a second tumor in the subject), and the like.

In some instances, the methods of the present disclosure may be employed to treat a subject with a drug resistant cancer, such as a multi-drug resistant cancer. Multidrug resistance (MDR) is the mechanism by which many cancers develop resistance to chemotherapy drugs, resulting in minimal cell death and the expansion of drug-resistant tumors. MDR cancers may involve one or more resistance mechanisms including but not limited to e.g., increased expression of efflux pumps, decreased absorption of drug, inhibition of cell death or apoptosis, modulating drug metabolism, and the like. In some instances, the methods of the present disclosure may prevent, reverse or circumvent MDR.

In some instances, methods of the present disclosure may include treating a subject having a cancer that is resistant to a first agent with an effective amount of a subject antibody described herein in combination with a second agent that is different from the first agent. For example, in some instances, cancer of a subject may be resistant to a first chemotherapeutic and the subject may be treated by administering an effective amount of a subject antibody as described herein in combination with a second chemotherapeutic that is different from the first. Various combinations of first and second chemotherapeutics may be employed depending on e.g., the type of cancer to be treated, the likelihood of developing resistance, etc.

Numerous cancers are known to develop drug resistance. For this and other reasons the methods of the present disclosure may find use in treating various cancers including but not limited to, e.g., Acute Lymphoblastic Leukemia (ALL), Acute Myeloid Leukemia (AML), Adrenocortical Carcinoma, AIDS-Related Cancers (e.g., Kaposi Sarcoma, Lymphoma, etc.). Anal Cancer, Appendix Cancer, Astrocytomas, Atypical Teratoid/Rhabdoid Tumor, Basal Cell Carcinoma. Bile Duct Cancer (Extrahepatic), Bladder Cancer, Bone Cancer (e.g., Ewing Sarcoma, Osteosarcoma and Malignant Fibrous Histiocytoma, etc.), Brain Stem Glioma, Brain Tumors (e.g., Astrocytomas, Central Nervous System Embryonal Tumors, Central Nervous System Germ Cell Tumors, Craniopharyngioma, Ependymoma, etc.), Breast Cancer (e.g., female breast cancer, male breast cancer, childhood breast cancer, etc.), Bronchial Tumors, Burkitt Lymphoma, Carcinoid Tumor (e.g., Childhood, Gastrointestinal, etc.), Carcinoma of Unknown Primary, Cardiac (Heart) Tumors, Central Nervous System (e.g., Atypical Teratoid/Rhabdoid Tumor, Embryonal Tumors, Germ Cell Tumor, Lymphoma, etc.), Cervical Cancer, Childhood Cancers, Chordoma, Chronic Lymphocytic Leukemia (CLL), Chronic Myelogenous Leukemia (CML), Chronic Myeloproliferative Neoplasms, Colon Cancer, Colorectal Cancer, Craniopharyngioma, Cutaneous T-Cell Lymphoma, Duct (e.g., Bile Duct, Extrahepatic, etc.). Ductal Carcinoma In Situ (DCIS), Embryonal Tumors, Endometrial Cancer, Ependymoma, Esophageal Cancer, Esthesioneuroblastoma, Ewing Sarcoma, Extracranial Germ Cell Tumor, Extragonadal Germ Cell Tumor, Extrahepatic Bile Duct Cancer, Eye Cancer (e.g., Intraocular Melanoma. Retinoblastoma, etc.), Fibrous Histiocytoma of Bone (e.g., Malignant, Osteosarcoma, ect.), Gallbladder Cancer, Gastric (Stomach) Cancer, Gastrointestinal Carcinoid Tumor. Gastrointestinal Stromal Tumors (GIST), Germ Cell Tumor (e.g., Extracranial, Extragonadal, Ovarian, Testicular, etc.), Gestational Trophoblastic Disease, Glioma, Hairy Cell Leukemia, Head and Neck Cancer, Heart Cancer, Hepatocellular (Liver) Cancer, Histiocytosis (e.g., Langerhans Cell, etc.), Hodgkin Lymphoma, Hypopharyngeal Cancer, intraocular Melanoma, Islet Cell Tumors (e.g., Pancreatic Neuroendocrine Tumors, etc.), Kaposi Sarcoma, Kidney Cancer (e.g., Renal Cell, Wilms Tumor, Childhood Kidney Tumors, etc.), Langerhans Cell Histiocytosis, Laryngeal Cancer, Leukemia (e.g., Acute Lymphoblastic (ALL), Acute Myeloid (AML). Chronic Lymphocytic (CLL), Chronic Myelogenous (CML), Hairy Cell, etc.), Lip and Oral Cavity Cancer, Liver Cancer (Primary), Lobular Carcinoma In Situ (LCIS), Lung Cancer (e.g., Non-Small Cell, Small Cell, etc.), Lymphoma (e.g., AIDS-Related, Burkitt, Cutaneous T-Cell, Hodgkin, Non-Hodgkin, Primary Central Nervous System (CNS), etc.), Macroglobulinemia (e.g., Waldenström, etc.), Male Breast Cancer, Malignant Fibrous Histiocytoma of Bone and Osteosarcoma, Melanoma, Merkel Cell Carcinoma, Mesothelioma, Metastatic Squamous Neck Cancer with Occult Primary, Midline Tract Carcinoma Involving NUT Gene, Mouth Cancer, Multiple Endocrine Neoplasia Syndromes, Multiple Myeloma/

Plasma Cell Neoplasm, Mycosis Fungoides, Myelodysplastic Syndromes, Myelodysplastic/Myeloproliferative Neoplasms, Myelogenous Leukemia (e.g., Chronic (CML), etc.), Myeloid Leukemia (e.g., Acute (AML), etc.), Myeloproliferative Neoplasms (e.g., Chronic, etc.). Nasal Cavity and Paranasal Sinus Cancer. Nasopharyngeal Cancer, Neuroblastoma, Non-Hodgkin Lymphoma, Non-Small Cell Lung Cancer, Oral Cancer, Oral Cavity Cancer (e.g., Lip, etc.), Oropharyngeal Cancer, Osteosarcoma and Malignant Fibrous Histiocytoma of Bone, Ovarian Cancer (e.g., Epithelial, Germ Cell Tumor, Low Malignant Potential Tumor, etc.), Pancreatic Cancer, Pancreatic Neuroendocrine Tumors (Islet Cell Tumors), Papillomatosis, Paraganglioma, Paranasal Sinus and Nasal Cavity Cancer, Parathyroid Cancer, Penile Cancer. Pharyngeal Cancer, Pheochromocytoma, Pituitary Tumor. Pleuropulmonary Blastoma, Primary Central Nervous System (CNS) Lymphoma, Prostate Cancer, Rectal Cancer, Renal Cell (Kidney) Cancer, Renal Pelvis and Ureter, Transitional Cell Cancer, Retinoblastoma, Rhabdomyosarcoma, Salivary Gland Cancer, Sarcoma (e.g., Ewing. Kaposi, Osteosarcoma, Rhabdomyosarcoma, Soft Tissue, Uterine, etc.). Sézary Syndrome. Skin Cancer (e.g., Childhood, Melanoma, Merkel Cell Carcinoma, Nonmelanoma, etc.), Small Cell Lung Cancer, Small Intestine Cancer, Soft Tissue Sarcoma, Squamous Cell Carcinoma, Squamous Neck Cancer (e.g., with Occult Primary, Metastatic, etc.), Stomach (Gastric) Cancer, T-Cell Lymphoma, Testicular Cancer, Throat Cancer, Thymoma and Thymic Carcinoma, Thyroid Cancer, Transitional Cell Cancer of the Renal Pelvis and Ureter, Ureter and Renal Pelvis Cancer, Urethral Cancer, Uterine Cancer (e.g., Endometrial, etc.), Uterine Sarcoma, Vaginal Cancer. Vulvar Cancer, Waldenstrom Macroglobulinemia, Wilms Tumor, and the like.

The methods of treating described herein may, in some instances, be performed in a subject that has previously undergone one or more conventional treatments. For example, in the case of oncology, the methods described herein may, in some instances, be performed following a conventional cancer therapy including but not limited to e.g., conventional chemotherapy, conventional radiation therapy, conventional immunotherapy, surgery, etc. In some instances, the methods described herein may be used when a subject has not responded to or is refractory to a conventional therapy. In some instances, the methods described herein may be used when a subject has responded to a conventional therapy.

In some instances, the method of the present disclosure may be employed to target, treat or clear a subject for minimal residual disease (MRD) remaining after a prior cancer therapy. Targeting, treating and/or clearance of MRD may be pursued using the instant methods whether the MRD is or has been determined to be refractory to the prior treatment or not. In some instances, a method of the present disclosure may be employed to target, treat and/or clear a subject of MRD following a determination that the MRD is refractory to a prior treatment or one or more available treatment options other than those employing the herein described multi-specific antibodies.

In some instances, the instant methods may be employed prophylactically for surveillance. For example, a subject in need thereof may be administered a treatment involving one or more of the herein described antibodies when the subject does not have detectable disease but is at risk of developing a recurrent cancer, including e.g., a drug resistant cancer. In some instances, a prophylactic approach may be employed when a subject is at particularly high risk of developing a primary cancer that would be predicted to be drug resistant or expected to become drug resistant. In some instances, a prophylactic approach may be employed when a subject has been previously treated for a cancer and is at risk of reoccurrence or development of drug resistance.

In some instances, methods of the present disclosure may involve analyzing a cancer for expression of one or more markers or therapeutic targets. For example, in some instances, methods may involve analyzing a sample of a cancer from a subject to determine whether the cancer expresses ABCC1 above a predetermined threshold.

In some instances, whether a subject is treated with an antibody of the present disclosure may depend on the results of ABCC1 expression assessment. For example, in some instances, if a cancer expresses ABCC1 at or above a predetermined threshold then the subject may be treated with an anti-ABCC1 antibody of the present disclosure and if the cancer expresses ABCC1 below the predetermined threshold then the subject may not be treated with an anti-ABCC1 antibody of the present disclosure.

Any convenient assay may be employed for analyzing ABCC1 levels, including but not limited to e.g., flow cytometry, nucleic acid-based assays (e.g., amplification, sequencing, etc.), cell cytometry, immunohistochemistry, and the like. Any convenient biological sample may be employed, including but not limited to e.g., cancer biopsy samples, Useful predetermined thresholds for assessing expression of one or more markers and/or targets may be determined by any convenient and appropriate method, including comparison of the measured level of expression to a corresponding control. For example, in some instances, a useful predetermined threshold for the level of ABCC1 in a sample may correspond to a level of ABCC1 measured in a reference cell, such as a healthy/normal cell.

Methods of Making

As summarized above, methods of the present disclosure also include methods or making and/or identifying antibodies as described herein. A subject antibody can be produced by any known method, e.g., conventional synthetic methods for protein synthesis: recombinant DNA methods; etc.

Where a subject antibody is a single chain polypeptide, it can be synthesized using standard chemical peptide synthesis techniques. Where a polypeptide is chemically synthesized, the synthesis may proceed via liquid-phase or solid-phase. Solid phase polypeptide synthesis (SPPS), in which the C-terminal amino acid of the sequence is attached to an insoluble support followed by sequential addition of the remaining amino acids in the sequence, is an example of a suitable method for the chemical synthesis of a subject antibody. Various forms of SPPS, such as Fmoc and Boc, are available for synthesizing a subject antibody.

Standard recombinant methods can be used for production of a subject antibody. For example, nucleic acids encoding light and heavy chain variable regions, optionally linked to constant regions, are inserted into expression vectors. The light and heavy chains can be cloned in the same or different expression vectors. The DNA segments encoding immunoglobulin chains are operably linked to control sequences in the expression vector(s) that ensure the expression of immunoglobulin polypeptides. Expression control sequences include, but are not limited to, promoters (e.g., naturally-associated or heterologous promoters), signal sequences, enhancer elements, and transcription termination sequences. The expression control sequences can be eukaryotic promoter systems in vectors capable of transforming or transfecting eukaryotic host cells (e.g., COS or CHO cells). Once the vector has been incorporated into the appropriate host, the host is maintained under conditions suitable for high level expression of the nucleotide sequences, and the collection and purification of the antibodies.

Because of the degeneracy of the genetic code, a variety of nucleic acid sequences can encode each immunoglobulin amino acid sequence. The desired nucleic acid sequences can be produced by de novo solid-phase DNA synthesis or by polymerase chain reaction (PCR) mutagenesis of an earlier prepared variant of the desired polynucleotide. Oligonucleotide-mediated mutagenesis is an example of a suitable method for preparing substitution, deletion and insertion variants of target polypeptide DNA. See Adelman et al., DNA 2:183 (1983). Briefly, the target polypeptide DNA is altered by hybridizing an oligonucleotide encoding the desired mutation to a single-stranded DNA template. After hybridization, a DNA polymerase is used to synthesize an entire second complementary strand of the template that incorporates the oligonucleotide primer, and encodes the selected alteration in the target polypeptide DNA.

Suitable expression vectors are typically replicable in the host organisms either as episomes or as an integral part of the host chromosomal DNA. Commonly, expression vectors contain selection markers (e.g., ampicillin-resistance, hygromycin-resistance, tetracycline resistance, kanamycin resistance or neomycin resistance) to permit detection of those cells transformed with the desired DNA sequences.

*Escherichia coli* is an example of a prokaryotic host cell that can be used for cloning a subject antibody-encoding polynucleotide. Other microbial hosts suitable for use include bacilli, such as *Bacillus subtilis*, and other enterobacteriaceae, such as *Salmonella, Serratia*, and various *Pseudomonas* species.

Other microbes, such as yeast, are also useful for expression. *Saccharomyces* (e.g., *S. cerevisae*) and *Pichia* are examples of suitable yeast host cells, with suitable vectors having expression control sequences (e.g., promoters), an origin of replication, termination sequences and the like as desired. Typical promoters include 3-phosphoglycerate kinase and other glycolytic enzymes. Inducible yeast promoters include, among others, promoters from alcohol dehydrogenase, isocytochrome C, and enzymes responsible for maltose and galactose utilization.

In addition to microorganisms, mammalian cells (e.g., mammalian cells grown in in vitro cell culture) can also be used to express and produce the polypeptides of the present invention (e.g., polynucleotides encoding immunoglobulins or fragments thereof). See Winnacker, From Genes to Clones, VCH Publishers, N.Y., N.Y. (1987). Suitable mammalian host cells include CHO cell lines, various Cos cell lines, HeLa cells, HEK cells, myeloma cell lines, and transformed B-cells or hybridomas. Expression vectors for these cells can include expression control sequences, such as an origin of replication, a promoter, and an enhancer (Queen et al., Immunol. Rev. 89:49 (1986)), and necessary processing information sites, such as ribosome binding sites, RNA splice sites, polyadenylation sites, and transcriptional terminator sequences. Examples of suitable expression control sequences are promoters derived from immunoglobulin genes. SV40, adenovirus, bovine papilloma virus, cytomegalovirus and the like. See Co at al., J. Immunol. 148: 1149 (1992).

Once synthesized (either chemically or recombinantly), the whole antibodies, their dimers, individual light and heavy chains, or other forms of a subject antibody (e.g., scFv, etc.) can be purified according to standard procedures of the art, including ammonium sulfate precipitation, affinity columns, column chromatography, high performance liquid chromatography (HPLC) purification, gel electrophoresis, and the like (see generally Scopes, Protein Purification (Springer-Verlag, N.Y., (1982)). A subject antibody can be substantially pure, e.g., at least about 80% to 85% pure, at least about 85% to 90% pure, at least about 90% to 95% pure, or 98% to 99%, or more, pure, e.g., free from contaminants such as cell debris, macromolecules other than a subject antibody, etc.

Kits

Aspects of the present disclosure also include kits. The kits may include, e.g., any combination of the antibodies, reagents, compositions, formulations, cells, nucleic acids, expression vectors, or the like, described herein. A subject kit can include one or more of: a subject antibody, a nucleic acid encoding the same, or a cell comprising a subject nucleic acid. Kits may be configured for various purposes, including e.g., treatment kits (e.g., where a kit may include an anti-ABCC1 antibody and e.g., one or more additional active agents, such as a chemotherapeutic), kits for producing antibodies, kits for screening antibodies, and the like.

Optional components of the kit will vary and may, e.g., include: a buffer; a protease inhibitor; etc. Where a subject kit comprises a subject nucleic acid, the nucleic acid may also have restrictions sites, multiple cloning sites, primer sites, etc. The various components of the kit may be present in separate containers or certain compatible components may be pre-combined into a single container, as desired.

In addition to above-mentioned components, a subject kit can include instructions for using the components of the kit to practice a subject method. The instructions for practicing a subject method are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. compact disc-read only memory (CD-ROM), digital versatile disk (DVD), diskette, etc. In yet other embodiments, the actual instructions are not present in the kit, but means for obtaining the instructions from a remote source. e.g. via the internet, are provided. An example of this embodiment is a kit that includes a web address where the instructions can be viewed and/or from which the instructions can be downloaded. As with the instructions, this means for obtaining the instructions is recorded on a suitable substrate.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

General methods in molecular and cellular biochemistry can be found in such standard textbooks as Molecular Cloning: A Laboratory Manual, 3rd Ed. (Sambrook et al., HaRBor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998), the disclosures of which are incorporated herein by reference. Reagents, cloning vectors, cells, and kits for methods referred to in, or related to, this disclosure are available from commercial vendors such as BioRad, Agilent Technologies, Thermo Fisher Scientific.

Sigma-Aldrich, New England Biolabs (NEB), Takara Bio USA, Inc., and the like, as well as repositories such as e.g., Addgene. Inc., American Type Culture Collection (ATCC), and the like.

Example 1: Generation of Antibodies that Bind Specifically to Cells Expressing ABCC1

Materials and Methods

Antibody Generation

Wild type (WT) human and cynolomgus ABCC1, full length and truncated versions, were used to immunize mice or rats. Spleen and lymph node cells from the vaccinated animals were fused with SP2/0 myeloma cells (hybridoma technology). Hybridoma supernatants were screened for the presence of anti-ABCC1 antibodies by flow cytometry. CDRs from selected murine IgGs were cloned into mammalian IgG1 backbone expression vectors for full-length IgG1 antibody expression and production in HEK 293 host cells via transfection using standard protocols and as described below.

Expression Vectors

For the generation of the antibody expression vectors, the variable regions of heavy and light chain DNA sequences were subcloned in frame with either the human IgG1 constant heavy chain or the human IgG1 kappa constant light chain pre-inserted into the respective generic recipient expression vectors optimized for expression in mammalian cell lines. The genes to be expressed were cloned into the pCI-neo Mammalian Expression Vector (Promega) that uses the full-length human cytomegalovirus (CMV) immediate-early promoter for high level gene expression. The two antibody chains were cloned into two different vectors.

The N-terminal signal sequences from mouse IgG heavy chain and kappa light chain were used for the secreted expression of the heavy and light chain, respectively. The signal peptide was cleaved during expression, leaving intact N-terminus. In the Fab constructs, the C-terminus of the CH1 IgG1 constant region was fused with a 6× His tag for purification.

Production of mAb

Antibody constructs were expressed using polymer-based co-transfection of Expi293 cells (A14527, ThermoFisher) cells growing in suspension with the mammalian expression vectors following the manufacturer's recommendations.

About six days after transfection the cells were harvested by centrifugation. In detail, 1 ug of total encoding DNA per 1 ml of transfected culture was diluted into of Opti-MEMO medium (Life Technologies), and incubated with Expifectamine reagent (Life Technologies) in the same medium for 20 min. The mixture was then added into the Expi293® cells growing in suspension in Expi293® Expression medium (Life Technologies) at 2.5 million cells/mi at 37° C. with and overlay of 8% of C02 in air. After 6 days, the medium containing the antibody construct was harvested by centrifugation.

Purification of mAbs

To purify antibody formats containing the human Fc, 10 μl of MabSelect™ SuRe™ (GE Healthcare) per 1 ml of supernatant were added to the harvested medium and kept stirring at 4° C. overnight. The next day, the protein A resin was applied in a 24 well filter plate using a vacuum manifold unit (Pall Lifesciences, USA). The resin was washed with PBS and the antibody eluted in 50 mM phosphate pH 3 and neutralized with 10×PBS pH 13.

Analytical Test for mAbs (GXII Reduced and Non-Reduced)

Purity and monomer content of the final protein preparation was determined by high-throughput analysis on the Caliper's LabChip GXII using Protein Express LabChip Kit (Perkin-Elmer) as described by the manufacturer. The chip was automatically primed on the instrument with polymer solution containing 0.2% SDS and fluorescent staining dye. The destain channels were filled with polymer solution free of SDS and dye. Briefly, proteins in reducing and not reducing conditions were prepared by mixing a small volume (2-5 μL) of sample with the caliper sample buffer with or without DDT. The samples were denatured at 75° C. for 5 minutes, centrifuged at 2000 g for 3 minutes, and then run. Electropherograms were generated by LabChip GXII Touch software (Perkin Elmer).

Analytical Test for mAbs (HPLC)

Purity and monomer content of the final protein preparation was determined by high-throughput analysis on HPLC. Size exclusion chromatography (SEC) was performed using an Advancebio SEC 300A 4.6×300 mm, 2.7 um (p/n PL1580-5301) (Agilent Technologies) on an Infinity 1260 Agilent HPLC system. Injections were made under isocratic elution conditions using a mobile phase of PBS, 400 mM sodium chloride, pH 7.4, and detected with absorbance at 280 nm. Quantification is based on the relative area of detected peaks.

A subject antibody can be substantially pure, e.g., at least about 80% to 85% pure, at least about 85% to 90% pure, at least about 90% to 95% pure, or 98% to 99%, or more, pure, e.g., free from contaminants such as cell debris, macromolecules other than a subject antibody, etc.

Monoclonal Antibody Titration Binding to KPC1

Binding titration of recombinant antibodies to KPC1 transfectants was performed by serial dilution of antibodies from about 666 nM, Diluted antibody in flow cytometry buffer was incubated with cells on ice for 30 min. After 2 washes with flow cytometry buffer, bound antibody was detected with PE-labeled F(ab')$_2$ fragment goat anti-human IgG (Jackson ImmunoResearch) diluted 1:200 in flow cytometry buffer and incubated with cells for 20 min on ice. After 2 washes with flow cytometry buffer fluorescence was measured on an Attune NxT flow cytometer. Data were analyzed with GraphPad Prism 8.0 software to determine EC50's.

Cell Binding Assays.

Antibody binding to cells was evaluated by flow cytometry. 293T cells stably transfected to express human or cynomolgus ABCC1 were washed once in flow cytometry buffer (PBS+2% FBS+0.02% sodium azide), resuspended at 2×10^6 cells/mL in flow cytometry buffer, and dispensed into 96-well microtiter plates at 0.1 mL/well. Recombinant antibodies were added to cells at 5 ug/mL for initial binding confirmation, or serially diluted from 100 ug/mL in flow cytometry buffer. After incubating cells on ice for 30 min, cells were washed twice with flow cytometry buffer. Bound antibody was detected with PE-labeled F(ab')$_2$ fragment goat anti-human IgG (Jackson ImmunoResearch) and evaluated on an Attune NxT flow cytometer. EC50 is calculated to be the concentration of antibody that gives half maximal response.

ABCC1 Efflux Assay.

HEK 293T cells expressing human ABCC1 were washed several times and aliquoted into 96-well plates as 50 μl aliquots/well at a cell density of $1\times10^6$ cells per ml in phenol red-free DMEM. Cells were mixed with 50 μl antibodies and incubated for 1.5 h at 37° C. The cells were then washed twice and finally resuspended in 200 ml PBS. Calcein AM fluorescence was measured by flow cytometry.

Cytotoxicity Assay

The effect of anti-ABCC1 antibodies on vincristine cytotoxicity was evaluated on 293T cells stably transfected to express ABCC1. Cells were plated in 0.05 mL of Assay Media (DMEM+10% FBS) at 5000 cells/well in white, flat bottom 96-well tissue culture plates. Vincristine was prepared at 2× final assay concentration by serial dilution from 200 uM in assay media containing test antibodies or control antibodies at 100 ug/mL (2× final concentration). An equivalent volume (0.05 mL) of the vicristine/antibody mixture was added to the 293T_ABCC1 cells in 96-well plates. The plates were then incubated at 37° C. in 5% $CO_2$. After about 72-96 hr plates were equilibrated to room temperature and cell viability assessed using Promega® CellTiter-Glo® Luminescent Cell Viability Assay according to the manufacturer's recommended protocol. Luminescence was measured on a Molecular Devices® FlexStation® 3 Multi-Mode Microplate Reader and data analyzed using GraphPad Prism 8.0 software. Half maximal inhibitory concentration (IC50) is the concentration of drug (vuncristine or other chemotherapy cytotoxic agent) where the response (cell growth) is reduced by 50%.

CT26 Syngeneic Xenograft Mouse Model.

Syngeneic models are allografts immortalized from mouse cancer cell lines, which are then grafted back into the same inbred immunocompetent mouse strain. CT26 is an N-nitroso-N-methylurethane-(NNMU) induced undifferentiated fibroblastic colon carcinoma cell line established from BALB/c mice with aggressive colon carcinoma. C26 cells were purchased from ATCC® (CRL-2638™) and maintained in RPMI-1640 medium supplemented with 10% FBS and 1% penicillin, 1% streptomycin at 37° C., 5% $CO_2$. Cell lines used were authentic and confirmed to be mycoplasma negative. The cells are adherent with a fibroblast morphology and will form tumors and metastases post implantation into syngeneic BALB/c mice or immunocompromised mice.

$1\times10^6$ cells diluted inPBS:Matrigel (1:1) were subcutaneously implanted using a 27G insulin syringe into anesthetized 54-week old female Balb/c mice under aseptic conditions. All animal maintenance, handling, surveillance, and animal procedures were performed in accordance with an approval from the APLAC protocol.

Once tumors reached 100-150 mm$^3$, mice were randomized into 6 groups of five mice each:

1. Control isotype 3 mg/kg,
2. Control isotype 3 mg/kg+Doxorubicin 2 mg/kg
3. KNJY C1-831 3 mg/kg
4. KNJY C1-831 3 mg/kg+Doxorubicin
5. KNJY C1-787A 3 mg/kg
6. KNJY C1-787A 3 mg/kg+Doxorubicin 2 mg/kg.

Doxorubicin is soluble in water. All test articles were dosed intraperitoneally twice a week for two consecutive weeks. Antibodies were dosed 4 hr prior to Doxorubicin.

Tumors were measured three times a week using a calibrated Vernier Caliper and tumor volume calculated as per the formula ½*L*S*S, where L is the long axis and S is the short axis of the tumor. Body weights were recorded before treatment started and were continuously monitored throughout the study. Animals were euthanized when turning moribund according to the above-mentioned predefined criteria rapid weight loss, loss of ability to ambulate, labored respiration, or inability to drink or feed to avoid animal suffering.

Results

Table 3 lists the following characteristics of the anti-ABCC1 antibodies: binding to 293T cells stably transfected to express human ABCC1 measured by FACS and binding to 293T cells stably transfected to express cynomolgus ABCC1 measured by FACS.

| Antibody | Binding by FACS | Cynomolgus ABCC1 binding |
|---|---|---|
| C1.309 | + | + |
| C1.310 | + | + |
| C1.499 | + | + |
| C1.505 | + | +/− |
| C1.773 | + | + |
| C1.773a | + | + |
| C1.777a | + | + |
| C1.778b | + | + |
| C1.784a | + | + |
| C1.786a | + | + |
| C1.787a | + | + |

FIG. 1 depicts the results of titration binding of ten anti-ABCC1 monoclonal antibodies to the doxorubicin-resistant lung carcinoma cell line H69AR (ATCC® CRL-11351™) that endogenously expresses ABCC1 in the flow cytometry (FACS) assay described above. All antibodies tested show significant (>10-folds of background fluorescence mean intensity (FMI)) binding to the H89AR cells.

FIGS. 2A-28 depict the results of titration binding of the indicated anti-ABCC1 monoclonal antibodies to human and cynomolgus ABCC1-overexpressing rat C6 glioma cell lines in the FACS assay described above. All antibodies tested show significant binding to both C6 cells overexpressing human ABCC1 and C6 cells overexpressing cynomolgus ABCC1.

FIGS. 3A-3C, 4, 5A-5B, and 6A-6B show the results of titration binding of further anti-ABCC1 monoclonal antibodies to human and cynomolgus ABCC1-overexpressing rat C6 glioma cell lines in the FACS assay described above. "2$^{nd}$ Ab only" refers to a not primary antibody used as negative control. All anti-ABCC1 antibodies tested show significant binding, relative to negative control, to both C6 cells overexpressing human ABCC1 and C6 cells overexpressing cynomolgus ABCC1.

Figure 7A:
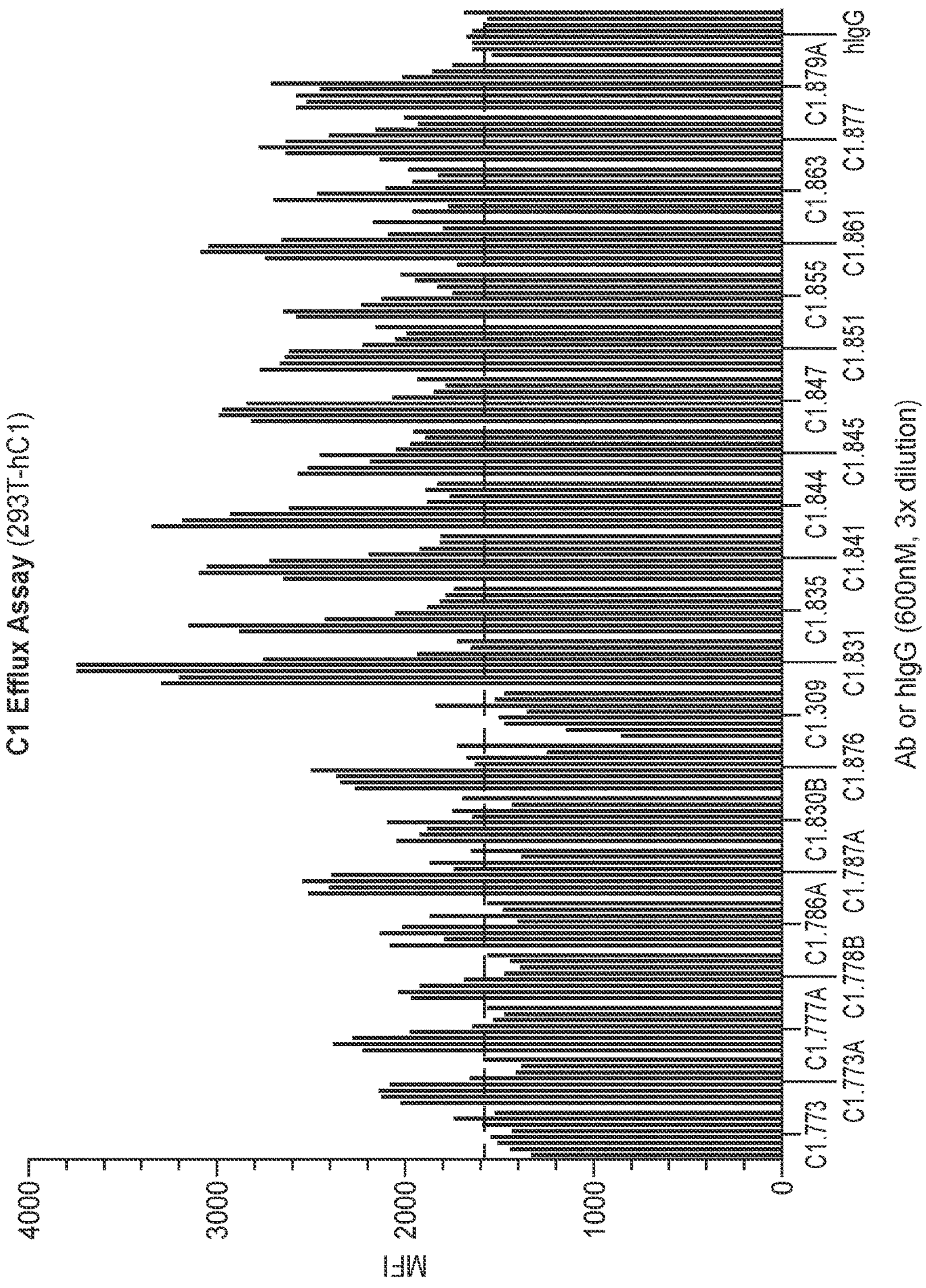
FIGS. 7A-7B show the results of ABCC1 efflux assay performed using HEK293T cells expressing human ABCC1.
Figure 7B:
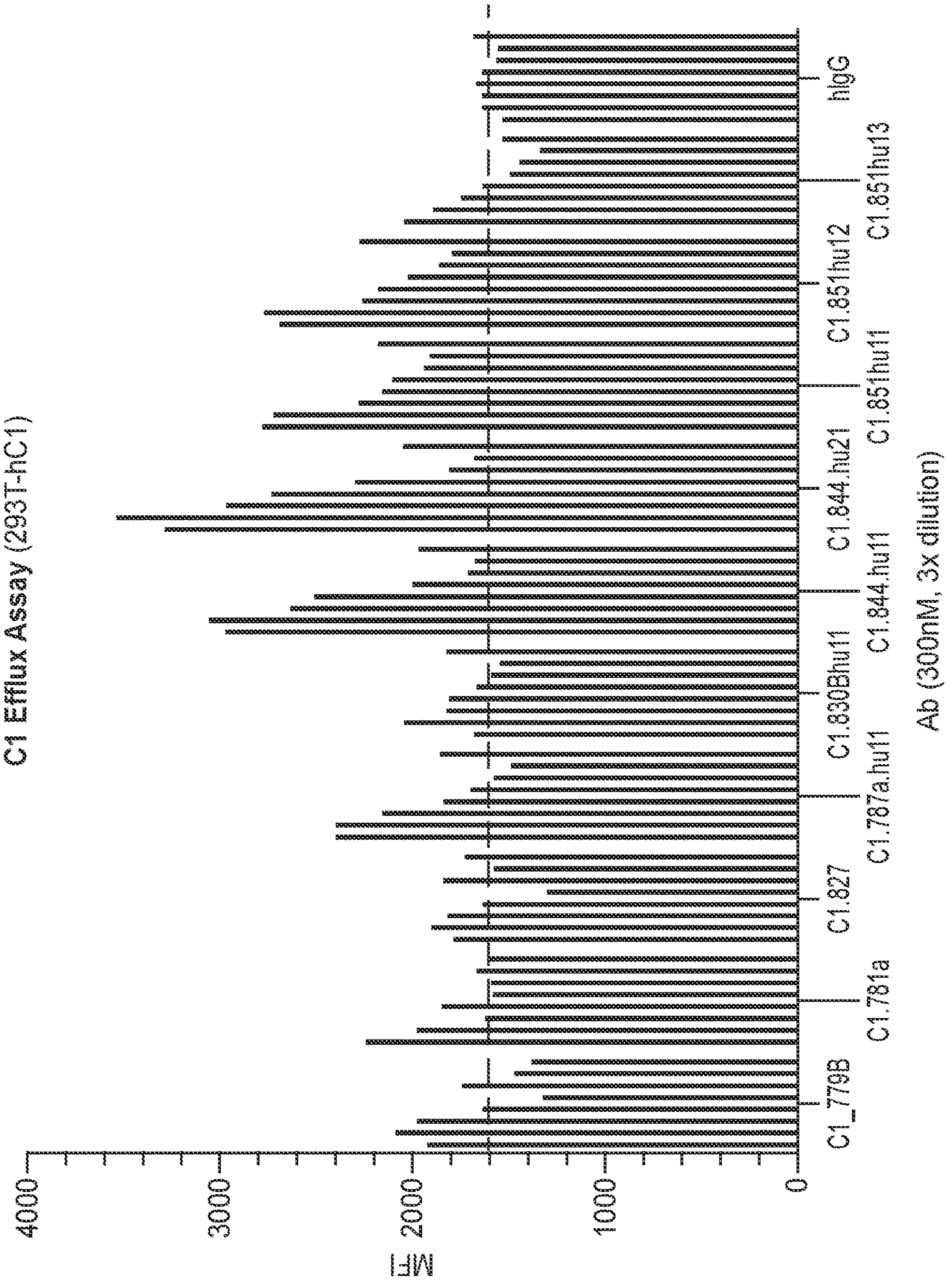

FIGS. 7A-7B show the results of ABCC1 efflux assay performed using HEK293T cells expressing human ABCC1. All anti-ABCC1 antibodies tested significantly inhibit the efflux function of the ABCC1 transporter.

Figure 8A:
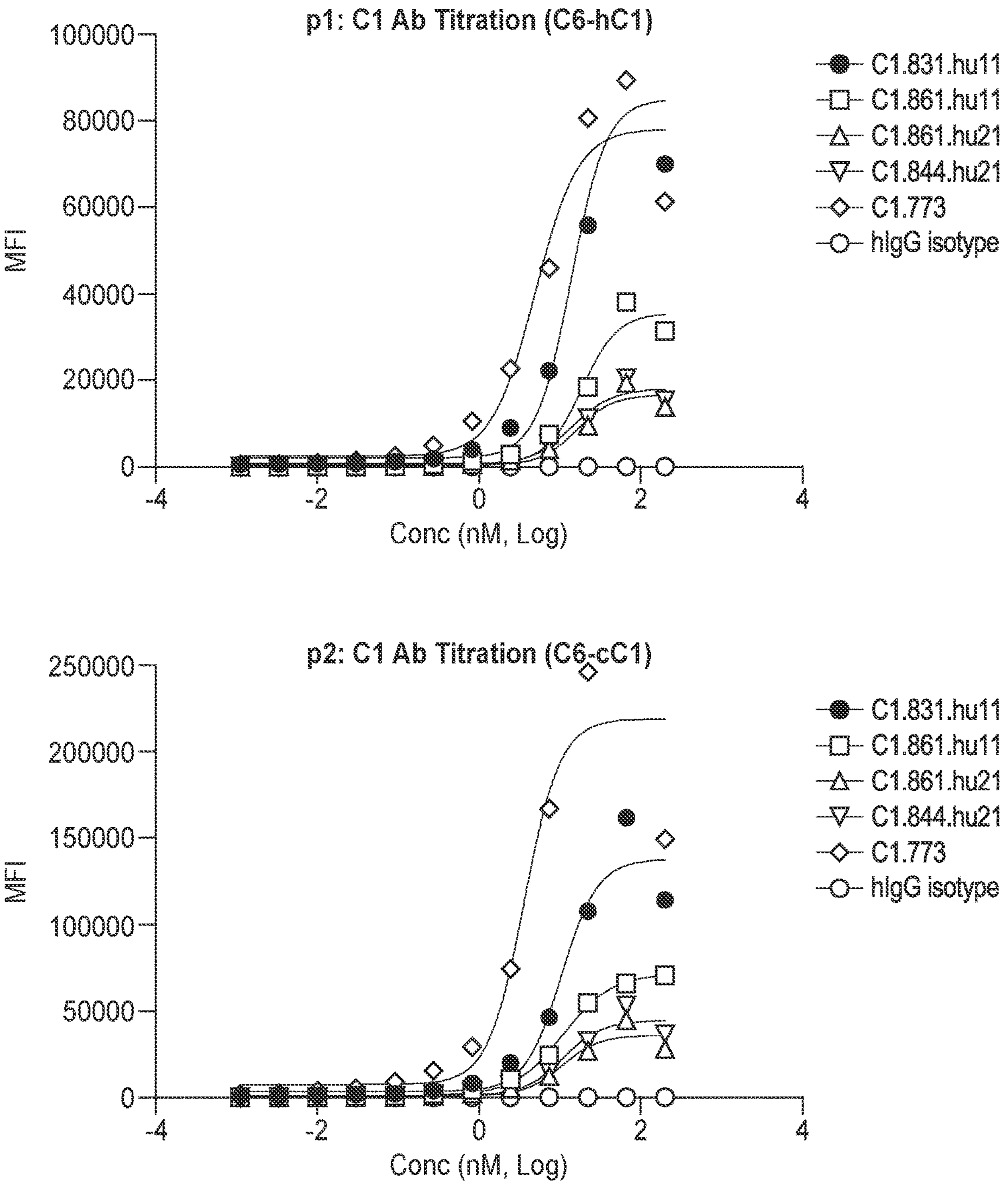
FIGS. 8A-8C present titration binding and efflux assay characterization of humanized anti-ABCC1 monoclonal antibodies.
Figure 8B:
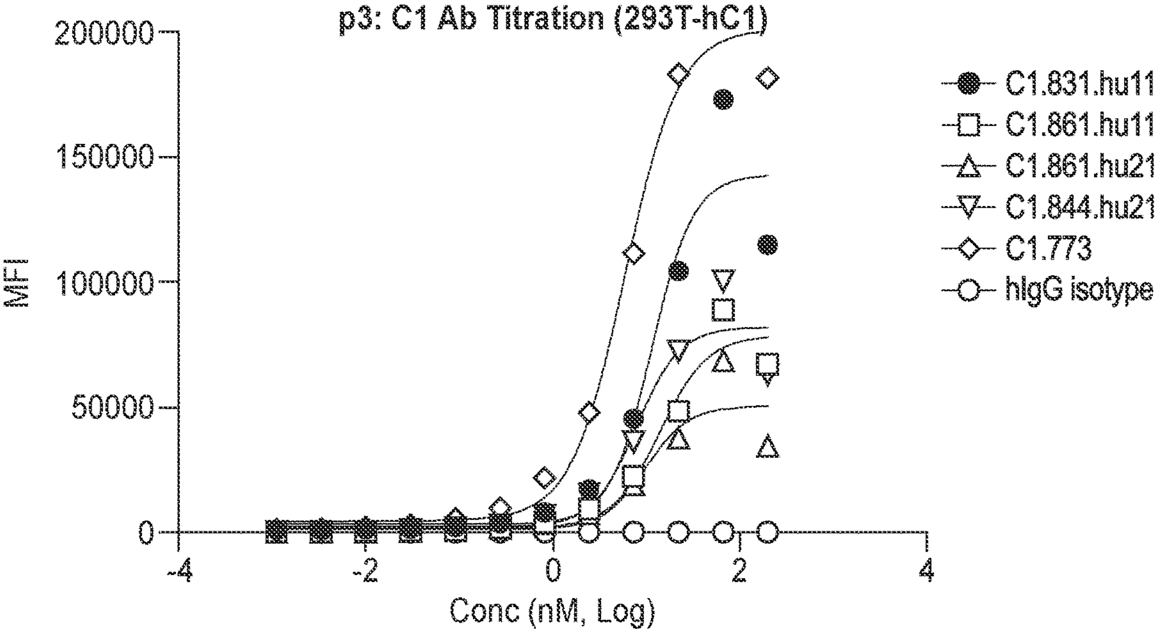
Figure 8C:
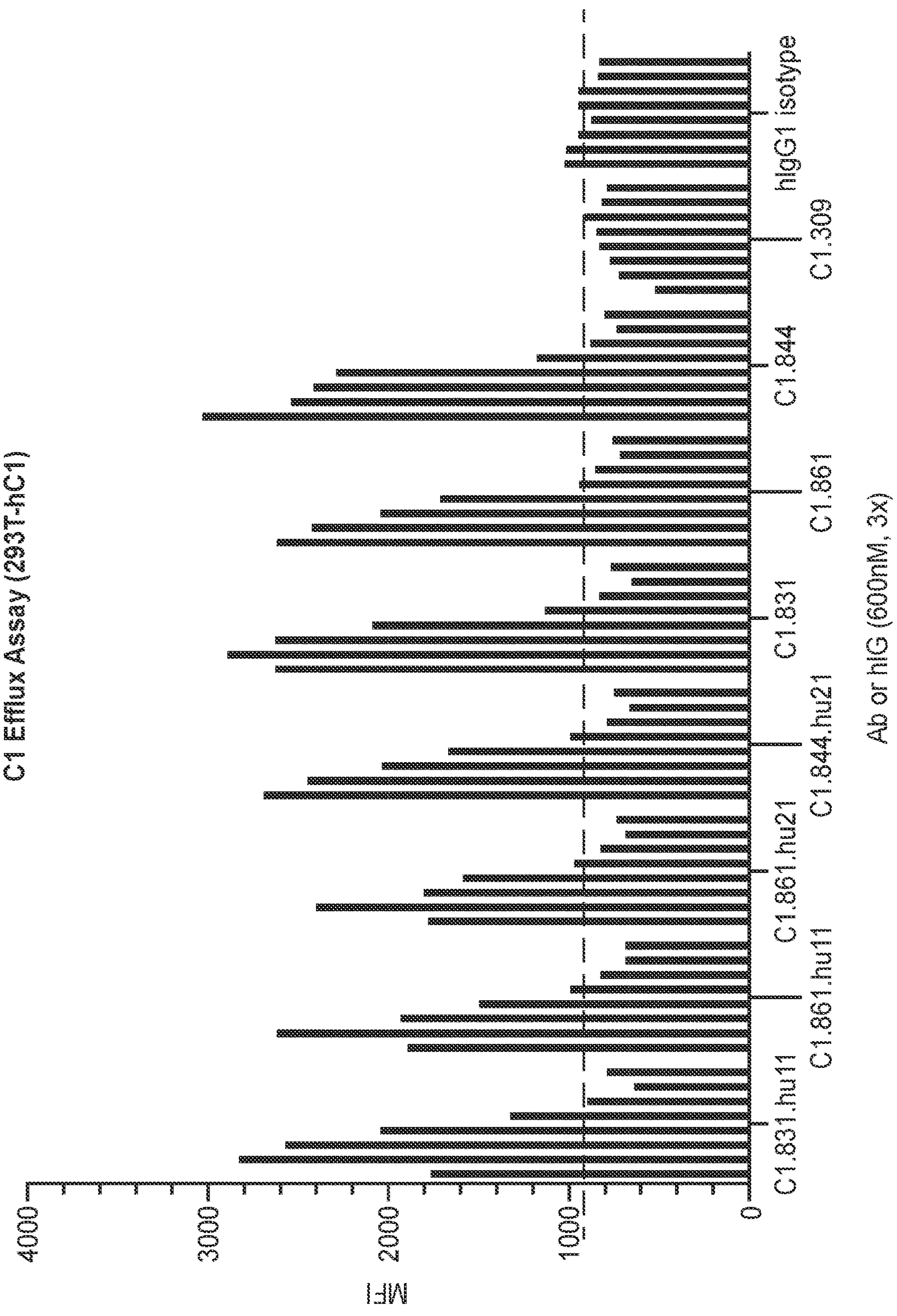

FIGS. 8A-8C present titration binding and efflux assay characterization of humanized anti-ABCC1 monoclonal antibodies. Humanized anti-ABCC1 antibodies C1.831.hu11, C1.861.hu11, C1.861.hu21, and C1.844.hu21 bind both human and cynomolgus ABCC1 in the titration binding assay and significantly inhibit the efflux function of the ABCC1 transporter in the efflux assay.

Figure 9A:
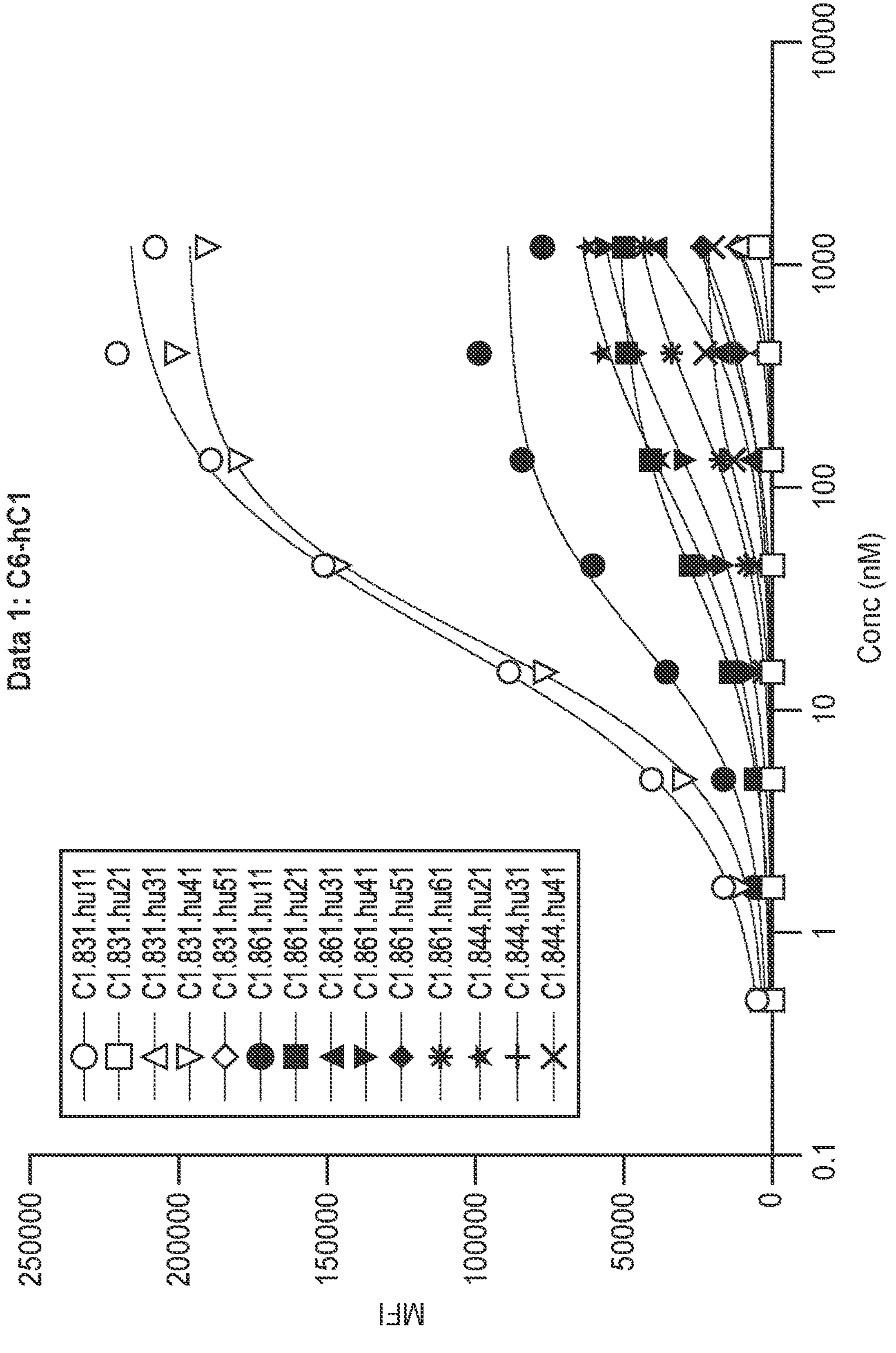
FIGS. 9A-9C show the binding of humanized anti-ABCC1 monoclonal antibodies to human and cynomolgus ABCC1 overexpressing rat C6 glioma cell lines.
Figure 9B:
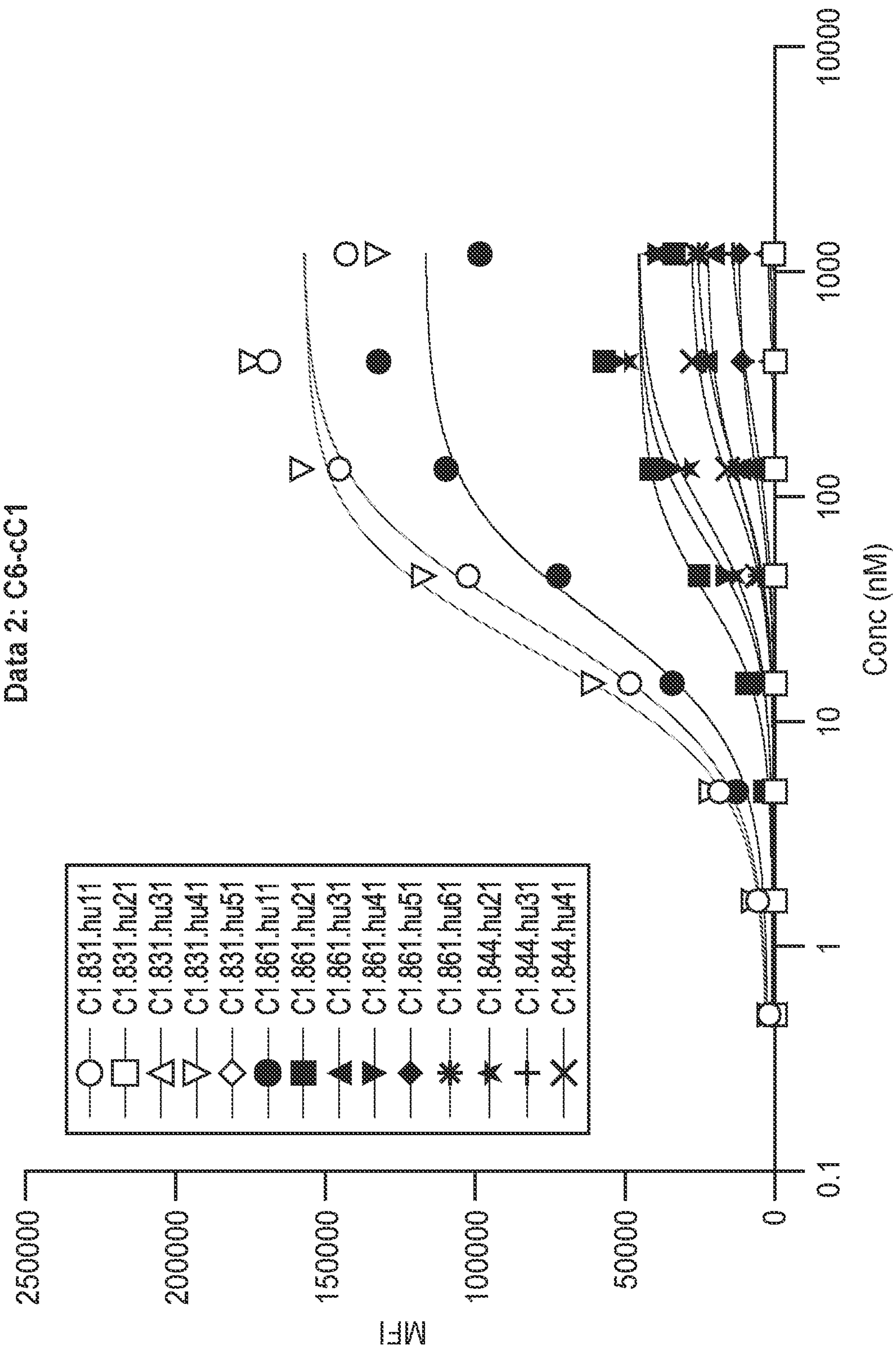
Figure 9C:
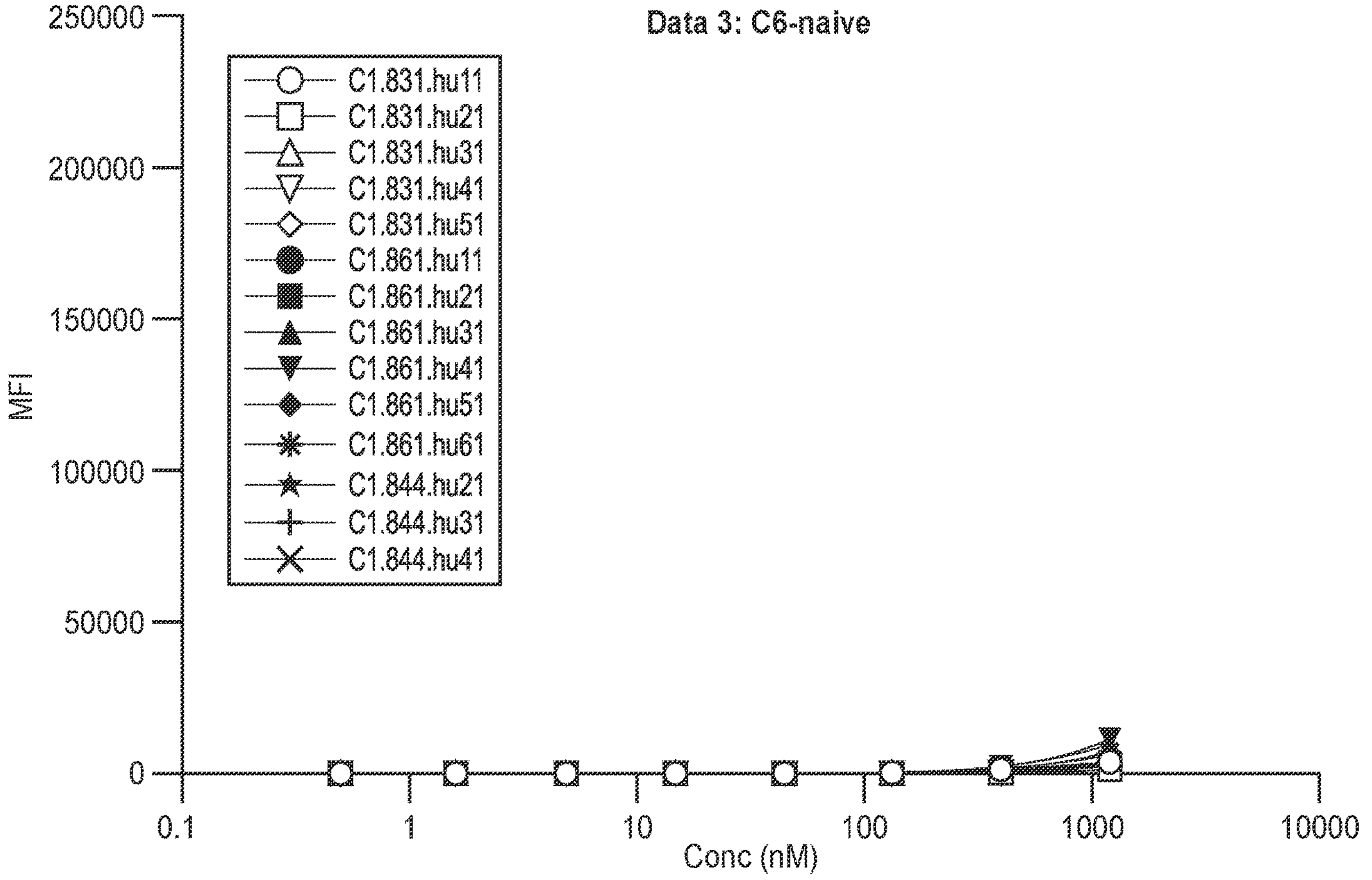

FIGS. 9A-9C show the binding of humanized variants of the anti-ABCC1 monoclonal antibodies C1.831, C1.861 and C1.844 to human and cynomolgus ABCC1 overexpressing rat C6 glioma cell lines. All humanized antibodies retain the ability to bind both human and cynomolgus ABCC1.

Figure 10A:
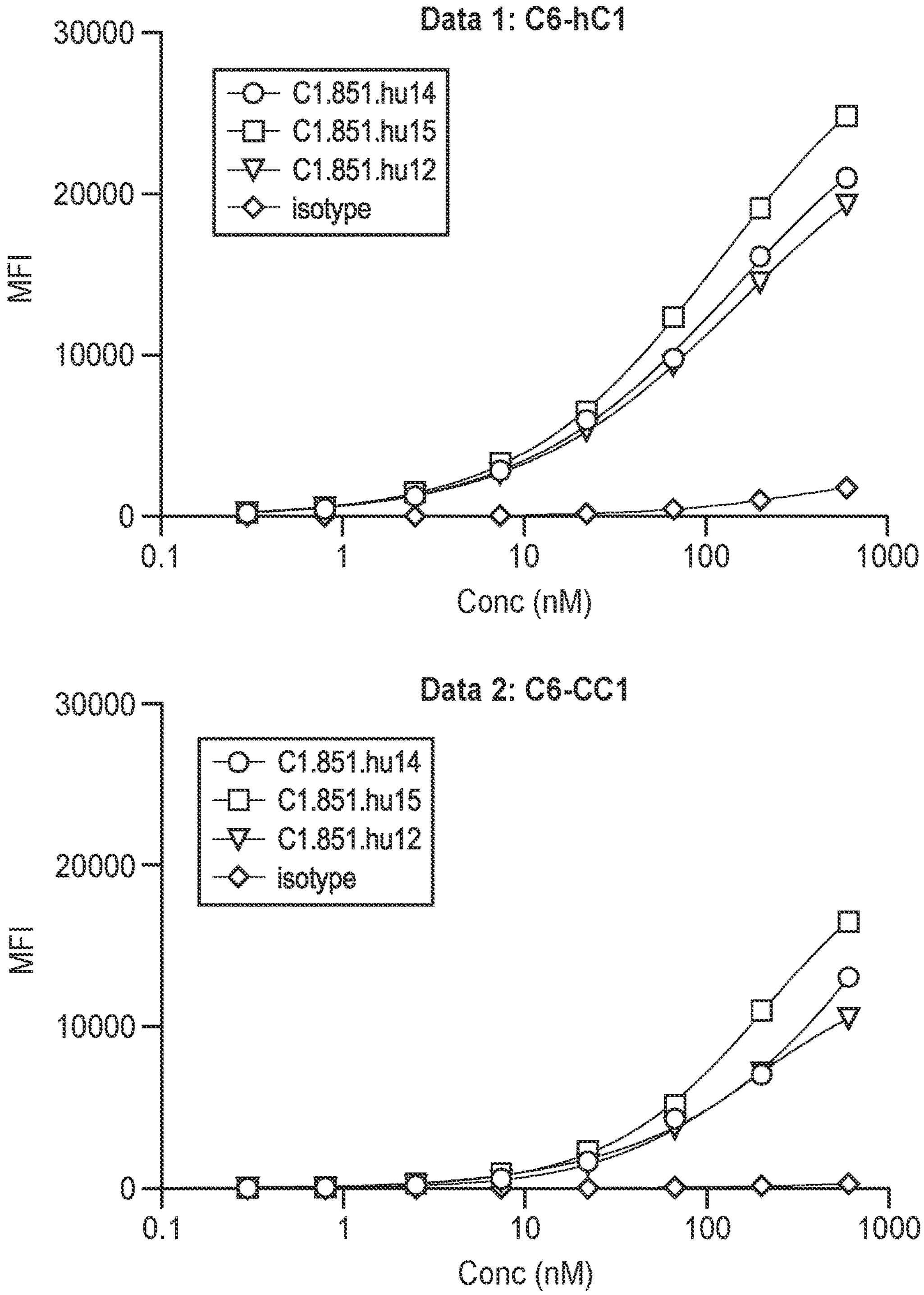
FIGS. 10A-10B show the binding of various humanized C1.851 anti-ABCC1 antibodies to human and cynomolgus ABCC1 overexpressing rat C6 glioma cell lines.
Figure 10B:
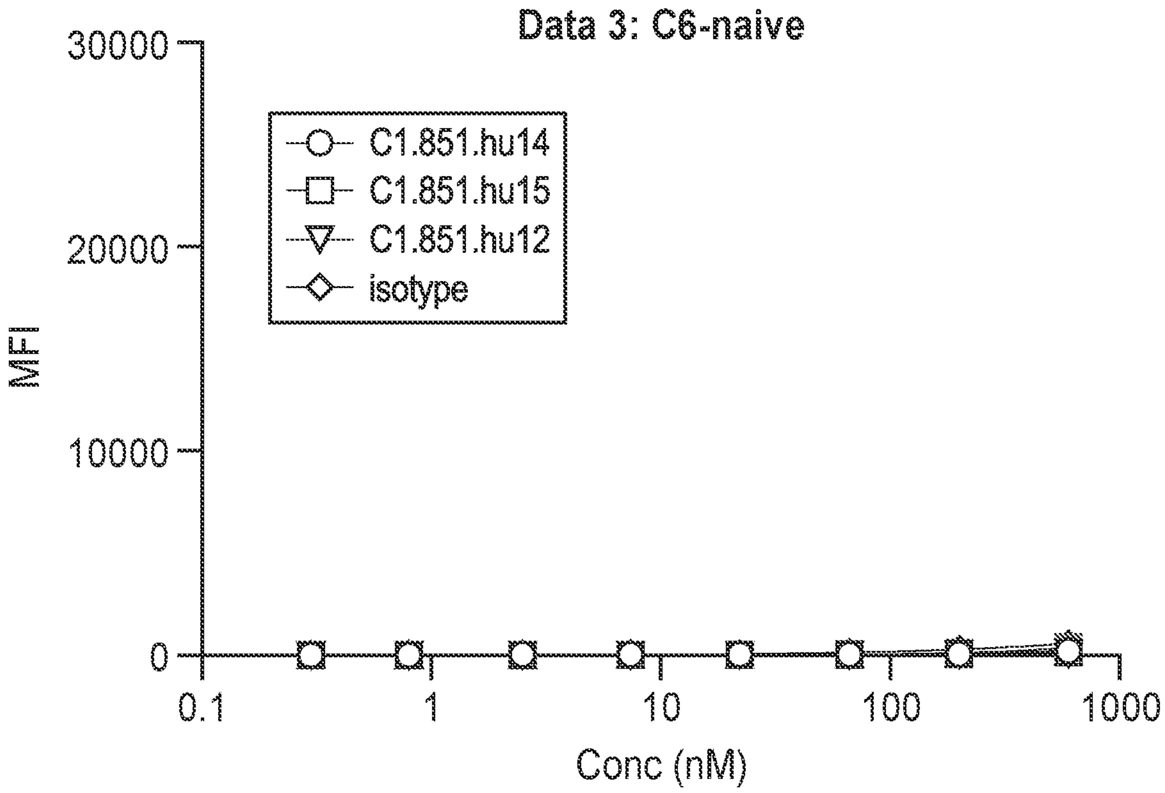

FIGS. 10A-10B show the binding of humanized anti-ABCC1 antibodies C1.851.12, C1.851.14 and C1.851.15 to human and cynomolgus ABCC1 overexpressing rat C6 glioma cell lines. All three antibodies retain the ability to bind both human and cynomolgus ABCC1.

Figure 11A:
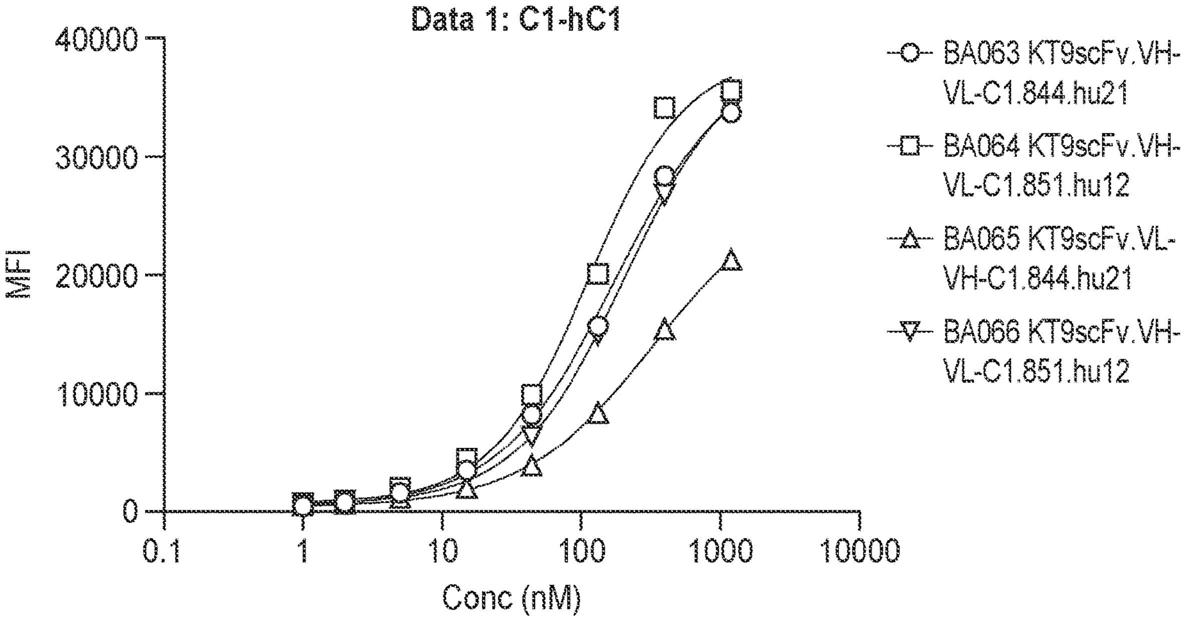
FIGS. 11A-11C present the binding of four humanized C1/KT9 bispecific antibodies to human and cynomolgus C6 cell lines, overexpressing ABCC1 and KT9, respectively. The schematic bispecific antibody structure is also shown. KT9 stands for PD-L1. The bispecific antibodies include the heavy and light chains from the indicated ABCC1 antibodies and a scFv region formed from the KT9 antibody.
Figure 11A:
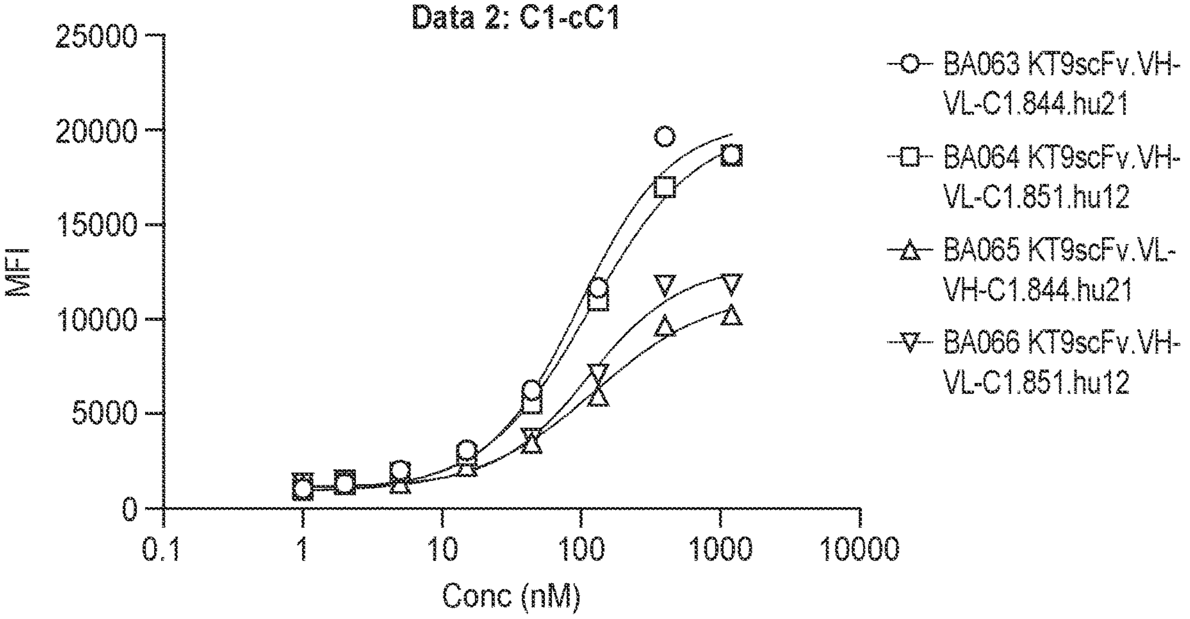
Figure 11B:
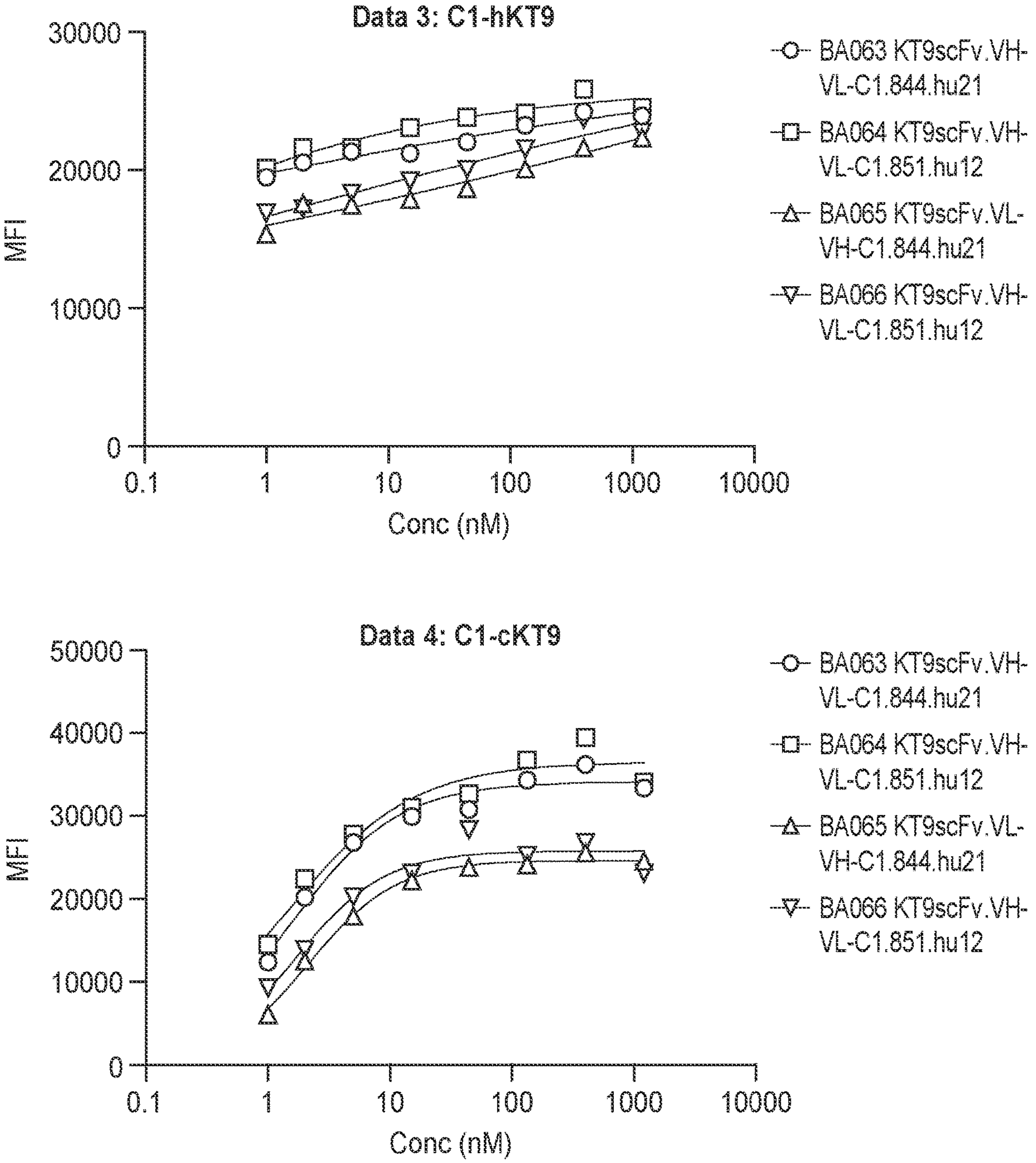
Figure 11C:
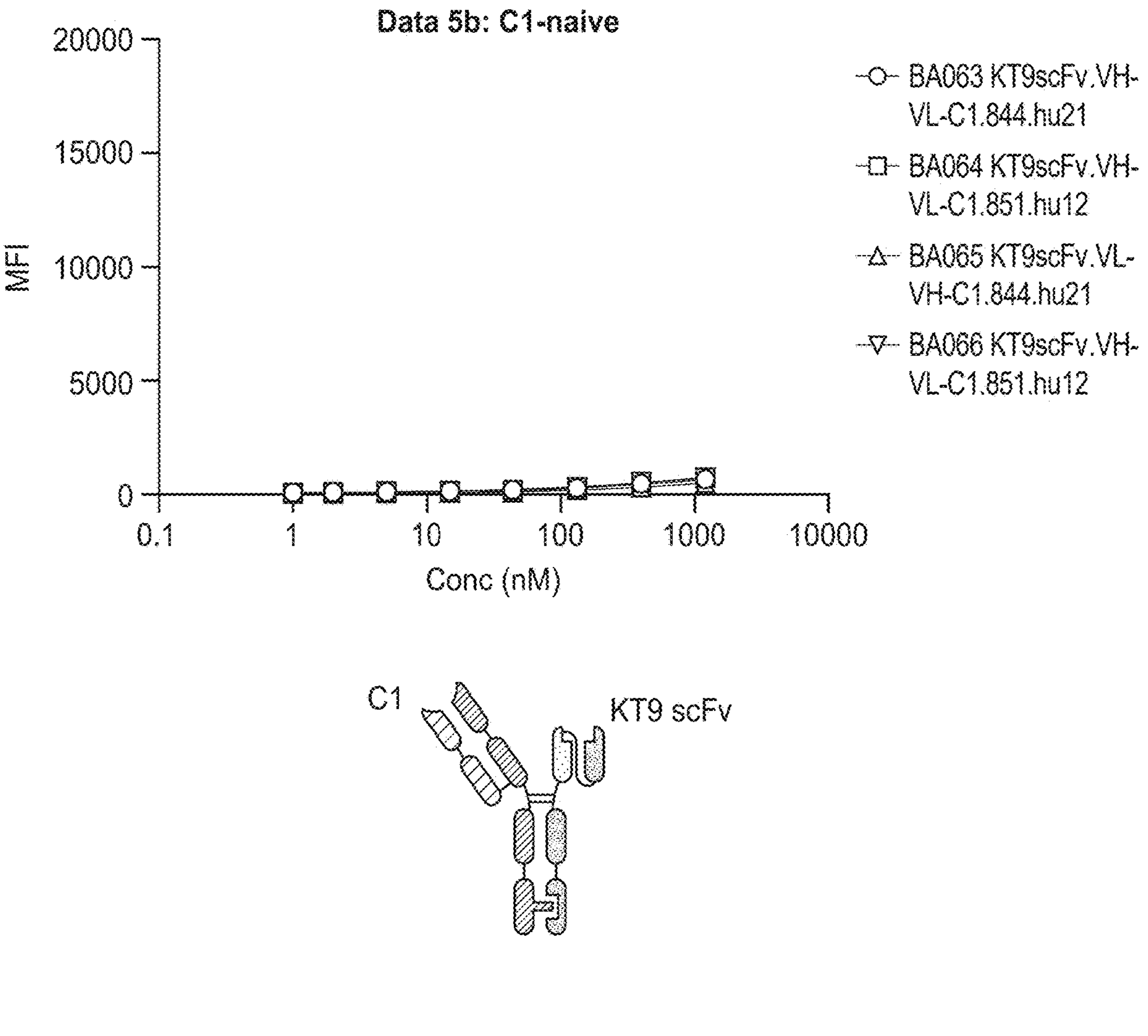

FIGS. 11A-11C present the binding of four humanized ABCC1/KT9 bispecific antibodies to human and cynomolgus C6 cell lines, overexpressing ABCC1 and KT9, respectively. The schematic bispecific antibody structure is also shown. KT9 stands for atezolizumab, an anti-PD-L1 monoclonal antibody. The bispecific antibodies include the heavy and light chains from the indicated ABCC1 antibodies and a scFv region formed from the KT9 antibody. All bispecific antibodies tested bind both C6 cells overexpressing ABCC1 and C6 cells overexpressing KT9.

Figure 12A:
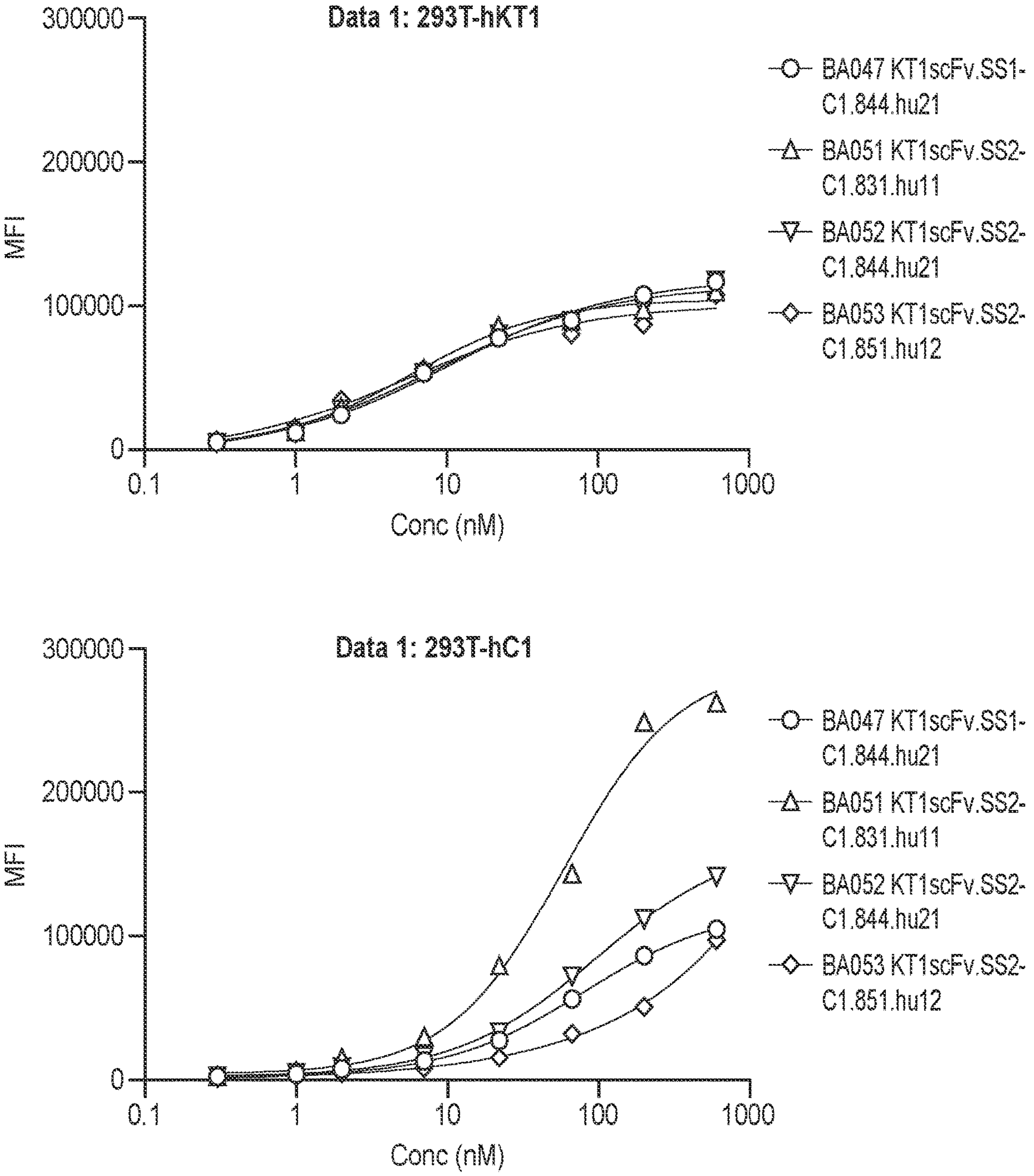
FIGS. 12A-12C present the binding of four humanized C1/KT1 bispecific antibodies to 293T cells expressing human ABCC1 and 293T cells expressing human or cynomolgus KT1, respectively. KT1 stands ErbB2. The bispecific antibodies include the heavy and light chains from the indicated anti-ABCC1 antibodies and a scFv region formed from the KT1 antibody.
Figure 12B:
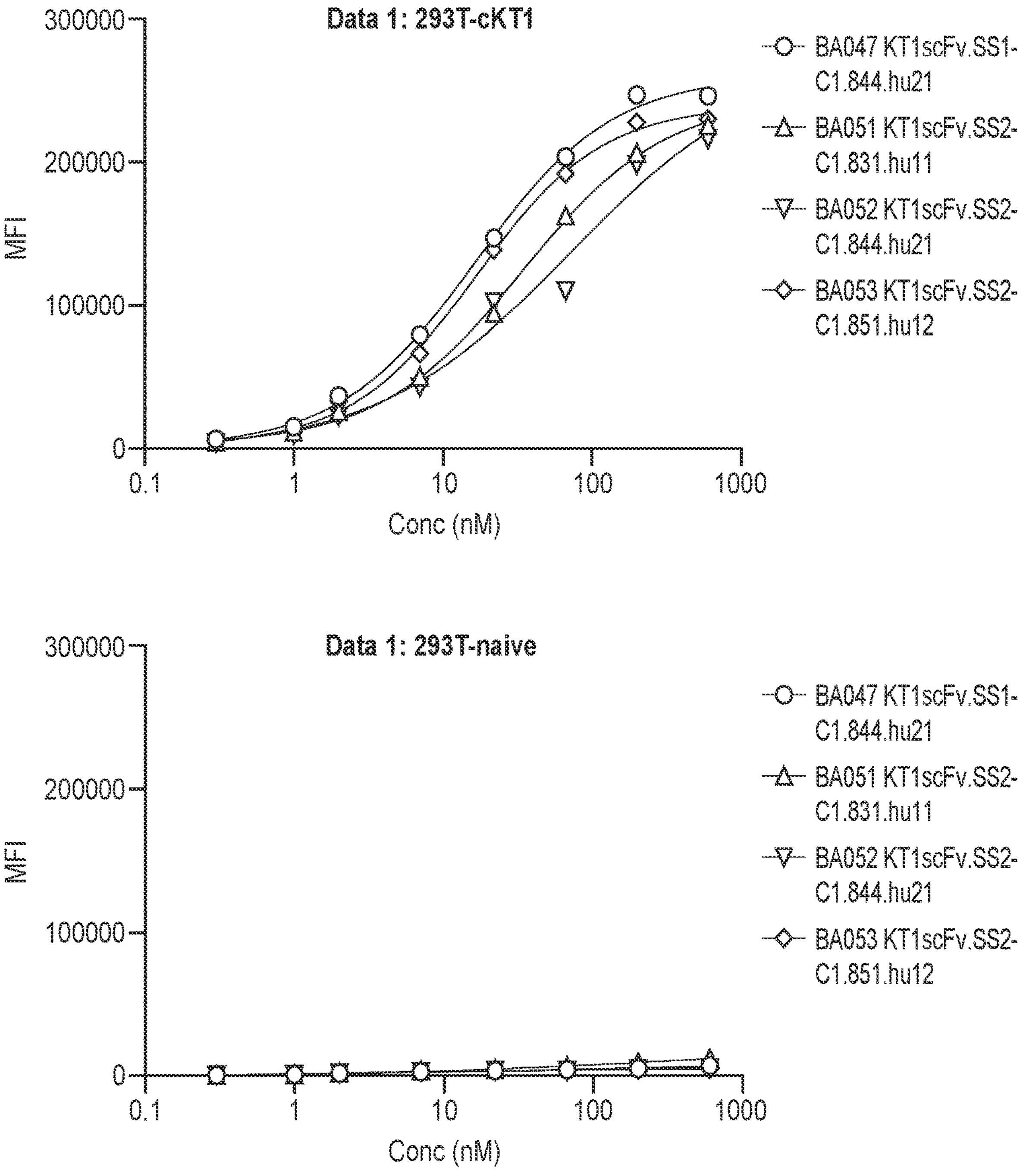
Figure 12C:
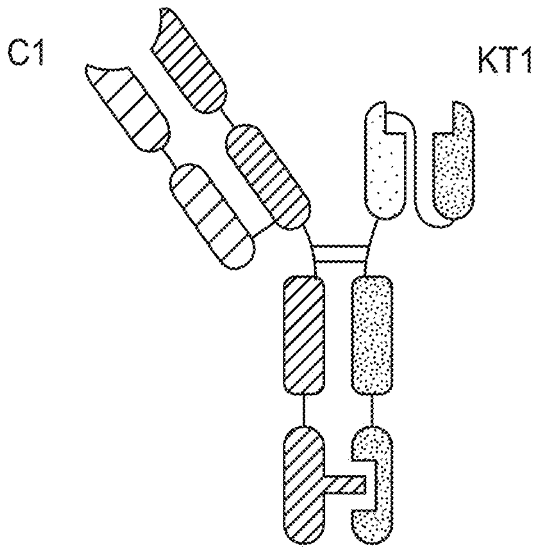
Figure 13A:
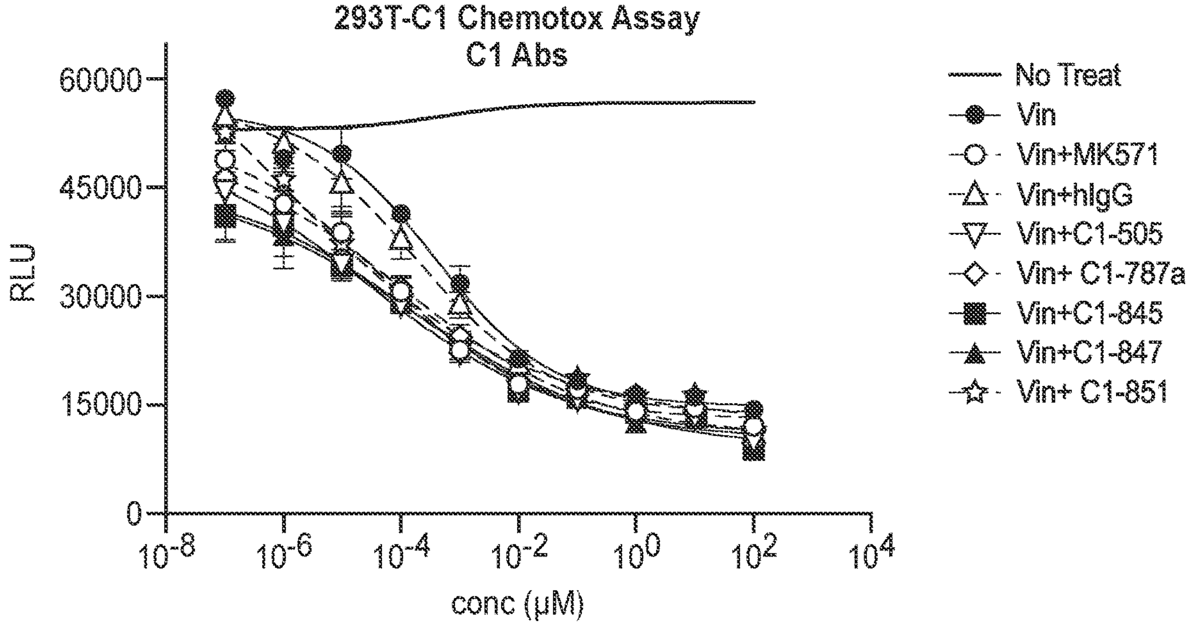
Figure 13A:
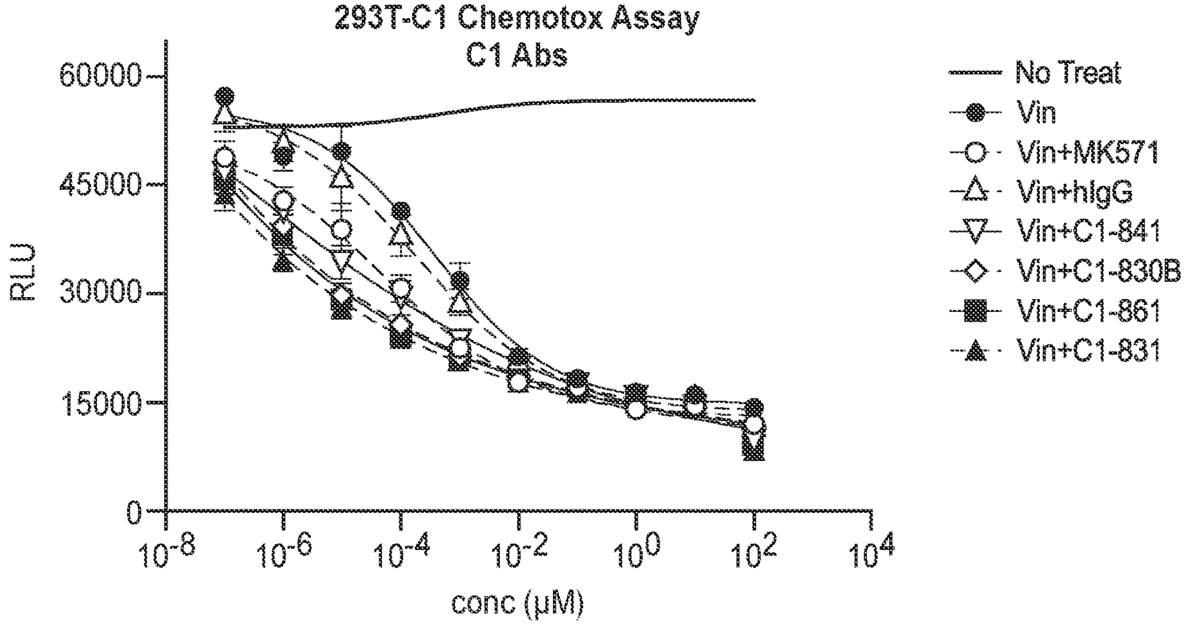
Figure 14A:
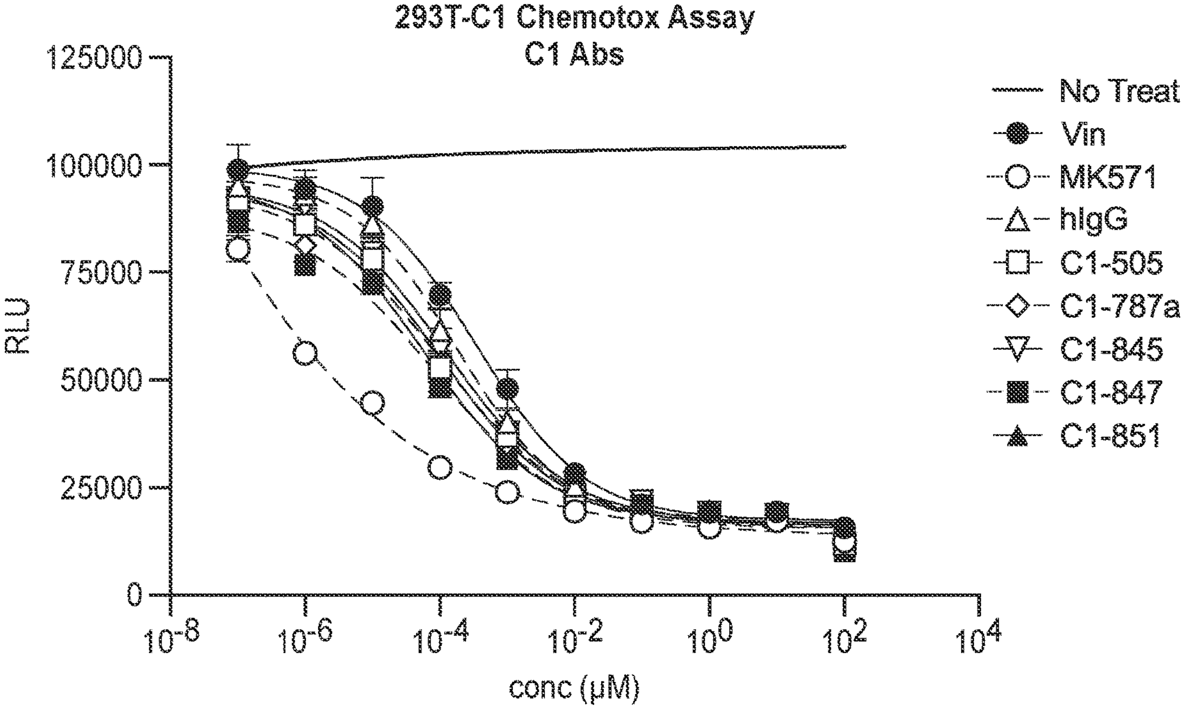
Figure 14B:
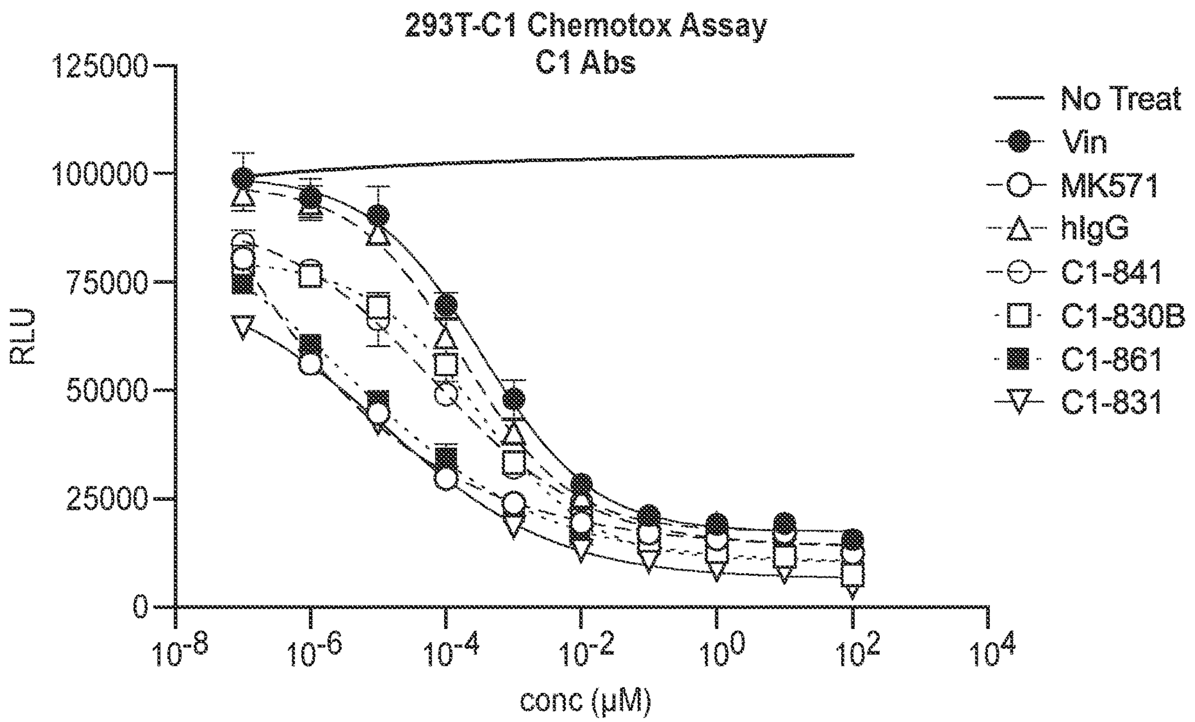
Figure 15:
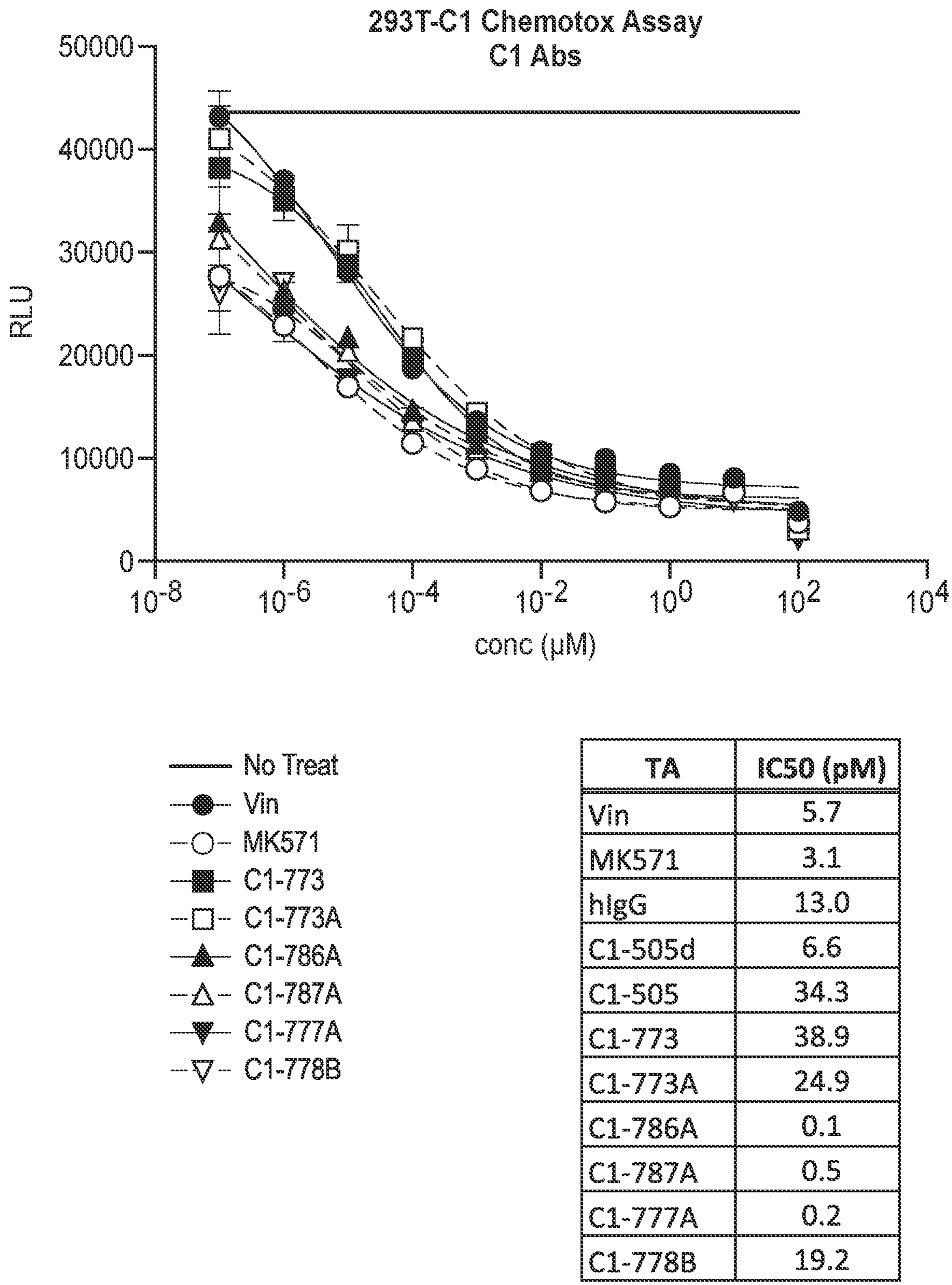

FIGS. 12A-12C present the binding of four humanized C1/KT1 bispecific antibodies to 293T cells expressing human ABCC1 and 293T cells expressing human or cynomolgus KT1, respectively. KT1 stands for trastuzumab, an anti-ErbB2 (anti-HER2) monoclonal antibody. The bispecific antibodies include the heavy and light chains from the indicated anti-ABCC1 antibodies and a scFv region formed from the KT1 antibody. The bispecific antibodies tested bind both 293T cells expressing human KT1 and 293T expressing cynomolgus KT1, and retain the ability to bind 293T cells expressing human ABCC1.

FIGS. 13A-13B, 14A-14B, and 15 show the effect of the tested anti-ABCC1 monoclonal antibodies on vincristine cytotoxicity in the 293T cytotoxicity assay. The tested anti-ABCC1 antibodies increase the cytotoxicity of vincristine in this assay. MK571 is a commercially available small molecule inhibitor of ABCC1-mediated transport.

Figure 16:
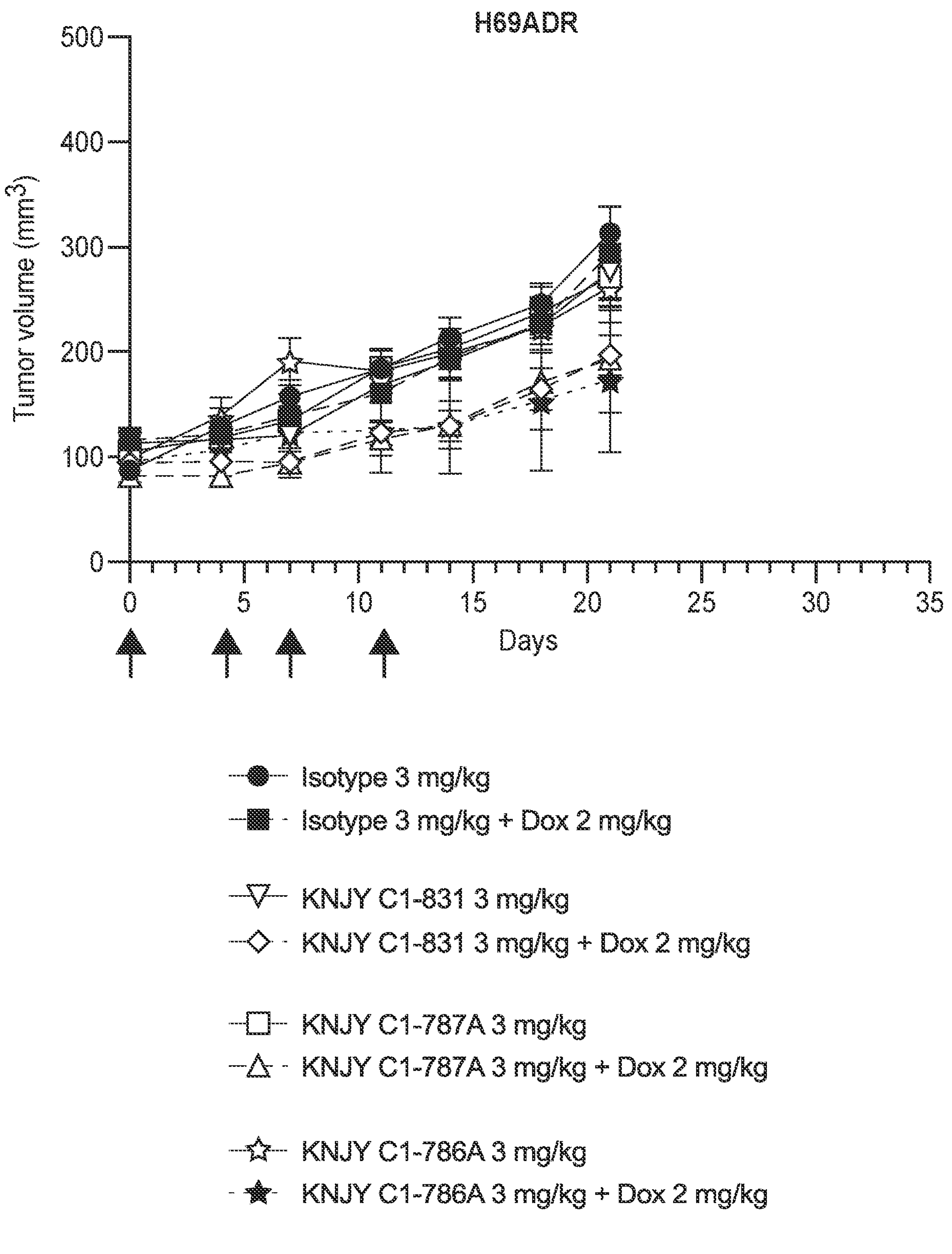
FIG. 16 shows that the three anti-ABCC1 monoclonal antibodies tested inhibit tumor growth in vivo in the H69AR cytotoxicity assay. The assay evaluates the effect of the tested antibodies on Adriamycin cytotoxicity on the H69AR cell line, which is an Adriamycin-selected, C1-positive variant of the human small cell lung cancer cell line, NCI-H69. Tumor formed from H69AR cell line is resistant to Adriamycin (Doxorubicin). All three of the anti-ABCC1 monoclonal antibodies tested sensitized the tumor to Adriamycin.

FIG. 16 shows that the three anti-ABCC1 monoclonal antibodies tested inhibit tumor growth in vivo in the H69AR cytotoxicity assay. The assay evaluates the effect of the tested antibodies on vincristine cytotoxicity on the H69AR cell line, which is an Adriamycin-selected, C1-positive variant of the human small cell lung cancer cell line, NCI-H69.

Figure 17:
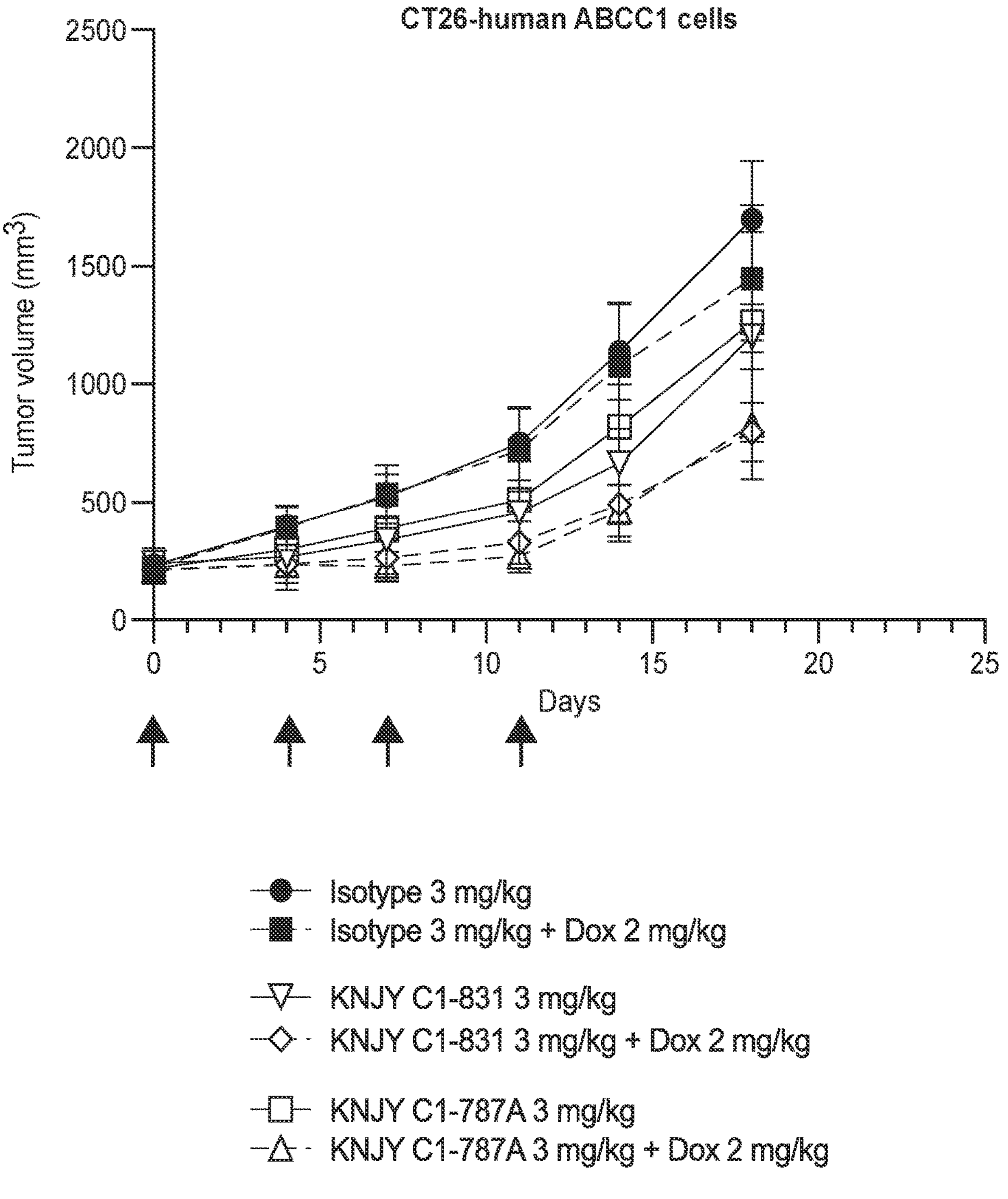
FIG. 17 shows that anti-ABCC1 monoclonal antibodies C1-831 and C1-737A inhibit tumor growth in vivo in the CT26 syngeneic mouse tumor model. The inhibition of tumor growth by these antibodies Is enhanced by doxorubicin.

FIG. 17 shows that anti-ABCC1 monoclonal antibodies C1-831 and C1-737A inhibit tumor growth in vivo in the CT26 syngeneic mouse tumor model.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. Moreover, nothing disclosed herein is intended to be dedicated to the public regardless of whether such disclosure is explicitly recited in the claims.

The scope of the present invention, therefore, is not intended to be limited to the exemplary embodiments shown and described herein. Rather, the scope and spirit of present invention is embodied by the appended claims. In the claims, 35 U.S.C. § 112(f) or 35 U.S.C. § 112(6) is expressly defined as being invoked for a limitation in the claim only when the exact phrase "means for" or the exact phrase "step for" is recited at the beginning of such limitation in the claim: if such exact phrase is not used in a limitation in the claim, then 35 U.S.C. § 112 (f) or 35 U.S.C. § 112(6) is not invoked.

What is claimed is:

1. An antibody that specifically binds to ATP Binding Cassette Subfamily C Member 1 (ABCC1) on the surface of a mammalian cell, the antibody comprising:
   - a variable heavy chain (VH) region comprising:
     - a heavy chain complementarity determining region (HCDR) 1 comprising the amino acid sequence: NNGVS (SEQ ID NO:40),
     - a HCDR 2 comprising the amino acid sequence: AIS-SGGNIYYNSAFKS (SEQ ID NO: 48), and
     - a HCDR 3 comprising the amino acid sequence: HRGYYGYNWGYFDY (SEQ ID NO: 65); and
   - a variable light chain (VL) region comprising:
     - a light chain complementarity determining region (LCDR) 1 comprising the amino acid sequence: KGSQNINNYLA (SEQ ID NO:113),
     - a LCDR 2 comprising the amino acid sequence: KTNSLQT (SEQ ID NO:126), and
     - a LCDR 3 comprising the amino acid sequence: YQYNNGYT (SEQ ID NO:142) or CQYNNGYT (SEQ ID NO:143) or YQYNQGYT (SEQ ID NO:148).

2. The antibody of claim 1, wherein the VH region comprises the amino acid sequence of SEQ ID NO:21 and the VL region comprises an amino acid sequence of SEQ ID NO:96.

3. The antibody of claim 1, wherein the VH region comprises the amino acid sequence of SEQ ID NO:27 and the VL region comprises an amino acid sequence of SEQ ID NO: 105.

4. The antibody of claim 1, wherein the antibody is humanized or is selected from the group consisting of a bispecific antibody, an lg monomer, a Fab fragment, a F (ab')2 fragment, a Fd fragment, a scFv, a scAb, a dAb, and a Fv.

5. One or more nucleic acids comprising one or more sequences encoding the antibody of claim 1 or one or more expression vectors comprising the one or more nucleic acids.

6. A host cell genetically modified with the one or more expression vectors of claim 5.

7. The host cell of claim 6, wherein the host cell is an immune effector cell comprising a chimeric antigen receptor (CAR) comprising an ABCC1 binding domain, a transmembrane domain, and an intracellular signaling domain, and wherein the ABCC1 binding domain comprises the VH region and the VL region.

8. A method of inhibiting efflux activity of ABCC1 expressed by a live cell, the method comprising contacting the cell with the antibody of claim 1.

9. The method of claim 8, wherein the cell is a cancer cell.

10. The method of claim 9, wherein the cancer cell is a multidrug resistant cancer cell.

11. The method of claim 10, wherein the cell is contacted with an inhibitor of ABCC1 mediated efflux and/or with a chemotherapy agent.

12. A bispecific antibody that binds to ATP Binding Cassette Subfamily C Member 1 (ABCC1) and to a tumor associated antigen (TAA) on the surface of a mammalian cell, the bispecific antibody comprising the VH region and the VL region of the antibody of claim 1.

13. The bispecific antibody of claim 12, wherein the VH region comprises an amino acid sequence having at least 85% identity to SEQ ID NO:27 and wherein the VL region comprises an amino acid sequence having at least 85% identity to SEQ ID NO:105.

14. The bispecific antibody of claim 12, wherein the VH region comprises the amino acid sequence of SEQ ID NO:27 and the VL region comprises an amino acid sequence of SEQ ID NO:105.

15. The bispecific antibody of claim 12, wherein the TAA is PD-L1 and the antibody comprises a VH region and a VL region of an antibody that binds to PD-L1,
   - wherein the VH region of the antibody that binds to PD-L1 comprises:
     - a HCDR 1 comprising the amino acid sequence: DSWIH (SEQ ID NO:25),
     - a HCDR 2 comprising the amino acid sequence: WISPYGGSTYYADSVKG (SEQ ID NO:169), and
     - a HCDR 3 comprising the amino acid sequence: RHWPGGFDY (SEQ ID NO:170); and
   - wherein the VL region of the antibody that binds to PD-L1 comprises:
     - a LCDR 1 comprising the amino acid sequence: RASQDVSTAVA (SEQ ID NO:171),
     - a LCDR 2 comprising the amino acid sequence: SASFLYS (SEQ ID NO:172), and
     - a LCDR 3 comprising the amino acid sequence: QQY-LYHPAT (SEQ ID NO:173).

16. The bispecific antibody of claim 15, wherein the VH region of the antibody that binds to PD-L1 comprises the amino acid sequence of SEQ ID NO:174 and wherein the VL region of the antibody that binds to PD-L1 comprises the amino acid sequence of SEQ ID NO:175.

17. The bispecific antibody of claim 14, wherein the TAA is ErbB2 and the antibody comprises a VH region and a VL region of an antibody that binds to ErbB2,
   - wherein the VH region of the antibody that binds to ErbB2 comprises:
     - HCDR 1 comprising the amino acid sequence: DTYIH (SEQ ID NO:177), HCDR 2 comprising the amino acid sequence: RIYPTNGYTRYADSVKG (SEQ ID NO:178) and HCDR 3 comprising the amino acid sequence: WGGDGFYAMDY (SEQ ID NO:179; and wherein the VL region of the antibody that binds to ErbB2 comprises:

LCDR 1 comprising the amino acid sequence: RASQDVNTAVA (SEQ ID NO:180),

LCDR 2 comprising the amino acid sequence: SASFLYS (SEQ ID NO:172), and

LCDR 3 comprising the amino acid sequence: QQHYTTPPT (SEQ ID NO:181).

18. The bispecific antibody of claim 17, wherein the VH region of the antibody that binds to ErbB2 comprises the amino acid sequence of SEQ ID NO:182 and wherein the VL region of the antibody that binds to ErbB2 comprises the amino acid sequence of SEQ ID NO:183.

19. A method of inhibiting efflux activity of ABCC1 expressed by a live cell, the method comprising contacting the cell with the bispecific antibody of claim 12.

20. The method of claim 19, wherein the cell is a cancer cell.

* * * * *

SEQUENCE LISTING

```
<160> NUMBER OF SEQ ID NOS: 184

<210> SEQ ID NO 1
<211> LENGTH: 122
<212> TYPE: PRT
<213> ORGANISM: Mus musculus

<400> SEQUENCE: 1

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Ser Tyr
            20                  25                  30

Asp Ile Thr Trp Ile Arg Gln Pro Pro Gly Lys Gly Leu Glu Trp Leu
        35                  40                  45

Gly Val Ile Trp Thr Gly Gly Gly Thr Asn Tyr Asn Ser Ala Phe Met
    50                  55                  60

Ser Arg Leu Ser Ile Ser Lys Asp Ser Ser Lys Ser Gln Val Phe Leu
65                  70                  75                  80

Lys Met Asn Ser Leu Arg Thr Asp Asp Thr Ala Ile Tyr Tyr Cys Val
```

```
                85                  90                  95

Arg Asp Leu Arg Tyr Gly Tyr Asp Gly Phe Trp Tyr Phe Asp Val Trp
            100                 105                 110

Gly Ala Gly Thr Thr Val Thr Val Ser Ser
        115                 120


<210> SEQ ID NO 2
<211> LENGTH: 122
<212> TYPE: PRT
<213> ORGANISM: Mus musculus

<400> SEQUENCE: 2

Gln Val Gln Met Lys Gln Ser Gly Pro Gly Leu Val Ala Pro Ser Gln
1               5                   10                  15

Ser Leu Ser Ile Thr Cys Thr Val Ser Gly Phe Ser Leu Thr Ser Tyr
            20                  25                  30

Asp Ile Thr Trp Ile Arg Gln Pro Pro Gly Lys Gly Leu Glu Trp Leu
        35                  40                  45

Gly Val Ile Trp Thr Gly Gly Gly Thr Asn Tyr Asn Ser Ala Phe Met
    50                  55                  60

Ser Arg Leu Ser Ile Ser Lys Asp Ser Ser Lys Ser Gln Val Phe Leu
65                  70                  75                  80

Lys Met Asn Ser Leu Arg Thr Asp Asp Thr Ala Ile Tyr Tyr Cys Val
                85                  90                  95

Arg Asp Leu Arg Tyr Gly Tyr Asp Gly Phe Trp Tyr Phe Asp Val Trp
            100                 105                 110

Gly Thr Gly Thr Thr Val Thr Val Ser Ser
        115                 120


<210> SEQ ID NO 3
<211> LENGTH: 122
<212> TYPE: PRT
<213> ORGANISM: Rattus norvegicus

<400> SEQUENCE: 3

Glu Val Glu Leu Lys Glu Ser Gly Pro Gly Leu Val Gln Pro Ser Gln
1               5                   10                  15

Thr Leu Ser Leu Thr Cys Thr Val Ser Gly Phe Ser Leu Thr Ser Asn
            20                  25                  30

Gly Val Ser Trp Val Arg Gln Pro Pro Gly Lys Gly Leu Glu Trp Ile
        35                  40                  45

Ala Ala Ile Ser Ser Gly Gly Asn Ile Tyr Tyr Asn Ser Ala Phe Lys
    50                  55                  60

Ser Arg Leu Ser Ile Ser Arg His Thr Ser Lys Ser Gln Val Leu Leu
65                  70                  75                  80

Lys Met Asn Ser Leu Gln Thr Glu Asp Thr Ala Met Tyr Phe Cys Val
                85                  90                  95

Arg His Arg Gly Tyr Tyr Gly Tyr Asn Trp Gly Tyr Phe Asp Tyr Trp
            100                 105                 110

Gly Gln Gly Ala Ser Val Thr Val Ser Ser
        115                 120


<210> SEQ ID NO 4
<211> LENGTH: 125
<212> TYPE: PRT
<213> ORGANISM: Rattus norvegicus

<400> SEQUENCE: 4
```

```
Glu Val Gln Leu Thr Glu Ser Gly Pro Gly Leu Val Gln Pro Ser Gln
1               5                   10                  15

Thr Leu Ser Leu Thr Cys Thr Val Ser Gly Phe Ser Leu Thr Ser Asn
            20                  25                  30

Gly Val Ser Trp Val Arg Leu Pro Pro Gly Lys Gly Leu Glu Trp Ile
        35                  40                  45

Ala Ala Ile Ser Ser Gly Gly Asn Ile Tyr Tyr Asn Ser Ala Leu Lys
    50                  55                  60

Ser Arg Leu Ser Ile Ser Arg Asp Thr Ser Lys Ser Gln Val Phe Leu
65                  70                  75                  80

Lys Met Asn Ser Leu Gln Thr Glu Asp Thr Ala Ile Tyr Phe Cys Thr
                85                  90                  95

Arg Glu Arg Gly Trp Asn Tyr Pro Gly Ile Thr Asn Gly Tyr Tyr Phe
            100                 105                 110

Asp Tyr Trp Gly Gln Gly Ala Ser Val Thr Val Ser Ser
        115                 120                 125


<210> SEQ ID NO 5
<211> LENGTH: 121
<212> TYPE: PRT
<213> ORGANISM: Rattus norvegicus

<400> SEQUENCE: 5

Glu Ile Gln Leu Ala Gln Ser Gly Pro Glu Leu Val Lys Pro Gly Ala
1               5                   10                  15

Ser Val Lys Met Ser Cys Lys Ala Ser Gly Tyr Ser Phe Ile Gly Tyr
            20                  25                  30

Phe Met Asn Trp Val Lys Gln Ser His Gly Lys Ser Leu Glu Trp Ile
        35                  40                  45

Gly Arg Ile Asn Pro Tyr Asn Gly Asp Thr Phe Tyr Asn Gln Lys Phe
    50                  55                  60

Lys Gly Lys Ala Thr Leu Thr Val Asp Lys Ser Ser Ser Thr Ala His
65                  70                  75                  80

Met Glu Leu Arg Ser Leu Thr Ser Glu Asp Ser Ala Leu Tyr Tyr Cys
                85                  90                  95

Thr Arg Ser Gly Trp Gly Tyr Asp Val Tyr Ser Phe Asp Tyr Trp Gly
            100                 105                 110

Gln Gly Thr Leu Val Thr Val Ser Ser
        115                 120


<210> SEQ ID NO 6
<211> LENGTH: 122
<212> TYPE: PRT
<213> ORGANISM: Rattus norvegicus

<400> SEQUENCE: 6

Glu Val Gln Leu Lys Glu Ser Gly Pro Gly Leu Val Gln Pro Ser Gln
1               5                   10                  15

Thr Leu Ser Leu Thr Cys Thr Val Ser Gly Phe Ser Leu Thr Ser Asn
            20                  25                  30

Gly Val Ser Trp Val Arg Gln Pro Pro Gly Lys Gly Leu Glu Trp Ile
        35                  40                  45

Ala Ala Ile Ser Ser Gly Gly Ser Ile Tyr Tyr Asn Ser Ala Phe Lys
    50                  55                  60

Ser Arg Leu Ser Ile Ser Arg His Thr Ser Lys Ser Gln Val Leu Leu
65                  70                  75                  80
```

```
Lys Met Asn Ser Leu Gln Thr Glu Asp Thr Ala Met Tyr Phe Cys Ala
                85                  90                  95

Arg His Arg Gly Tyr Tyr Gly Tyr Asn Trp Gly Tyr Phe Asp Tyr Trp
            100                 105                 110

Gly Gln Gly Ala Ser Val Thr Val Ser Ser
        115                 120


<210> SEQ ID NO 7
<211> LENGTH: 122
<212> TYPE: PRT
<213> ORGANISM: Rattus norvegicus

<400> SEQUENCE: 7

Glu Val Gln Leu Val Glu Ser Gly Pro Gly Leu Val Gln Pro Ser Gln
1               5                   10                  15

Thr Leu Ser Leu Thr Cys Thr Val Ser Gly Phe Ser Leu Thr Asn Asn
            20                  25                  30

Gly Val Ser Trp Val Arg Gln Pro Pro Gly Lys Gly Leu Glu Trp Ile
        35                  40                  45

Ala Ala Ile Ser Ser Gly Gly Ser Ile Tyr Tyr Asn Leu Ala Phe Lys
    50                  55                  60

Ser Arg Leu Ser Ile Ser Arg Asn Thr Ser Lys Gly His Val Leu Leu
65                  70                  75                  80

Lys Met Asn Ser Leu Gln Thr Glu Asp Thr Ala Met Tyr Phe Cys Val
                85                  90                  95

Arg His Arg Gly Tyr Tyr Gly Phe Asn Trp Gly Tyr Phe Asp Tyr Trp
            100                 105                 110

Gly Gln Gly Val Met Val Thr Val Ser Ser
        115                 120


<210> SEQ ID NO 8
<211> LENGTH: 122
<212> TYPE: PRT
<213> ORGANISM: Rattus norvegicus

<400> SEQUENCE: 8

Glu Val Gln Arg Lys Glu Ser Gly Pro Gly Leu Val Gln Pro Ser Gln
1               5                   10                  15

Thr Leu Ser Leu Thr Cys Thr Val Ser Gly Phe Ser Leu Thr Asn Asn
            20                  25                  30

Gly Val Ser Trp Val Arg Gln Pro Pro Gly Lys Gly Leu Glu Trp Ile
        35                  40                  45

Ala Ala Ile Ser Ser Gly Gly Ser Ile Tyr Tyr Asn Ser Ala Phe Lys
    50                  55                  60

Ser Arg Leu Ser Ile Ser Arg Ile Thr Ser Lys Ser Gln Val Leu Leu
65                  70                  75                  80

Lys Met Asn Ser Leu Gln Thr Glu Asp Thr Ala Met Tyr Phe Cys Ala
                85                  90                  95

Arg His Arg Gly Tyr Tyr Gly Tyr Asn Trp Gly Tyr Phe Asp Tyr Trp
            100                 105                 110

Gly Gln Gly Val Met Val Thr Val Ser Ser
        115                 120


<210> SEQ ID NO 9
<211> LENGTH: 122
<212> TYPE: PRT
<213> ORGANISM: Rattus norvegicus
```

<400> SEQUENCE: 9

```
Glu Val Lys Leu Glu Glu Ser Gly Pro Gly Leu Val Gln Pro Ser Gln
1               5                   10                  15

Thr Leu Ser Leu Thr Cys Thr Val Ser Gly Phe Ser Leu Thr Asn Asn
            20                  25                  30

Gly Val Ser Trp Val Arg Gln Pro Pro Gly Lys Gly Leu Glu Trp Ile
        35                  40                  45

Ala Ala Met Ser Ser Gly Gly Asn Ile Tyr Tyr Asn Ser Ala Phe Lys
    50                  55                  60

Ser Arg Leu Ser Ile Ser Arg Asp Thr Ser Lys Ser Gln Val Leu Leu
65                  70                  75                  80

Lys Met Ser Ser Leu Gln Thr Glu Asp Thr Ala Met Tyr Phe Cys Gly
                85                  90                  95

Arg His Arg Gly Tyr Tyr Trp Tyr Asn Trp Gly Phe Phe Asp Tyr Trp
            100                 105                 110

Gly Gln Gly Ala Ser Val Thr Val Ser Ser
        115                 120
```

<210> SEQ ID NO 10
<211> LENGTH: 123
<212> TYPE: PRT
<213> ORGANISM: Rattus norvegicus

<400> SEQUENCE: 10

```
Glu Val Gln Leu Thr Glu Ser Gly Leu Gly Leu Val Gln Pro Ser Gln
1               5                   10                  15

Thr Leu Ser Leu Thr Cys Ser Val Ser Gly Phe Ser Leu Thr Ser Tyr
            20                  25                  30

Asn Val His Trp Val Arg Gln Pro Thr Gly Lys Gly Leu Glu Trp Met
        35                  40                  45

Gly Val Ile Trp Thr Gly Gly Tyr Thr Asp Ser Asn Ser Pro Leu Lys
    50                  55                  60

Ser Arg Leu Ser Ile Thr Arg Asp Thr Ser Lys Ser Gln Val Phe Leu
65                  70                  75                  80

Lys Met Asn Ser Leu Gln Ser Glu Asp Ile Ala Thr Tyr Tyr Cys Ala
                85                  90                  95

Arg Glu Arg His Thr Met Gly Ile Thr Lys Ser Trp Tyr Phe Asp Tyr
            100                 105                 110

Trp Gly Gln Gly Val Met Val Thr Val Ser Ser
        115                 120
```

<210> SEQ ID NO 11
<211> LENGTH: 122
<212> TYPE: PRT
<213> ORGANISM: Rattus norvegicus

<400> SEQUENCE: 11

```
Glu Val Gln Leu Thr Glu Ser Gly Pro Gly Leu Val Gln Pro Ser Gln
1               5                   10                  15

Thr Leu Ser Leu Thr Cys Thr Val Ser Gly Phe Ser Leu Thr Ser Asn
            20                  25                  30

Gly Val Ser Trp Val Arg Gln Pro Pro Gly Lys Gly Leu Glu Trp Ile
        35                  40                  45

Ala Ala Ile Ser Ser Gly Gly Ser Thr Tyr Tyr Asn Ser Ala Phe Lys
    50                  55                  60
```

```
Ser Arg Leu Ser Ile Ser Arg His Thr Ser Lys Ser Gln Val Leu Leu
65                  70                  75                  80

Asn Met Asn Ser Leu Gln Thr Glu Asp Thr Ala Met Tyr Phe Cys Ala
                85                  90                  95

Arg His Arg Gly Tyr Tyr Trp Ser Asn Trp Gly Tyr Phe Asp Tyr Trp
            100                 105                 110

Gly Gln Gly Val Met Val Thr Val Ser Ser
        115                 120


<210> SEQ ID NO 12
<211> LENGTH: 120
<212> TYPE: PRT
<213> ORGANISM: Rattus norvegicus

<400> SEQUENCE: 12

Glu Val Lys Leu Leu Glu Ser Gly Pro Gly Leu Val Gln Pro Ser Gln
1               5                   10                  15

Thr Leu Ser Leu Thr Cys Thr Val Ser Gly Phe Ser Leu Thr Ser Asn
            20                  25                  30

Gly Val Ile Trp Val Arg Gln Pro Pro Gly Lys Gly Leu Glu Trp Ile
        35                  40                  45

Ala Ala Ile Ser Ser Gly Gly Asn Ile Tyr Tyr Asn Ser Gly Leu Lys
    50                  55                  60

Ser Arg Leu Gly Ile Ser Arg Asp Thr Ser Lys Ser Gln Val Phe Leu
65                  70                  75                  80

Lys Met Asn Ser Leu Gln Thr Glu Asp Thr Ala Ile Tyr Phe Cys Thr
                85                  90                  95

Arg Ala Arg Gly Thr Thr Thr Ala Tyr Phe Met Asp Ala Trp Gly Gln
            100                 105                 110

Gly Ala Ser Val Thr Val Ser Ser
        115                 120


<210> SEQ ID NO 13
<211> LENGTH: 125
<212> TYPE: PRT
<213> ORGANISM: Rattus norvegicus

<400> SEQUENCE: 13

Glu Val Gln Leu Thr Glu Ser Gly Pro Gly Leu Val Gln Pro Ser Gln
1               5                   10                  15

Thr Leu Ser Leu Thr Cys Thr Val Ser Gly Phe Ser Leu Thr Ser Asn
            20                  25                  30

Gly Val Ser Trp Val Arg Leu Pro Pro Gly Lys Gly Leu Glu Trp Ile
        35                  40                  45

Ala Ala Ile Ser Ser Gly Gly Asn Ile Tyr Tyr Asn Ser Ala Leu Lys
    50                  55                  60

Ser Arg Leu Ser Ile Ser Arg Asp Thr Ser Lys Ser Gln Val Phe Leu
65                  70                  75                  80

Lys Met Asn Ser Leu Gln Thr Glu Asp Thr Ala Ile Tyr Phe Cys Thr
                85                  90                  95

Arg Glu Arg Gly Trp Asn Tyr Pro Gly Ile Thr Asn Gly Tyr Tyr Phe
            100                 105                 110

Asp Tyr Trp Gly Gln Gly Thr Ser Val Thr Val Ser Ser
        115                 120                 125


<210> SEQ ID NO 14
<211> LENGTH: 122
```

```
<212> TYPE: PRT
<213> ORGANISM: Rattus norvegicus

<400> SEQUENCE: 14

Glu Val Gln Leu Val Glu Ser Gly Pro Gly Leu Val Gln Pro Ser Gln
1               5                   10                  15

Thr Leu Ser Leu Thr Cys Thr Val Ser Gly Phe Ser Leu Thr Asn Asn
            20                  25                  30

Gly Val Ser Trp Val Arg Gln Pro Pro Gly Lys Gly Leu Glu Trp Ile
        35                  40                  45

Ala Ala Ile Ser Asn Gly Gly Asn Ile Tyr His Asn Ser Ala Leu Lys
    50                  55                  60

Ser Arg Leu Ser Ile Ser Arg Asn Thr Ala Lys Ser Gln Val Leu Leu
65                  70                  75                  80

Lys Met Asn Ser Leu Gln Thr Glu Asp Thr Ala Met Tyr Phe Cys Ala
                85                  90                  95

Arg His Arg Gly Tyr Tyr Gly Tyr Asn Trp Gly Tyr Phe Asp Tyr Trp
            100                 105                 110

Gly Gln Gly Ala Ser Val Thr Val Ser Ser
        115                 120


<210> SEQ ID NO 15
<211> LENGTH: 123
<212> TYPE: PRT
<213> ORGANISM: Rattus norvegicus

<400> SEQUENCE: 15

Glu Val Gln Leu Lys Glu Ser Gly Pro Gly Leu Val Arg Pro Ser Gln
1               5                   10                  15

Thr Leu Ser Leu Thr Cys Ser Val Ser Gly Phe Ser Leu Thr Asn Tyr
            20                  25                  30

Asn Val His Trp Val Arg Gln Pro Thr Gly Lys Gly Leu Glu Trp Met
        35                  40                  45

Gly Ile Ile Trp Thr Gly Gly Tyr Thr Asp Tyr Asn Ser Asp Leu Lys
    50                  55                  60

Ser Arg Leu Ser Ile Thr Arg Asp Thr Ser Lys Ser Gln Val Phe Leu
65                  70                  75                  80

Lys Met Asn Gly Leu Gln Thr Glu Asp Val Ala Thr Tyr Tyr Cys Ala
                85                  90                  95

Arg Glu Arg His Thr Met Gly Ile Thr Lys Ser Trp Tyr Phe Asp Tyr
            100                 105                 110

Trp Gly Gln Gly Ala Ser Val Thr Val Ser Ser
        115                 120


<210> SEQ ID NO 16
<211> LENGTH: 125
<212> TYPE: PRT
<213> ORGANISM: Rattus norvegicus

<400> SEQUENCE: 16

Glu Val Gln Leu Thr Glu Ser Gly Pro Gly Leu Val Gln Pro Ser Gln
1               5                   10                  15

Thr Leu Ser Leu Thr Cys Thr Val Ser Gly Phe Ser Leu Thr Ser Asn
            20                  25                  30

Gly Val Ser Trp Val Arg Gln Pro Pro Gly Lys Gly Leu Glu Trp Ile
        35                  40                  45

Ala Ala Ile Ser Ser Gly Gly Asn Ile Tyr Tyr Asn Ser Val Leu Lys
```

```
    50                  55                  60

Ser Arg Leu Ser Ile Ser Arg Asp Thr Ser Lys Ser Gln Val Phe Leu
65                  70                  75                  80

Lys Met Ser Ser Val Gln Thr Glu Asp Thr Ala Ile Tyr Phe Cys Thr
                85                  90                  95

Arg Glu Arg Gly Trp Asn Tyr Pro Phe Ile Thr Asn Gly Tyr Tyr Phe
            100                 105                 110

Asp Tyr Trp Gly Gln Gly Val Met Val Thr Val Ser Ser
        115                 120                 125


<210> SEQ ID NO 17
<211> LENGTH: 122
<212> TYPE: PRT
<213> ORGANISM: Rattus norvegicus

<400> SEQUENCE: 17

Glu Val Gln Leu Leu Glu Ser Gly Pro Gly Leu Val Gln Pro Ser Gln
1               5                   10                  15

Thr Leu Ser Leu Thr Cys Thr Val Ser Gly Phe Ser Leu Thr Asn Asn
            20                  25                  30

Gly Val Ser Trp Val Arg Gln Pro Pro Gly Lys Gly Leu Glu Trp Val
        35                  40                  45

Ala Ala Met Ser Ser Gly Gly Asn Ile Tyr Tyr Asn Ser Ala Phe Lys
    50                  55                  60

Ser Arg Leu Ser Ile Ser Arg His Thr Ser Lys Ser Gln Val Leu Leu
65                  70                  75                  80

Lys Met Asn Ser Leu Gln Thr Glu Asp Thr Ala Met Tyr Phe Cys Ala
                85                  90                  95

Arg His Arg Gly Tyr Tyr Gly Tyr Asn Trp Gly Tyr Phe Asp Tyr Trp
            100                 105                 110

Gly Gln Gly Val Met Val Thr Val Ser Ser
        115                 120


<210> SEQ ID NO 18
<211> LENGTH: 120
<212> TYPE: PRT
<213> ORGANISM: Rattus norvegicus

<400> SEQUENCE: 18

Glu Val Gln Leu Lys Glu Ser Gly Pro Gly Leu Val Gln Pro Ser Gln
1               5                   10                  15

Thr Leu Ser Leu Thr Cys Thr Val Ser Gly Phe Ser Leu Thr Ser Asn
            20                  25                  30

Gly Val Ile Trp Val Arg Gln Pro Pro Gly Lys Gly Leu Glu Trp Ile
        35                  40                  45

Ala Ala Ile Ser Ser Gly Gly Asn Ile Tyr Tyr Asn Ser Gly Leu Lys
    50                  55                  60

Ser Arg Leu Gly Ile Ser Arg Asp Thr Ser Lys Ser Gln Val Phe Leu
65                  70                  75                  80

Lys Met Asn Ser Leu Gln Thr Glu Asp Thr Ala Ile Tyr Phe Cys Thr
                85                  90                  95

Arg Ala Arg Gly Thr Thr Thr Ala Tyr Val Met Asp Ala Trp Gly Gln
            100                 105                 110

Gly Ala Ser Val Thr Val Ser Ser
        115                 120
```

<210> SEQ ID NO 19
<211> LENGTH: 122
<212> TYPE: PRT
<213> ORGANISM: Rattus norvegicus

<400> SEQUENCE: 19

```
Glu Val Gln Leu Val Glu Ser Gly Pro Gly Leu Val Gln Pro Ser Gln
1               5                   10                  15

Thr Leu Ser Leu Thr Cys Thr Val Ser Gly Phe Ser Leu Thr Asn Asn
            20                  25                  30

Gly Val Ser Trp Val Arg Gln Pro Pro Gly Lys Gly Leu Glu Trp Ile
        35                  40                  45

Ala Ala Ile Ser Ser Gly Gly Ser Ile Tyr Tyr Asn Leu Ala Phe Lys
    50                  55                  60

Ser Arg Leu Ser Ile Ser Arg Asn Thr Ser Lys Gly Gln Val Leu Leu
65                  70                  75                  80

Lys Met Asn Ser Leu Gln Thr Glu Asp Thr Ala Met Tyr Phe Cys Ala
                85                  90                  95

Arg His Arg Gly Tyr Tyr Gly Tyr Asn Trp Gly Tyr Phe Asp Tyr Trp
            100                 105                 110

Gly Gln Gly Ala Ser Val Thr Val Ser Ser
        115                 120
```

<210> SEQ ID NO 20
<211> LENGTH: 122
<212> TYPE: PRT
<213> ORGANISM: Rattus norvegicus

<400> SEQUENCE: 20

```
Glu Val Gln Leu Lys Glu Ser Gly Pro Gly Leu Val Gln Pro Ser Gln
1               5                   10                  15

Thr Leu Ser Leu Thr Cys Thr Val Ser Gly Phe Ser Leu Thr Asn Asn
            20                  25                  30

Gly Val Ser Trp Val Arg Gln Pro Pro Gly Lys Gly Leu Glu Trp Ile
        35                  40                  45

Ala Ala Ile Ser Ser Gly Gly Asn Ile Tyr His Asn Ser Ala Leu Lys
    50                  55                  60

Ser Arg Leu Ser Ile Ser Arg Asn Thr Ala Gln Ser Gln Val Leu Leu
65                  70                  75                  80

Lys Met Asn Ser Leu Gln Thr Glu Asp Thr Ala Met Tyr Phe Cys Ala
                85                  90                  95

Arg His Arg Gly Tyr Tyr Gly Tyr Asn Trp Gly Tyr Phe Asp Tyr Trp
            100                 105                 110

Gly Gln Gly Thr Leu Val Thr Val Ser Ser
        115                 120
```

<210> SEQ ID NO 21
<211> LENGTH: 122
<212> TYPE: PRT
<213> ORGANISM: Rattus norvegicus

<400> SEQUENCE: 21

```
Glu Val Gln Leu Lys Glu Ser Gly Pro Gly Leu Val Gln Pro Ser Gln
1               5                   10                  15

Thr Leu Ser Leu Thr Cys Thr Val Ser Gly Phe Ser Leu Thr Asn Asn
            20                  25                  30

Gly Val Ser Trp Ile Arg Gln Pro Pro Gly Lys Gly Leu Glu Trp Ile
        35                  40                  45
```

```
Ala Ala Ile Ser Ser Gly Gly Asn Ile Tyr Tyr Asn Ser Ala Phe Lys
    50                  55                  60

Ser Arg Leu Ser Ile Ser Arg Asn Thr Ser Lys Arg Gln Val Leu Leu
65                  70                  75                  80

Lys Met Asn Ser Leu Gln Thr Glu Asp Thr Ala Met Tyr Phe Cys Ala
                85                  90                  95

Arg His Arg Gly Tyr Tyr Gly Tyr Asn Trp Gly Tyr Phe Asp Tyr Trp
            100                 105                 110

Gly Gln Gly Ala Ser Val Thr Val Ser Ser
        115                 120


<210> SEQ ID NO 22
<211> LENGTH: 122
<212> TYPE: PRT
<213> ORGANISM: Rattus norvegicus

<400> SEQUENCE: 22

Glu Val Gln Leu Lys Glu Ser Gly Pro Gly Leu Val Gln Pro Ser Gln
1               5                   10                  15

Thr Leu Ser Leu Thr Cys Thr Val Ser Gly Phe Ser Leu Thr Ser Asn
            20                  25                  30

Gly Val Ser Trp Val Arg Gln Pro Pro Gly Lys Gly Leu Glu Trp Ile
        35                  40                  45

Ala Ala Ile Ser Asn Gly Gly Asn Ile Tyr Tyr Asn Ser Ala Phe Lys
    50                  55                  60

Ser Arg Leu Ser Ile Ser Arg His Thr Ser Lys Ser Gln Val Leu Leu
65                  70                  75                  80

Lys Met Asn Ser Leu Gln Thr Glu Asp Thr Ala Met Tyr Phe Cys Ala
                85                  90                  95

Arg His Arg Gly Tyr Tyr Gly Tyr Asn Trp Gly Tyr Phe Asp Tyr Trp
            100                 105                 110

Gly Gln Gly Ala Ser Val Thr Val Ser Ser
        115                 120


<210> SEQ ID NO 23
<211> LENGTH: 120
<212> TYPE: PRT
<213> ORGANISM: Rattus norvegicus

<400> SEQUENCE: 23

Glu Val Gln Leu Lys Glu Ser Gly Pro Gly Leu Val Gln Pro Ser Gln
1               5                   10                  15

Thr Leu Ser Leu Thr Cys Thr Val Ser Gly Phe Ser Leu Thr Ser Asn
            20                  25                  30

Gly Val Thr Trp Val Arg Gln Pro Pro Gly Lys Gly Leu Glu Trp Ile
        35                  40                  45

Ala Ala Ile Ser Ser Gly Gly Asn Ile Tyr Tyr Asn Ser Ala Val Lys
    50                  55                  60

Ser Arg Leu Ser Ile Ser Arg Asp Thr Ser Lys Ser Gln Val Phe Leu
65                  70                  75                  80

Lys Met Asn Ser Leu Gln Thr Glu Asp Thr Ala Ile Tyr Phe Cys Thr
                85                  90                  95

Arg Ala Arg Gly Thr Thr Thr Ala Tyr Val Met Asp Ala Trp Gly Gln
            100                 105                 110

Gly Ala Ser Val Thr Val Ser Ser
        115                 120
```

<210> SEQ ID NO 24
<211> LENGTH: 122
<212> TYPE: PRT
<213> ORGANISM: Rattus norvegicus

<400> SEQUENCE: 24

```
Gln Val Gln Leu Lys Glu Ser Gly Pro Gly Leu Val Gln Pro Ser Gln
1               5                   10                  15

Thr Leu Ser Leu Thr Cys Thr Val Ser Gly Phe Ser Leu Thr Asn Asn
            20                  25                  30

Gly Val Ser Trp Val Arg Gln Pro Pro Gly Lys Gly Leu Glu Trp Ile
        35                  40                  45

Ala Ala Met Ser Ser Gly Gly Ser Ile Tyr Tyr Asn Ser Ala Phe Lys
    50                  55                  60

Ser Arg Leu Ser Ile Ser Arg His Thr Ser Lys Ser Gln Val Leu Leu
65                  70                  75                  80

Gln Met Asn Ser Leu Gln Thr Glu Asp Thr Ala Met Tyr Phe Cys Thr
                85                  90                  95

Arg His Arg Gly Tyr Tyr Gly Tyr Asn Trp Gly Tyr Phe Asp Tyr Trp
            100                 105                 110

Gly Gln Gly Val Met Val Thr Val Ser Ser
        115                 120
```

<210> SEQ ID NO 25
<211> LENGTH: 5
<212> TYPE: PRT
<213> ORGANISM: Rattus norvegicus

<400> SEQUENCE: 25

```
Asp Ser Trp Ile His
1               5
```

<210> SEQ ID NO 26
<211> LENGTH: 123
<212> TYPE: PRT
<213> ORGANISM: Artificial sequence
<220> FEATURE:
<223> OTHER INFORMATION: humanized sequence

<400> SEQUENCE: 26

```
Glu Val Gln Leu Gln Glu Ser Gly Pro Gly Leu Val Lys Pro Ser Gln
1               5                   10                  15

Thr Leu Ser Leu Thr Cys Ala Val Tyr Gly Phe Ser Leu Thr Asn Tyr
            20                  25                  30

Asn Val His Trp Val Arg Gln Pro Pro Gly Lys Gly Leu Glu Trp Met
        35                  40                  45

Gly Ile Ile Trp Thr Gly Gly Tyr Thr Asp Tyr Asn Ser Asp Leu Lys
    50                  55                  60

Ser Arg Leu Thr Ile Ser Arg Asp Thr Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Glu Arg His Thr Met Gly Ile Thr Lys Ser Trp Tyr Phe Asp Tyr
            100                 105                 110

Trp Gly Gln Gly Thr Leu Val Thr Val Ser Ser
        115                 120
```

<210> SEQ ID NO 27
<211> LENGTH: 122
<212> TYPE: PRT
<213> ORGANISM: Artificial sequence
<220> FEATURE:
<223> OTHER INFORMATION: humanized sequence

<400> SEQUENCE: 27

```
Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Asn Asn
            20                  25                  30

Gly Val Ser Trp Ile Arg Gln Pro Pro Gly Lys Gly Leu Glu Trp Ile
        35                  40                  45

Ala Ala Ile Ser Ser Gly Gly Asn Ile Tyr Tyr Asn Ser Ala Phe Lys
    50                  55                  60

Ser Arg Leu Thr Ile Ser Arg Asp Thr Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg His Arg Gly Tyr Tyr Gly Tyr Asn Trp Gly Tyr Phe Asp Tyr Trp
            100                 105                 110

Gly Gln Gly Thr Leu Val Thr Val Ser Ser
        115                 120
```

<210> SEQ ID NO 28
<211> LENGTH: 122
<212> TYPE: PRT
<213> ORGANISM: Artificial sequence
<220> FEATURE:
<223> OTHER INFORMATION: humanized sequence

<400> SEQUENCE: 28

```
Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Ser Asn
            20                  25                  30

Gly Val Ser Trp Val Arg Gln Pro Pro Gly Lys Gly Leu Glu Trp Ile
        35                  40                  45

Ala Ala Ile Ser Ser Gly Gly Ser Thr Tyr Tyr Asn Ser Ala Phe Lys
    50                  55                  60

Ser Arg Leu Thr Ile Ser Arg Asp Thr Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg His Arg Gly Tyr Tyr Trp Ser Asn Trp Gly Tyr Phe Asp Tyr Trp
            100                 105                 110

Gly Gln Gly Thr Leu Val Thr Val Ser Ser
        115                 120
```

<210> SEQ ID NO 29
<211> LENGTH: 125
<212> TYPE: PRT
<213> ORGANISM: Artificial sequence
<220> FEATURE:
<223> OTHER INFORMATION: humanized sequence

<400> SEQUENCE: 29

```
Glu Val Gln Leu Gln Glu Ser Gly Pro Gly Leu Val Lys Pro Ser Glu
1               5                   10                  15
```

```
Thr Leu Ser Leu Thr Cys Thr Val Ser Gly Phe Ser Leu Thr Ser Asn
            20                  25                  30

Gly Val Ser Trp Val Arg Gln Pro Pro Gly Lys Gly Leu Glu Trp Ile
        35                  40                  45

Ala Ala Ile Ser Ser Gly Gly Asn Ile Tyr Tyr Asn Ser Val Leu Lys
    50                  55                  60

Ser Arg Leu Thr Ile Ser Arg Asp Thr Ser Lys Asn Gln Val Ser Leu
65                  70                  75                  80

Lys Leu Ser Ser Val Thr Ala Ala Asp Thr Ala Val Tyr Tyr Cys Thr
                85                  90                  95

Arg Glu Arg Gly Trp Asn Tyr Pro Phe Ile Thr Asn Gly Tyr Tyr Phe
            100                 105                 110

Asp Tyr Trp Gly Gln Gly Thr Leu Val Thr Val Ser Ser
        115                 120                 125


<210> SEQ ID NO 30
<211> LENGTH: 125
<212> TYPE: PRT
<213> ORGANISM: Artificial sequence
<220> FEATURE:
<223> OTHER INFORMATION: humanized sequence

<400> SEQUENCE: 30

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Ser Gln
            20                  25                  30

Gly Val Ser Trp Val Arg Gln Pro Pro Gly Lys Gly Leu Glu Trp Ile
        35                  40                  45

Ala Ala Ile Ser Ser Gly Gly Asn Ile Tyr Tyr Asn Ser Val Leu Lys
    50                  55                  60

Ser Arg Leu Thr Ile Ser Arg Asp Thr Ser Lys Asn Gln Val Ser Leu
65                  70                  75                  80

Lys Leu Ser Ser Val Thr Ala Ala Asp Thr Ala Val Tyr Tyr Cys Thr
                85                  90                  95

Arg Glu Arg Gly Trp Asn Tyr Pro Phe Ile Thr Ser Gly Tyr Tyr Phe
            100                 105                 110

Asp Tyr Trp Gly Gln Gly Thr Leu Val Thr Val Ser Ser
        115                 120                 125


<210> SEQ ID NO 31
<211> LENGTH: 120
<212> TYPE: PRT
<213> ORGANISM: Artificial sequence
<220> FEATURE:
<223> OTHER INFORMATION: humanized sequence

<400> SEQUENCE: 31

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Ser Asn
            20                  25                  30

Gly Val Ile Trp Val Arg Gln Pro Pro Gly Lys Gly Leu Glu Trp Ile
        35                  40                  45

Ala Ala Ile Ser Ser Gly Gly Asn Ile Tyr Tyr Asn Ser Gly Leu Lys
    50                  55                  60

Ser Arg Leu Thr Ile Ser Arg Asp Thr Ser Lys Asn Gln Val Ser Leu
```

```
65                  70                  75                  80

Lys Leu Ser Ser Val Thr Ala Ala Asp Thr Ala Val Tyr Tyr Cys Thr
                85                  90                  95

Arg Ala Arg Gly Thr Thr Thr Ala Tyr Val Met Asp Ala Trp Gly Gln
            100                 105                 110

Gly Thr Leu Val Thr Val Ser Ser
        115                 120


<210> SEQ ID NO 32
<211> LENGTH: 120
<212> TYPE: PRT
<213> ORGANISM: Artificial sequence
<220> FEATURE:
<223> OTHER INFORMATION: humanized sequence

<400> SEQUENCE: 32

Glu Val Gln Leu Val Glu Ser Gly Gly Gly Leu Ile Gln Pro Gly Gly
1               5                   10                  15

Ser Leu Arg Leu Ser Cys Ala Val Ser Gly Phe Ser Leu Thr Ser Asn
            20                  25                  30

Gly Val Ile Trp Val Arg Gln Pro Pro Gly Lys Gly Leu Glu Trp Ile
        35                  40                  45

Ala Ala Ile Ser Ser Gly Gly Asn Ile Tyr Tyr Asn Ser Gly Leu Lys
    50                  55                  60

Ser Arg Leu Thr Ile Ser Arg Asp Thr Ser Lys Asn Thr Val Tyr Leu
65                  70                  75                  80

Gln Met Asn Ser Leu Arg Ala Glu Asp Thr Ala Val Tyr Tyr Cys Thr
                85                  90                  95

Arg Ala Arg Gly Thr Thr Thr Ala Tyr Val Met Asp Ala Trp Gly Gln
            100                 105                 110

Gly Thr Leu Val Thr Val Ser Ser
        115                 120


<210> SEQ ID NO 33
<211> LENGTH: 120
<212> TYPE: PRT
<213> ORGANISM: Artificial sequence
<220> FEATURE:
<223> OTHER INFORMATION: humanized sequence

<400> SEQUENCE: 33

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Ser Asn
            20                  25                  30

Gly Val Thr Trp Val Arg Gln Pro Pro Gly Lys Gly Leu Glu Trp Ile
        35                  40                  45

Ala Ala Ile Ser Ser Gly Gly Asn Ile Tyr Tyr Asn Ser Ala Val Lys
    50                  55                  60

Ser Arg Leu Thr Ile Ser Arg Asp Thr Ser Lys Asn Gln Val Ser Leu
65                  70                  75                  80

Lys Leu Ser Ser Val Thr Ala Ala Asp Thr Ala Val Tyr Tyr Cys Thr
                85                  90                  95

Arg Ala Arg Gly Thr Thr Thr Ala Tyr Val Met Asp Ala Trp Gly Gln
            100                 105                 110

Gly Thr Thr Val Thr Val Ser Ser
        115                 120
```

<210> SEQ ID NO 34
<211> LENGTH: 120
<212> TYPE: PRT
<213> ORGANISM: Artificial sequence
<220> FEATURE:
<223> OTHER INFORMATION: humanized sequence

<400> SEQUENCE: 34

```
Glu Val Gln Leu Val Glu Ser Gly Gly Gly Leu Ile Gln Pro Gly Gly
1               5                   10                  15

Ser Leu Arg Leu Ser Cys Ala Val Ser Gly Phe Ser Leu Thr Ser Asn
            20                  25                  30

Gly Val Thr Trp Val Arg Gln Pro Pro Gly Lys Gly Leu Glu Trp Ile
        35                  40                  45

Ala Ala Ile Ser Ser Gly Gly Asn Ile Tyr Tyr Asn Ser Ala Val Lys
    50                  55                  60

Ser Arg Leu Thr Ile Ser Arg Asp Thr Ser Lys Asn Thr Val Tyr Leu
65                  70                  75                  80

Gln Met Asn Ser Leu Arg Ala Glu Asp Thr Ala Val Tyr Phe Cys Thr
                85                  90                  95

Arg Ala Arg Gly Thr Thr Thr Ala Tyr Val Met Asp Ala Trp Gly Gln
            100                 105                 110

Gly Thr Thr Val Thr Val Ser Ser
        115                 120
```

<210> SEQ ID NO 35
<211> LENGTH: 120
<212> TYPE: PRT
<213> ORGANISM: Artificial sequence
<220> FEATURE:
<223> OTHER INFORMATION: humanized sequence

<400> SEQUENCE: 35

```
Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Ser Ser
            20                  25                  30

Gly Val Thr Trp Val Arg Gln Pro Pro Gly Lys Gly Leu Glu Trp Ile
        35                  40                  45

Ala Ala Ile Ser Ser Gly Gly Asn Ile Tyr Tyr Asn Ser Ala Val Lys
    50                  55                  60

Ser Arg Leu Thr Ile Ser Arg Asp Thr Ser Lys Asn Gln Val Ser Leu
65                  70                  75                  80

Lys Leu Ser Ser Val Thr Ala Ala Asp Thr Ala Val Tyr Tyr Cys Thr
                85                  90                  95

Arg Ala Arg Gly Thr Thr Thr Ala Tyr Val Met Asp Ala Trp Gly Gln
            100                 105                 110

Gly Thr Thr Val Thr Val Ser Ser
        115                 120
```

<210> SEQ ID NO 36
<211> LENGTH: 120
<212> TYPE: PRT
<213> ORGANISM: Artificial sequence
<220> FEATURE:
<223> OTHER INFORMATION: humanized sequence

<400> SEQUENCE: 36

```
Glu Val Gln Leu Val Glu Ser Gly Gly Gly Leu Ile Gln Pro Gly Gly
```

```
1               5                   10                  15

Ser Leu Arg Leu Ser Cys Ala Val Ser Gly Phe Ser Leu Thr Ser Ser
            20                  25                  30

Gly Val Thr Trp Val Arg Gln Pro Pro Gly Lys Gly Leu Glu Trp Ile
        35                  40                  45

Ala Ala Ile Ser Ser Gly Gly Asn Ile Tyr Tyr Asn Ser Ala Val Lys
    50                  55                  60

Ser Arg Leu Thr Ile Ser Arg Asp Thr Ser Lys Asn Thr Val Tyr Leu
65                  70                  75                  80

Gln Met Asn Ser Leu Arg Ala Glu Asp Thr Ala Val Tyr Phe Cys Thr
                85                  90                  95

Arg Ala Arg Gly Thr Thr Thr Ala Tyr Val Met Asp Ala Trp Gly Gln
            100                 105                 110

Gly Thr Thr Val Thr Val Ser Ser
        115                 120


<210> SEQ ID NO 37
<211> LENGTH: 5
<212> TYPE: PRT
<213> ORGANISM: Mus musculus

<400> SEQUENCE: 37

Ser Tyr Asp Ile Thr
1               5


<210> SEQ ID NO 38
<211> LENGTH: 5
<212> TYPE: PRT
<213> ORGANISM: Unknown
<220> FEATURE:
<223> OTHER INFORMATION: Rattus norvegicus or humanized sequence

<400> SEQUENCE: 38

Ser Asn Gly Val Ser
1               5


<210> SEQ ID NO 39
<211> LENGTH: 5
<212> TYPE: PRT
<213> ORGANISM: Rattus norvegicus

<400> SEQUENCE: 39

Gly Tyr Phe Met Asn
1               5


<210> SEQ ID NO 40
<211> LENGTH: 5
<212> TYPE: PRT
<213> ORGANISM: Unknown
<220> FEATURE:
<223> OTHER INFORMATION: Rattus norvegicus or humanized sequence

<400> SEQUENCE: 40

Asn Asn Gly Val Ser
1               5


<210> SEQ ID NO 41
<211> LENGTH: 5
<212> TYPE: PRT
<213> ORGANISM: Rattus norvegicus

<400> SEQUENCE: 41
```

Ser Tyr Asn Val His
1 5

<210> SEQ ID NO 42
<211> LENGTH: 5
<212> TYPE: PRT
<213> ORGANISM: Unknown
<220> FEATURE:
<223> OTHER INFORMATION: Rattus norvegicus or humanized sequence

<400> SEQUENCE: 42

Ser Asn Gly Val Ile
1 5

<210> SEQ ID NO 43
<211> LENGTH: 5
<212> TYPE: PRT
<213> ORGANISM: Unknown
<220> FEATURE:
<223> OTHER INFORMATION: Rattus norvegicus or humanized sequence

<400> SEQUENCE: 43

Asn Tyr Asn Val His
1 5

<210> SEQ ID NO 44
<211> LENGTH: 5
<212> TYPE: PRT
<213> ORGANISM: Unknown
<220> FEATURE:
<223> OTHER INFORMATION: Rattus norvegicus or humanized sequence

<400> SEQUENCE: 44

Ser Asn Gly Val Thr
1 5

<210> SEQ ID NO 45
<211> LENGTH: 5
<212> TYPE: PRT
<213> ORGANISM: Artificial sequence
<220> FEATURE:
<223> OTHER INFORMATION: humanized sequence

<400> SEQUENCE: 45

Ser Gln Gly Val Ser
1 5

<210> SEQ ID NO 46
<211> LENGTH: 5
<212> TYPE: PRT
<213> ORGANISM: Artificial sequence
<220> FEATURE:
<223> OTHER INFORMATION: humanized sequence

<400> SEQUENCE: 46

Ser Ser Gly Val Thr
1 5

<210> SEQ ID NO 47
<211> LENGTH: 16
<212> TYPE: PRT
<213> ORGANISM: Mus musculus

<400> SEQUENCE: 47

Val Ile Trp Thr Gly Gly Gly Thr Asn Tyr Asn Ser Ala Phe Met Ser
1 5 10 15

<210> SEQ ID NO 48
<211> LENGTH: 16
<212> TYPE: PRT
<213> ORGANISM: Unknown
<220> FEATURE:
<223> OTHER INFORMATION: Rattus norvegicus or humanized sequence

<400> SEQUENCE: 48

Ala Ile Ser Ser Gly Gly Asn Ile Tyr Tyr Asn Ser Ala Phe Lys Ser
1 5 10 15

<210> SEQ ID NO 49
<211> LENGTH: 16
<212> TYPE: PRT
<213> ORGANISM: Rattus norvegicus

<400> SEQUENCE: 49

Ala Ile Ser Ser Gly Gly Asn Ile Tyr Tyr Asn Ser Ala Leu Lys Ser
1 5 10 15

<210> SEQ ID NO 50
<211> LENGTH: 17
<212> TYPE: PRT
<213> ORGANISM: Rattus norvegicus

<400> SEQUENCE: 50

Arg Ile Asn Pro Tyr Asn Gly Asp Thr Phe Tyr Asn Gln Lys Phe Lys
1 5 10 15

Gly

<210> SEQ ID NO 51
<211> LENGTH: 16
<212> TYPE: PRT
<213> ORGANISM: Rattus norvegicus

<400> SEQUENCE: 51

Ala Ile Ser Ser Gly Gly Ser Ile Tyr Tyr Asn Ser Ala Phe Lys Ser
1 5 10 15

<210> SEQ ID NO 52
<211> LENGTH: 16
<212> TYPE: PRT
<213> ORGANISM: Rattus norvegicus

<400> SEQUENCE: 52

Ala Ile Ser Ser Gly Gly Ser Ile Tyr Tyr Asn Leu Ala Phe Lys Ser
1 5 10 15

<210> SEQ ID NO 53
<211> LENGTH: 16
<212> TYPE: PRT
<213> ORGANISM: Rattus norvegicus

<400> SEQUENCE: 53

Ala Met Ser Ser Gly Gly Asn Ile Tyr Tyr Asn Ser Ala Phe Lys Ser
1 5 10 15

<210> SEQ ID NO 54
<211> LENGTH: 16
<212> TYPE: PRT
<213> ORGANISM: Rattus norvegicus

<400> SEQUENCE: 54

Val Ile Trp Thr Gly Gly Tyr Thr Asp Ser Asn Ser Pro Leu Lys Ser 1 5 10 15

<210> SEQ ID NO 55
<211> LENGTH: 16
<212> TYPE: PRT
<213> ORGANISM: Unknown
<220> FEATURE:
<223> OTHER INFORMATION: Rattus norvegicus or humanized sequence

<400> SEQUENCE: 55

Ala Ile Ser Ser Gly Gly Ser Thr Tyr Tyr Asn Ser Ala Phe Lys Ser
1 5 10 15

<210> SEQ ID NO 56
<211> LENGTH: 16
<212> TYPE: PRT
<213> ORGANISM: Artificial sequence
<220> FEATURE:
<223> OTHER INFORMATION: humanized sequence

<400> SEQUENCE: 56

Ala Ile Ser Ser Gly Gly Asn Ile Tyr Tyr Asn Ser Gly Leu Lys Ser
1 5 10 15

<210> SEQ ID NO 57
<211> LENGTH: 16
<212> TYPE: PRT
<213> ORGANISM: Rattus norvegicus

<400> SEQUENCE: 57

Ala Ile Ser Asn Gly Gly Asn Ile Tyr His Asn Ser Ala Leu Lys Ser
1 5 10 15

<210> SEQ ID NO 58
<211> LENGTH: 16
<212> TYPE: PRT
<213> ORGANISM: Unknown
<220> FEATURE:
<223> OTHER INFORMATION: Rattus norvegicus or humanized sequence

<400> SEQUENCE: 58

Ile Ile Trp Thr Gly Gly Tyr Thr Asp Tyr Asn Ser Asp Leu Lys Ser
1 5 10 15

<210> SEQ ID NO 59
<211> LENGTH: 16
<212> TYPE: PRT
<213> ORGANISM: Unknown
<220> FEATURE:
<223> OTHER INFORMATION: Rattus norvegicus or humanized sequence

<400> SEQUENCE: 59

Ala Ile Ser Ser Gly Gly Asn Ile Tyr Tyr Asn Ser Val Leu Lys Ser
1 5 10 15

<210> SEQ ID NO 60
<211> LENGTH: 16
<212> TYPE: PRT
<213> ORGANISM: Rattus norvegicus

<400> SEQUENCE: 60

Ala Ile Ser Ser Gly Gly Asn Ile Tyr His Asn Ser Ala Leu Lys Ser
1 5 10 15

<210> SEQ ID NO 61
<211> LENGTH: 16

<212> TYPE: PRT
<213> ORGANISM: Rattus norvegicus

<400> SEQUENCE: 61

Ala Ile Ser Asn Gly Gly Asn Ile Tyr Tyr Asn Ser Ala Phe Lys Ser
1 5 10 15

<210> SEQ ID NO 62
<211> LENGTH: 16
<212> TYPE: PRT
<213> ORGANISM: Unknown
<220> FEATURE:
<223> OTHER INFORMATION: Rattus norvegicus or humanized sequence

<400> SEQUENCE: 62

Ala Ile Ser Ser Gly Gly Asn Ile Tyr Tyr Asn Ser Ala Val Lys Ser
1 5 10 15

<210> SEQ ID NO 63
<211> LENGTH: 16
<212> TYPE: PRT
<213> ORGANISM: Rattus norvegicus

<400> SEQUENCE: 63

Ala Met Ser Ser Gly Gly Ser Ile Tyr Tyr Asn Ser Ala Phe Lys Ser
1 5 10 15

<210> SEQ ID NO 64
<211> LENGTH: 14
<212> TYPE: PRT
<213> ORGANISM: Mus musculus

<400> SEQUENCE: 64

Asp Leu Arg Tyr Gly Tyr Asp Gly Phe Trp Tyr Phe Asp Val
1 5 10

<210> SEQ ID NO 65
<211> LENGTH: 14
<212> TYPE: PRT
<213> ORGANISM: Unknown
<220> FEATURE:
<223> OTHER INFORMATION: Rattus norvegicus or humanized sequence

<400> SEQUENCE: 65

His Arg Gly Tyr Tyr Gly Tyr Asn Trp Gly Tyr Phe Asp Tyr
1 5 10

<210> SEQ ID NO 66
<211> LENGTH: 17
<212> TYPE: PRT
<213> ORGANISM: Rattus norvegicus

<400> SEQUENCE: 66

Glu Arg Gly Trp Asn Tyr Pro Gly Ile Thr Asn Gly Tyr Tyr Phe Asp
1 5 10 15

Tyr

<210> SEQ ID NO 67
<211> LENGTH: 12
<212> TYPE: PRT
<213> ORGANISM: Rattus norvegicus

<400> SEQUENCE: 67

Ser Gly Trp Gly Tyr Asp Val Tyr Ser Phe Asp Tyr
1 5 10

<210> SEQ ID NO 68
<211> LENGTH: 14
<212> TYPE: PRT
<213> ORGANISM: Rattus norvegicus

<400> SEQUENCE: 68

His Arg Gly Tyr Tyr Gly Phe Asn Trp Gly Tyr Phe Asp Tyr
1 5 10

<210> SEQ ID NO 69
<211> LENGTH: 14
<212> TYPE: PRT
<213> ORGANISM: Rattus norvegicus

<400> SEQUENCE: 69

His Arg Gly Tyr Tyr Trp Tyr Asn Trp Gly Phe Phe Asp Tyr
1 5 10

<210> SEQ ID NO 70
<211> LENGTH: 15
<212> TYPE: PRT
<213> ORGANISM: Unknown
<220> FEATURE:
<223> OTHER INFORMATION: Rattus norvegicus or humanized sequence

<400> SEQUENCE: 70

Glu Arg His Thr Met Gly Ile Thr Lys Ser Trp Tyr Phe Asp Tyr
1 5 10 15

<210> SEQ ID NO 71
<211> LENGTH: 14
<212> TYPE: PRT
<213> ORGANISM: Unknown
<220> FEATURE:
<223> OTHER INFORMATION: Rattus norvegicus or humanized sequence

<400> SEQUENCE: 71

His Arg Gly Tyr Tyr Trp Ser Asn Trp Gly Tyr Phe Asp Tyr
1 5 10

<210> SEQ ID NO 72
<211> LENGTH: 12
<212> TYPE: PRT
<213> ORGANISM: Rattus norvegicus

<400> SEQUENCE: 72

Ala Arg Gly Thr Thr Thr Ala Tyr Phe Met Asp Ala
1 5 10

<210> SEQ ID NO 73
<211> LENGTH: 17
<212> TYPE: PRT
<213> ORGANISM: Unknown
<220> FEATURE:
<223> OTHER INFORMATION: Rattus norvegicus or humanized sequence

<400> SEQUENCE: 73

Glu Arg Gly Trp Asn Tyr Pro Phe Ile Thr Asn Gly Tyr Tyr Phe Asp
1 5 10 15

Tyr

<210> SEQ ID NO 74
<211> LENGTH: 12
<212> TYPE: PRT

<213> ORGANISM: Unknown
<220> FEATURE:
<223> OTHER INFORMATION: Rattus norvegicus or humanized sequence

<400> SEQUENCE: 74

Ala Arg Gly Thr Thr Thr Ala Tyr Val Met Asp Ala
1 5 10

<210> SEQ ID NO 75
<211> LENGTH: 17
<212> TYPE: PRT
<213> ORGANISM: Artificial sequence
<220> FEATURE:
<223> OTHER INFORMATION: synthetic sequence

<400> SEQUENCE: 75

Glu Arg Gly Trp Asn Tyr Pro Phe Ile Thr Ser Gly Tyr Tyr Phe Asp
1 5 10 15

Tyr

<210> SEQ ID NO 76
<211> LENGTH: 112
<212> TYPE: PRT
<213> ORGANISM: Unknown
<220> FEATURE:
<223> OTHER INFORMATION: Mus musculus or humanized sequence

<400> SEQUENCE: 76

Asp Val Val Met Thr Gln Thr Pro Leu Ser Leu Pro Val Ser Leu Gly
1 5 10 15

Asp Gln Ala Ser Ile Ser Cys Arg Ser Ser Gln Ser Ile Val His Ser
20 25 30

Asn Gly Asn Thr Tyr Leu Glu Trp Tyr Leu Gln Lys Pro Gly Gln Ser
35 40 45

Pro Lys Leu Leu Ile Tyr Lys Val Ser Asn Arg Phe Ser Gly Val Pro
50 55 60

Asp Arg Phe Ser Gly Ser Gly Thr Gly Thr Asp Phe Thr Leu Lys Ile
65 70 75 80

Ser Arg Val Glu Ala Glu Asp Leu Gly Val Tyr Tyr Cys Phe Gln Gly
85 90 95

Ser His Val Pro Arg Thr Phe Gly Gly Gly Thr Lys Leu Glu Ile Lys
100 105 110

<210> SEQ ID NO 77
<211> LENGTH: 107
<212> TYPE: PRT
<213> ORGANISM: Unknown
<220> FEATURE:
<223> OTHER INFORMATION: Mus musculus or humanized sequence

<400> SEQUENCE: 77

Asp Val Val Met Thr Gln Ala Pro Ser Ser Leu Ser Ala Ser Leu Gly
1 5 10 15

Glu Arg Ile Ser Leu Thr Cys Arg Ala Ser Gln Asp Ile Tyr Gly Ser
20 25 30

Leu Asn Trp Phe Gln Gln Lys Pro Asp Gly Thr Ile Lys Leu Leu Ile
35 40 45

Tyr Gly Thr Ser Ser Leu Asp Ser Gly Val Pro Lys Arg Phe Ser Gly
50 55 60

Ser Arg Ser Gly Ser Asp Tyr Ser Leu Thr Ile Ser Ser Leu Glu Ser
65 70 75 80

```
Glu Asp Phe Ala Asp Tyr Tyr Cys Leu Gln Tyr Ala Ser Ser Pro Tyr
                85                  90                  95

Thr Phe Gly Gly Gly Thr Lys Leu Glu Ile Lys
            100                 105


<210> SEQ ID NO 78
<211> LENGTH: 106
<212> TYPE: PRT
<213> ORGANISM: Rattus norvegicus

<400> SEQUENCE: 78

Asp Ile Gln Met Thr Gln Ser Pro Ser Leu Leu Ser Ala Ser Val Gly
1               5                   10                  15

Asp Arg Val Thr Leu Ser Cys Lys Gly Ser Gln Asn Ile Asn Asn Tyr
            20                  25                  30

Leu Ala Trp Tyr Gln Gln Lys Leu Gly Gly Ala Pro Lys Leu Leu Ile
        35                  40                  45

Tyr Lys Thr Asn Ser Leu Gln Thr Gly Ile Pro Ser Arg Phe Ser Gly
    50                  55                  60

Ser Gly Ser Gly Thr Asp Tyr Thr Leu Thr Ile Ser Ser Leu His Ser
65                  70                  75                  80

Glu Asp Leu Ala Thr Tyr Tyr Cys Tyr Gln Tyr Asn Asn Trp Tyr Thr
                85                  90                  95

Phe Gly Pro Gly Thr Lys Leu Glu Leu Lys
            100                 105


<210> SEQ ID NO 79
<211> LENGTH: 106
<212> TYPE: PRT
<213> ORGANISM: Rattus norvegicus

<400> SEQUENCE: 79

Asp Ile Val Leu Thr Gln Ser Pro Ser Leu Leu Ser Ala Ser Val Gly
1               5                   10                  15

Asp Arg Val Ile Leu Ser Cys Lys Ala Gly Gln Lys Ile Asn Asn Tyr
            20                  25                  30

Leu Ala Trp Tyr Gln Gln Lys Leu Gly Glu Ala Pro Lys Leu Leu Ile
        35                  40                  45

Tyr Asn Ala Asn Ser Leu Gln Thr Gly Ile Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Val Ala Thr Tyr Phe Cys Gln Gln Tyr Asn Ser Trp Tyr Thr
                85                  90                  95

Phe Gly Ala Gly Thr Lys Leu Glu Ile Lys
            100                 105


<210> SEQ ID NO 80
<211> LENGTH: 107
<212> TYPE: PRT
<213> ORGANISM: Rattus norvegicus

<400> SEQUENCE: 80

Asp Ile Gln Met Thr Gln Thr Pro Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30
```

```
Leu Asn Trp Tyr Gln Gln Lys Pro Asp Gly Thr Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Trp
                85                  90                  95

Thr Phe Gly Gly Gly Thr Lys Leu Glu Ile Lys
            100                 105


<210> SEQ ID NO 81
<211> LENGTH: 106
<212> TYPE: PRT
<213> ORGANISM: Rattus norvegicus

<400> SEQUENCE: 81

Asn Ile Gln Leu Thr Gln Ser Pro Ser Leu Leu Ser Ala Ser Val Gly
1               5                   10                  15

Asp Arg Val Thr Leu Ser Cys Lys Gly Ser Gln Asn Ile Asn Asn Tyr
            20                  25                  30

Leu Ala Trp Tyr Gln Gln Lys Leu Gly Glu Ala Pro Lys Leu Leu Ile
        35                  40                  45

Tyr Lys Thr Asn Ser Leu Gln Thr Gly Ile Pro Ser Arg Phe Ser Gly
    50                  55                  60

Ser Gly Ser Gly Thr Asp Tyr Thr Leu Thr Ile Ser Ser Leu His Ser
65                  70                  75                  80

Glu Asp Leu Ala Thr Tyr Tyr Cys Ser Gln Tyr Asn Asn Gly Tyr Thr
                85                  90                  95

Phe Gly Ala Gly Thr Lys Leu Glu Ile Lys
            100                 105


<210> SEQ ID NO 82
<211> LENGTH: 106
<212> TYPE: PRT
<213> ORGANISM: Rattus norvegicus

<400> SEQUENCE: 82

Asn Ile Gln Leu Thr Gln Ser Pro Ser Leu Leu Ser Ala Ser Val Gly
1               5                   10                  15

Asp Arg Val Thr Leu Ser Cys Lys Gly Ser Gln Asn Ile Asn Asn Tyr
            20                  25                  30

Leu Ala Trp Tyr Gln Gln Lys Leu Gly Glu Ala Pro Lys Leu Leu Ile
        35                  40                  45

Tyr Lys Thr Asn Ser Leu Gln Thr Gly Ile Pro Ser Arg Phe Ser Gly
    50                  55                  60

Ser Gly Ser Gly Thr Asp Tyr Thr Leu Thr Ile Ser Ser Leu His Ser
65                  70                  75                  80

Glu Asp Leu Ala Thr Tyr Tyr Cys Tyr Gln Tyr Asn Asp Gly Tyr Thr
                85                  90                  95

Phe Gly Ala Gly Thr Lys Leu Glu Leu Lys
            100                 105


<210> SEQ ID NO 83
<211> LENGTH: 110
<212> TYPE: PRT
<213> ORGANISM: Rattus norvegicus
```

```
<400> SEQUENCE: 83

Asn Ile Gln Leu Thr Gln Ser Pro Ser Leu Leu Ser Ala Ser Val Gly
1               5                   10                  15

Asp Arg Val Thr Leu Ser Cys Lys Gly Ser Gln Asn Ile Asp Asn Tyr
            20                  25                  30

Leu Ala Trp Tyr Gln Gln Lys Leu Gly Glu Pro Pro Lys Leu Leu Ile
        35                  40                  45

Tyr Lys Thr Asn Ser Leu Gln Thr Gly Ile Pro Ser Arg Phe Ser Gly
    50                  55                  60

Ser Gly Ser Gly Thr Asp Tyr Thr Leu Thr Ile Ser Ser Leu His Ser
65                  70                  75                  80

Glu Asp Leu Ala Thr Tyr Tyr Cys Tyr Gln Tyr Asn Asn Gly Tyr Thr
                85                  90                  95

Phe Gly Ala Gly Thr Lys Leu Glu Leu Lys Arg Ala Asp Ala
            100                 105                 110


<210> SEQ ID NO 84
<211> LENGTH: 106
<212> TYPE: PRT
<213> ORGANISM: Rattus norvegicus

<400> SEQUENCE: 84

Asn Ile Gln Leu Thr Gln Ser Pro Ser Leu Leu Ser Ala Ser Val Gly
1               5                   10                  15

Asp Arg Val Thr Leu Ser Cys Lys Gly Ser Gln Asn Ile Asn Asn Tyr
            20                  25                  30

Leu Ala Trp Tyr Gln Gln Lys Leu Gly Glu Ala Pro Lys Leu Leu Ile
        35                  40                  45

Tyr Lys Thr Asn Ser Leu Gln Thr Gly Ile Pro Ser Arg Phe Ser Gly
    50                  55                  60

Ser Gly Ser Gly Thr Asp Phe Thr Leu Thr Ile Ser Ser Leu His Ser
65                  70                  75                  80

Glu Asp Leu Ala Thr Tyr Tyr Cys Cys Gln Tyr Asn Asn Gly Tyr Thr
                85                  90                  95

Phe Gly Ala Gly Thr Lys Leu Glu Leu Lys
            100                 105


<210> SEQ ID NO 85
<211> LENGTH: 107
<212> TYPE: PRT
<213> ORGANISM: Rattus norvegicus

<400> SEQUENCE: 85

Asp Val Gln Met Thr Gln Ser Pro Ala Ser Leu Ser Ala Ser Leu Gly
1               5                   10                  15

Glu Thr Ile Ser Ile Glu Cys Leu Ala Ser Glu Gly Ile Phe Ser Tyr
            20                  25                  30

Leu Ala Trp Tyr Gln Gln Lys Pro Gly Lys Ser Pro Gln Leu Leu Ile
        35                  40                  45

Tyr Gly Ala Asn Thr Leu Gln Ala Gly Val Pro Ser Arg Phe Ser Gly
    50                  55                  60

Ser Gly Ser Gly Thr Gln Tyr Ser Leu Lys Ile Ser Ser Met Gln Pro
65                  70                  75                  80

Glu Asp Glu Gly Asp Tyr Phe Cys Gln Gln Ser Tyr Lys Phe Pro Val
                85                  90                  95

Thr Phe Gly Ser Gly Thr Lys Leu Glu Leu Lys
```

100 105

<210> SEQ ID NO 86
<211> LENGTH: 106
<212> TYPE: PRT
<213> ORGANISM: Rattus norvegicus

<400> SEQUENCE: 86

Asn Ile Gln Leu Thr Gln Ser Pro Ser Leu Leu Ser Ala Ser Val Gly
1 5 10 15

Asp Arg Val Thr Leu Ser Cys Lys Gly Ser Gln Asn Ile Asn Asn Tyr
20 25 30

Leu Ala Trp Tyr Gln Gln Lys Leu Gly Glu Ala Pro Lys Leu Leu Ile
35 40 45

Tyr Lys Thr Asn Ser Leu Gln Thr Gly Ile Pro Ser Arg Phe Ser Gly
50 55 60

Ser Gly Ser Gly Thr Asp Tyr Thr Leu Thr Leu Ser Ser Leu His Ser
65 70 75 80

Glu Asp Leu Ala Thr Tyr Tyr Cys Cys Gln Tyr Asn Asp Gly Tyr Thr
85 90 95

Phe Gly Ala Gly Thr Lys Leu Glu Leu Lys
100 105

<210> SEQ ID NO 87
<211> LENGTH: 114
<212> TYPE: PRT
<213> ORGANISM: Rattus norvegicus

<400> SEQUENCE: 87

Glu Thr Val Met Thr Gln Ser Pro Ser Ser Leu Ala Val Ser Ala Gly
1 5 10 15

Glu Thr Val Thr Met Asn Cys Lys Ser Ser Gln Ser Leu Leu Tyr Ser
20 25 30

Gly Asn Gln Lys Asn Tyr Leu Ala Trp Tyr Gln Gln Lys Pro Gly Gln
35 40 45

Ser Pro Lys Leu Leu Ile Tyr Trp Ala Ser Thr Arg Gln Ser Gly Val
50 55 60

Pro Asp Arg Phe Ile Gly Ser Gly Ser Gly Thr Asp Phe Thr Leu Thr
65 70 75 80

Ile Ser Ser Val Gln Ala Glu Asp Leu Ala Ile Tyr Tyr Cys Gln Gln
85 90 95

Tyr Tyr Asp Thr Leu Met Lys Met Phe Gly Ala Gly Thr Lys Leu Glu
100 105 110

Ile Lys

<210> SEQ ID NO 88
<211> LENGTH: 106
<212> TYPE: PRT
<213> ORGANISM: Rattus norvegicus

<400> SEQUENCE: 88

Asn Ile Gln Val Thr Gln Ser Pro Ser Leu Leu Ser Ala Ser Val Gly
1 5 10 15

Asp Arg Val Thr Leu Ser Cys Lys Gly Ser Gln Asn Ile Tyr Asn Tyr
20 25 30

Leu Ala Trp Tyr Gln Gln Lys Leu Gly Glu Ala Pro Lys Leu Leu Ile
35 40 45

```
Tyr Lys Thr Asn Ser Leu Gln Thr Gly Ile Pro Ser Arg Phe Ser Gly
    50                  55                  60

Ser Gly Ser Gly Thr Asp Tyr Thr Leu Thr Ile Ser Ser Leu His Ser
65                  70                  75                  80

Glu Asp Leu Ala Thr Tyr Tyr Cys Cys Gln Tyr Asn Asn Gly Tyr Thr
                85                  90                  95

Phe Gly Ala Gly Thr Lys Leu Glu Leu Lys
            100                 105


<210> SEQ ID NO 89
<211> LENGTH: 107
<212> TYPE: PRT
<213> ORGANISM: Rattus norvegicus

<400> SEQUENCE: 89

Asp Ile Leu Met Thr Gln Ser Pro Ala Ser Leu Ser Ala Ser Leu Gly
1               5                   10                  15

Glu Thr Ile Ser Ile Glu Cys Leu Ala Ser Glu Gly Ile Phe Ser Tyr
            20                  25                  30

Leu Gly Trp Tyr Gln Gln Lys Pro Gly Lys Ser Pro Gln Leu Leu Ile
        35                  40                  45

Tyr Gly Ala Asn Ser Leu Gln Ala Gly Val Pro Ser Arg Phe Ser Gly
    50                  55                  60

Ser Gly Ser Gly Thr Gln Tyr Ser Leu Lys Ile Ser Ser Met Gln Pro
65                  70                  75                  80

Glu Asp Glu Gly Asp Tyr Phe Cys Gln Gln Ser Tyr Lys Phe Pro Val
                85                  90                  95

Thr Phe Gly Ser Gly Thr Lys Leu Glu Leu Lys
            100                 105


<210> SEQ ID NO 90
<211> LENGTH: 106
<212> TYPE: PRT
<213> ORGANISM: Rattus norvegicus

<400> SEQUENCE: 90

Glu Ile Met Leu Thr Gln Ser Pro Ser Leu Leu Ser Ala Ser Val Gly
1               5                   10                  15

Asp Arg Val Thr Leu Ser Cys Lys Ala Gly Gln Asn Ile Asn Asn Tyr
            20                  25                  30

Leu Ala Trp Tyr Gln Gln Lys Leu Gly Glu Ala Pro Lys Leu Leu Ile
        35                  40                  45

Tyr Asn Ala Asn Ser Leu Gln Thr Gly Ile Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Val Ala Thr Tyr Phe Cys Gln Gln Tyr Asn Ser Trp Tyr Thr
                85                  90                  95

Phe Gly Ala Gly Thr Lys Leu Glu Ile Lys
            100                 105


<210> SEQ ID NO 91
<211> LENGTH: 106
<212> TYPE: PRT
<213> ORGANISM: Rattus norvegicus

<400> SEQUENCE: 91

Asn Ile Gln Leu Thr Gln Ser Pro Ser Leu Leu Ser Ala Ser Val Gly
```

```
1               5                   10                  15

Asp Arg Val Thr Leu Ser Cys Lys Gly Ser Gln Asn Ile Tyr Asn Tyr
            20                  25                  30

Leu Ala Trp Tyr Gln Gln Lys Leu Gly Glu Ala Pro Lys Leu Leu Ile
        35                  40                  45

Tyr Lys Thr Asn Ser Leu Gln Thr Asp Ile Pro Ser Arg Phe Ser Gly
    50                  55                  60

Ser Gly Ser Gly Thr Asp Tyr Thr Leu Thr Ile Ser Ser Leu His Ser
65                  70                  75                  80

Glu Asp Leu Ala Thr Tyr Tyr Cys Cys Gln Tyr Asn Asn Gly Tyr Thr
                85                  90                  95

Phe Gly Ala Gly Thr Lys Leu Glu Leu Lys
            100                 105
```

<210> SEQ ID NO 92
<211> LENGTH: 106
<212> TYPE: PRT
<213> ORGANISM: Rattus norvegicus

<400> SEQUENCE: 92

```
Asn Ile Gln Leu Thr Gln Ser Pro Ser Leu Leu Ser Ala Ser Val Gly
1               5                   10                  15

Asp Ser Val Ser Leu Arg Cys Lys Gly Ser Gln Asn Ile Tyr Asn Tyr
            20                  25                  30

Leu Ala Trp Tyr Gln Gln Lys Leu Gly Glu Ala Pro Lys Leu Leu Ile
        35                  40                  45

Tyr Lys Thr Asn Asn Leu Gln Thr Gly Ile Pro Ser Arg Phe Ser Gly
    50                  55                  60

Ser Gly Ser Gly Thr Asp Tyr Thr Leu Thr Ile Ser Ser Leu Asn Ser
65                  70                  75                  80

Glu Asp Leu Ala Thr Tyr Tyr Cys Cys Gln Tyr Asn Asn Gly Tyr Thr
                85                  90                  95

Phe Gly Ala Gly Thr Lys Leu Glu Leu Lys
            100                 105
```

<210> SEQ ID NO 93
<211> LENGTH: 114
<212> TYPE: PRT
<213> ORGANISM: Rattus norvegicus

<400> SEQUENCE: 93

```
Asp Ile Val Met Thr Gln Ser Pro Ser Ser Leu Ala Val Ser Ala Gly
1               5                   10                  15

Glu Thr Val Asn Ile Asn Cys Lys Ser Ser Gln Ser Leu Leu Tyr Ser
            20                  25                  30

Val Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Gln Ser Gly Val
    50                  55                  60

Pro Asp Arg Phe Ile Gly Ser Gly Ser Gly Thr Asp Phe Thr Leu Thr
65                  70                  75                  80

Ile Ser Ser Val Gln Ala Glu Asp Leu Ala Ile Tyr Tyr Cys Gln Gln
                85                  90                  95

Tyr Tyr Asp Thr Leu Met Lys Met Phe Gly Ala Gly Thr Lys Leu Glu
            100                 105                 110

Leu Lys
```

<210> SEQ ID NO 94
<211> LENGTH: 106
<212> TYPE: PRT
<213> ORGANISM: Rattus norvegicus

<400> SEQUENCE: 94

```
Asn Ile Gln Leu Thr Gln Ser Pro Ser Leu Leu Ser Ala Ser Val Gly
1               5                   10                  15

Asp Arg Val Thr Leu Ser Cys Lys Gly Ser Gln Asn Ile Asn Asn Tyr
            20                  25                  30

Leu Ala Trp Tyr Gln Gln Lys Leu Gly Glu Ala Pro Lys Leu Leu Ile
        35                  40                  45

Tyr Lys Thr Asn Ser Leu Gln Thr Gly Ile Pro Ser Arg Phe Ser Gly
    50                  55                  60

Ser Gly Ser Gly Ser Asp Tyr Thr Leu Thr Ile Ser Ser Leu His Ser
65                  70                  75                  80

Glu Asp Leu Ala Thr Tyr Tyr Cys Tyr Gln Tyr Asn Asp Gly Tyr Thr
                85                  90                  95

Phe Gly Ala Gly Thr Lys Leu Glu Leu Lys
            100                 105
```

<210> SEQ ID NO 95
<211> LENGTH: 106
<212> TYPE: PRT
<213> ORGANISM: Rattus norvegicus

<400> SEQUENCE: 95

```
Asn Ile Gln Leu Thr Gln Ser Pro Ser Leu Leu Ser Ala Ser Val Gly
1               5                   10                  15

Asp Arg Val Thr Leu Ser Cys Lys Gly Ser Gln Asn Ile Tyr Asn Tyr
            20                  25                  30

Leu Ala Trp Tyr Gln Gln Lys Leu Gly Glu Ala Pro Lys Leu Leu Ile
        35                  40                  45

Tyr Lys Thr Asn Ser Leu Gln Thr Gly Ile Pro Ser Arg Phe Ser Gly
    50                  55                  60

Ser Gly Ser Gly Thr Asp Tyr Thr Leu Thr Ile Ser Ser Leu His Ser
65                  70                  75                  80

Glu Asp Leu Ala Thr Tyr Tyr Cys Cys Gln Tyr Asn Asn Gly Tyr Thr
                85                  90                  95

Phe Gly Ala Gly Thr Lys Leu Glu Leu Lys
            100                 105
```

<210> SEQ ID NO 96
<211> LENGTH: 107
<212> TYPE: PRT
<213> ORGANISM: Rattus norvegicus

<400> SEQUENCE: 96

```
Asn Ile Gln Leu Thr Gln Ser Pro Ser Leu Leu Ser Ala Ser Val Gly
1               5                   10                  15

Asp Arg Val Thr Leu Ser Cys Lys Gly Ser Gln Asn Ile Asn Asn Tyr
            20                  25                  30

Leu Ala Trp Tyr Gln Gln Lys Leu Gly Glu Ala Pro Lys Leu Leu Ile
        35                  40                  45

Tyr Lys Thr Asn Ser Leu Gln Thr Gly Ile Pro Ser Arg Phe Ser Gly
    50                  55                  60
```

-continued

```
Ser Gly Ser Gly Thr Asp Tyr Thr Leu Thr Ile Ser Ser Leu His Ser
65                  70                  75                  80

Glu Asp Leu Ala Thr Tyr Tyr Cys Cys Gln Tyr Asn Asn Gly Tyr Thr
                85                  90                  95

Phe Gly Ala Gly Thr Lys Leu Glu Leu Lys Arg
            100                 105


<210> SEQ ID NO 97
<211> LENGTH: 106
<212> TYPE: PRT
<213> ORGANISM: Rattus norvegicus

<400> SEQUENCE: 97

Asn Ile Gln Leu Thr Gln Ser Pro Ser Leu Leu Ser Ala Ser Val Gly
1               5                   10                  15

Asp Arg Val Thr Leu Ser Cys Lys Gly Ser Gln Asn Ile Asn Asn Tyr
            20                  25                  30

Leu Gly Trp Tyr Gln Gln Lys Leu Gly Glu Ala Pro Arg Leu Leu Ile
        35                  40                  45

Tyr Lys Thr Asn Ser Leu Gln Thr Gly Ile Pro Ser Arg Phe Ser Gly
    50                  55                  60

Ser Gly Ser Gly Thr Asp Tyr Thr Leu Thr Ile Ser Ser Leu His Ser
65                  70                  75                  80

Glu Asp Leu Ala Thr Tyr Tyr Cys Tyr Gln Tyr Asn Asn Gly Tyr Thr
                85                  90                  95

Phe Gly Ala Gly Thr Lys Leu Glu Leu Lys
            100                 105


<210> SEQ ID NO 98
<211> LENGTH: 114
<212> TYPE: PRT
<213> ORGANISM: Rattus norvegicus

<400> SEQUENCE: 98

Asp Val Val Leu Thr Gln Ser Pro Ser Ser Leu Ala Val Ser Ala Gly
1               5                   10                  15

Glu Thr Val Thr Ile Asn Cys Lys Ser Ser Gln Ser Leu Leu Tyr Ser
            20                  25                  30

Gly Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Gln Ser Gly Val
    50                  55                  60

Pro Asp Arg Phe Ile Gly Ser Gly Ser Gly Thr Asp Phe Thr Leu Thr
65                  70                  75                  80

Ile Ser Ser Val Gln Ala Glu Asp Leu Ala Ile Tyr Tyr Cys Gln Gln
                85                  90                  95

Tyr Tyr Asp Val Leu Met Asn Met Phe Gly Ala Gly Thr Lys Leu Glu
            100                 105                 110

Ile Lys


<210> SEQ ID NO 99
<211> LENGTH: 106
<212> TYPE: PRT
<213> ORGANISM: Rattus norvegicus

<400> SEQUENCE: 99

Asn Ile Gln Met Thr Gln Ser Pro Ser Leu Leu Ser Ala Ser Val Gly
1               5                   10                  15
```

```
Asp Arg Val Thr Leu Ser Cys Lys Gly Ser Gln Asn Ile Tyr Asn Tyr
            20                  25                  30

Leu Ala Trp Tyr Gln Gln Lys Leu Gly Glu Ala Pro Lys Leu Leu Ile
        35                  40                  45

Tyr Lys Thr Ser Ser Leu Gln Ala Gly Ile Pro Ser Arg Phe Ser Gly
    50                  55                  60

Ser Gly Ser Asp Thr Asp Tyr Thr Leu Thr Ile Ser Ser Leu His Ser
65                  70                  75                  80

Glu Asp Leu Ala Thr Tyr Tyr Cys Cys Gln Tyr Asn Asn Gly Tyr Thr
                85                  90                  95

Phe Gly Ala Gly Thr Lys Leu Glu Ile Lys
            100                 105


<210> SEQ ID NO 100
<211> LENGTH: 106
<212> TYPE: PRT
<213> ORGANISM: Rattus norvegicus

<400> SEQUENCE: 100

Asp Ile Gln Leu Thr Gln Ser Pro Ser Leu Leu Ser Ala Ser Val Gly
1               5                   10                  15

Asp Ser Val Ser Leu Arg Cys Lys Gly Ser Gln Asn Ile Tyr Asn Tyr
            20                  25                  30

Leu Ala Trp Tyr Gln Gln Lys Leu Gly Glu Ala Pro Lys Leu Leu Ile
        35                  40                  45

Tyr Lys Thr Asn Asn Leu Gln Thr Gly Ile Pro Ser Arg Phe Ser Gly
    50                  55                  60

Ser Gly Ser Gly Thr Asp Tyr Thr Leu Thr Ile Ser Ser Leu Asn Ser
65                  70                  75                  80

Glu Asp Leu Ala Thr Tyr Tyr Cys Cys Gln Tyr Asn Asn Gly Tyr Thr
                85                  90                  95

Phe Gly Ala Gly Thr Lys Val Glu Leu Lys
            100                 105


<210> SEQ ID NO 101
<211> LENGTH: 106
<212> TYPE: PRT
<213> ORGANISM: Rattus norvegicus

<400> SEQUENCE: 101

Asp Ile Val Met Thr Gln Ser Pro Ser Leu Leu Ser Ala Ser Val Gly
1               5                   10                  15

Asp Arg Val Thr Leu Ser Cys Lys Gly Ser Gln Asn Ile Asn Asn Tyr
            20                  25                  30

Leu Ala Trp Tyr Gln Gln Lys Leu Gly Glu Ala Pro Lys Leu Leu Ile
        35                  40                  45

Tyr Glu Thr Asn Ser Leu Gln Thr Gly Ile Pro Ser Arg Phe Ser Gly
    50                  55                  60

Ser Gly Ser Gly Thr Asp Tyr Thr Leu Thr Leu Ser Ser Leu His Ser
65                  70                  75                  80

Glu Asp Leu Ala Thr Tyr Tyr Cys Tyr Gln Tyr Asn Asp Gly Tyr Thr
                85                  90                  95

Phe Gly Ala Gly Thr Lys Leu Glu Ile Lys
            100                 105


<210> SEQ ID NO 102
```

<211> LENGTH: 114
<212> TYPE: PRT
<213> ORGANISM: Rattus norvegicus

<400> SEQUENCE: 102

Asp Ile Gln Leu Thr Gln Ser Pro Ser Leu Leu Ser Ala Ser Val Gly
1 5 10 15

Asp Arg Val Thr Leu Ser Cys Lys Gly Ser Gln Asn Ile Asn Asn Tyr
20 25 30

Leu Ala Trp Tyr Gln Gln Lys Val Gly Glu Ala Pro Lys Leu Leu Ile
35 40 45

Tyr Lys Thr Asn Ser Leu Gln Thr Gly Ile Pro Ser Arg Phe Ser Gly
50 55 60

Ser Gly Ser Gly Thr Asp Tyr Thr Leu Thr Ile Ser Ser Leu His Ser
65 70 75 80

Glu Asp Leu Ala Thr Tyr Tyr Cys Tyr Gln Tyr Asn Asn Gly Tyr Thr
85 90 95

Phe Gly Ala Gly Thr Lys Leu Glu Leu Lys Arg Ala Asp Ala Ala Pro
100 105 110

Thr Val

<210> SEQ ID NO 103
<211> LENGTH: 107
<212> TYPE: PRT
<213> ORGANISM: Artificial sequence
<220> FEATURE:
<223> OTHER INFORMATION: humanized sequence

<400> SEQUENCE: 103

Asp Ile Gln Met Thr Gln Ser Pro Ser Ser Leu Ser Ala Ser Val Gly
1 5 10 15

Asp Arg Val Thr Ile Thr Cys Leu Ala Ser Glu Gly Ile Phe Ser Tyr
20 25 30

Leu Gly Trp Tyr Gln Gln Lys Pro Gly Lys Ser Pro Lys Leu Leu Ile
35 40 45

Tyr Gly Ala Asn Ser Leu Gln Ala Gly Val Pro Ser Arg Phe Ser Gly
50 55 60

Ser Gly Ser Gly Thr Asp Tyr Thr Leu Thr Ile Ser Ser Leu Gln Pro
65 70 75 80

Glu Asp Phe Ala Thr Tyr Tyr Cys Gln Gln Ser Tyr Lys Phe Pro Val
85 90 95

Thr Phe Gly Gln Gly Thr Lys Leu Glu Ile Lys
100 105

<210> SEQ ID NO 104
<211> LENGTH: 106
<212> TYPE: PRT
<213> ORGANISM: Artificial sequence
<220> FEATURE:
<223> OTHER INFORMATION: humanized sequence

<400> SEQUENCE: 104

Asp Ile Gln Leu Thr Gln Ser Pro Ser Ser Leu Ser Ala Ser Val Gly
1 5 10 15

Asp Arg Val Thr Ile Thr Cys Lys Gly Ser Gln Asn Ile Asn Asn Tyr
20 25 30

Leu Ala Trp Tyr Gln Gln Lys Pro Gly Lys Ala Pro Lys Leu Leu Ile
35 40 45

```
Tyr Lys Thr Asn Ser Leu Gln Thr Gly Ile Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Cys Gln Tyr Asn Asn Gly Tyr Thr
                85                  90                  95

Phe Gly Gln Gly Thr Lys Leu Glu Ile Lys
            100                 105


<210> SEQ ID NO 105
<211> LENGTH: 106
<212> TYPE: PRT
<213> ORGANISM: Artificial sequence
<220> FEATURE:
<223> OTHER INFORMATION: humanized sequence

<400> SEQUENCE: 105

Asp Ile Gln Leu Thr Gln Ser Pro Ser Ser Leu Ser Ala Ser Val Gly
1               5                   10                  15

Asp Arg Val Thr Ile Thr Cys Lys Gly Ser Gln Asn Ile Asn Asn Tyr
            20                  25                  30

Leu Ala Trp Tyr Gln Gln Lys Pro Gly Lys Ala Pro Lys Leu Leu Ile
        35                  40                  45

Tyr Lys Thr Asn Ser Leu Gln Thr Gly Ile Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Tyr Gln Tyr Asn Asn Gly Tyr Thr
                85                  90                  95

Phe Gly Gln Gly Thr Lys Leu Glu Ile Lys
            100                 105


<210> SEQ ID NO 106
<211> LENGTH: 106
<212> TYPE: PRT
<213> ORGANISM: Artificial sequence
<220> FEATURE:
<223> OTHER INFORMATION: humanized sequence

<400> SEQUENCE: 106

Asp Ile Gln Leu Thr Gln Ser Pro Ser Ser Leu Ser Ala Ser Val Gly
1               5                   10                  15

Asp Arg Val Thr Ile Thr Cys Lys Gly Ser Gln Asn Ile Asn Asn Tyr
            20                  25                  30

Leu Ala Trp Tyr Gln Gln Lys Pro Gly Lys Ala Pro Lys Leu Leu Ile
        35                  40                  45

Tyr Lys Thr Asn Ser Leu Gln Thr Gly Ile Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Ser Gln Tyr Asn Asn Gly Tyr Thr
                85                  90                  95

Phe Gly Gln Gly Thr Lys Leu Glu Ile Lys
            100                 105


<210> SEQ ID NO 107
<211> LENGTH: 106
<212> TYPE: PRT
<213> ORGANISM: Artificial sequence
```

<220> FEATURE:
<223> OTHER INFORMATION: humanized sequence

<400> SEQUENCE: 107

```
Asp Ile Gln Leu Thr Gln Ser Pro Ser Ser Leu Ser Ala Ser Val Gly
1               5                   10                  15

Asp Arg Val Thr Ile Thr Cys Lys Gly Ser Gln Asn Ile Asn Asn Tyr
            20                  25                  30

Leu Ala Trp Tyr Gln Gln Lys Pro Gly Lys Ala Pro Lys Leu Leu Ile
        35                  40                  45

Tyr Lys Thr Asn Ser Leu Gln Thr Gly Ile Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Cys Gln Tyr Asn Asp Gly Tyr Thr
                85                  90                  95

Phe Gly Gln Gly Thr Lys Leu Glu Ile Lys
            100                 105
```

<210> SEQ ID NO 108
<211> LENGTH: 106
<212> TYPE: PRT
<213> ORGANISM: Artificial sequence
<220> FEATURE:
<223> OTHER INFORMATION: humanized sequence

<400> SEQUENCE: 108

```
Asp Ile Gln Leu Thr Gln Ser Pro Ser Ser Leu Ser Ala Ser Val Gly
1               5                   10                  15

Asp Arg Val Thr Ile Thr Cys Lys Ala Gly Gln Asn Ile Asn Asn Tyr
            20                  25                  30

Leu Ala Trp Tyr Gln Gln Lys Pro Gly Lys Ala Pro Lys Leu Leu Ile
        35                  40                  45

Tyr Asn Ala Asn Ser Leu Gln Thr Gly Ile Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Tyr Asn Ser Trp Tyr Thr
                85                  90                  95

Phe Gly Gln Gly Thr Lys Leu Glu Ile Lys
            100                 105
```

<210> SEQ ID NO 109
<211> LENGTH: 114
<212> TYPE: PRT
<213> ORGANISM: Artificial sequence
<220> FEATURE:
<223> OTHER INFORMATION: humanized sequence

<400> SEQUENCE: 109

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Tyr Ser
            20                  25                  30

Val Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Gln Ser Gly Val
    50                  55                  60
```

```
Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Asp Thr Leu Met Lys Met Phe Gly Ala Gly Thr Lys Leu Glu
            100                 105                 110

Leu Lys


<210> SEQ ID NO 110
<211> LENGTH: 114
<212> TYPE: PRT
<213> ORGANISM: Artificial sequence
<220> FEATURE:
<223> OTHER INFORMATION: humanized sequence

<400> SEQUENCE: 110

Asp Val Gln Leu Thr Gln Ser Pro Ser Ser Leu Ser Ala Ser Val Gly
1               5                   10                  15

Asp Arg Val Thr Ile Thr Cys Lys Ser Ser Gln Ser Leu Leu Tyr Ser
            20                  25                  30

Gly Asn Gln Lys Asn Tyr Leu Ala Trp Tyr Gln Gln Lys Pro Gly Lys
        35                  40                  45

Ser Pro Lys Leu Leu Ile Tyr Trp Ala Ser Thr Arg Gln Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Val Ala Thr Tyr Tyr Cys Gln Gln
                85                  90                  95

Tyr Tyr Asp Val Leu Met Asn Met Phe Gly Gly Gly Thr Lys Leu Glu
            100                 105                 110

Ile Lys


<210> SEQ ID NO 111
<211> LENGTH: 16
<212> TYPE: PRT
<213> ORGANISM: Mus musculus

<400> SEQUENCE: 111

Arg Ser Ser Gln Ser Ile Val His Ser Asn Gly Asn Thr Tyr Leu Glu
1               5                   10                  15


<210> SEQ ID NO 112
<211> LENGTH: 11
<212> TYPE: PRT
<213> ORGANISM: Mus musculus

<400> SEQUENCE: 112

Arg Ala Ser Gln Asp Ile Tyr Gly Ser Leu Asn
1               5                   10


<210> SEQ ID NO 113
<211> LENGTH: 11
<212> TYPE: PRT
<213> ORGANISM: Unknown
<220> FEATURE:
<223> OTHER INFORMATION: Rattus norvegicus or humanized sequence

<400> SEQUENCE: 113

Lys Gly Ser Gln Asn Ile Asn Asn Tyr Leu Ala
1               5                   10
```

<210> SEQ ID NO 114
<211> LENGTH: 11
<212> TYPE: PRT
<213> ORGANISM: Rattus norvegicus

<400> SEQUENCE: 114

Lys Ala Gly Gln Lys Ile Asn Asn Tyr Leu Ala
1 5 10

<210> SEQ ID NO 115
<211> LENGTH: 11
<212> TYPE: PRT
<213> ORGANISM: Rattus norvegicus

<400> SEQUENCE: 115

Arg Ala Ser Gln Asp Ile Ser Asn Tyr Leu Asn
1 5 10

<210> SEQ ID NO 116
<211> LENGTH: 11
<212> TYPE: PRT
<213> ORGANISM: Rattus norvegicus

<400> SEQUENCE: 116

Lys Gly Ser Gln Asn Ile Asp Asn Tyr Leu Ala
1 5 10

<210> SEQ ID NO 117
<211> LENGTH: 11
<212> TYPE: PRT
<213> ORGANISM: Rattus norvegicus

<400> SEQUENCE: 117

Leu Ala Ser Glu Gly Ile Phe Ser Tyr Leu Ala
1 5 10

<210> SEQ ID NO 118
<211> LENGTH: 17
<212> TYPE: PRT
<213> ORGANISM: Unknown
<220> FEATURE:
<223> OTHER INFORMATION: Rattus norvegicus or humanized sequence

<400> SEQUENCE: 118

Lys Ser Ser Gln Ser Leu Leu Tyr Ser Gly Asn Gln Lys Asn Tyr Leu
1 5 10 15

Ala

<210> SEQ ID NO 119
<211> LENGTH: 11
<212> TYPE: PRT
<213> ORGANISM: Rattus norvegicus

<400> SEQUENCE: 119

Lys Gly Ser Gln Asn Ile Tyr Asn Tyr Leu Ala
1 5 10

<210> SEQ ID NO 120
<211> LENGTH: 11
<212> TYPE: PRT
<213> ORGANISM: Unknown
<220> FEATURE:
<223> OTHER INFORMATION: Rattus norvegicus or humanized sequence

<400> SEQUENCE: 120

```
Leu Ala Ser Glu Gly Ile Phe Ser Tyr Leu Gly
1               5                   10


<210> SEQ ID NO 121
<211> LENGTH: 11
<212> TYPE: PRT
<213> ORGANISM: Unknown
<220> FEATURE:
<223> OTHER INFORMATION: Rattus norvegicus or humanized sequence

<400> SEQUENCE: 121

Lys Ala Gly Gln Asn Ile Asn Asn Tyr Leu Ala
1               5                   10


<210> SEQ ID NO 122
<211> LENGTH: 17
<212> TYPE: PRT
<213> ORGANISM: Unknown
<220> FEATURE:
<223> OTHER INFORMATION: Rattus norvegicus or humanized sequence

<400> SEQUENCE: 122

Lys Ser Ser Gln Ser Leu Leu Tyr Ser Val Asn Gln Lys Asn Tyr Leu
1               5                   10                  15

Ala


<210> SEQ ID NO 123
<211> LENGTH: 11
<212> TYPE: PRT
<213> ORGANISM: Rattus norvegicus

<400> SEQUENCE: 123

Lys Gly Ser Gln Asn Ile Asn Asn Tyr Leu Gly
1               5                   10


<210> SEQ ID NO 124
<211> LENGTH: 7
<212> TYPE: PRT
<213> ORGANISM: Mus musculus

<400> SEQUENCE: 124

Lys Val Ser Asn Arg Phe Ser
1               5


<210> SEQ ID NO 125
<211> LENGTH: 7
<212> TYPE: PRT
<213> ORGANISM: Mus musculus

<400> SEQUENCE: 125

Gly Thr Ser Ser Leu Asp Ser
1               5


<210> SEQ ID NO 126
<211> LENGTH: 7
<212> TYPE: PRT
<213> ORGANISM: Unknown
<220> FEATURE:
<223> OTHER INFORMATION: Rattus norvegicus or humanized sequence

<400> SEQUENCE: 126

Lys Thr Asn Ser Leu Gln Thr
1               5
```

<210> SEQ ID NO 127
<211> LENGTH: 7
<212> TYPE: PRT
<213> ORGANISM: Unknown
<220> FEATURE:
<223> OTHER INFORMATION: Rattus norvegicus or humanized sequence

<400> SEQUENCE: 127

Asn Ala Asn Ser Leu Gln Thr
1               5

<210> SEQ ID NO 128
<211> LENGTH: 7
<212> TYPE: PRT
<213> ORGANISM: Rattus norvegicus

<400> SEQUENCE: 128

Tyr Thr Ser Arg Leu His Ser
1               5

<210> SEQ ID NO 129
<211> LENGTH: 7
<212> TYPE: PRT
<213> ORGANISM: Rattus norvegicus

<400> SEQUENCE: 129

Gly Ala Asn Thr Leu Gln Ala
1               5

<210> SEQ ID NO 130
<211> LENGTH: 7
<212> TYPE: PRT
<213> ORGANISM: Unknown
<220> FEATURE:
<223> OTHER INFORMATION: Rattus norvegicus or humanized sequence

<400> SEQUENCE: 130

Trp Ala Ser Thr Arg Gln Ser
1               5

<210> SEQ ID NO 131
<211> LENGTH: 7
<212> TYPE: PRT
<213> ORGANISM: Rattus norvegicus

<400> SEQUENCE: 131

Gly Ala Asn Ser Leu Gln Ala
1               5

<210> SEQ ID NO 132
<211> LENGTH: 7
<212> TYPE: PRT
<213> ORGANISM: Rattus norvegicus

<400> SEQUENCE: 132

Lys Thr Asn Asn Leu Gln Thr
1               5

<210> SEQ ID NO 133
<211> LENGTH: 7
<212> TYPE: PRT
<213> ORGANISM: Rattus norvegicus

<400> SEQUENCE: 133

Lys Thr Ser Ser Leu Gln Ala
1               5

```
<210> SEQ ID NO 134
<211> LENGTH: 7
<212> TYPE: PRT
<213> ORGANISM: Rattus norvegicus

<400> SEQUENCE: 134

Glu Thr Asn Ser Leu Gln Thr
1               5


<210> SEQ ID NO 135
<211> LENGTH: 9
<212> TYPE: PRT
<213> ORGANISM: Mus musculus

<400> SEQUENCE: 135

Phe Gln Gly Ser His Val Pro Arg Thr
1               5


<210> SEQ ID NO 136
<211> LENGTH: 9
<212> TYPE: PRT
<213> ORGANISM: Mus musculus

<400> SEQUENCE: 136

Leu Gln Tyr Ala Ser Tyr Pro Tyr Thr
1               5


<210> SEQ ID NO 137
<211> LENGTH: 8
<212> TYPE: PRT
<213> ORGANISM: Rattus norvegicus

<400> SEQUENCE: 137

Tyr Gln Tyr Asn Asn Trp Tyr Thr
1               5


<210> SEQ ID NO 138
<211> LENGTH: 8
<212> TYPE: PRT
<213> ORGANISM: Unknown
<220> FEATURE:
<223> OTHER INFORMATION: Rattus norvegicus or humanized sequence

<400> SEQUENCE: 138

Gln Gln Tyr Asn Ser Trp Tyr Thr
1               5


<210> SEQ ID NO 139
<211> LENGTH: 9
<212> TYPE: PRT
<213> ORGANISM: Rattus norvegicus

<400> SEQUENCE: 139

Gln Gln Gly Asn Thr Leu Pro Trp Thr
1               5


<210> SEQ ID NO 140
<211> LENGTH: 8
<212> TYPE: PRT
<213> ORGANISM: Unknown
<220> FEATURE:
<223> OTHER INFORMATION: Rattus norvegicus or humanized sequence

<400> SEQUENCE: 140
```

Ser Gln Tyr Asn Asn Gly Tyr Thr
1 5

<210> SEQ ID NO 141
<211> LENGTH: 8
<212> TYPE: PRT
<213> ORGANISM: Rattus norvegicus

<400> SEQUENCE: 141

Tyr Gln Tyr Asn Asp Gly Tyr Thr
1 5

<210> SEQ ID NO 142
<211> LENGTH: 8
<212> TYPE: PRT
<213> ORGANISM: Unknown
<220> FEATURE:
<223> OTHER INFORMATION: Rattus norvegicus or humanized sequence

<400> SEQUENCE: 142

Tyr Gln Tyr Asn Asn Gly Tyr Thr
1 5

<210> SEQ ID NO 143
<211> LENGTH: 8
<212> TYPE: PRT
<213> ORGANISM: Unknown
<220> FEATURE:
<223> OTHER INFORMATION: Rattus norvegicus or humanized sequence

<400> SEQUENCE: 143

Cys Gln Tyr Asn Asn Gly Tyr Thr
1 5

<210> SEQ ID NO 144
<211> LENGTH: 9
<212> TYPE: PRT
<213> ORGANISM: Unknown
<220> FEATURE:
<223> OTHER INFORMATION: Rattus norvegicus or humanized sequence

<400> SEQUENCE: 144

Gln Gln Ser Tyr Lys Phe Pro Val Thr
1 5

<210> SEQ ID NO 145
<211> LENGTH: 8
<212> TYPE: PRT
<213> ORGANISM: Unknown
<220> FEATURE:
<223> OTHER INFORMATION: Rattus norvegicus or humanized sequence

<400> SEQUENCE: 145

Cys Gln Tyr Asn Asp Gly Tyr Thr
1 5

<210> SEQ ID NO 146
<211> LENGTH: 10
<212> TYPE: PRT
<213> ORGANISM: Unknown
<220> FEATURE:
<223> OTHER INFORMATION: Rattus norvegicus or humanized sequence

<400> SEQUENCE: 146

Gln Gln Tyr Tyr Asp Thr Leu Met Lys Met
1 5 10

<210> SEQ ID NO 147
<211> LENGTH: 10
<212> TYPE: PRT
<213> ORGANISM: Unknown
<220> FEATURE:
<223> OTHER INFORMATION: Rattus norvegicus or humanized sequence

<400> SEQUENCE: 147

Gln Gln Tyr Tyr Asp Val Leu Met Asn Met
1 5 10

<210> SEQ ID NO 148
<211> LENGTH: 8
<212> TYPE: PRT
<213> ORGANISM: Artificial sequence
<220> FEATURE:
<223> OTHER INFORMATION: humanized sequence

<400> SEQUENCE: 148

Tyr Gln Tyr Asn Gln Gly Tyr Thr
1 5

<210> SEQ ID NO 149
<211> LENGTH: 8
<212> TYPE: PRT
<213> ORGANISM: Artificial sequence
<220> FEATURE:
<223> OTHER INFORMATION: humanized sequence

<400> SEQUENCE: 149

Tyr Gln Tyr Asn Ser Gly Tyr Thr
1 5

<210> SEQ ID NO 150
<211> LENGTH: 1531
<212> TYPE: PRT
<213> ORGANISM: Homo sapiens

<400> SEQUENCE: 150

Met Ala Leu Arg Gly Phe Cys Ser Ala Asp Gly Ser Asp Pro Leu Trp
1 5 10 15

Asp Trp Asn Val Thr Trp Asn Thr Ser Asn Pro Asp Phe Thr Lys Cys
20 25 30

Phe Gln Asn Thr Val Leu Val Trp Val Pro Cys Phe Tyr Leu Trp Ala
35 40 45

Cys Phe Pro Phe Tyr Phe Leu Tyr Leu Ser Arg His Asp Arg Gly Tyr
50 55 60

Ile Gln Met Thr Pro Leu Asn Lys Thr Lys Thr Ala Leu Gly Phe Leu
65 70 75 80

Leu Trp Ile Val Cys Trp Ala Asp Leu Phe Tyr Ser Phe Trp Glu Arg
85 90 95

Ser Arg Gly Ile Phe Leu Ala Pro Val Phe Leu Val Ser Pro Thr Leu
100 105 110

Leu Gly Ile Thr Met Leu Leu Ala Thr Phe Leu Ile Gln Leu Glu Arg
115 120 125

Arg Lys Gly Val Gln Ser Ser Gly Ile Met Leu Thr Phe Trp Leu Val
130 135 140

Ala Leu Val Cys Ala Leu Ala Ile Leu Arg Ser Lys Ile Met Thr Ala
145 150 155 160

Leu Lys Glu Asp Ala Gln Val Asp Leu Phe Arg Asp Ile Thr Phe Tyr
165 170 175

```
Val Tyr Phe Ser Leu Leu Leu Ile Gln Leu Val Leu Ser Cys Phe Ser
            180                 185                 190

Asp Arg Ser Pro Leu Phe Ser Glu Thr Ile His Asp Pro Asn Pro Cys
        195                 200                 205

Pro Glu Ser Ser Ala Ser Phe Leu Ser Arg Ile Thr Phe Trp Trp Ile
    210                 215                 220

Thr Gly Leu Ile Val Arg Gly Tyr Arg Gln Pro Leu Glu Gly Ser Asp
225                 230                 235                 240

Leu Trp Ser Leu Asn Lys Glu Asp Thr Ser Glu Gln Val Val Pro Val
                245                 250                 255

Leu Val Lys Asn Trp Lys Lys Glu Cys Ala Lys Thr Arg Lys Gln Pro
            260                 265                 270

Val Lys Val Val Tyr Ser Ser Lys Asp Pro Ala Gln Pro Lys Glu Ser
        275                 280                 285

Ser Lys Val Asp Ala Asn Glu Glu Val Glu Ala Leu Ile Val Lys Ser
    290                 295                 300

Pro Gln Lys Glu Trp Asn Pro Ser Leu Phe Lys Val Leu Tyr Lys Thr
305                 310                 315                 320

Phe Gly Pro Tyr Phe Leu Met Ser Phe Phe Phe Lys Ala Ile His Asp
                325                 330                 335

Leu Met Met Phe Ser Gly Pro Gln Ile Leu Lys Leu Leu Ile Lys Phe
            340                 345                 350

Val Asn Asp Thr Lys Ala Pro Asp Trp Gln Gly Tyr Phe Tyr Thr Val
        355                 360                 365

Leu Leu Phe Val Thr Ala Cys Leu Gln Thr Leu Val Leu His Gln Tyr
    370                 375                 380

Phe His Ile Cys Phe Val Ser Gly Met Arg Ile Lys Thr Ala Val Ile
385                 390                 395                 400

Gly Ala Val Tyr Arg Lys Ala Leu Val Ile Thr Asn Ser Ala Arg Lys
                405                 410                 415

Ser Ser Thr Val Gly Glu Ile Val Asn Leu Met Ser Val Asp Ala Gln
            420                 425                 430

Arg Phe Met Asp Leu Ala Thr Tyr Ile Asn Met Ile Trp Ser Ala Pro
        435                 440                 445

Leu Gln Val Ile Leu Ala Leu Tyr Leu Leu Trp Leu Asn Leu Gly Pro
    450                 455                 460

Ser Val Leu Ala Gly Val Ala Val Met Val Leu Met Val Pro Val Asn
465                 470                 475                 480

Ala Val Met Ala Met Lys Thr Lys Thr Tyr Gln Val Ala His Met Lys
                485                 490                 495

Ser Lys Asp Asn Arg Ile Lys Leu Met Asn Glu Ile Leu Asn Gly Ile
            500                 505                 510

Lys Val Leu Lys Leu Tyr Ala Trp Glu Leu Ala Phe Lys Asp Lys Val
        515                 520                 525

Leu Ala Ile Arg Gln Glu Glu Leu Lys Val Leu Lys Lys Ser Ala Tyr
    530                 535                 540

Leu Ser Ala Val Gly Thr Phe Thr Trp Val Cys Thr Pro Phe Leu Val
545                 550                 555                 560

Ala Leu Cys Thr Phe Ala Val Tyr Val Thr Ile Asp Glu Asn Asn Ile
                565                 570                 575

Leu Asp Ala Gln Thr Ala Phe Val Ser Leu Ala Leu Phe Asn Ile Leu
            580                 585                 590
```

```
Arg Phe Pro Leu Asn Ile Leu Pro Met Val Ile Ser Ser Ile Val Gln
        595                 600                 605

Ala Ser Val Ser Leu Lys Arg Leu Arg Ile Phe Leu Ser His Glu Glu
    610                 615                 620

Leu Glu Pro Asp Ser Ile Glu Arg Arg Pro Val Lys Asp Gly Gly Gly
625                 630                 635                 640

Thr Asn Ser Ile Thr Val Arg Asn Ala Thr Phe Thr Trp Ala Arg Ser
                645                 650                 655

Asp Pro Pro Thr Leu Asn Gly Ile Thr Phe Ser Ile Pro Glu Gly Ala
            660                 665                 670

Leu Val Ala Val Val Gly Gln Val Gly Cys Gly Lys Ser Ser Leu Leu
        675                 680                 685

Ser Ala Leu Leu Ala Glu Met Asp Lys Val Glu Gly His Val Ala Ile
    690                 695                 700

Lys Gly Ser Val Ala Tyr Val Pro Gln Gln Ala Trp Ile Gln Asn Asp
705                 710                 715                 720

Ser Leu Arg Glu Asn Ile Leu Phe Gly Cys Gln Leu Glu Glu Pro Tyr
                725                 730                 735

Tyr Arg Ser Val Ile Gln Ala Cys Ala Leu Leu Pro Asp Leu Glu Ile
            740                 745                 750

Leu Pro Ser Gly Asp Arg Thr Glu Ile Gly Glu Lys Gly Val Asn Leu
        755                 760                 765

Ser Gly Gly Gln Lys Gln Arg Val Ser Leu Ala Arg Ala Val Tyr Ser
    770                 775                 780

Asn Ala Asp Ile Tyr Leu Phe Asp Asp Pro Leu Ser Ala Val Asp Ala
785                 790                 795                 800

His Val Gly Lys His Ile Phe Glu Asn Val Ile Gly Pro Lys Gly Met
                805                 810                 815

Leu Lys Asn Lys Thr Arg Ile Leu Val Thr His Ser Met Ser Tyr Leu
            820                 825                 830

Pro Gln Val Asp Val Ile Ile Val Met Ser Gly Gly Lys Ile Ser Glu
        835                 840                 845

Met Gly Ser Tyr Gln Glu Leu Leu Ala Arg Asp Gly Ala Phe Ala Glu
    850                 855                 860

Phe Leu Arg Thr Tyr Ala Ser Thr Glu Gln Glu Gln Asp Ala Glu Glu
865                 870                 875                 880

Asn Gly Val Thr Gly Val Ser Gly Pro Gly Lys Glu Ala Lys Gln Met
                885                 890                 895

Glu Asn Gly Met Leu Val Thr Asp Ser Ala Gly Lys Gln Leu Gln Arg
            900                 905                 910

Gln Leu Ser Ser Ser Ser Ser Tyr Ser Gly Asp Ile Ser Arg His His
        915                 920                 925

Asn Ser Thr Ala Glu Leu Gln Lys Ala Glu Ala Lys Lys Glu Glu Thr
    930                 935                 940

Trp Lys Leu Met Glu Ala Asp Lys Ala Gln Thr Gly Gln Val Lys Leu
945                 950                 955                 960

Ser Val Tyr Trp Asp Tyr Met Lys Ala Ile Gly Leu Phe Ile Ser Phe
                965                 970                 975

Leu Ser Ile Phe Leu Phe Met Cys Asn His Val Ser Ala Leu Ala Ser
            980                 985                 990

Asn Tyr Trp Leu Ser Leu Trp Thr  Asp Asp Pro Ile Val  Asn Gly Thr
        995                 1000                1005

Gln Glu  His Thr Lys Val Arg  Leu Ser Val Tyr Gly  Ala Leu Gly
```

```
    1010                1015                1020

Ile Ser  Gln Gly Ile Ala Val  Phe Gly Tyr Ser Met  Ala Val Ser
    1025                1030                1035

Ile Gly  Gly Ile Leu Ala Ser  Arg Cys Leu His Val  Asp Leu Leu
    1040                1045                1050

His Ser  Ile Leu Arg Ser Pro  Met Ser Phe Phe Glu  Arg Thr Pro
    1055                1060                1065

Ser Gly  Asn Leu Val Asn Arg  Phe Ser Lys Glu Leu  Asp Thr Val
    1070                1075                1080

Asp Ser  Met Ile Pro Glu Val  Ile Lys Met Phe Met  Gly Ser Leu
    1085                1090                1095

Phe Asn  Val Ile Gly Ala Cys  Ile Val Ile Leu Leu  Ala Thr Pro
    1100                1105                1110

Ile Ala  Ala Ile Ile Ile Pro  Pro Leu Gly Leu Ile  Tyr Phe Phe
    1115                1120                1125

Val Gln  Arg Phe Tyr Val Ala  Ser Ser Arg Gln Leu  Lys Arg Leu
    1130                1135                1140

Glu Ser  Val Ser Arg Ser Pro  Val Tyr Ser His Phe  Asn Glu Thr
    1145                1150                1155

Leu Leu  Gly Val Ser Val Ile  Arg Ala Phe Glu Glu  Gln Glu Arg
    1160                1165                1170

Phe Ile  His Gln Ser Asp Leu  Lys Val Asp Glu Asn  Gln Lys Ala
    1175                1180                1185

Tyr Tyr  Pro Ser Ile Val Ala  Asn Arg Trp Leu Ala  Val Arg Leu
    1190                1195                1200

Glu Cys  Val Gly Asn Cys Ile  Val Leu Phe Ala Ala  Leu Phe Ala
    1205                1210                1215

Val Ile  Ser Arg His Ser Leu  Ser Ala Gly Leu Val  Gly Leu Ser
    1220                1225                1230

Val Ser  Tyr Ser Leu Gln Val  Thr Thr Tyr Leu Asn  Trp Leu Val
    1235                1240                1245

Arg Met  Ser Ser Glu Met Glu  Thr Asn Ile Val Ala  Val Glu Arg
    1250                1255                1260

Leu Lys  Glu Tyr Ser Glu Thr  Glu Lys Glu Ala Pro  Trp Gln Ile
    1265                1270                1275

Gln Glu  Thr Ala Pro Pro Ser  Ser Trp Pro Gln Val  Gly Arg Val
    1280                1285                1290

Glu Phe  Arg Asn Tyr Cys Leu  Arg Tyr Arg Glu Asp  Leu Asp Phe
    1295                1300                1305

Val Leu  Arg His Ile Asn Val  Thr Ile Asn Gly Gly  Glu Lys Val
    1310                1315                1320

Gly Ile  Val Gly Arg Thr Gly  Ala Gly Lys Ser Ser  Leu Thr Leu
    1325                1330                1335

Gly Leu  Phe Arg Ile Asn Glu  Ser Ala Glu Gly Glu  Ile Ile Ile
    1340                1345                1350

Asp Gly  Ile Asn Ile Ala Lys  Ile Gly Leu His Asp  Leu Arg Phe
    1355                1360                1365

Lys Ile  Thr Ile Ile Pro Gln  Asp Pro Val Leu Phe  Ser Gly Ser
    1370                1375                1380

Leu Arg  Met Asn Leu Asp Pro  Phe Ser Gln Tyr Ser  Asp Glu Glu
    1385                1390                1395

Val Trp  Thr Ser Leu Glu Leu  Ala His Leu Lys Asp  Phe Val Ser
    1400                1405                1410
```

```
Ala Leu  Pro Asp Lys Leu Asp  His Glu Cys Ala Glu  Gly Gly Glu
    1415                 1420                 1425

Asn Leu  Ser Val Gly Gln Arg  Gln Leu Val Cys Leu  Ala Arg Ala
    1430                 1435                 1440

Leu Leu  Arg Lys Thr Lys Ile  Leu Val Leu Asp Glu  Ala Thr Ala
    1445                 1450                 1455

Ala Val  Asp Leu Glu Thr Asp  Asp Leu Ile Gln Ser  Thr Ile Arg
    1460                 1465                 1470

Thr Gln  Phe Glu Asp Cys Thr  Val Leu Thr Ile Ala  His Arg Leu
    1475                 1480                 1485

Asn Thr  Ile Met Asp Tyr Thr  Arg Val Ile Val Leu  Asp Lys Gly
    1490                 1495                 1500

Glu Ile  Gln Glu Tyr Gly Ala  Pro Ser Asp Leu Leu  Gln Gln Arg
    1505                 1510                 1515

Gly Leu  Phe Tyr Ser Met Ala  Lys Asp Ala Gly Leu  Val
    1520                 1525                 1530


<210> SEQ ID NO 151
<211> LENGTH: 33
<212> TYPE: PRT
<213> ORGANISM: Homo sapiens

<400> SEQUENCE: 151

Met Ala Leu Arg Gly Phe Cys Ser Ala Asp Gly Ser Asp Pro Leu Trp
1               5                   10                  15

Asp Trp Asn Val Thr Trp Asn Thr Ser Asn Pro Asp Phe Thr Lys Cys
            20                  25                  30

Phe


<210> SEQ ID NO 152
<211> LENGTH: 5
<212> TYPE: PRT
<213> ORGANISM: Homo sapiens

<400> SEQUENCE: 152

Arg Ser Arg Gly Ile
1               5


<210> SEQ ID NO 153
<211> LENGTH: 18
<212> TYPE: PRT
<213> ORGANISM: Homo sapiens

<400> SEQUENCE: 153

Ser Lys Ile Met Thr Ala Leu Lys Glu Asp Ala Gln Val Asp Leu Phe
1               5                   10                  15

Arg Asp


<210> SEQ ID NO 154
<211> LENGTH: 26
<212> TYPE: PRT
<213> ORGANISM: Homo sapiens

<400> SEQUENCE: 154

Met Met Phe Ser Gly Pro Gln Ile Leu Lys Leu Leu Ile Lys Phe Val
1               5                   10                  15

Asn Asp Thr Lys Ala Pro Asp Trp Gln Gly
            20                  25
```

<210> SEQ ID NO 155
<211> LENGTH: 22
<212> TYPE: PRT
<213> ORGANISM: Homo sapiens

<400> SEQUENCE: 155

Val Thr Ile Asp Glu Asn Asn Ile Leu Asp Ala Gln Thr Ala Phe Val
1               5                   10                  15

Ser Leu Ala Leu Phe Asn
            20

<210> SEQ ID NO 156
<211> LENGTH: 37
<212> TYPE: PRT
<213> ORGANISM: Homo sapiens

<400> SEQUENCE: 156

Ala Leu Ala Ser Asn Tyr Trp Leu Ser Leu Trp Thr Asp Asp Pro Ile
1               5                   10                  15

Val Asn Gly Thr Gln Glu His Thr Lys Val Arg Leu Ser Val Tyr Gly
            20                  25                  30

Ala Leu Gly Ile Ser
        35

<210> SEQ ID NO 157
<211> LENGTH: 1329
<212> TYPE: PRT
<213> ORGANISM: Homo sapiens

<400> SEQUENCE: 157

Met Asp Pro Asn Pro Cys Pro Glu Ser Ser Ala Ser Phe Leu Ser Arg
1               5                   10                  15

Ile Thr Phe Trp Trp Ile Thr Gly Leu Ile Val Arg Gly Tyr Arg Gln
            20                  25                  30

Pro Leu Glu Gly Ser Asp Leu Trp Ser Leu Asn Lys Glu Asp Thr Ser
        35                  40                  45

Glu Gln Val Val Pro Val Leu Val Lys Asn Trp Lys Lys Glu Cys Ala
    50                  55                  60

Lys Thr Arg Lys Gln Pro Val Lys Val Val Tyr Ser Ser Lys Asp Pro
65                  70                  75                  80

Ala Gln Pro Lys Glu Ser Ser Lys Val Asp Ala Asn Glu Glu Val Glu
                85                  90                  95

Ala Leu Ile Val Lys Ser Pro Gln Lys Glu Trp Asn Pro Ser Leu Phe
            100                 105                 110

Lys Val Leu Tyr Lys Thr Phe Gly Pro Tyr Phe Leu Met Ser Phe Phe
        115                 120                 125

Phe Lys Ala Ile His Asp Leu Met Met Phe Ser Gly Pro Gln Ile Leu
    130                 135                 140

Lys Leu Leu Ile Lys Phe Val Asn Asp Thr Lys Ala Pro Asp Trp Gln
145                 150                 155                 160

Gly Tyr Phe Tyr Thr Val Leu Leu Phe Val Thr Ala Cys Leu Gln Thr
                165                 170                 175

Leu Val Leu His Gln Tyr Phe His Ile Cys Phe Val Ser Gly Met Arg
            180                 185                 190

Ile Lys Thr Ala Val Ile Gly Ala Val Tyr Arg Lys Ala Leu Val Ile
        195                 200                 205

Thr Asn Ser Ala Arg Lys Ser Ser Thr Val Gly Glu Ile Val Asn Leu

```
    210                 215                 220

Met Ser Val Asp Ala Gln Arg Phe Met Asp Leu Ala Thr Tyr Ile Asn
225                 230                 235                 240

Met Ile Trp Ser Ala Pro Leu Gln Val Ile Leu Ala Leu Tyr Leu Leu
                245                 250                 255

Trp Leu Asn Leu Gly Pro Ser Val Leu Ala Gly Val Ala Val Met Val
            260                 265                 270

Leu Met Val Pro Val Asn Ala Val Met Ala Met Lys Thr Lys Thr Tyr
        275                 280                 285

Gln Val Ala His Met Lys Ser Lys Asp Asn Arg Ile Lys Leu Met Asn
    290                 295                 300

Glu Ile Leu Asn Gly Ile Lys Val Leu Lys Leu Tyr Ala Trp Glu Leu
305                 310                 315                 320

Ala Phe Lys Asp Lys Val Leu Ala Ile Arg Gln Glu Glu Leu Lys Val
                325                 330                 335

Leu Lys Lys Ser Ala Tyr Leu Ser Ala Val Gly Thr Phe Thr Trp Val
            340                 345                 350

Cys Thr Pro Phe Leu Val Ala Leu Cys Thr Phe Ala Val Tyr Val Thr
        355                 360                 365

Ile Asp Glu Asn Asn Ile Leu Asp Ala Gln Thr Ala Phe Val Ser Leu
    370                 375                 380

Ala Leu Phe Asn Ile Leu Arg Phe Pro Leu Asn Ile Leu Pro Met Val
385                 390                 395                 400

Ile Ser Ser Ile Val Gln Ala Ser Val Ser Leu Lys Arg Leu Arg Ile
                405                 410                 415

Phe Leu Ser His Glu Glu Leu Glu Pro Asp Ser Ile Glu Arg Arg Pro
            420                 425                 430

Val Lys Asp Gly Gly Gly Thr Asn Ser Ile Thr Val Arg Asn Ala Thr
        435                 440                 445

Phe Thr Trp Ala Arg Ser Asp Pro Pro Thr Leu Asn Gly Ile Thr Phe
    450                 455                 460

Ser Ile Pro Glu Gly Ala Leu Val Ala Val Val Gly Gln Val Gly Cys
465                 470                 475                 480

Gly Lys Ser Ser Leu Leu Ser Ala Leu Leu Ala Glu Met Asp Lys Val
                485                 490                 495

Glu Gly His Val Ala Ile Lys Gly Ser Val Ala Tyr Val Pro Gln Gln
            500                 505                 510

Ala Trp Ile Gln Asn Asp Ser Leu Arg Glu Asn Ile Leu Phe Gly Cys
        515                 520                 525

Gln Leu Glu Glu Pro Tyr Tyr Arg Ser Val Ile Gln Ala Cys Ala Leu
    530                 535                 540

Leu Pro Asp Leu Glu Ile Leu Pro Ser Gly Asp Arg Thr Glu Ile Gly
545                 550                 555                 560

Glu Lys Gly Val Asn Leu Ser Gly Gly Gln Lys Gln Arg Val Ser Leu
                565                 570                 575

Ala Arg Ala Val Tyr Ser Asn Ala Asp Ile Tyr Leu Phe Asp Asp Pro
            580                 585                 590

Leu Ser Ala Val Asp Ala His Val Gly Lys His Ile Phe Glu Asn Val
        595                 600                 605

Ile Gly Pro Lys Gly Met Leu Lys Asn Lys Thr Arg Ile Leu Val Thr
    610                 615                 620

His Ser Met Ser Tyr Leu Pro Gln Val Asp Val Ile Ile Val Met Ser
625                 630                 635                 640
```

```
Gly Gly Lys Ile Ser Glu Met Gly Ser Tyr Gln Glu Leu Leu Ala Arg
                645                 650                 655

Asp Gly Ala Phe Ala Glu Phe Leu Arg Thr Tyr Ala Ser Thr Glu Gln
            660                 665                 670

Glu Gln Asp Ala Glu Glu Asn Gly Val Thr Gly Val Ser Gly Pro Gly
        675                 680                 685

Lys Glu Ala Lys Gln Met Glu Asn Gly Met Leu Val Thr Asp Ser Ala
    690                 695                 700

Gly Lys Gln Leu Gln Arg Gln Leu Ser Ser Ser Ser Ser Tyr Ser Gly
705                 710                 715                 720

Asp Ile Ser Arg His His Asn Ser Thr Ala Glu Leu Gln Lys Ala Glu
                725                 730                 735

Ala Lys Lys Glu Glu Thr Trp Lys Leu Met Glu Ala Asp Lys Ala Gln
            740                 745                 750

Thr Gly Gln Val Lys Leu Ser Val Tyr Trp Asp Tyr Met Lys Ala Ile
        755                 760                 765

Gly Leu Phe Ile Ser Phe Leu Ser Ile Phe Leu Phe Met Cys Asn His
    770                 775                 780

Val Ser Ala Leu Ala Ser Asn Tyr Trp Leu Ser Leu Trp Thr Asp Asp
785                 790                 795                 800

Pro Ile Val Asn Gly Thr Gln Glu His Thr Lys Val Arg Leu Ser Val
                805                 810                 815

Tyr Gly Ala Leu Gly Ile Ser Gln Gly Ile Ala Val Phe Gly Tyr Ser
            820                 825                 830

Met Ala Val Ser Ile Gly Gly Ile Leu Ala Ser Arg Cys Leu His Val
        835                 840                 845

Asp Leu Leu His Ser Ile Leu Arg Ser Pro Met Ser Phe Phe Glu Arg
    850                 855                 860

Thr Pro Ser Gly Asn Leu Val Asn Arg Phe Ser Lys Glu Leu Asp Thr
865                 870                 875                 880

Val Asp Ser Met Ile Pro Glu Val Ile Lys Met Phe Met Gly Ser Leu
                885                 890                 895

Phe Asn Val Ile Gly Ala Cys Ile Val Ile Leu Leu Ala Thr Pro Ile
            900                 905                 910

Ala Ala Ile Ile Ile Pro Pro Leu Gly Leu Ile Tyr Phe Phe Val Gln
        915                 920                 925

Arg Phe Tyr Val Ala Ser Ser Arg Gln Leu Lys Arg Leu Glu Ser Val
    930                 935                 940

Ser Arg Ser Pro Val Tyr Ser His Phe Asn Glu Thr Leu Leu Gly Val
945                 950                 955                 960

Ser Val Ile Arg Ala Phe Glu Glu Gln Glu Arg Phe Ile His Gln Ser
                965                 970                 975

Asp Leu Lys Val Asp Glu Asn Gln Lys Ala Tyr Tyr Pro Ser Ile Val
            980                 985                 990

Ala Asn Arg Trp Leu Ala Val Arg  Leu Glu Cys Val Gly  Asn Cys Ile
        995                 1000                 1005

Val Leu  Phe Ala Ala Leu Phe  Ala Val Ile Ser Arg  His Ser Leu
    1010                 1015                 1020

Ser Ala  Gly Leu Val Gly Leu  Ser Val Ser Tyr Ser  Leu Gln Val
    1025                 1030                 1035

Thr Thr  Tyr Leu Asn Trp Leu  Val Arg Met Ser Ser  Glu Met Glu
    1040                 1045                 1050
```

```
Thr Asn  Ile Val Ala Val Glu  Arg Leu Lys Glu Tyr  Ser Glu Thr
    1055                 1060                 1065

Glu Lys  Glu Ala Pro Trp Gln  Ile Gln Glu Thr Ala  Pro Pro Ser
    1070                 1075                 1080

Ser Trp  Pro Gln Val Gly Arg  Val Glu Phe Arg Asn  Tyr Cys Leu
    1085                 1090                 1095

Arg Tyr  Arg Glu Asp Leu Asp  Phe Val Leu Arg His  Ile Asn Val
    1100                 1105                 1110

Thr Ile  Asn Gly Gly Glu Lys  Val Gly Ile Val Gly  Arg Thr Gly
    1115                 1120                 1125

Ala Gly  Lys Ser Ser Leu Thr  Leu Gly Leu Phe Arg  Ile Asn Glu
    1130                 1135                 1140

Ser Ala  Glu Gly Glu Ile Ile  Ile Asp Gly Ile Asn  Ile Ala Lys
    1145                 1150                 1155

Ile Gly  Leu His Asp Leu Arg  Phe Lys Ile Thr Ile  Ile Pro Gln
    1160                 1165                 1170

Asp Pro  Val Leu Phe Ser Gly  Ser Leu Arg Met Asn  Leu Asp Pro
    1175                 1180                 1185

Phe Ser  Gln Tyr Ser Asp Glu  Glu Val Trp Thr Ser  Leu Glu Leu
    1190                 1195                 1200

Ala His  Leu Lys Asp Phe Val  Ser Ala Leu Pro Asp  Lys Leu Asp
    1205                 1210                 1215

His Glu  Cys Ala Glu Gly Gly  Glu Asn Leu Ser Val  Gly Gln Arg
    1220                 1225                 1230

Gln Leu  Val Cys Leu Ala Arg  Ala Leu Leu Arg Lys  Thr Lys Ile
    1235                 1240                 1245

Leu Val  Leu Asp Glu Ala Thr  Ala Ala Val Asp Leu  Glu Thr Asp
    1250                 1255                 1260

Asp Leu  Ile Gln Ser Thr Ile  Arg Thr Gln Phe Glu  Asp Cys Thr
    1265                 1270                 1275

Val Leu  Thr Ile Ala His Arg  Leu Asn Thr Ile Met  Asp Tyr Thr
    1280                 1285                 1290

Arg Val  Ile Val Leu Asp Lys  Gly Glu Ile Gln Glu  Tyr Gly Ala
    1295                 1300                 1305

Pro Ser  Asp Leu Leu Gln Gln  Arg Gly Leu Phe Tyr  Ser Met Ala
    1310                 1315                 1320

Lys Asp  Ala Gly Leu Val
    1325


<210> SEQ ID NO 158
<211> LENGTH: 1531
<212> TYPE: PRT
<213> ORGANISM: Macaca fascicularis

<400> SEQUENCE: 158

Met Ala Leu Arg Gly Phe Cys Ser Ala Asp Gly Ser Asp Pro Leu Trp
1               5                   10                  15

Asp Trp Asn Val Thr Trp Tyr Thr Ser Asn Pro Asp Phe Thr Lys Cys
            20                  25                  30

Phe Gln Asn Thr Val Leu Val Trp Val Pro Cys Phe Tyr Leu Trp Ala
        35                  40                  45

Cys Phe Pro Phe Tyr Phe Leu Tyr Leu Ser Arg His Asp Arg Gly Tyr
    50                  55                  60

Ile Gln Met Thr Leu Leu Asn Lys Thr Lys Thr Ala Leu Gly Phe Leu
65                  70                  75                  80
```

```
Leu Trp Ile Val Cys Trp Ala Asp Leu Phe Tyr Ser Phe Trp Glu Arg
                85                  90                  95

Ser Arg Gly Ile Phe Leu Ala Pro Val Phe Leu Val Ser Pro Thr Leu
            100                 105                 110

Leu Gly Ile Thr Met Leu Leu Ala Thr Phe Leu Ile Gln Leu Glu Arg
        115                 120                 125

Arg Lys Gly Val Gln Ser Ser Gly Ile Met Leu Thr Phe Trp Leu Val
    130                 135                 140

Ala Leu Leu Cys Ala Leu Ala Ile Leu Arg Ser Lys Ile Met Thr Ala
145                 150                 155                 160

Leu Lys Glu Asp Val Gln Val Asp Leu Phe Arg Asp Met Thr Phe Tyr
                165                 170                 175

Val Tyr Phe Ser Leu Val Leu Ile Gln Leu Val Leu Ser Cys Phe Ser
            180                 185                 190

Asp Arg Ser Pro Leu Phe Ser Glu Thr Ile His Asp Pro Asn Pro Cys
        195                 200                 205

Pro Glu Ser Ser Ala Ser Phe Leu Ser Arg Ile Thr Phe Trp Trp Ile
    210                 215                 220

Thr Gly Leu Ile Val Arg Gly Tyr Arg Gln Pro Leu Glu Gly Ser Asp
225                 230                 235                 240

Leu Trp Ser Leu Asn Lys Glu Asp Thr Ser Glu Gln Val Val Pro Val
                245                 250                 255

Leu Val Lys Asn Trp Lys Lys Glu Cys Ala Lys Thr Arg Lys Gln Pro
            260                 265                 270

Val Lys Val Val Tyr Ser Ser Lys Asp Pro Ala Gln Pro Lys Asp Ser
        275                 280                 285

Ser Lys Val Asp Ala Asn Glu Glu Val Glu Ala Leu Ile Val Lys Ser
    290                 295                 300

Pro Gln Lys Glu Trp Asn Pro Ser Leu Phe Lys Val Leu Tyr Lys Thr
305                 310                 315                 320

Phe Gly Pro Tyr Phe Leu Met Ser Phe Phe Phe Lys Ala Ile His Asp
                325                 330                 335

Leu Met Met Phe Ser Gly Pro Glu Ile Leu Lys Leu Leu Ile Asn Phe
            340                 345                 350

Val Asn Asp Thr Lys Ala Pro Asp Trp Gln Gly Tyr Phe Tyr Thr Ala
        355                 360                 365

Leu Leu Phe Val Ala Ala Cys Leu Gln Thr Leu Val Leu His Gln Tyr
    370                 375                 380

Phe His Ile Cys Phe Val Ser Gly Met Arg Ile Lys Thr Ala Val Ile
385                 390                 395                 400

Gly Ala Val Tyr Arg Lys Ala Leu Val Ile Thr Asn Ala Ala Arg Lys
                405                 410                 415

Ser Ser Thr Val Gly Glu Ile Val Asn Leu Met Ser Val Asp Ala Gln
            420                 425                 430

Arg Phe Met Asp Leu Ala Thr Tyr Ile Asn Met Ile Trp Ser Ala Pro
        435                 440                 445

Leu Gln Val Ile Leu Ala Leu Tyr Leu Leu Trp Arg Asn Leu Gly Pro
    450                 455                 460

Pro Ile Leu Ala Gly Val Ala Val Met Val Leu Met Val Pro Val Asn
465                 470                 475                 480

Ala Val Met Ala Met Lys Thr Lys Thr Tyr Gln Val Ala His Met Lys
                485                 490                 495
```

```
Ser Lys Asp Asn Arg Ile Lys Leu Met Asn Glu Ile Leu Asn Gly Ile
            500                 505                 510

Lys Val Leu Lys Leu Tyr Ala Trp Glu Leu Ala Phe Lys Asp Lys Val
        515                 520                 525

Leu Ala Ile Arg Gln Glu Glu Leu Lys Val Leu Lys Lys Ser Ala Tyr
    530                 535                 540

Leu Ala Ala Val Gly Thr Phe Thr Trp Val Cys Thr Pro Phe Leu Val
545                 550                 555                 560

Ala Leu Cys Thr Phe Ala Val Tyr Val Thr Ile Asp Lys Asn Asn Val
                565                 570                 575

Leu Asp Ala Gln Lys Ala Phe Val Ser Leu Ala Leu Phe Asn Ile Leu
            580                 585                 590

Arg Phe Pro Leu Asn Ile Leu Pro Met Val Ile Ser Ser Ile Val Gln
        595                 600                 605

Ala Ser Val Ser Leu Lys Arg Leu Arg Ile Phe Leu Ser His Glu Glu
    610                 615                 620

Leu Glu Pro Asp Ser Ile Glu Arg Arg Pro Val Lys Asp Gly Gly Asp
625                 630                 635                 640

Thr Asn Ser Ile Thr Val Arg Asn Ala Thr Phe Thr Trp Ala Arg Ser
                645                 650                 655

Asp Pro Pro Thr Leu Asn Gly Ile Thr Phe Ser Ile Pro Glu Gly Ala
            660                 665                 670

Leu Val Ala Val Val Gly Gln Val Gly Cys Gly Lys Ser Ser Leu Leu
        675                 680                 685

Ser Ala Leu Leu Ala Glu Met Asp Lys Val Glu Gly His Val Ala Leu
    690                 695                 700

Lys Gly Ser Val Ala Tyr Val Pro Gln Gln Ala Trp Ile Gln Asn Asp
705                 710                 715                 720

Ser Leu Gln Glu Asn Ile Leu Phe Gly Cys Gln Leu Glu Glu Pro Tyr
                725                 730                 735

Tyr Arg Ser Val Ile Gln Ala Cys Ala Leu Leu Pro Asp Leu Glu Ile
            740                 745                 750

Leu Pro Ser Gly Asp Arg Thr Glu Ile Gly Glu Lys Gly Val Asn Leu
        755                 760                 765

Ser Gly Gly Gln Lys Gln Arg Val Ser Leu Ala Arg Ala Val Tyr Cys
    770                 775                 780

Asn Ala Asp Ile Tyr Leu Phe Asp Asp Pro Leu Ser Ala Val Asp Ala
785                 790                 795                 800

His Val Gly Lys His Ile Phe Glu Asn Val Ile Gly Pro Lys Gly Met
                805                 810                 815

Leu Lys Asn Lys Thr Arg Ile Leu Val Thr His Ser Met Ser Tyr Leu
            820                 825                 830

Pro Gln Val Asp Val Ile Ile Val Met Ser Gly Gly Lys Ile Ser Glu
        835                 840                 845

Met Gly Ser Tyr Gln Glu Leu Leu Ala Arg Asp Gly Ala Phe Ala Glu
    850                 855                 860

Phe Leu Arg Thr Tyr Ala Ser Ala Glu Gln Glu Gln Asp Pro Glu Asp
865                 870                 875                 880

Asn Gly Val Thr Gly Val Ser Gly Pro Gly Lys Glu Ala Lys Gln Met
                885                 890                 895

Glu Asn Gly Met Leu Val Thr Asp Ser Ala Gly Lys Gln Leu Gln Arg
            900                 905                 910

Gln Leu Ser Ser Ser Ser Ser Tyr Ser Gly Asp Val Ser Arg Gln His
```

```
        915                 920                 925

Asn Ser Thr Ala Glu Leu Gln Lys Asp Gly Ala Lys Lys Glu Glu Thr
    930                 935                 940

Trp Lys Leu Met Glu Ala Asp Lys Ala Gln Thr Gly Gln Val Lys Leu
945                 950                 955                 960

Ser Val Tyr Trp Asp Tyr Met Lys Ala Ile Gly Leu Phe Ile Ser Phe
                965                 970                 975

Leu Ser Ile Phe Leu Phe Ile Cys Asn His Val Ala Ala Leu Ala Ser
            980                 985                 990

Asn Tyr Trp Leu Ser Leu Trp Thr  Asp Asp Pro Ile Val  Asn Gly Thr
        995                 1000                1005

Gln Glu  His Thr Lys Val Arg  Leu Ser Val Tyr Gly  Ala Leu Gly
    1010                 1015                1020

Ile Ser  Gln Gly Ile Ala Val  Phe Gly Tyr Ser Met  Ala Val Ser
    1025                 1030                1035

Ile Gly  Gly Ile Leu Ala Ser  Arg Cys Leu His Val  Asp Leu Leu
    1040                 1045                1050

His Ser  Ile Leu Arg Ser Pro  Met Ser Phe Phe Glu  Arg Thr Pro
    1055                 1060                1065

Ser Gly  Asn Leu Val Asn Arg  Phe Ser Lys Glu Leu  Asp Thr Val
    1070                 1075                1080

Asp Ser  Met Ile Pro Glu Val  Ile Lys Met Phe Met  Gly Ser Leu
    1085                 1090                1095

Phe Asn  Val Ile Gly Ala Cys  Ile Val Ile Leu Leu  Ala Thr Pro
    1100                 1105                1110

Ile Ala  Ala Ile Ile Ile Pro  Pro Leu Gly Leu Ile  Tyr Phe Phe
    1115                 1120                1125

Val Gln  Arg Phe Tyr Val Ala  Ser Ser Arg Gln Leu  Lys Arg Leu
    1130                 1135                1140

Glu Ser  Val Ser Arg Ser Pro  Val Tyr Ser His Phe  Asn Glu Thr
    1145                 1150                1155

Leu Leu  Gly Val Ser Val Ile  Arg Ala Phe Glu Glu  Gln Glu Arg
    1160                 1165                1170

Phe Ile  His Gln Ser Asp Leu  Lys Val Asp Glu Asn  Gln Lys Ala
    1175                 1180                1185

Tyr Tyr  Pro Ser Ile Val Ala  Asn Arg Trp Leu Ala  Val Arg Leu
    1190                 1195                1200

Glu Cys  Val Gly Asn Cys Ile  Val Leu Phe Ala Ala  Leu Phe Ala
    1205                 1210                1215

Val Ile  Ser Arg His Ser Leu  Ser Ala Gly Leu Val  Gly Leu Ser
    1220                 1225                1230

Val Ser  Tyr Ser Leu Gln Val  Thr Thr Tyr Leu Asn  Trp Leu Val
    1235                 1240                1245

Arg Met  Ser Ser Glu Met Glu  Thr Asn Ile Val Ala  Val Glu Arg
    1250                 1255                1260

Leu Lys  Glu Tyr Ser Glu Thr  Glu Lys Glu Ala Pro  Trp Gln Ile
    1265                 1270                1275

Gln Glu  Thr Ala Pro Pro Ser  Asn Trp Pro Gln Val  Gly Arg Val
    1280                 1285                1290

Glu Phe  Arg Asn Tyr Cys Leu  Arg Tyr Arg Glu Asp  Leu Asp Phe
    1295                 1300                1305

Val Leu  Arg His Ile Asn Val  Thr Ile Asn Gly Gly  Glu Lys Val
    1310                 1315                1320
```

```
Gly Ile  Val Gly Arg Thr Gly  Ala Gly Lys Ser Ser  Leu Thr Leu
    1325                 1330                 1335

Gly Leu  Phe Arg Ile Asn Glu  Ser Ala Glu Gly Glu  Ile Ile Ile
    1340                 1345                 1350

Asp Gly  Ile Asn Ile Ala Arg  Ile Gly Leu His Asp  Leu Arg Phe
    1355                 1360                 1365

Lys Ile  Thr Ile Ile Pro Gln  Asp Pro Val Leu Phe  Ser Gly Ser
    1370                 1375                 1380

Leu Arg  Met Asn Leu Asp Pro  Phe Ser Gln Tyr Ser  Asp Glu Glu
    1385                 1390                 1395

Val Trp  Thr Ser Leu Glu Leu  Ala His Leu Lys Gly  Phe Val Ser
    1400                 1405                 1410

Ala Leu  Pro Asp Lys Leu Asp  His Glu Cys Ala Glu  Gly Gly Glu
    1415                 1420                 1425

Asn Leu  Ser Val Gly Gln Arg  Gln Leu Val Cys Leu  Ala Arg Ala
    1430                 1435                 1440

Leu Leu  Arg Lys Thr Lys Ile  Leu Val Leu Asp Glu  Ala Thr Ala
    1445                 1450                 1455

Ala Val  Asp Leu Glu Thr Asp  Asp Leu Ile Gln Ser  Thr Ile Arg
    1460                 1465                 1470

Thr Gln  Phe Glu Asp Cys Thr  Val Leu Thr Ile Ala  His Arg Leu
    1475                 1480                 1485

Asn Thr  Ile Met Asp Tyr Thr  Arg Val Ile Val Leu  Asp Lys Gly
    1490                 1495                 1500

Glu Ile  Gln Glu Tyr Gly Ala  Pro Ser Asp Leu Leu  Gln Gln Arg
    1505                 1510                 1515

Gly Leu  Phe Tyr Asn Met Ala  Arg Asp Ala Gly Leu  Val
    1520                 1525                 1530
```

<210> SEQ ID NO 159
<211> LENGTH: 1329
<212> TYPE: PRT
<213> ORGANISM: Macaca fascicularis

<400> SEQUENCE: 159

```
Met Asp Pro Asn Pro Cys Pro Glu Ser Ser Ala Ser Phe Leu Ser Arg
1               5                   10                  15

Ile Thr Phe Trp Trp Ile Thr Gly Leu Ile Val Arg Gly Tyr Arg Gln
            20                  25                  30

Pro Leu Glu Gly Ser Asp Leu Trp Ser Leu Asn Lys Glu Asp Thr Ser
        35                  40                  45

Glu Gln Val Val Pro Val Leu Val Lys Asn Trp Lys Lys Glu Cys Ala
    50                  55                  60

Lys Thr Arg Lys Gln Pro Val Lys Val Val Tyr Ser Ser Lys Asp Pro
65                  70                  75                  80

Ala Gln Pro Lys Asp Ser Ser Lys Val Asp Ala Asn Glu Glu Val Glu
                85                  90                  95

Ala Leu Ile Val Lys Ser Pro Gln Lys Glu Trp Asn Pro Ser Leu Phe
            100                 105                 110

Lys Val Leu Tyr Lys Thr Phe Gly Pro Tyr Phe Leu Met Ser Phe Phe
        115                 120                 125

Phe Lys Ala Ile His Asp Leu Met Met Phe Ser Gly Pro Glu Ile Leu
    130                 135                 140

Lys Leu Leu Ile Asn Phe Val Asn Asp Thr Lys Ala Pro Asp Trp Gln
```

-continued

```
145                 150                 155                 160

Gly Tyr Phe Tyr Thr Ala Leu Leu Phe Val Ala Ala Cys Leu Gln Thr
                165                 170                 175

Leu Val Leu His Gln Tyr Phe His Ile Cys Phe Val Ser Gly Met Arg
            180                 185                 190

Ile Lys Thr Ala Val Ile Gly Ala Val Tyr Arg Lys Ala Leu Val Ile
        195                 200                 205

Thr Asn Ala Ala Arg Lys Ser Ser Thr Val Gly Glu Ile Val Asn Leu
    210                 215                 220

Met Ser Val Asp Ala Gln Arg Phe Met Asp Leu Ala Thr Tyr Ile Asn
225                 230                 235                 240

Met Ile Trp Ser Ala Pro Leu Gln Val Ile Leu Ala Leu Tyr Leu Leu
                245                 250                 255

Trp Arg Asn Leu Gly Pro Pro Ile Leu Ala Gly Val Ala Val Met Val
            260                 265                 270

Leu Met Val Pro Val Asn Ala Val Met Ala Met Lys Thr Lys Thr Tyr
        275                 280                 285

Gln Val Ala His Met Lys Ser Lys Asp Asn Arg Ile Lys Leu Met Asn
    290                 295                 300

Glu Ile Leu Asn Gly Ile Lys Val Leu Lys Leu Tyr Ala Trp Glu Leu
305                 310                 315                 320

Ala Phe Lys Asp Lys Val Leu Ala Ile Arg Gln Glu Glu Leu Lys Val
                325                 330                 335

Leu Lys Lys Ser Ala Tyr Leu Ala Ala Val Gly Thr Phe Thr Trp Val
            340                 345                 350

Cys Thr Pro Phe Leu Val Ala Leu Cys Thr Phe Ala Val Tyr Val Thr
        355                 360                 365

Ile Asp Lys Asn Asn Val Leu Asp Ala Gln Lys Ala Phe Val Ser Leu
    370                 375                 380

Ala Leu Phe Asn Ile Leu Arg Phe Pro Leu Asn Ile Leu Pro Met Val
385                 390                 395                 400

Ile Ser Ser Ile Val Gln Ala Ser Val Ser Leu Lys Arg Leu Arg Ile
                405                 410                 415

Phe Leu Ser His Glu Glu Leu Glu Pro Asp Ser Ile Glu Arg Arg Pro
            420                 425                 430

Val Lys Asp Gly Gly Asp Thr Asn Ser Ile Thr Val Arg Asn Ala Thr
        435                 440                 445

Phe Thr Trp Ala Arg Ser Asp Pro Pro Thr Leu Asn Gly Ile Thr Phe
    450                 455                 460

Ser Ile Pro Glu Gly Ala Leu Val Ala Val Val Gly Gln Val Gly Cys
465                 470                 475                 480

Gly Lys Ser Ser Leu Leu Ser Ala Leu Leu Ala Glu Met Asp Lys Val
                485                 490                 495

Glu Gly His Val Ala Leu Lys Gly Ser Val Ala Tyr Val Pro Gln Gln
            500                 505                 510

Ala Trp Ile Gln Asn Asp Ser Leu Gln Glu Asn Ile Leu Phe Gly Cys
        515                 520                 525

Gln Leu Glu Glu Pro Tyr Tyr Arg Ser Val Ile Gln Ala Cys Ala Leu
    530                 535                 540

Leu Pro Asp Leu Glu Ile Leu Pro Ser Gly Asp Arg Thr Glu Ile Gly
545                 550                 555                 560

Glu Lys Gly Val Asn Leu Ser Gly Gly Gln Lys Gln Arg Val Ser Leu
                565                 570                 575
```

-continued

```
Ala Arg Ala Val Tyr Cys Asn Ala Asp Ile Tyr Leu Phe Asp Asp Pro
            580                 585                 590

Leu Ser Ala Val Asp Ala His Val Gly Lys His Ile Phe Glu Asn Val
        595                 600                 605

Ile Gly Pro Lys Gly Met Leu Lys Asn Lys Thr Arg Ile Leu Val Thr
    610                 615                 620

His Ser Met Ser Tyr Leu Pro Gln Val Asp Val Ile Ile Val Met Ser
625                 630                 635                 640

Gly Gly Lys Ile Ser Glu Met Gly Ser Tyr Gln Glu Leu Leu Ala Arg
                645                 650                 655

Asp Gly Ala Phe Ala Glu Phe Leu Arg Thr Tyr Ala Ser Ala Glu Gln
            660                 665                 670

Glu Gln Asp Pro Glu Asp Asn Gly Val Thr Gly Val Ser Gly Pro Gly
        675                 680                 685

Lys Glu Ala Lys Gln Met Glu Asn Gly Met Leu Val Thr Asp Ser Ala
    690                 695                 700

Gly Lys Gln Leu Gln Arg Gln Leu Ser Ser Ser Ser Ser Tyr Ser Gly
705                 710                 715                 720

Asp Val Ser Arg Gln His Asn Ser Thr Ala Glu Leu Gln Lys Asp Gly
                725                 730                 735

Ala Lys Lys Glu Glu Thr Trp Lys Leu Met Glu Ala Asp Lys Ala Gln
            740                 745                 750

Thr Gly Gln Val Lys Leu Ser Val Tyr Trp Asp Tyr Met Lys Ala Ile
        755                 760                 765

Gly Leu Phe Ile Ser Phe Leu Ser Ile Phe Leu Phe Ile Cys Asn His
    770                 775                 780

Val Ala Ala Leu Ala Ser Asn Tyr Trp Leu Ser Leu Trp Thr Asp Asp
785                 790                 795                 800

Pro Ile Val Asn Gly Thr Gln Glu His Thr Lys Val Arg Leu Ser Val
                805                 810                 815

Tyr Gly Ala Leu Gly Ile Ser Gln Gly Ile Ala Val Phe Gly Tyr Ser
            820                 825                 830

Met Ala Val Ser Ile Gly Gly Ile Leu Ala Ser Arg Cys Leu His Val
        835                 840                 845

Asp Leu Leu His Ser Ile Leu Arg Ser Pro Met Ser Phe Phe Glu Arg
    850                 855                 860

Thr Pro Ser Gly Asn Leu Val Asn Arg Phe Ser Lys Glu Leu Asp Thr
865                 870                 875                 880

Val Asp Ser Met Ile Pro Glu Val Ile Lys Met Phe Met Gly Ser Leu
                885                 890                 895

Phe Asn Val Ile Gly Ala Cys Ile Val Ile Leu Leu Ala Thr Pro Ile
            900                 905                 910

Ala Ala Ile Ile Ile Pro Pro Leu Gly Leu Ile Tyr Phe Phe Val Gln
        915                 920                 925

Arg Phe Tyr Val Ala Ser Ser Arg Gln Leu Lys Arg Leu Glu Ser Val
    930                 935                 940

Ser Arg Ser Pro Val Tyr Ser His Phe Asn Glu Thr Leu Leu Gly Val
945                 950                 955                 960

Ser Val Ile Arg Ala Phe Glu Glu Gln Glu Arg Phe Ile His Gln Ser
                965                 970                 975

Asp Leu Lys Val Asp Glu Asn Gln Lys Ala Tyr Tyr Pro Ser Ile Val
            980                 985                 990
```

```
Ala Asn Arg Trp Leu Ala Val Arg  Leu Glu Cys Val Gly  Asn Cys Ile
        995                 1000                 1005

Val Leu  Phe Ala Ala Leu Phe  Ala Val Ile Ser Arg  His Ser Leu
    1010                 1015                 1020

Ser Ala  Gly Leu Val Gly Leu  Ser Val Ser Tyr Ser  Leu Gln Val
    1025                 1030                 1035

Thr Thr  Tyr Leu Asn Trp Leu  Val Arg Met Ser Ser  Glu Met Glu
    1040                 1045                 1050

Thr Asn  Ile Val Ala Val Glu  Arg Leu Lys Glu Tyr  Ser Glu Thr
    1055                 1060                 1065

Glu Lys  Glu Ala Pro Trp Gln  Ile Gln Glu Thr Ala  Pro Pro Ser
    1070                 1075                 1080

Asn Trp  Pro Gln Val Gly Arg  Val Glu Phe Arg Asn  Tyr Cys Leu
    1085                 1090                 1095

Arg Tyr  Arg Glu Asp Leu Asp  Phe Val Leu Arg His  Ile Asn Val
    1100                 1105                 1110

Thr Ile  Asn Gly Gly Glu Lys  Val Gly Ile Val Gly  Arg Thr Gly
    1115                 1120                 1125

Ala Gly  Lys Ser Ser Leu Thr  Leu Gly Leu Phe Arg  Ile Asn Glu
    1130                 1135                 1140

Ser Ala  Glu Gly Glu Ile Ile  Ile Asp Gly Ile Asn  Ile Ala Arg
    1145                 1150                 1155

Ile Gly  Leu His Asp Leu Arg  Phe Lys Ile Thr Ile  Ile Pro Gln
    1160                 1165                 1170

Asp Pro  Val Leu Phe Ser Gly  Ser Leu Arg Met Asn  Leu Asp Pro
    1175                 1180                 1185

Phe Ser  Gln Tyr Ser Asp Glu  Glu Val Trp Thr Ser  Leu Glu Leu
    1190                 1195                 1200

Ala His  Leu Lys Gly Phe Val  Ser Ala Leu Pro Asp  Lys Leu Asp
    1205                 1210                 1215

His Glu  Cys Ala Glu Gly Gly  Glu Asn Leu Ser Val  Gly Gln Arg
    1220                 1225                 1230

Gln Leu  Val Cys Leu Ala Arg  Ala Leu Leu Arg Lys  Thr Lys Ile
    1235                 1240                 1245

Leu Val  Leu Asp Glu Ala Thr  Ala Ala Val Asp Leu  Glu Thr Asp
    1250                 1255                 1260

Asp Leu  Ile Gln Ser Thr Ile  Arg Thr Gln Phe Glu  Asp Cys Thr
    1265                 1270                 1275

Val Leu  Thr Ile Ala His Arg  Leu Asn Thr Ile Met  Asp Tyr Thr
    1280                 1285                 1290

Arg Val  Ile Val Leu Asp Lys  Gly Glu Ile Gln Glu  Tyr Gly Ala
    1295                 1300                 1305

Pro Ser  Asp Leu Leu Gln Gln  Arg Gly Leu Phe Tyr  Asn Met Ala
    1310                 1315                 1320

Arg Asp  Ala Gly Leu Val
    1325
```

<210> SEQ ID NO 160
<211> LENGTH: 5
<212> TYPE: PRT
<213> ORGANISM: Artificial sequence
<220> FEATURE:
<223> OTHER INFORMATION: synthetic sequence

<400> SEQUENCE: 160

Gly Ser Gly Gly Ser
1 5

<210> SEQ ID NO 161
<211> LENGTH: 4
<212> TYPE: PRT
<213> ORGANISM: Artificial sequence
<220> FEATURE:
<223> OTHER INFORMATION: synthetic sequence

<400> SEQUENCE: 161

Gly Gly Gly Ser
1

<210> SEQ ID NO 162
<211> LENGTH: 4
<212> TYPE: PRT
<213> ORGANISM: Artificial sequence
<220> FEATURE:
<223> OTHER INFORMATION: synthetic sequence

<400> SEQUENCE: 162

Gly Gly Ser Gly
1

<210> SEQ ID NO 163
<211> LENGTH: 5
<212> TYPE: PRT
<213> ORGANISM: Artificial sequence
<220> FEATURE:
<223> OTHER INFORMATION: synthetic sequence

<400> SEQUENCE: 163

Gly Gly Ser Gly Gly
1 5

<210> SEQ ID NO 164
<211> LENGTH: 5
<212> TYPE: PRT
<213> ORGANISM: Artificial sequence
<220> FEATURE:
<223> OTHER INFORMATION: synthetic sequence

<400> SEQUENCE: 164

Gly Ser Gly Ser Gly
1 5

<210> SEQ ID NO 165
<211> LENGTH: 5
<212> TYPE: PRT
<213> ORGANISM: Artificial sequence
<220> FEATURE:
<223> OTHER INFORMATION: synthetic sequence

<400> SEQUENCE: 165

Gly Ser Gly Gly Gly
1 5

<210> SEQ ID NO 166
<211> LENGTH: 5
<212> TYPE: PRT
<213> ORGANISM: Artificial sequence
<220> FEATURE:
<223> OTHER INFORMATION: synthetic sequence

<400> SEQUENCE: 166

Gly Gly Gly Ser Gly 1 5

<210> SEQ ID NO 167
<211> LENGTH: 5
<212> TYPE: PRT
<213> ORGANISM: Artificial sequence
<220> FEATURE:
<223> OTHER INFORMATION: synthetic sequence

<400> SEQUENCE: 167

Gly Ser Ser Ser Gly
1 5

<210> SEQ ID NO 168
<211> LENGTH: 15
<212> TYPE: PRT
<213> ORGANISM: Artificial sequence
<220> FEATURE:
<223> OTHER INFORMATION: synthetic sequence
<220> FEATURE:
<221> NAME/KEY: SITE
<222> LOCATION: (3)..(15)
<223> OTHER INFORMATION: Each amino acid at positions 3 to 15 is either present or absent

<400> SEQUENCE: 168

Gly Gly Gly Gly Gly Gly Gly Gly Gly Gly Gly Gly Gly Gly Gly
1 5 10 15

<210> SEQ ID NO 169
<211> LENGTH: 17
<212> TYPE: PRT
<213> ORGANISM: Artificial sequence
<220> FEATURE:
<223> OTHER INFORMATION: synthetic sequence

<400> SEQUENCE: 169

Trp Ile Ser Pro Tyr Gly Gly Ser Thr Tyr Tyr Ala Asp Ser Val Lys
1 5 10 15

Gly

<210> SEQ ID NO 170
<211> LENGTH: 9
<212> TYPE: PRT
<213> ORGANISM: Artificial sequence
<220> FEATURE:
<223> OTHER INFORMATION: synthetic sequence

<400> SEQUENCE: 170

Arg His Trp Pro Gly Gly Phe Asp Tyr
1 5

<210> SEQ ID NO 171
<211> LENGTH: 11
<212> TYPE: PRT
<213> ORGANISM: Artificial sequence
<220> FEATURE:
<223> OTHER INFORMATION: synthetic sequence

<400> SEQUENCE: 171

Arg Ala Ser Gln Asp Val Ser Thr Ala Val Ala
1 5 10

<210> SEQ ID NO 172
<211> LENGTH: 7
<212> TYPE: PRT
<213> ORGANISM: Artificial sequence
<220> FEATURE:
<223> OTHER INFORMATION: synthetic sequence

<400> SEQUENCE: 172

Ser Ala Ser Phe Leu Tyr Ser
1               5

<210> SEQ ID NO 173
<211> LENGTH: 9
<212> TYPE: PRT
<213> ORGANISM: Artificial sequence
<220> FEATURE:
<223> OTHER INFORMATION: synthetic sequence

<400> SEQUENCE: 173

Gln Gln Tyr Leu Tyr His Pro Ala Thr
1               5

<210> SEQ ID NO 174
<211> LENGTH: 118
<212> TYPE: PRT
<213> ORGANISM: Artificial sequence
<220> FEATURE:
<223> OTHER INFORMATION: synthetic sequence

<400> SEQUENCE: 174

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ser
        115

<210> SEQ ID NO 175
<211> LENGTH: 107
<212> TYPE: PRT
<213> ORGANISM: Artificial sequence
<220> FEATURE:
<223> OTHER INFORMATION: synthetic sequence

<400> SEQUENCE: 175

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

```
Glu Asp Phe Ala Thr Tyr Tyr Cys Gln Gln Tyr Leu Tyr His Pro Ala
                85                  90                  95

Thr Phe Gly Gln Gly Thr Lys Val Glu Ile Lys
            100                 105


<210> SEQ ID NO 176
<211> LENGTH: 240
<212> TYPE: PRT
<213> ORGANISM: Artificial sequence
<220> FEATURE:
<223> OTHER INFORMATION: synthetic sequence

<400> SEQUENCE: 176

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ser Gly Gly Gly Gly Ser Gly Gly Gly Gly Ser
        115                 120                 125

Gly Gly Gly Gly Ser Asp Ile Gln Met Thr Gln Ser Pro Ser Ser Leu
    130                 135                 140

Ser Ala Ser Val Gly Asp Arg Val Thr Ile Thr Cys Arg Ala Ser Gln
145                 150                 155                 160

Asp Val Ser Thr Ala Val Ala Trp Tyr Gln Gln Lys Pro Gly Lys Ala
                165                 170                 175

Pro Lys Leu Leu Ile Tyr Ser Ala Ser Phe Leu Tyr Ser Gly Val Pro
            180                 185                 190

Ser Arg Phe Ser Gly Ser Gly Ser Gly Thr Asp Phe Thr Leu Thr Ile
        195                 200                 205

Ser Ser Leu Gln Pro Glu Asp Phe Ala Thr Tyr Tyr Cys Gln Gln Tyr
    210                 215                 220

Leu Tyr His Pro Ala Thr Phe Gly Gln Gly Thr Lys Val Glu Ile Lys
225                 230                 235                 240


<210> SEQ ID NO 177
<211> LENGTH: 5
<212> TYPE: PRT
<213> ORGANISM: Artificial sequence
<220> FEATURE:
<223> OTHER INFORMATION: synthetic sequence

<400> SEQUENCE: 177

Asp Thr Tyr Ile His
1               5


<210> SEQ ID NO 178
<211> LENGTH: 17
<212> TYPE: PRT
```

<213> ORGANISM: Artificial sequence
<220> FEATURE:
<223> OTHER INFORMATION: synthetic sequence

<400> SEQUENCE: 178

Arg Ile Tyr Pro Thr Asn Gly Tyr Thr Arg Tyr Ala Asp Ser Val Lys
1               5                   10                  15

Gly

<210> SEQ ID NO 179
<211> LENGTH: 11
<212> TYPE: PRT
<213> ORGANISM: Artificial sequence
<220> FEATURE:
<223> OTHER INFORMATION: synthetic sequence

<400> SEQUENCE: 179

Trp Gly Gly Asp Gly Phe Tyr Ala Met Asp Tyr
1               5                   10

<210> SEQ ID NO 180
<211> LENGTH: 11
<212> TYPE: PRT
<213> ORGANISM: Artificial sequence
<220> FEATURE:
<223> OTHER INFORMATION: synthetic sequence

<400> SEQUENCE: 180

Arg Ala Ser Gln Asp Val Asn Thr Ala Val Ala
1               5                   10

<210> SEQ ID NO 181
<211> LENGTH: 9
<212> TYPE: PRT
<213> ORGANISM: Artificial sequence
<220> FEATURE:
<223> OTHER INFORMATION: synthetic sequence

<400> SEQUENCE: 181

Gln Gln His Tyr Thr Thr Pro Pro Thr
1               5

<210> SEQ ID NO 182
<211> LENGTH: 120
<212> TYPE: PRT
<213> ORGANISM: Artificial sequence
<220> FEATURE:
<223> OTHER INFORMATION: synthetic sequence

<400> SEQUENCE: 182

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln

```
            100                 105                 110

Gly Thr Leu Val Thr Val Ser Ser
        115                 120


<210> SEQ ID NO 183
<211> LENGTH: 107
<212> TYPE: PRT
<213> ORGANISM: Artificial sequence
<220> FEATURE:
<223> OTHER INFORMATION: synthetic sequence

<400> SEQUENCE: 183

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105


<210> SEQ ID NO 184
<211> LENGTH: 242
<212> TYPE: PRT
<213> ORGANISM: Artificial sequence
<220> FEATURE:
<223> OTHER INFORMATION: synthetic sequence

<400> SEQUENCE: 184

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Cys
            100                 105                 110

Gly Thr Leu Val Thr Val Ser Ser Gly Gly Gly Gly Ser Gly Gly Gly
        115                 120                 125

Gly Ser Gly Gly Gly Gly Ser Asp Ile Gln Met Thr Gln Ser Pro Ser
    130                 135                 140

Ser Leu Ser Ala Ser Val Gly Asp Arg Val Thr Ile Thr Cys Arg Ala
145                 150                 155                 160

Ser Gln Asp Val Asn Thr Ala Val Ala Trp Tyr Gln Gln Lys Pro Gly
                165                 170                 175
```

-continued

```
Lys Cys Pro Lys Leu Leu Ile Tyr Ser Ala Ser Phe Leu Tyr Ser Gly
            180                 185                 190

Val Pro Ser Arg Phe Ser Gly Ser Arg Ser Gly Thr Asp Phe Thr Leu
        195                 200                 205

Thr Ile Ser Ser Leu Gln Pro Glu Asp Phe Ala Thr Tyr Tyr Cys Gln
    210                 215                 220

Gln His Tyr Thr Thr Pro Pro Thr Phe Gly Gln Gly Thr Lys Val Glu
225                 230                 235                 240

Ile Lys
```